(12) United States Patent
Beck et al.

(10) Patent No.: US 9,163,263 B2
(45) Date of Patent: *Oct. 20, 2015

(54) IDENTIFICATION OF ISOPRENE SYNTHASE VARIANTS WITH IMPROVED PROPERTIES FOR THE PRODUCTION OF ISOPRENE

(71) Applicants: Danisco US Inc., Palo Alto, CA (US); The Goodyear Tire & Rubber Company, Akron, OH (US)

(72) Inventors: Zachary Q. Beck, Palo Alto, CA (US); David A. Estell, San Francisco, CA (US); Jeffrey V. Miller, Menlo Park, CA (US); James Ngai, San Jose, CA (US); Christopher L. Rife, Redwood City, CA (US); Derek H. Wells, Palo Alto, CA (US)

(73) Assignees: The Goodyear Tire & Rubber Company, Akron, OH (US); Danisco US Inc., Palo Alto, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/801,971

(22) Filed: Mar. 13, 2013

(65) Prior Publication Data

US 2013/0330796 A1    Dec. 12, 2013

Related U.S. Application Data

(60) Provisional application No. 61/641,823, filed on May 2, 2012.

(51) Int. Cl.
C12P 5/00     (2006.01)
C12N 9/88     (2006.01)

(52) U.S. Cl.
CPC . C12P 5/007 (2013.01); C12N 9/88 (2013.01); C12Y 402/03027 (2013.01)

(58) Field of Classification Search
None
See application file for complete search history.

(56) References Cited

U.S. PATENT DOCUMENTS

| | | |
|---|---|---|
| 1,344,713 A | 6/1920 | Peters |
| 3,686,349 A | 8/1972 | Schliebs et al. |
| 4,570,029 A | 2/1986 | Kulprathipanja et al. |
| 4,647,344 A | 3/1987 | Lindner et al. |
| 4,683,195 A | 7/1987 | Mullis et al. |
| 4,683,202 A | 7/1987 | Mullis |
| 4,703,007 A | 10/1987 | Mulholland et al. |
| 4,846,872 A | 7/1989 | Kamuro et al. |
| 4,965,188 A | 10/1990 | Mullis et al. |
| 5,322,770 A | 6/1994 | Gelfand |
| 5,349,126 A | 9/1994 | Chappell et al. |
| 5,380,831 A | 1/1995 | Adang et al. |
| 5,436,391 A | 7/1995 | Fujimoto et al. |
| 5,545,816 A | 8/1996 | Ausich et al. |
| 5,849,970 A | 12/1998 | Fall et al. |
| 5,874,276 A | 2/1999 | Fowler et al. |
| 6,022,725 A | 2/2000 | Fowler et al. |
| 6,106,888 A | 8/2000 | Dale et al. |
| 6,176,176 B1 | 1/2001 | Dale et al. |
| 6,268,328 B1 | 7/2001 | Mitchinson et al. |
| 6,270,739 B1 | 8/2001 | Barnicki et al. |
| 6,294,653 B1 | 9/2001 | Mayfield |
| 6,582,914 B1 | 6/2003 | Caldwell et al. |
| 6,806,076 B1 | 10/2004 | Miyake et al. |
| 6,989,257 B2 | 1/2006 | Berry et al. |
| 6,998,471 B2 | 2/2006 | Hallahan et al. |
| 7,129,392 B2 | 10/2006 | Hahn et al. |
| 7,132,268 B2 | 11/2006 | Miyake et al. |
| 7,132,527 B2 | 11/2006 | Payne et al. |
| 7,172,886 B2 | 2/2007 | Keasling et al. |
| 7,183,089 B2 | 2/2007 | Keasling et al. |
| 7,208,298 B2 | 4/2007 | Miyake et al. |
| 7,241,587 B2 | 7/2007 | Dodge et al. |
| 7,262,041 B2 | 8/2007 | Baldwin et al. |
| 7,364,885 B2 | 4/2008 | Miyake et al. |
| 7,371,558 B2 | 5/2008 | Cervin et al. |
| 7,531,333 B2 | 5/2009 | Miyake et al. |
| 7,659,097 B2 | 2/2010 | Renninger et al. |
| 7,785,858 B2 | 8/2010 | Kozlov et al. |
| 8,173,410 B2 | 5/2012 | Bott et al. |
| 8,288,148 B2 | 10/2012 | Cervin et al. |
| 8,420,360 B2 | 4/2013 | Calabria et al. |
| 8,518,686 B2 | 8/2013 | Beck et al. |
| 8,709,785 B2 | 4/2014 | Cervin et al. |
| 2002/0095818 A1 | 7/2002 | Jain et al. |
| 2003/0033626 A1 | 2/2003 | Hahn et al. |
| 2004/0005678 A1 | 1/2004 | Keasling et al. |
| 2004/0219629 A1 | 11/2004 | Cheng et al. |
| 2005/0287655 A1 | 12/2005 | Tabata et al. |
| 2006/0009647 A1 | 1/2006 | Yeates et al. |

(Continued)

FOREIGN PATENT DOCUMENTS

| | | |
|---|---|---|
| DE | 196 29 568 C1 | 1/1998 |
| EP | 0 215 594 A2 | 3/1987 |

(Continued)

OTHER PUBLICATIONS

Altschul, S.F. et al. (1990). "Basic Local Alignment Search Tool," *J. Mol. Biol.* 215:403-410.

Altschul, S.F. et al. (1996). "Local Alignment Statistics," Chapter 27 in *Multiple Alignment and Phylogenetic Trees*, American Press, Inc. 266:460-480.

Altschul, S.F. et al. (1997). "Gapped BLAST and PSI-BLAST: A New Generation of Protein Database Search Programs," *Nucleic Acids Research* 25(17):3389-3402.

(Continued)

*Primary Examiner* — Nashaat Nashed
(74) *Attorney, Agent, or Firm* — Mintz, Levin, Cohn, Ferris, Glovsky and Popeo, P.C.

(57) ABSTRACT

The invention provides for compositions and methods for producing isoprene using isoprene synthase variants with improved properties.

15 Claims, 45 Drawing Sheets

(56) References Cited

U.S. PATENT DOCUMENTS

| | | |
|---|---|---|
| 2006/0020095 A1 | 1/2006 | Gandon-Pain |
| 2008/0038805 A1 | 2/2008 | Melis |
| 2008/0178354 A1 | 7/2008 | Chappell |
| 2009/0155874 A1 | 6/2009 | Clark et al. |
| 2009/0203102 A1 | 8/2009 | Cervin et al. |
| 2009/0282545 A1 | 11/2009 | Eichelberger et al. |
| 2010/0003716 A1 | 1/2010 | Cervin et al. |
| 2010/0048964 A1 | 2/2010 | Calabria et al. |
| 2010/0086978 A1 | 4/2010 | Beck et al. |
| 2010/0113846 A1 | 5/2010 | McAuliffe et al. |
| 2010/0196977 A1 | 8/2010 | Chotani et al. |
| 2010/0196982 A1 | 8/2010 | Anderson |
| 2010/0285549 A1 | 11/2010 | Muramatsu et al. |
| 2010/0297749 A1 | 11/2010 | Aravanis et al. |
| 2011/0045563 A1 | 2/2011 | Melis |
| 2011/0076743 A1 | 3/2011 | Beck et al. |
| 2011/0159557 A1 | 6/2011 | Beck et al. |
| 2011/0178261 A1 | 7/2011 | Feher et al. |
| 2013/0045891 A1* | 2/2013 | Beck et al. ............... 506/10 |
| 2013/0078699 A1 | 3/2013 | Cervin et al. |
| 2013/0252303 A1 | 9/2013 | Beck et al. |
| 2013/0260432 A1 | 10/2013 | Bott et al. |

FOREIGN PATENT DOCUMENTS

| | | |
|---|---|---|
| EP | 0 215 594 A3 | 3/1987 |
| EP | 0 215 594 B1 | 3/1987 |
| EP | 0 215 594 B2 | 3/1987 |
| EP | 0 238 023 A2 | 9/1987 |
| EP | 0 238 023 A3 | 9/1987 |
| EP | 0 238 023 B1 | 9/1987 |
| EP | 0 238 023 B2 | 9/1987 |
| EP | 0 244 234 A2 | 11/1987 |
| EP | 0 244 234 A3 | 11/1987 |
| EP | 0 244 234 B1 | 11/1987 |
| EP | 0 244 234 B2 | 11/1987 |
| EP | 1 118 855 A2 | 7/2001 |
| EP | 1 118 855 A3 | 7/2001 |
| JP | 2006-271379 A | 10/2006 |
| JP | 2008-035831 A | 2/2008 |
| JP | 2008/61506 A | 3/2008 |
| JP | 2008-182950 A | 8/2008 |
| JP | 2009-207402 A | 9/2009 |
| KR | 2001-0084864 A | 9/2001 |
| RU | 2027760 C1 | 9/2000 |
| RU | 2 197 461 C2 | 1/2003 |
| WO | WO-95/04134 A1 | 2/1995 |
| WO | WO-95/11913 A1 | 5/1995 |
| WO | WO-96/35796 A1 | 11/1996 |
| WO | WO-92/02550 A3 | 1/1998 |
| WO | WO-98/02550 A2 | 1/1998 |
| WO | WO-00/17327 A2 | 3/2000 |
| WO | WO-00/17327 A3 | 3/2000 |
| WO | WO-00/17327 A9 | 3/2000 |
| WO | WO-01/58839 A1 | 8/2001 |
| WO | WO-02/076189 A1 | 10/2002 |
| WO | WO-02/099095 A2 | 12/2002 |
| WO | WO-02/099095 A3 | 12/2002 |
| WO | WO-2004/033646 A2 | 4/2004 |
| WO | WO-2004/033646 A3 | 4/2004 |
| WO | WO-2004/111214 A1 | 12/2004 |
| WO | WO-2005/001036 A2 | 1/2005 |
| WO | WO-2005/001036 C1 | 1/2005 |
| WO | WO-2005/007682 A2 | 1/2005 |
| WO | WO-2005/007682 A3 | 1/2005 |
| WO | WO-2005/078074 A2 | 8/2005 |
| WO | WO-2005/078074 A3 | 8/2005 |
| WO | WO-2006/063752 A1 | 6/2006 |
| WO | WO-2006/085899 A2 | 8/2006 |
| WO | WO-2006/085899 A3 | 8/2006 |
| WO | WO-2007/018062 A1 | 2/2007 |
| WO | WO-2007/136847 A2 | 11/2007 |
| WO | WO-2007/136847 A3 | 11/2007 |
| WO | WO-2007/140339 A2 | 12/2007 |
| WO | WO-2007/140339 A3 | 12/2007 |
| WO | WO-2007/140339 A8 | 12/2007 |
| WO | WO-2008/002472 A2 | 1/2008 |
| WO | WO-2008/002472 A3 | 1/2008 |
| WO | WO-2008/003078 A2 | 1/2008 |
| WO | WO-2008/003078 A3 | 1/2008 |
| WO | WO-2008/003078 A8 | 1/2008 |
| WO | WO-2008/137092 A2 | 11/2008 |
| WO | WO-2008/137092 A3 | 11/2008 |
| WO | WO-2008/153925 A2 | 12/2008 |
| WO | WO-2008/153925 A3 | 12/2008 |
| WO | WO-2008/153925 A9 | 12/2008 |
| WO | WO-2008/153934 A2 | 12/2008 |
| WO | WO-2008/153934 A3 | 12/2008 |
| WO | WO-2008/153935 A2 | 12/2008 |
| WO | WO-2008/153935 A3 | 12/2008 |
| WO | WO-2009/036067 A2 | 3/2009 |
| WO | WO-2009/036067 A3 | 3/2009 |
| WO | WO-2009/064910 A2 | 5/2009 |
| WO | WO-2009/064910 A3 | 5/2009 |
| WO | WO-2009/076676 A2 | 6/2009 |
| WO | WO-2009/076676 A3 | 6/2009 |
| WO | WO-2009/100231 A2 | 8/2009 |
| WO | WO-2009/100231 A3 | 8/2009 |
| WO | WO-2009/132220 A2 | 10/2009 |
| WO | WO-2009/132220 A3 | 10/2009 |
| WO | WO-2009/132220 A9 | 10/2009 |
| WO | WO-2010/003007 A2 | 1/2010 |
| WO | WO-2010/003007 A3 | 1/2010 |
| WO | WO-2010/005525 A1 | 1/2010 |
| WO | WO-2010/013077 A1 | 2/2010 |
| WO | WO-2010/031062 A1 | 3/2010 |
| WO | WO-2010/031068 A1 | 3/2010 |
| WO | WO-2010/031076 A2 | 3/2010 |
| WO | WO-2010/031076 A3 | 3/2010 |
| WO | WO-2010/031077 A1 | 3/2010 |
| WO | WO-2010/031079 A1 | 3/2010 |
| WO | WO-2010/078457 A2 | 7/2010 |
| WO | WO-2010/078457 A3 | 7/2010 |
| WO | WO-2010/124146 A2 | 10/2010 |
| WO | WO-2010/124146 A3 | 10/2010 |
| WO | WO-2010/148150 A1 | 12/2010 |
| WO | WO-2010/148256 A1 | 12/2010 |
| WO | WO-2011/000026 A1 | 1/2011 |
| WO | WO-2011/034863 A1 | 3/2011 |
| WO | WO-2011/159853 A1 | 12/2011 |
| WO | WO 2012/058494 * | 5/2012 |

OTHER PUBLICATIONS

Anderson, M.S. et al. (Nov. 15, 1989). "Isopentenyl Diphosphate: Dimethylallyl Diphosphate Isomerase. An Improved Purification of the Enzyme and Isolation of the Gene from *Saccharomyces cerevisiae*," *J. Biol. Chem.* 264(32):19169-19175.

Baldwin, S.A. et. al. (1978). "Novel Kinetic and Structural Properties of the Class-I D-Fructose 1,6-Bisphosphate Aldolase from *Escherichia coli* (Crookes' Strain)," *Biochem. J.* 169(3):643-652.

Bellion, E. et al. (1993). "Methylamine Utilization in Yeast and Bacteria: Studies Using in vivo NMR," Chapter 32 in *Microbial Growth on $C_1$ Compounds*, Murrell, J.C. et al. eds, Intercept Ltd: Andover, UK, pp. 415-432.

Berka, R.M. et al. (1989). "The Development of Gene Expression Systems for Filamentous Fungi," *Biotechnology Advances* 7(2):127-154.

Bhayana, V. et al. (1984). "Amino Acid Sequence of *Escherichia coli* Citrate Synthase," *Biochemistry* 23:2900-2905 (Figure 5).

Bologna, F.P. et al. (Aug. 2007). "*Escherichia coli* Malic Enzymes: Two Isoforms with Substantial Differences in Kinetic Properties, Metabolic Regulation, and Structure," *Journal of Bacteriology* 189(16):5937-5946.

Bologna, F.P. et al. (2010). "Characterization of *Escherichia coli* EutD: a Phosphotransacetylase of the Ethanolamine Operon," *The Journal of Microbiology* 48(5):629-636.

Bouvier, F. et al. (2005). "Biogenesis, Molecular Regulation and Function of Plant Isoprenoids," *Progress in Lipid Research* 44:357-429.

Branlant, G. et al. (1985). "Nucleotide Sequence of the *Escherichia coli* Gap Gene. Different evolutionary behavior of the $NAD^+$-binding

(56) References Cited

OTHER PUBLICATIONS domain and of the catalytic domain of D-glyceraldehyde-3-phosphate dehydrogenase," *Eur. J. Biochem.* 150:61-66.
Bunch, P.K. et al. (1997). "The *ldh*A Gene Encoding the Fermentative Lactate Dehydrogenase of *Escherichia coli*," *Microbiology* 143:187-195.
Campbell, E.I. et al. (1989). "Improved Transformation Efficiency of *Aspergillus niger* Using the Homologous *nia*D Gene for Nitrate Reductase," *Current Genetics* 16:53-56.
Dawes, E.A. et al. (1966). "The Route to Ethanol Formation in *Zymomonas mobilis*," *Biochem. J.* 98:795-803.
Devereux, J. et al. (1984). "A Comprehensive Set of Sequence Analysis Programs for the VAX," *Nucleic Acids Research* 12(1):387-395.
Dhe-Paganon, S. et al. (1994). "Mechanism of Mevalonate Pyrophosphate Decarboxylase: Evidence for a Carbocationic Transition State," *Biochemistry* 33(45):13355-13362.
Duckworth, H.W. et al. (1987). "Structural Basis for Regulation in Gram-Negative Bacterial Citrate Synthases," *Biochem. Soc. Symp.* 54:83-92.
Egan, S.E. et al. (Jul. 1992). "Molecular Characterization of the Entner-Doudoroff Pathway in *Escherichia coli*: Sequence Analysis and Localization of Promoters for the *edd-eda* Operon," *Journal of Bacteriology* 174(14):4638-4646.
Feng, D-F. et al. (1987). "Progressive Sequence Alignment as a Prerequisite to Correct Phylogenetic Trees," *Journal of Molecular Evolution* 25:351-360.
Fowler, Z.L. et. al. (Sep. 2009). "Increased Malonyl Coenzyme A Biosynthesis by Tuning the *Escherichia coli* Metabolic Network and Its Application to Flavanone Production," *Applied and Environmental Microbiology* 75(18):5831-5839.
GenBank Accession No. AB198180, last updated on May 10, 2005, located at <http://www.ncbi.nlm.nih.gov/nuccore/63108309>, last visited on Jun. 2, 2010, 2 pages.
GenBank Accession No. AB266390, last updated on Aug. 11, 2006, located at <http://www.ebi.ac.uk/ena/data/view/AB266390&display=text>, last visited on May 13, 2014, 2 pages.
GenBank Accession No. AB540131.1, last updated on Oct. 9, 2013, located at <http://www.ncbi.nlm.nih.gov/nuccore/299758081>, last visited on May 13, 2014, 2 pages.
GenBank Accession No. AJ294819.1, last updated Apr. 15, 2005, located at <http://www.ncbi.nlm.nih.gov/nuccore/AJ294819.1>, last visited on Dec. 7, 2011, 2 pages.
GenBank Accession No. AJ457070, last updated on Apr. 15, 2005, located at <http://www.ncbi.nlm.nih.gov/nuccore/38092202>, last visited on Jun. 2, 2010, 2 pages.
GenBank Accession No. AM410988.1, last updated Aug. 14, 2008, located at <http://www.ncbi.nlm.nih.gov/nuccore/AM410988.1>, last visited on Dec. 7, 2011, 2 pages.
GenBank Accession No. AY182241, last updated on May 4, 2004, located at <http://www.ncbi.nlm.nih.gov/nuccore/32265057>, last visited on Jun. 2, 2010, 2 pages.
GenBank Accession No. AY279379, last updated on Mar. 11, 2005, located at <http://www.ncbi.nlm.nih.gov/nuccore/AY279379>, last visited on May 13, 2014, 2 pages.
GenBank Accession No. AY316691, last updated on Feb. 15, 2005, located at <http://www.ncbi.nlm.nih.gov/nuccore/35187003>, last visited on Jun. 2, 2010, 2 pages.
GenBank Accession No. AY341431, last updated on Feb. 15, 2005, located at <http://www.ncbi.nlm.nih.gov/nuccore/33358228>, last visited on Jun. 2, 2010, 3 pages.
GenBank Accession No. CAC35696, last updated on Apr. 15, 2005, located at <http://www.ncbi.nlm.nih.gov/protein/CAC35696>, last visited on May 13, 2014, 2 pages.
GenBank Accession No. EF147555.1, last updated Mar. 24, 2009, located at <http://www.ncbi.nlm.nih.gov/nuccore/EF147555.1>, last visited on Dec. 7, 2011, 2 pages.
GenBank Accession No. EF638224.1, last updated May 3, 2010, located at <http://www.ncbi.nlm.nih.gov/nuccore/EF638224.1>, last visited on Dec. 7, 2011, 2 pages.

GenBank Accession No. EU693027, last updated on May 27, 2008, located at <http://www.ncbi.nlm.nih.gov/nuccore/189017053>, last visited on Jun. 2, 2010, 2 pages.
GenBank Accession No. JN173037, created Jan. 19, 2012, last updated on Apr. 17, 2013, located at http://www.ebi.ac.uk/ena/data/view/JN173037&display=text, last visited on May 13, 2014, 2 pages.
GenBank Accession No. JN173038, created Jan. 19, 2012, last updated on Apr. 17, 2013, located at http://www.ebi.ac.uk/ena/data/view/JN173038&display=text, last visited on May 13, 2014, 2 pages.
GenBank Accession No. JN173039, created Jan. 19, 2012, last updated on Apr. 17, 2013, located at http://www.ebi.ac.uk/ena/data/view/JN173039&display=text, last visited on May 13, 2014, 2 pages.
GenBank Accession No. JN173040, created Jan. 19, 2012, last updated on Apr. 17, 2013, located at http://www.ebi.ac.uk/ena/data/view/JN173040&display=text, last visited on May 13, 2014, 2 pages.
GenBank Accession No. JN173041, created Jan. 19, 2012, last updated on Apr. 17, 2013, located at http://www.ebi.ac.uk/ena/data/view/JN173041&display=text, last visited on May 13, 2014, 2 pages.
GenBank Accession No. JN173042, created Jan. 19, 2012, last updated on Apr. 17, 2013, located at http://www.ebi.ac.uk/ena/data/view/JN173042&display=text, last visited on May 13, 2014, 2 pages.
GenBank Accession No. JN173043, created Jan. 19, 2012, last updated on Apr. 17, 2013, located at http://www.ebi.ac.uk/ena/data/view/JN173043&display=text, last visited on May 13, 2014, 2 pages.
GenBank Accession No. NC_001416, last updated on Mar. 11, 2011, located at http://www.ncbi.nlm.nih.gov/nuccore/9626243?report=genbank, last visited on May 13, 2014, 42 pages.
Greenberg, J.P. et al. (1993). "Sub-Parts Per Billion Detection of Isoprene Using a Reduction Gas Detector with a Portable Gas Chromatograph," *Atmospheric Environment* 27A(16):2689-2692.
Hedl, M. et al. (Apr. 2002). "*Enterococcus faecalis* Acetoacetyl-Coenzyme a Thiolase/3-Hydroxy-3-Methylglutaryl-Coenzyme A Reductase, a Dual-Function Protein of Isopentenyl Diphosphate Biosynthesis," *Journal of Bacteriology* 184(8):2116-2122.
Henikoff, S. et al. (Nov. 1992). "Amino Acid Substitution Matrices from Protein Blocks," *Proc. Natl. Acad. Sci. USA* 89:10915:10919.
Higgins, D.G. et al. (1989). "Fast and Sensitive Multiple Sequence Alignments on a Microcomputer," *Cabios Communications* 5(2):151-153.
Hoeffler, J-F. et al. (2002). "Isoprenoid Biosynthesis via the Methylerythritol Phosphate Pathway. Mechanistic Investigations of the 1-Deoxy-D-Xylulose 5-Phosphate Reductoisomerase," *Eur. J. Biochem.* 269:4446-4457.
Hunter, B.K. (1985). "Formaldehyde Metabolism by *Escherichia coli*. Carbon and Solvent Deuterium Incorporation into Glycerol, 1,2-Propanediol, and 1,3-Propanediol," *Biochemistry* 24(15):4148-4155.
Ilmén, M. et al. (Apr. 1997). "Regulation of Cellulase Gene Expression in the Filamentous Fungus *Trichoderma reesei*," *Appl. Environ. Microbiol.* 63(4):1298-1306.
Iwakura, M. et al. (1979). "Studies on Regulatory Functions of Malic Enzymes," *J. Biochem.* 85:1355-1365.
Julsing, M.K. et al. (Jul. 2007, e-pub. Apr. 26, 2007). "Functional Analysis of Genes Involved in the Biosynthesis of Isoprene in *Bacillus subtilis*," *Applied Microbiol. Biotechnol.* 75(6):1377-1384.
Kakuda, H. et al. (1994). "Identification and Characterization of the *ack*A (Acetate Kinase A)-*pta* (Phosphotransacetylase) Operon and Complementation Analysis of Acetate Utilization by an *ackA-pta* Deletion Mutant of *Escherichia coli*," *J. Biochem.* 116:916-922.
Karlin, S. et al. (Jun. 1993). "Applications and Statistics for Multiple High-scoring Segments in Molecular Sequences," *Proc. Natl. Acad. Sci. USA* 90:5873-5877.
Kotlarz, D. et al. (1975). "Regulation of the Amount and of the Activity of Phosphofructokinases and Pyruvate Kinases in *Escherichia coli*," *Biochimica et Biophysica Acta* 381:257-268.
Kuzma, J. et al. (1995). "Bacteria Produce the Volatile Hydrocarbon Isoprene," *Current Microbiology* 30:97-103.
Lindberg, P. et al. (2010). "Engineering a Platform for Photosynthetic Isoprene Production in Cyanobacteria, Using *Synechocystis* as the Model Organism," *Metabolic Engineering* 12(1):70-79.

(56) References Cited

OTHER PUBLICATIONS

Lüttgen, H. et al. (Feb. 1, 2000). "Biosynthesis of Terpenoids: YchB Protein *Escherichia coli* Phosphorylates the 2-Hydroxy Group of 4-Diphosphocytidyl-2C-Methyl-D-Erythritol," *PNAS* 97(3):1062-1067.

Maurus, R. et al. (2003). "Insights into the Evolution of Allosteric Properties. The NADH Binding Site of Hexameric Type II Citrate Synthases," *Biochemistry* 42:5555-5565.

Meile, L. et al. (May 2001). "Characterization of the D-Xylulose 5-Phosphate/D-Fructose 6-Phosphate Phosphoketolase Gene (*xfp*) from *Bifidobacterium lactis*," *Journal of Bacteriology* 183(9):2929-2936.

Miller, B. et al. (2001, e-pub. May 10, 2001). "First Isolation of an Isoprene Synthase Gene from Poplar and Successful Expression of the Gene in *Escherichia coli*," *Planta* 213(3):483-487.

Murrell, J.C. et al. (1993). "Detection of Methylotrophic Bacteria in Natural Samples by Molecular Probing Techniques," *Chemosphere* 26(1-4):1-11.

Needleman, S.B. et al. (1970). "A General Method Applicable to the Search for Similarities in the Amino Acid Sequence of Two Proteins," *J. Mol. Biol.* 48:443-453.

Ner, S.S. et al. (Nov. 8, 1983). "Complete Sequence of the *glt* A Gene Encoding Citrate Synthase in *Escherichia coli*," *Biochemistry* 22(23):5243-5249.

Ogasawara, H. et al. (2007). "PdhR (Pyruvate Dehydrogenase Complex Regulator) Controls the Respiratory Electron Transport System in *Escherichia coli*," *Journal of Bacteriology* 189(15):5534-5541.

Oh, M-K. et al. (Apr. 12, 2002). "Global Expression Profiling of Acetate-grown *Escherichia coli*," *The Journal of Biological Chemistry* 277(15):13175-13183.

Okamura, E. et al. (Jun. 22, 2010). "Unprecedented Acetoacetyl-coenzyme a Synthesizing Enzyme of the Thiolase Superfamily Involved in the Mevalonate Pathway," *PNAS* 107(25):11265-11270.

Oulmouden, A. et al. (1991). "Nucleotide Sequence of the *ERG12* Gene of *Saccharomyces cerevisiae* Encoding Mevalonate Kinase," *Curr. Genet.* 19:9-14.

Pearson, W.R. et al. (Apr. 1988). "Improved Tools for Biological Sequence Comparison," *Proc. Natl. Acad. Sci. USA* 85:2444-2448.

Peekhaus, N. et al. (Jul. 1998). "What's for Dinner?: Entner-Doudoroff Metabolism in *Escherichia coli*," *Journal of Bacteriology* 180(14):3495-3502.

Pourquié, J. et al. (1988). "Scale Up of Cellulase Production and Utilization," in *Biochemistry and Genetics of Cellulose Degradation*, Aubert, J.-P. et al. eds., Academic Press: San Diego, CA, pp. 71-86.

Quant, P.A. et al. (1989). "Treatment of Rats With Glucagon or Mannoheptulose Increases Mitochondrial 3-Hydroxy-3-Methylglutaryl-CoA Synthase Activity and Decreases Succinyl-CoA Content in Liver," *Biochem. J.* 262:159-164.

Rohdich, F. et al. (Oct. 12, 1999). "Cytidine 5'-Triphosphate-Dependent Biosynthesis of Isoprenoids: YgbP Protein of *Escherichia coli* Catalyzes the Formation of 4-Diphosphocytidyl-2-*C*-Methylerythritol," *PNAS* 96(21):11758-11763.

Rohdich, F. et al. (Jun. 6, 2000). "Biosynthesis of Terpenoids: 4-Diphosphocytidyl-2C-Methyl-D-Erythritol Synthase of *Arabidopsis thaliana*," *PNAS* 97(12):6451-6456.

Romanos, M.A. et al. (1992). "Foreign Gene Expression in Yeast: a Review," *Yeast* 8(6):423-488.

Sánchez, A.M. et al. (2005). "Novel Pathway Engineering Design of The Anaerobic Central Metabolic Pathway in *Escherichia coli* to Increase Succinate Yield and Productivity," *Metabolic Engineering* 7:229-239.

Sharkey, T.D. et al. (Feb. 2005). "Evolution of the Isoprene Biosynthetic Pathway in Kudzu," *Plant Physiology* 137:700-712.

Shimizu, M. et al. (1969). "Phosphotransacetylase of *Escherichia coli* B, Purification and Properties," *Biochimica et Biophysica Acta* 191:550-558.

Silver, G.M. et al. (1991). "Enzymatic Synthesis of Isoprene from Dimethylallyl Diphosphate in Aspen Leaf Extracts," *Plant Physiol.* 97:1588-1591.

Silver, G.M. et al. (Jun. 2, 1995). "Characterization of Aspen Isoprene Synthase, an Enzyme Responsible for Leaf Isoprene Emission to the Atmosphere," *The Journal of Biological Chemistry* 270(22):13010-13016.

Smith, T.F. et al. (1981). "Comparison of Biosequences," *Advances in Applied Mathematics* 2:482-489.

Sprenger, G.A. (1995). "Genetics of Pentose-Phosphate Pathway Enzymes of *Escherichia coli* K-12," *Arch. Microbiol.* 164:324-330.

Sprenger, G.A. et al. (Nov. 1997). "Identification of a Thiamin-Dependent Synthase in *Escherichia coli* Required for the Formation of the 1-Deoxy-D-Xylulose 5-Phosphate Precursor to Isoprenoids, Thiamin, and Pyridoxol," *Proc. Natl. Acad. Sci. USA* 94:12857-12862.

Stokell, D.J. et al. (Sep. 12, 2003). "Probing the Roles of Key Residues in the Unique Regulatory NADH Binding Site of Type II Citrate Synthase of *Escherichia coli*," *The Journal of Biological Chemistry* 278(37):35435-35443.

Stulke, J. et al. (2000). "Regulation of Carbon Catabolism in *Bacillus* Species," *Annu. Rev. Microbiol.* 54:849-880.

Sulter, G.J. et al. (1990). "Proliferation and Metabolic Significance of Peroxisomes in *Candida boidinii* During Growth on D-Alanine or Oleic Acid as the Sole Carbon Source," *Arch. Microbiol.* 153:485-489.

Sutherlin, A. et al. (Aug. 2002). "*Enterococcus faecalis* 3-Hydroxy-3-Methylglutaryl Coenzyme A Synthase, an Enzyme of Isopentenyl Diphosphate Biosynthesis," *Journal of Bacteriology* 184(15):4065-4070.

Tabata, K. et al. (2004). "Production of Mevalonate by a Metabolically-engineered *Escherichia coli*," *Biotechnology Letters* 26:1487-1491.

Teymouri, F. et al. (2005, e-pub. Feb. 24, 2005). "Optimization of the Ammonia Fiber Explosion (AFEX) Treatment Parameters for Enzymatic Hydrolysis of Corn Stover," *Bioresource Technology* 96:2014-2018.

Tsay, Y.H. et al. (Feb. 1991). "Cloning and Characterization of *ERG8*, an Essential Gene of *Saccharomyces cerevisiae* That Encodes Phosphomevalonate Kinase," *Molecular and Cellular Biology* 11(2):620-631.

Underwood, S.A. et al. (2002). "Flux through Citrate Synthase Limits the Growth of Ethanologenic *Escherichia coli* KO11 During Xylose Fermentation," *Applied and Environmental Microbiology* 68(3):1071-1081.

UniProt Database Accession No. H2CSU6, Mar. 21, 2012, located at http://www.uniprot.org/uniprot/H2CSU6.txt, last visited on May 13, 2014, 1 page.

Wagner, W.P. et al. (Aug. 1999). "Three Distinct Phases of Isoprene Formation During Growth and Sporulation of *Bacillus subtilis*," *Journal of Bacteriology* 181(15):4700-4703.

Weissermel, K. et al. (2003). "Isoprene," in *Industrial Organic Chemistry*, 4th Completely Revised Edition, translated by Lindley, C.R. et al., Wiley-VCH GmbH & Co. KGaA, Weinheim, Germany, pp. 117-122.

Wiegand, G. et al. (1986). "Citrate Synthase: Structure, Control, and Mechanism," *Ann. Rev. Biophys. Biophys. Chem.* 15:97-117.

Wilkins, K. (1996). "Volatile Metabolites from Actinomycetes," *Chemosphere* 32(7):1427-1434.

Wolfe, A.J. (2005). "The Acetate Switch," *Microbiol. Mol. Biol. Rev.* 69(1):12-50.

Yamada, K. et al. (1989). "Production of Glycerol from Methanol by a Mutant Strain of *Candida boidinii* No. 2201," *Agric. Biol. Chem.* 53(2):541-543.

Zepeck, F. et al. (2005, e-pub. Oct. 14, 2005). "Biosynthesis of Isoprenoids. Purification and Properties of IspG Protein from *Escherichia coli*," *J. Org. Chem.* 70:9168-9174.

International Search Report mailed on Jan. 31, 2014 for PCT Patent Application No. PCT/US2013/039151 filed on May 1, 2013, 6 pages.

Alper, H. et al. (2008). "Uncovering the Gene Knockout Landscape for Improved Lycopene Production in *E. coli*," *Appl. Microbiol. Biotechnol.* 10 pages.

Alterthum, F. et al. (Aug. 1989). "Efficient Ethanol Production from Glucose, Lactose, and Xylose by Recombinant *Escherichia coli*," *Applied Environmental Microbiology* 55(8):1943-1948.

(56) References Cited

OTHER PUBLICATIONS

Alves, R. et al. (Nov. 2000). "Effect of Overall Feedback Inhibition in Unbranched Biosynthetic Pathways," *Biophysical Journal* 79(5):2290-2304.

Andreassi, J.L. et al. (2004, e-pub. Dec. 4, 2004). "*Streptococcus pneumoniae* Isoprenoid Biosynthesis is Downregulated by Diphosphomevalonate: An Antimicrobial Target," *Biochemistry* 43(51):16461-16466.

Andreassi, J.L. et al. (2007, e-pub. Mar. 30, 2007). "Crystal Structure of the *Streptococcus pneumoniae* Mevalonate Kinase in Complex with Diphosphomevalonate," *Protein Science* 16:983-989.

Aon, J.C. et al. (Feb. 2008, e-pub. Dec. 14, 2007). "Suppressing Posttranslational Gluconoylation of Heterologous Proteins by Metabolic Engineering of *Escherichia coli*," *Applied and Environmental Microbiology* 74(4):950-958.

Arai, Y. et al. (2004). "Production of Polyhydroxybutyrate by Polycistronic Expression of Bacterial Genes in Tobacco Plastid," *Plant Cell Physiol.* 45(9):1176-1184.

Ashby, M.N. et al. (Aug. 5, 1990). "Elucidation of the Deficiency in Two Yeast Coenzyme Q Mutants: Characterization of the Structural Gene Encoding Hexaprenyl Pyrophosphate Synthetase," *The Journal of Biological Chemistry* 265(22):13157-13164.

Ausubel, F. M. et al. eds. (1987). "Introduction of DNA into Mammalian Cells," Chapter 9 in *Current Protocols in Molecular Biology*.

Baba, T. et al. (Feb. 21, 2006). "Construction of *Escherichia coli* K-12 In-Frame, Single-Gene Knockout Mutants: The Keio Collection," *Molecular Systems Biology* pp. 1-11.

Barkovich, R. et al. (2001, e-pub. Dec. 1, 2000). "Metabolic Engineering of Isoprenoids," *Metabolic Engineering* 3:27-39.

Beaucage, S.L. et al. (1981). "Deoxynucleoside Phosphoramidites—A New Class of Key Intermediates for Deoxypolynucleotide Synthesis," *Tetrahedron Letters* 22(20):1859-1862.

Berman, H. et al. (2007, e-pub. Nov. 16, 2006). "The Worldwide Protein Data Bank (wwPDB): Ensuring a Single, Uniform Archive of PDB Data," *Nucleic Acids Research* 35:D301-D303.

Beytia, E. et al. (Oct. 25, 1970). "Purification and Mechanism of Action of Hog Liver Mevalonic Kinase," *The Journal of Biological Chemistry* 245(20):5450-5458.

Bock, R. et al. (2000). "Extranuclear Inheritance: Plastid Genetics: Manipulation of Plastid Genomes and Biotechnological Applications," *Progress in Botany* 61:76-90.

Bock, R. (2001). "Transgenic Plastids in Basic Research and Plant Biotechnology," *J. Mol. Biol.* 312:425-438.

Bock, R. et al. (Jun. 2004). "Taming Plastids for a Green Future," *Trends in Biotechnology* 22(6):311-318.

Boel, E. et al. (1984). "Two Different Types of Intervening Sequences in the Glucoamylase Gene from *Aspergillus niger*," *The EMBO Journal* 3(7):1581-1585.

Boynton, J.E. et al. (1993). "Chloroplast Transformation in *Chlamydomonas*," *Methods in Enzymology* 217(37):510-536.

Broun, P. et al. (Nov. 13, 1998). "Catalytic Plasticity of Fatty Acid Modification Enzymes Underlying Chemical Diversity of Plant Lipids," *Science* 282:1315-1317.

Brünger, A.T. et al. (1998). "*Crystallography & NMR System*: A New Software Suite for Macromolecular Structure Determination," *Acta Cryst.* D54:905-921.

Bubunenko, M. et al. (Apr. 2007). "Essentiality of Ribosomal and Transcription Antitermination Proteins Analyzed by Systematic Gene Replacement in *Escherichia coli*," *Journal of Bacteriology* 189(7):2844-2853.

Campbell, J.W. et al. (Oct. 2001). "*Escherichia coli* FadR Positively Regulates Transcription of the *fabB* Fatty Acid Biosynthetic Gene," *J. Bacteriol.* 183(20):5982-5990.

Campos, N. et al. (2001). "*Escherichia coli* Engineering to Synthesize Isopentenyl Diphosphate and Dimethylallyl Diphosphate from Mevalonate: A Novel System for the Genetic Analysis of the 2-C-Methyl-D-Erythritol 4-Phospate Pathway for Isoprenoid Biosynthesis," *Biochem. J.* 353:59-67.

Cao, Q.-N. et al. (2000). "Penicillopepsin-JT2, a Recombinant Enzyme from *Penicillium janthinellum* and the Contribution of a Hydrogen Bond in Subsite $S_3$ to $k_{cat}$," *Protein Science* 9:991-1001.

Chamberlin, M. et al. (Oct. 17, 1970). "New RNA Polymerase from *Escherichia coli* Infected with Bacteriophage T7," *Nature* 228:227-231.

Champenoy, S. et al. (1998). "Expression of the Yeast Mevalonate Kinase Gene in Transgenic Tobacco," *Molecular Breeding* 4:291-300.

Chan, W. et al. (2007, e-pub. Apr. 10, 2007). "A Recombineering Based Approach for High-Throughput Conditional Knockout Targeting Vector Construction," *Nucleic Acids Research* 35(8):e64, 13 pages.

Chappell, J. et al. (1995). "Is the Reaction Catalyzed by 3-Hydroxy-3-Methylglutaryl-Coenzyme A Reductase a Rate-Limiting Step for Isoprenoid Biosynthesis in Plants?" *Plant Physiology* 109:1337-1343.

Chemler, J.A. et al. (May 23, 2006). "Biosynthesis of Isoprenoids, Polyunsaturated Fatty Acids and Flavonoids in *Saccharomyces cerevisiae*," *Microbial Cell Factories* 5:20, 9 pages.

Cherepanov, P.P. et al. (1995). "Gene Disruption in *Escherichia coli*: $Tc^R$ and $Km^R$ Cassettes with the Option of Flp-Catalyzed Excision of the Antibiotic-Resistance Determinant," *Gene* 158(1):9-14.

Chica, R.A. et al. (2005). "Semi-Rational Approaches to Engineering Enzyme Activity: Combining the Benefits of Directed Evolution and Rational Design," *Current Opinion in Biotechnology* 16:378-384.

Cho, H.-J. et al. (1995). "Expression Pattern of Bacterial Polycistronic Genes in Tobacco Cells," *Journal of Fermentation and Bioengineering* 80(2):111-117.

Clarke, S. (1992). "Protein Isoprenylation and Methylation at Carboxyl-Terminal Cysteine Residues," *Annu. Rev. Biochem.* 61:355-386.

Clough, S.J. et al. (1998). "Floral Dip: A Simplified Method for *Agrobacterium*-Mediated Transformation of *Arabidopsis thaliana*," *The Plant Journal* 16(6):735-743.

Collaborative Computational Project, No. 4. (1994). "The *CCP4* Suite: Programs for Protein Crystallography," *Acta Cryst.* D50:760-763.

Cordier, H. et al. (1999). "Heterologous Expression in *Saccharomyces cerevisiae* of an *Arabidopsis thaliana* cDNA Encoding Mevalonate Diphosphate Decarboxylase," *Plant Molecular Biology* 39:953-967.

Cunningham, F.X. et al. (1998). "Genes and Enzymes of Carotenoid Biosynthesis in Plants," *Ann. Rev. Plant Physiol. Plant Mol. Biol.* 49:557-583.

Cunningham, F.X. et al. (Oct. 2000). "Evidence of a Role for LytB in the Nonmevalonate Pathway of Isoprenoid Biosynthesis," *Journal of Bacteriology* 182(20):5841-5848.

Dale, G.E. et al. (2003). "The Protein as a Variable in Protein Crystallization," *Journal of Structural Biology* 142:88-97.

Dale, P.J. (1992). "Spread of Engineered Genes to Wild Relatives," *Plant Physiol.* 100:13-15.

Daniell, H. (1997). "Transformation and Foreign Gene Expression in Plants Mediated by Microprojectile Bombardment," Chapter 35 in *Methods in Molecular Biology, Recombinant Gene Expression Protocols*, Tuan, R. ed., Humana Press, Inc., Totowa, NJ, 62:463-489.

Daniell, H. et al. (Apr. 1998) "Containment of Herbicide Resistance Through Genetic Engineering of the Chloroplast Genome," *Nature Biotechnology* 16:345-348.

Datsenko, K.A. et al. (Jun. 6, 2000). "One-Step Inactivation of Chromosomal Genes in *Escherichia coli* K-12 Using PCR Products," *PNAS* 97(12):6640-6645.

Datta, S. et al. (2006). "A Set of Recombineering Plasmids for Gram-Negative Bacteria," *Gene* 379:109-115.

Datukishvili, N.T. et al. (2001). "Isolation and Purification of Protein Responsible for the Conversion of Dimethylallylpyrophosphate from Poplar Leaves into Isoprene," *Russian Journal of Plant Physiology* 48(2):222-225.

Davidson, S. (Oct.-Dec. 2003). "Light Factories," located at <http://www.publish.csiro.au/?act=view_file&file_id=EC117p10.pdf>, last visited on Oct. 2, 2008.

(56) References Cited

OTHER PUBLICATIONS

Davis, I.W. et al. (2007). "MolProbity: All-Atom Contacts and Structure Validation for Proteins and Nucleic Acids," *Nucleic Acids Research* 35:W375-W383.

De Cosa, B. et al. (Jan. 2001). "Overexpression of the *Bt* cry2Aa2operon in Chloroplasts Leads to Formation of Insecticidal Crystals," *Nature Biotechnology* 19:71-74.

Del Campo, E. M. et al. (1997). "Plastid *ndhD* Gene of Barley, Sequence and Transcript Editing (Accesion No. Y12258) (PGR 97-090)," *Plant Physiol.* 114:747-749.

Della-Cioppa, G. et al. (1987). "Protein Trafficking in Plant Cells," *Plant Physiol*.84:965-968.

Deppenmeier, U. et al. (2002). "The Genome of *Methanosarcina mazei*: Evidence for Lateral Gene Transfer Between Bacteria and Archaea," *J. Mol. Microbiol. Biotechnol*. 4(4):453-461.

Deroles, S.C. et al. (1988). "Expression and Inheritance of Kanamycin Resistance in a Large Number of Transgenic Petunias Generated by *Agrobacterium*-Mediated Transformation," *Plant Molecular Biology* 11:355-364.

Dettmer, K. et al. (2000). "Stability of Reactive Low Boiling Hydrocarbons on Carbon Based Adsorbents Typically Used for Adsorptive Enrichment and Thermal Desorption," *Fresenius J. Anal. Chem.* 366:70-78.

Devos, D. et al. (2000). "Practical Limits of Function Prediction," *Proteins: Structure, Function, and Genetics* 41:98-107.

Dewick, P.M. et al. (2002, e-pub. Jan. 22, 2002). "The Biosynthesis of $C_5$—$C_{25}$ Terpenoid Compounds," *Nat. Prod. Rep.* 19:181-222.

Dorsey, J.K. et al. (Sep. 25, 1968). "The Inhibition of Mevalonic Kinase by Geranyl and Farnesyl Pyrophosphates," *The Journal of Biological Chemistry* 243(18):4667-4670.

Doumith, M. et al. (2000, e-pub. Aug. 25, 2000). "Analysis of Genes Involved in 6-Deoxyhexose Biosynthesis and Transfer in *Saccharopolyspora erythraea*," *Mol. Gen Genet*. 264:477-485.

Dynan, W.S. et al. (Aug. 29, 1985). "Control of Eukaryotic Messenger RNA Synthesis by Sequence-Specific DNA-Binding Proteins," *Nature* 316:774-778.

Eisenreich, W. et al. (Sep. 1998). "The Deoxyxylulose Phosphate Pathway of Terpenoid Biosynthesis in Plants and Microorganisms," *Chemistry and Biology* 5(9):R221-R233.

Eisenreich, W. et al, (Feb. 2001). "Deoxyxylulose Phosphate Pathway to Terpenoids," *Trends in Plant Science* 6(2):78-84.

Elroy-Stein, O. et al. (Aug. 1989). "Cap-Independent Translation of mRNA Conferred by Encephalomyocarditis Virus 5' Sequence Improves the Performance of the Vaccinia Virus/Bacteriophage T7 Hybrid Expression System," *PNAS USA* 86:6126-6130.

EMBL-EBI Accession No. A0PFK2, last updated on Mar. 2, 2010, located at <http://srs.ebi.ac.uk/srsbin/cgi-bin/wgetz?-e+[UNIPROT:A0PFK2_POPNI]+-newId>, last visited on Jun. 2, 2010, 2 pages.

EMBL-EBI Accession No. A9PGR5, last updated on Mar. 2, 2010, located at <http://srs.ebi.ac.uk/srsbin/cgi-bin/wgetz?-e+[UNIPROT:A9PGR5_POPTR]+-newId>, last visited on Jun. 2, 2010, 2 pages.

EMBL-EBI Accession No. AB198180, last updated May 10, 2005, located at <http://www.ebi.ac.uk/cgi-bin/dbfetch?db=embl&id=ab198180&Subm . . . >, last visited on Jul. 8, 2009, 2 pages.

EMBL-EBI Accession No. AY341431, last updated Apr. 16, 2005, located at <http://www.ebi.ac.uk/cgi-bin/dbfetch?db=embl&id=AY341431∈ . . . >, last visited on Nov. 26, 2009, 2 pages.

Emsley, P. et al. (2004). "*Coot*: Model-Building Tools for Molecular Graphics," *Acta Crystallographica* D60:2126-2132.

Emsley, P. et al. (2010). "Features and Development of *Coot*," *Acta Crystallographica* D66:486-501.

Extended European Search Report mailed on Jun. 14, 2011, for EP Patent Application No. 08860589.4, filed on Dec. 15, 2008, 10 pages.

Fall, R. (Sep. 12, 2003). "Final Technical Report: DE-FG03-97ER20274, Microbial Production of Isoprene. Dates Covered: Jun. 15, 2000 to Jun. 14, 2003," located at <http://www.osti.gov/scitech/servlets/purl/814920>, last visited on Nov. 11, 2013, 4 pages.

Farmer, W.R. et al. (May 2000). "Improving Lycopene Production in *Escherichia coli* by Engineering Metabolic Control," *Nature Biotechnology* 18:533-537.

Finkelstein, D.B. (1992). "Transformation," Chapter 6 in *Biotechnology of Filamentous Fungi*, Butterworth-Heinemann: Boston, MA, pp. 113-156.

Flores, S. et al. (Aug. 20, 2004, e-pub. Jul. 23, 2004). "Growth-Rate Recovery of *Escherichia coli* Cultures Carrying a Multicopy Plasmid, by Engineering of the Pentose-Phosphate Pathway," *Biotechnology and Bioengineering* 87(4):485-494.

Fu, Z. et al. (2008, e-pub. Feb. 27, 2008). "Biochemical and Structural Basis for Feedback Inhibition of Mevalonate Kinase and Isoprenoid Metabolism," *Biochemistry* 47:3715-3724.

Gallie, D.R. et al. (1989). "Eukaryotic Viral 5'-Leader Sequences Act as Translational Enhancers in Eukaryotes and Prokaryotes," in *Molecular Biology of RNA*, Cech, T.R. ed., Alan R. Liss, Inc: New York, NY, pp. 237-256.

Garret, T.A. et al. (May 15, 1998). "Accumulation of a Lipid A Precursor Lacking the 4'-Phosphate Following Inactivation of the *Escherichia coli lpxK* Gene," *The Journal of Biological Chemistry* 273(20):12457-12465.

Geneseq Database Accession No. AFB74822, "Monoterpene synthetase protein SEQ ID No. 4." Retrieved from EBI accession No. GSP:AFB74822 (Apr. 19, 2007), located at http://ibis/exam/dbfetch.jsp?id=GSP:AFB74822, last visited on Apr. 17, 2012, 2 pages.

Goedegebuur, F. et al. (2002, e-pub. May 7, 2002). "Cloning and Relational Analysis of 15 Novel Fungal Endoglucanases from Family 12 Glycosyl Hydrolase," *Curr. Genet*. 41:89-98.

Goldschmidt-Clermont, M. (1991). "Transgenic Expression of Aminoglycoside Adenine Transferase in the Chloroplast: A Selectable Marker for Site-Directed Transformation of Chlamydomonas," *Nucleic Acids Res*. 19(15):4083-4089.

Goodwin, T.W. (1971). "Biosynthesis of Carotenoids and Plant Triterpenes: The Fifth CIBA Medal Lecture," *Biochem. J.* 123(3):293-329.

Grāwert, T. et al. (2004, e-pub. Sep. 21, 2004). "IspH Protein of *Escherichia coli*: Studies on Iron—Sulfur Cluster Implementation and Catalysis," *Journal American Chemistry Society* 126:12847-12855.

Grochowski, L.L. et al. (May 2006). "*Methanocaldococcus jannaschii* Uses a Modified Mevalonate Pathway for Biosynthesis of Isopentenyl Diphosphate," *Journal of Bacteriology* 188(9):3192-3198.

Guda, C. et al. (2000). "Stable Expression for a Biodegradable Protein-Based Polymer in Tobacco Chloroplasts," *Plant Cell Reports* 19:257-262.

Guerineau, F. et al. (1991). "Effect of Deletions in the Cauliflower Mosaic Virus Polyadenylation Sequence on the Choice of the Polyadenylation Sites in Tobacco Protoplasts," *Mol. Gen. Genet.* 226:141-144.

Guo, D.-A. et al. (1995). "Developmental Regulation of Sterol Biosynthesis in *Zea mays*," *Lipids* 30(3):203-219.

Hahn, F.M. et al. (May 12, 1995). "Isolation of *Schizosaccharomyces pombe* Isopentenyl Diphosphate Isomerase in cDNA Clones by Complementation and Synthesis of the Enzyme in *Escherichia coli*," *The Journal of Biological Chemistry* 270(19):11298-11303.

Hahn, F.M. et al. (Feb. 1996). "Open Reading Frame 176 in the Photosynthesis Gene Cluster of *Rhodobacter capsulatus* Encodes *idi*, a Gene for Isopentenyl Diphosphate Isomerase," *Journal of Bacteriology* 178(3):619-624.

Hahn, F.M. et al. (Aug. 1999). "*Escherichia coli* Open Reading Frame 696 is *idi*, a Nonessential Gene Encoding Isopentenyl Diphosphate Isomerase," *Journal of Bacteriology* 181(15):4499-4504.

Hahn, F.M. et al. (Jan. 2001). "1-Deoxy D-Xylulose 5-Phosphate Synthase, the Gene Product of Open Reading Frame (ORF) 2816 and ORF 2895 in *Rhodobacter capsulatus*," *Journal of Bacteriology* 183(1):1-11.

Hamano, Y. et al. (2001). "Cloning of a Gene Cluster Encoding Enzymes Responsible for the Mevalonate Pathway from a Terpenoid-Antibiotic-Producing *Streptomyces* Strain," *Biosci. Biotechnol. Biochem*. 65(7):1627-1635.

(56) References Cited

OTHER PUBLICATIONS

Hamilton, C.M. et al. (Sep. 1989). "New Method for Generating Deletions and Gene Replacements in *Escherichia coli*," *Journal of Bacteriology* 171(9):4617-4622.

Hanai, T. et al. (Dec. 2007). "Engineered Synthetic Pathway for Isopropanol Production in *Escherichia coli*," *Applied and Environmental Microbiology* 73(24):7814-7818.

Harker, M. et al. (1999). "Expression of Prokaryotic 1-Deoxy-D-Xylulose-5-Phosphatases in *Escherichia coli* Increases Carotenoid and Ubiquinone Biosynthesis," *FEBS Letters* 448:115-119.

Harkki, A. et al. (Jun. 1989). "A Novel Fungal Expression System: Secretion of Active Calf Chymosin from the Filamentous Fungus *Trichoderma reesei*," *Bio/Technology* 7:596-603.

Hedl, M. et al. (Apr. 2004). "Class II 3-Hydroxy-3-Methylglutaryl Coenzyme A Reductases," *Journal of Bacteriology* 186(7):1927-1932.

Hellman, U. et al. (1995). "Improvement of an "In-Gel" Digestion Procedure for the Micropreparation of Internal Protein Fragments for Amino Acid Fragments for Amino Acid Sequencing," *Analytical Biochemistry* 224:451-455.

Herbers, K. et al. (Jun. 1996). "Manipulating Metabolic Partitioning in Transgenic Plants", *TIBTECH* 14:198-205.

Herz, S. et al. (Mar. 14, 2000). "Biosynthesis of Terpenoids: YgbB Protein Converts 4-Diphosphocytidyl-2C-Methyl-D-Erythritol 2-Phosphate to 2C-Methyl-D-Erythritol 2,4-Cyclodiphosphate," *PNAS* 97(6):2486-2490.

Hinson, D.D. et al. (1997). "Post-Translation Regulation of Mevalonate Kinase by Intermediates of the Cholesterol and Nonsterol Isoprene Biosynthetic Pathways," *Journal of Lipid Research* 38:2216-2223.

Huang, K.-X. et al. (1999). "Overexpression, Purification, and Characterization of the Thermostable Mevalonate Kinase from *Methanococcus jannaschii*," *Protein Expression and Purification* 17:33-40.

Hyatt, D.C. et al. (Mar. 27, 2007). "Structure of Limonene Synthase, A Simple Model for Terpenoid Cyclase Catalysis," *PNAS* 104(13):5360-5365.

Innis, M.A. et al. (Apr. 5, 1985). "Expression, Glycosylation, and Secretion of an *Aspergillus* Glucoamylase by *Saccharomyces cerevisiae*," *Science* 228:21-26.

Jenkins, L.S. et al. (Jan. 1987). "Genetic and Molecular Characterization of the Genes Involved in Short-Chain Fatty Acid Degradation in *Escherichia coli*: The *ato* System," *Journal of Bacteriology* 169(1):42-52.

Jeong, D-W. et al. (2007). "Cloning and Characterization of a Gene Encoding Phosphoketolase in a *Lactobacillus paraplantarum* Isolated from *Kimchi*," *Journal of Microbiology and Biotechnology* 17(5):822-829.

Jeong, S-W. et al. (2004, e-pub. Jan. 21, 2004). "Dicistronic Expression of the Green Fluorescent Protein and Antibiotic Resistance Genes in the Plastid for Selection and Tracking of Plastid-Transformed Cells in Tobacco," *Plant Cell Rep* 22:747-751.

Jobling, S.A. et al. (Feb. 12, 1987). "Enhanced Translation of Chimaeric Messenger RNAs Containing a Plant Viral Untranslated Leader Sequence," *Nature* 235:622-625.

Jones, E.Y. et al. (1991). "Methodology Employed for the Structure Determination of Tumour Necrosis Factor, a Case of High Non-Crystallographic Symmetry," *Acta Cryst* A47:753-770.

Jones, K.L. et al. (2000). "Low-Copy Plasmids Can Perform as Well as or Better Than High-Copy Plasmids for Metabolic Engineering of Bacteria," *Metabolic Engineering* 2:238-338.

Joshi, C.P. (1987). "Putative Polyadenylation Signals in Nuclear Genes of Higher Plants: A Compilation and Analysis," *Nucleic Acids Research* 15(23):9627-9640.

Kacian, D.L. et al. (Oct. 1972). "A Replicating RNA Molecule Suitable for a Detailed Analysis of Extracellular Evolution and Replication," *Proc. Natl. Acad. Sci. USA* 69(10):3038-3042.

Kajiwara, S. et al. (1997). "Expression of an Exogenous Isopentenyl Diphosphate Isomerase Gene Enhances Isoprenoid Biosynthesis in *Escherichia coli*," *Biochem. J.* 324:421-426.

Kampranis, S.C. et al. (Jun. 2007). "Rational Conversion of Substrate and Product Specificity in a *Salvia* Monoterpene Synthase: Structural Insights into the Evolution of Terpene Synthase Function," *The Plant Cell* 19:1994-2005.

Kaneda, K. et al. (Jan. 30, 2001). "An Unusual Isopentenyl Diphosphate Isomerase Found in the Mevalonate Pathway Gene Cluster from *Streptomyces* sp. Strain CL190," *PNAS* 98(3):932-937.

Karl, T. et al. (2003). "Dynamic Measurements of Partition Coefficients Using Proton-Transfer-Reaction Mass Spectrometry (PTR-MS)," *International Journal of Mass Spectrometry* 223-224:383-395.

Kavanagh, T.A. et al. (Jul. 1999). "Homeologous Plastid DNA Transformation in Tobacco is Mediated by Multiple Recombination Events," *Genetics* 152(3):1111-1122.

Keasling, J.D. (Mar. 29, 2004). "Genetic Tools for Metabolic Enzyme Production in *Escherichia coli*," presented at NIGMS 2004 PSI Protein Production & Crystallization Workshop, Bethesda, MD, Mar. 29-31, 2004, located at <http://www-nmr.cabm.rutgers.edu/labdocuments/workshops/psi_ppcw_32904/ppcw_32904.html>, last visited on Jun. 4, 2010, 66 pages.

Keasling, J.D. (May 7, 2005). "Drugs from Bugs: Engineering Microorganisms to Produce New Drugs," *presented at* Engineering a Better World: *Our Environment, Our Health*, Berkeley, CA, May 7, 2005, 62 pages.

Keasling, J.D. (Sep. 23, 2007). "Engineering Microbes for Production of Low-Cost, Effective, Anti-Malarial Drugs," presented at *Enzyme Engineering XIX*, Harrison Hot Springs, British Columbia, Canada, Sep. 23-28, 2007, 152 pages.

Keegan, R.M. et al. (2007). "Automated Search-Model Discovery and Preparation for Structure Solution by Molecular Replacement," *Acta Crystallographica* D63:447-457.

Keeler, K.H. et al. (1996). "Movement of Crop Transgenes into Wild Plants," Chapter 20 in *Herbicide Resistant Crops: Agricultural, Environmental, Economic, Regulatory, and Technical Aspects*, Duke, S.O. ed., Lewis Publishers: Boca Raton, FL., pp. 303-330.

Kelly, J.M. et al. (1985). "Transformation of *Aspergillus niger* by the *amd*S Gene of *Aspergillus nidulans*," *The EMBO Journal* 4(2):475-479.

Khan, M.S. et al. (Sep. 1999). "Fluorescent Antibiotic Resistance Marker for Tracking Plastid Transformation in Higher Plants," *Nature Biotechnology* 17:910-914.

Kieser, T. eds. et al. (Jul. 2000). "Introduction of DNA into *Streptomyces*," Chapter 10 in *Practical Streptomyces Genetics*, pp. 229-252.

Kisselev, L. (Jan. 2002). "Polypeptide Release Factors in Prokaryotes and Eukaryotes: Same Function, Different Structure," *Structure* 10:8-9.

Klein-Marcuschamer, D. et al. (2007, e-pub. Aug. 2, 2007). "Engineering Microbial Cell Factories for Biosynthesis of Isoprenoid Molecules: Beyond Lycopene," *TRENDS in Biotechnology* 25(9):417-424.

Klein-Marcuschamer, D. et al. (Feb. 19, 2008). "Assessing the Potential of Mutational Strategies to Elicit New Phenotypes in Industrial Strains," *PNAS* 105(7):2319-2324.

Koga, Y. et al. (Mar. 2007). "Biosynthesis of Ether-Type Polar Lipids in Archaea and Evolutionary Considerations," *Microbiology and Molecular Biology Reviews* 71(1):97-120.

Köksal, M. et al. (2010, e-pub. Jul. 17, 2010). "Structure of Isoprene Synthase Illuminates the Chemical Mechanism of Teragram Atmospheric Carbon Emission," *J. Mol. Biol*. pp. 1-11.

Kooter, J. M., et al. (Sep. 1999). "Listening to the Silent Genes: Transgene Silencing, Gene Regulation and Pathogen Control," *Trends in Plant Science* 4(9):340-347.

Kota, M. et al. (Mar. 1999). "Overexpression of the *Bacillus thuringiensis* (Bt) Cry2Aa2 Protein in Chloroplasts Confers Resistance to Plants Against Susceptible and Bt-Resistant Insects," *Proc. Natl. Acad. Sci. USA* 96:1840-1845.

Kozak, M. (Oct. 25, 1991). "Structural Features in Eukaryotic mRNAs That Modulate the Initiation of Translation," *The Journal of Biological Chemistry* 266(30):19867-19870.

Kozak, M. (1999). "Initiation of Translation in Prokaryotes and Eukaryotes," *Gene* 234:187-208.

(56) References Cited

OTHER PUBLICATIONS

Kunkel, T. A. (Jan. 1985). "Rapid and Efficient Site-Specific Mutagenesis without Phenotypic Selection," *Proc. Natl. Acad. Sci. USA* 82:488-492.

Kuzuyama, T. et al. (1998). "Direct Formation of 2-C Methyl-D-Erythritol 4-Phosphate from 1-Deoxy-D-Xylulose 5-Phosphate by 1-Deoxy-D-Xylulose 5-Phosphate Reductoisomerase, a New Enzyme in the Non-Mevalonate Pathway to Isopentenyl Diphosphate," *Tetrahedron Letters* 39:4509-4512.

Kuzuyama, T. et al. (1998). "Fosmidomycin, a Specific Inhibitor of 1-Deoxy-D-Xylulose 5-Phosphate Reductoisomerase in the Nonmevalonate Pathway for Terpenoid Biosynthesis," *Tetrahedron Letters* 39:7913-7916.

Lange, B.M. et al. (Nov. 23, 1999). "Isopentenyl Diphosphate Biosynthesis via a Mevalonate-Independent Pathway: Isopentenyl Monophosphate Kinase Catalyzes the Terminal Enzymatic Step," *PNAS* 96(24):13714-13719.

Lange, B.M. et al. (Sep. 2001). "Isoprenoid Biosynthesis. Metabolite Profiling of Peppermint Oil Gland Secretory Cells and Application to Herbicide Target Analysis," *Plant Physiology* 127:305-314.

Law, C.K. (1984). "Heat and Mass Transfer in Combustion: Fundamental Concepts and Analytical Techniques," *Progress in Energy and Combustion Science* 10:295-318.

Lehning, A. et al. (1999). "Isoprene Synthase Activity and Its Relation to Isoprene Emission in *Quercus robur* L. Leaves," *Plant, Cell and Environment* 22:495-504.

Lerner, C.G. et al. (1990). "Low Copy Number Plasmids for Regulated Low-Level Expression of Cloned Genes in *Escherichia coli* with Blue/White Insert Screening Capability," *Nucleic Acids Research* 18(15):4631.

Li, W. et al. (2010, e-pub. Nov. 1, 2009). "Non-Redundant Patent Sequence Databases with Value-Added Annotations at Two Levels," *Nucleic Acids Research* 38:D52-D56.

Lichtenthaler, H.K. (1999). "The 1-Deoxy-D-Xylulose-5-Phosphate Pathway of Isoprenoid Biosynthesis in Plants," *Annu. Rev. Plant Physiol. Plant Mol. Biol.* 50:47-65.

Lichtenthaler, H.K. et al. (1997). "Biosynthesis of Isoprenoids in Higher Plant Chloroplasts Proceeds via a Mevalonate-Independent Pathway," *FEBS Letters* 400:271-274.

Lin, X.-M. et al. (2008, e-pub. Apr. 26, 2008). "Proteomic Analysis of Nalidixic Acid Resistance in *Escherichia coli*: Identification and Functional Characterization of OM Proteins," *Journal of Proteome Research* pp. A-G.

Lluch, M.A. et al. (2000). "Molecular Cloning and Expression Analysis of the Mevalonate Kinase Gene from *Arabidopsis thaliana*," *Plant Molecular Biology* 42:365-376.

Lois, L.M. et al. (Mar. 1998). "Cloning and Characterization of a Gene from *Escherichia coli* Encoding a Transketolase-Like Enzyme that Catalyzes the Synthesis of D-1-Deoxyxylulose 5-Phosphate, a Common Precursor for Isoprenoid, Thiamin, and Pyridoxol Biosynthesis," *Proc. Natl. Acad. Sci. USA* 95:2105-2110.

Loivamäki, M. et al. (Jun. 2007). "*Arabidopsis*, a Model to Study Biological Functions of Isoprene Emission?" *Plant Physiology* 144:1066-1078.

Lommel, S.A. et al. (1991). "Identification of the Maize Chlorotic Mottle Virus Capsid Protein Cistron and Characterization of its Subgenomic Messenger RNA," *Virology* 181:382-385.

Lücker, J. et al. (2002). "Monoterpene Biosynthesis in Lemon (*Citrus Limon*). cDNA Isolation and Functional Analysis of Four Monoterpene Synthases," *European Journal of Biochemistry* 269:3160-3171.

Luli, G.W. et al. (Apr. 1990). "Comparison of Growth, Acetate Production, and Acetate Inhibition of *Escherichia coli* in Batch and Fed-Batch Fermentations," *Applied and Environmental Microbiology* 56(4):1004-1011.

Macejak, D.G. et al. (Sep. 5, 1991). "Internal Initiation of Translation Mediated by the 5' Leader of a Cellular mRNA," *Nature* 353:90-94.

Mahmoud, S.S. et al. (Jul. 17, 2001). "Metabolic Engineering of Essential Oil Yield and Composition in Mint by Altering Expression of Deoxyxylulose Phosphate Reductoisomerase and Menthofuran Synthase," *PNAS* 98(15):8915-8920.

Maldonado-Mendoza, I.E. et al. (Jul. 1997). "Molecular Characterization of Three Differentially Expressed Members of the *Camptotheca acuminata* 3-Hydroxy-3-Methylglutaryl CoA Reductase (HMGR) Gene Family," *Plant Molecular Biology* 34(5):781-790.

Mann, V. et al. (Aug. 2000). "Metabolic Engineering of Astaxanthin Production in Tobacco Flowers," *Nature Biotechnology* 18:888-892.

Martin, V.J.J. et al. (Dec. 5, 2001). "The In Vivo Synthesis of Plant Sesquiterpenes by *Escherichia coli*," *Biotechnology and Bioengineering* 75(5):497-503.

Martin, V.J.J. et al. (Jul. 2003). "Engineering a Mevalonate Pathway in *Escherichia coli* for Production of Terpenoids," *Nature Biotechnology* 21(7):796-802.

Martin, W. et al. (May 14, 1998). "Gene Transfer to the Nucleus and the Evolution of Chloroplasts," *Nature* 393:162-165.

Mash Ego, M.R. et al. (2007, e-pub. Nov. 8, 2006). "Microbial Metabolomics: Past, Present and Future Methodologies," *Biotechnol. Lett.* 29:1-16.

Matsuoka, S. et al. (Feb. 25, 1991). "Variable Product Specificity of Microsomal Dehydrodolichyl Diphosphate Synthase from Rat Liver," *The Journal of Biological Chemistry* 266(6):3464-3468.

Matteucci, M.D. et al. (1981). "Synthesis of Deoxyoligonucleotides on a Polymer Support," *J. American Chemical Society* 103(11):3185-3191.

Matthews, P.D. et al. (2000). "Metabolic Engineering of Carotenoid Accumulation in *Escherichia coli* by Modulation of the Isoprenoid Precursor Pool with Expression of Deoxyxylulose Phosphate Synthase," *Appl. Microbiol. Biotechnol.* 53:396-400.

Maury, J. et al. (2005, e-pub. Jul. 5, 2005). "Microbial Isoprenoid Production: An Example of Green Chemistry through Metabolic Engineering," *Adv. Biochem. Engin/Biotechnol.* 100:19-51.

McPherson, A. (2004). "Introduction to Protein Crystallization," *Methods* 34:254-265.

Meinkoth, J. et al. (1984). "Hybridization of Nucleic Acids Immobilized on Solid Supports," *Analytical Biochemistry* 138:267-284.

Meyer, P. et al. (1996). "Homology-Dependent Gene Silencing in Plants," *Ann. Rev. Plant Physiol. Plant Mol. Biol.* 47:23-48.

Miao, L. et al. (2006, e-pub. Mar. 15, 2006). "Effect of Culture Conditions on Mycelial Growth, Antibacterial Activity, and Metabolite Profiles of the Marine-derived Fungus *Arthrinium c.f. saccharicola*," *Appl. Microbiol. Biotechnol.* 72:1063-1073.

Millen, R.S. et al. (Mar. 2001). "Many Parallel Losses of *infA* from Chloroplast DNA During Angiosperm Evolution with Multiple Independent Transfers to the Nucleus," *The Plant Cell* 13:645-658.

Miller, B. (2001). "Erstmalige Isolierung Eines Isoprenysthase-Gens und Heterologe Expression Des Aus Der Pappel Stammenden Gens Sowie Charakterisierung der Eingangsgene des Mevalonat-unabhängigen Isoprenoidbiosyntheseweges aus dem Cyanobakterium *Synechococcus leopoliensis*," located at <http://kups.ub.uni-koeln.de/883/>, last visited on Jun. 23, 2011, English Translation included, 2 pages.

Miller, J. "High-Throughput Screening for Protein Engineering of Industrial Enzymes," published by Genencor on Jun. 5, 2009, Online document-retrieved on Apr. 17, 2012, XP002673697, 29 pages.

Milne, P.J. et al. (1995). "Measurement of Vertical Distribution of Isoprene in Surface Seawater, its Chemical Fate, and its Emission from Several Phytoplankton Monocultures," *Marine Chemistry* 48:237-244.

Mo, H. et al. (2004). "Studies of the Isoprenoid-Mediated Inhibition of Mevalonate Synthesis Applied to Cancer Chemotherapy and Chemoprevention," *Exp. Biol. Med.* 229:567-585.

Mogen, B.D. et al. (Dec. 1990). "Upstream Sequences Other than AAUAAA are Required for Efficient Messenger RNA 3'-End Formation in Plants," *The Plant Cell* 2:1261-1272.

Monson, R.K. et al. (1992). "Relationships Among Isoprene Emission Rate, Photosynthesis, and Isoprene Synthase Activity as Influenced by Temperature," *Plant Physiol.* 98:1175-1180.

Munroe, D. et al. (1990). "Tales of Poly(A): a Review," *Gene* 91:151-158.

Murray, E.E. et al. (1989). "Codon Usage in Plant Genes," *Nucleic Acids Research* 17(2): 477-498.

(56) References Cited

OTHER PUBLICATIONS

Nakamura, C.E. et al. (2003). "Metabolic Engineering for the Microbial Production of 1,3-Propanediol," *Current Opinion in Biotechnology* 14:454-459.
Nanchen, A. et al. (Apr. 2008, e-pub. Jan. 25, 2008). "Cyclic AMP-Dependent Catabolite Repression is the Dominant Control Mechanism of Metabolic Fluxes Under Glucose Limitation in *Escherichia coli*," *Journal of Bacteriology* 190(7):2323-2330.
Nawrath, C. et al. (Dec. 1994). "Targeting of the Polyhydroxybutyrate Biosynthetic Pathway to the Plastids of *Arabidopsis thaliana* Results in High Levels of Polymer Accumulation," *Proc. Natl. Acad. Sci. USA* 91:12760-12764.
Neidhardt, F.C. et al. (Sep. 1974). "Culture Medium for Enterobacteria," *Journal of Bacteriology* 119(3):736-747.
Neidhardt, F.C. et al. (1990). "Table 1. Overall Macromolecular Composition of an Average *E. coli* B/r Cell$^a$," Chapter 1 in *Physiology of the Bacterial Cell: A Molecular Approach*, Sinauer Associates, Inc., Sunderland, MA, pp. 4.
Nevalainen, K.M.H. et al. (1992). "The Molecular Biology of *Trichoderma* and Its Application to the Expression of Both Homologous and Heterologous Genes," Chapter 6 in *Molecular Industrial Mycology, Systems and Applications for Filamentous Fungi*, Leong, S.A. et al. eds., Marcel Dekker Inc., New York, NY, pp. 129-148.
Newman, J.D. et al. (Nov. 5, 2006, e-pub. Jul. 28, 2006). "High-Level Production of Amorpha-4,11-Diene in a Two-Phase Partitioning Bioreactor of Metabolically Engineered *Escherichia coli*," *Biotechnology and Bioengineering* 95(4):684-691.
Newman, T. et al. (1994). "Genes Galore: A Summary of Methods for Accessing Results from Large-Scale Partial Sequencing of Anonymous *Arabidopsis* cDNA Clones," *Plant Physiology* 106:1241-1255.
Nielsen, K.M. et al. (1997). "Analysis and Developmental Profile of Carotenoid Pigments in Petals of Three Yellow Petunia Cultivars," *Scientia Horticulturae* 71:257-266.
Niinemets, Ü. et al. (Nov. 2002). "Stomatal Constraints May Affect Emission of Oxygenated Monoterpenoids from the Foliage of *Pinus pinea*," *Plant Physiology* 130:1371-1385.
Noronha, S.B. et al. (May 5, 2000). "Investigation of the TCA Cycle and the Glyoxylate Shunt in *Escherichia coli* BL21 and JM109 Using $^{13}$C-NMR/MS," *Biotechnology and Bioengineering* 68(3):316-327.
Nunberg, J.H. et al. (Nov. 1984). "Molecular Cloning and Characterization of the Glucoamylase Gene of *Aspergillus awamori*," *Mol. Cell. Biol.* 4(11):2306-2315.
Ondrey, G. et al. (Oct. 2008). "Bio-Based Isoprene," *Chemical Engineering, Access Intelligence Association*, Rockville, MA, 115(1):14.
Pachuk, C.J. et al. (2000). "Chain Reaction Cloning: A One-Step Method for Directional Ligation of Multiple DNA Fragments," *Gene* 243:19-25.
Perego, M. (1993). "Integrational Vectors for Genetic Manipulation in *Bacillus subtilis*," Chapter 42 in *Bacillus subtilis and Other Gram-Positive Bacteria: Biochemistry, Physiology, and Molecular Genetics*, Sonenshein et al. eds., American Society for Microbiology: Washington, D.C., pp. 615-624.
Phan, R.M. et al. (2001, e-pub. Sep. 13, 2001). "Synthesis of (*S*)-Isoprenoid Thiodiphosphates as Substrates and Inhibitors," *J. Org. Chem.* 66(20):6705-6710.
Phillips, T.A. et al. (Jul. 1984). "Ion Gene Product of *Escherichia coli* is a Heat-Shock Protein," *Journal of Bacteriology* 159(1):283-287.
Phue, J.-N. et al. (2004). "Transcription Levels of Key Metabolic Genes are the Cause for Different Glucose Utilization Pathways in *E. coli* B (BL21) and *E. coli* K (JM109)," *Journal of Biotechnology* 109:21-30.
Phue, J.-N. et al. (2005, e-pub. Aug. 11, 2005). "Impact of Dissolved Oxygen Concentration on Acetate Accumulation and Physiology of *E. coli* BL21, Evaluating Transcription Levels of Key Genes at Different Dissolved Oxygen Conditions," *Metabolic Engineering* 7:353-363.
Pilloff, D. et al. (Feb. 14, 2003). "The Kinetic Mechanism of Phosphomevalonate Kinase," *The Journal of Biological Chemistry* 278(7):4510-4515.

Pitera, D.J. et al. (2007, e-pub. Nov. 23, 2006). "Balancing a Heterologous Mevalonate Pathway for Improved Isoprenoid Production in *Escherichia coli*," *Metabolic Engineering* 9:193-207.
Pommer, H. et al. (1975). "Industrial Synthesis of Terpene Compounds," *Pure and Applied Chemistry* 43(3-4):527-551.
Potter, D. et al. (Oct. 10, 1997). "Identification of Catalytic Residues in Human Mevalonate Kinase," *The Journal of Biological Chemistry* 272(41):25449-25454.
Proudfoot, N. (Feb. 22, 1991). "Poly(A) Signals," *Cell* 64:671-674.
Ramos-Valdivia, A.C. et al. (1997). "Isopentenyl Diphosphate Isomerase: A Core Enzyme in Isoprenoid Biosynthesis: A Review of its Biochemistry and Function," *Natural Product Reports* 6:591-603.
Raschke, M. et al. (2004, e-pub. Oct. 28, 2004). "A High-Performance Liquid Chromatography Methods for the Analysis of Intermediates of the Deoxyxylulose Phosphate Pathway," *Analytical Biochemistry* 335:235-243.
Re, E.B. et al. (1995). "Co-Expression of Native and Introduced Genes Reveals Cryptic Regulation of HMG CoA Reductase Expression in *Arabidopsis*," *The Plant Journal* 7(5):771-784.
Reiling, K.K. et al. (Jul. 20, 2004, e-pub. Jun. 18, 2004). "Mono and Diterpene Production in *Escherichia coli*," *Biotechnology and Bioengineering* 87(2):200-212.
Rodríguez-Concepción, M. et al. (2000). "Genetic Evidence of Branching in the Isoprenoid Pathway for the Production of Isopentenyl Diphosphate and Dimethylallyl Diphosphate in *Escherichia coli*," *FEBS Letters* 473:328-332.
Rodríguez-Concepción, M. et al. (Nov. 2002). "Elucidation of the Methylerythritol Phosphate Pathway for Isoprenoid Biosynthesis in Bacteria and Plastids. A Metabolic Milestone Achieved Through Genomics," *Plant Physiology* 130:1079-1089.
Rodríguez-Villalón, A. et al. (2008). "Carotenoid Accumulation in Bacteria with Enhanced Supply of Isoprenoid Precursors by Upregulation of Exogenous or Endogenous Pathways," *Journal of Biotechnology* 135:78-84.
Rohmer, M. (1998). "Isoprenoid Biosynthesis via the Mevalonate-Independent Route, a Novel Target for Antibacterial Drugs?" *Progress in Drug Research* 50:137-154.
Röhrich, R.C. et al. (2005, e-pub. Nov. 2, 2005). "Reconstitution of an Apicoplast-Localised Electron Transfer Pathway Involved in the Isoprenoid Biosynthesis of *Plasmodium falciparum*," *FEBS Letters* 579:6433-6438.
Rondon, M.R. et al. (May 1999). "Toward Functional Genomics in Bacteria: Analysis of Gene Expression in *Escherichia coli* from a Bacterial Artificial Chromosome Library of *Bacillus cereus*," *Proc. Natl. Acad. Sci. USA* 96:6451-6455.
Rosenfeld, J. et al. (1992). "In-Gel Digestion of Proteins for Internal Sequence Analysis After One- or Two-Dimensional Gel Electrophoresis," *Analytical Biochemistry* 203:173-179.
Rost, B. et al. (2004). "The PredictProtein Server," *Nucleic Acids Research* 32:W321-W326.
Sánchez, C. et al. (Apr. 2002). "The Biosynthetic Gene Cluster for the Antitumor Rebeccamycin: Characterization and Generation of Indolocarbazole Derivatives," *Chemistry and Biology* 9(4):519-531.
Sander, R. (Apr. 8, 1999). *Compilation of Henry's Law Constants for Inorganic and Organic Species of Potential Importance in Environmental Chemistry*, 3:1-107.
Sanfaçon, H. et al. (1991). "A Dissection of the Cauliflower Mosaic Virus Polyadenylation Signal," *Genes & Development* 5:141-149.
Sasaki, K. et al. (2005, e-pub. Apr. 7, 2005). "Gene Expression and Characterization of Isoprene Synthase from *Populus alba*," *FEBS Letters* 579:2514-2518.
Schneider, D. et al. (Jul. 9, 2002). "Genomic Comparisons Among *Escherichia coli* Strains B, K-12, and O157:H7 Using IS Elements as Molecular Markers," *BMC Microbiology* 2:18, 8 pages.
Schnitzler, J.-P. et al. (2005, e-pub. Jul. 29, 2005). "Biochemical Properties of Isoprene Synthase in Poplar (*Populus x canescens*)," *Planta* 222(5):777-786.
Schöller, C. et al. (1997). "Volatile Metabolites from Some Gram-Negative Bacteria," *Chemosphere* 35(7):1487-1495.
Scott, E. et al. (2007, e-pub. Mar. 27, 2007). "Biomass in the Manufacture of Industrial Products—The Use of Proteins and Amino Acids," *Appl. Microbiol. Biotechnol.* 75:751-762.

(56) References Cited

OTHER PUBLICATIONS

Sen, S. et al. (2007). "Developments in Directed Evolution for Improving Enzyme Functions," *Appl. Biochem. Biotechnol.* 143:212-223.
Serino, G. et al. (1997). "A Negative Selection Scheme Based on the Expression of Cytosine Deaminase in Plastids," *The Plant Journal* 12(3):697-701.
Sharkey, T.D. et al. (Feb. 1, 2005). "Supplemental data for: Evolution of the Isoprene Biosynthetic Pathway in Kudzu," *Plant Physiology* 137(2):700-712.
Sheir-Neiss, G. et al. (Jul. 1984). "Characterization of the Secreted Cellulases of *Trichoderma reesei* Wild Type and Mutants During Controlled Fermentations," *Appl. Microbiol. Biotechnol.* 20(1):46-53.
Shelton, D. et al. (2004, e-pub. Nov. 26, 2004). "Isolation and Partial Characterization of a Putative Monoterpene Synthase from *Melaleuca alternifolia*," *Plant Physiology and Biochemistry* 42:875-882.
Shinozaki, K. et al. (1986). "The Complete Nucleotide Sequence of the Tobacco Chloroplast Genome: its Gene Organization and Expression," *The EMBO Journal* 5(9):2043-2049.
Shirk, M.C. et al. (2002, e-pub. Jul. 27, 2002). "Isoprene Formation in *Bacillus subtilis*: A Barometer of Central Carbon Assimilation in a Bioreactor?" *Biotechnol. Prog.* 18(5):1109-1115.
Sivy, T.L. et al. (2002). "Isoprene Synthase Activity Parallels Fluctuations of Isoprene Release During Growth of *Bacillus subtilis*," *Biochemical and Biophysical Research Communications* 294:71-75.
Siwko, M.E. et al. (2007, e-pub. Oct. 4, 2006). "Does Isoprene Protect Plant Membranes from Thermal Shock? A Molecular Dynamics Study," *Biochimica et Biophysica Acta* 1768:198-206.
Slabinski, L. et al. (2007). "The Challenge of Protein Structure Determination—Lessons from Structural Genomics," *Protein Science* 16:2472-2482.
Slater, S. et al. (Apr. 1992). "Production of Poly-(3-Hydroxybutyrate-Co-3-Hydroxyvalerate) in a Recombinant *Escherichia coli* Strain," *Applied and Environmental Microbiology* 58(4):1089-1094.
Slater, S. et al. (Oct. 1999). "Metabolic Engineering of *Arabidopsis* and *Brassica* for Poly(3-Hydroxybutyrate-co-3-Hydroxyvalerate) Copolymer Production," *Nature Biotechnology* 17:1011-1016.
Smit, A. et al. (2000). "Biosynthesis of Isoprenoids via Mevalonate in Archaea: The Lost Pathway," *Genome Research* 10:1468-1484.
Starks, C.M. et al. (Sep. 19, 1997). "Structural Basis for Cyclic Terpene Biosynthesis by Tobacco 5-Epi-Aristolochene Synthase," *Science* 277:1815-1820.
Staub, J. M. et al. (1995). "Expression of a Chimeric *uidA* Gene Indicates that Polycistronic mRNAs are Efficiently Translated in Tobacco Plastids," *The Plant Journal* 7(5):845-848.
Staub, J. M. et al. (Mar. 2000). "High-Yield Production of a Human Therapeutic Protein in Tobacco Chloroplast," *Nature Biotechnology* 18:333-338.
Steinbüchel, A. (2003). "Production of Rubber-Like Polymers by Microorganisms," *Current Opinion in Microbiology* 6:261-270.
Steller, I. et al. (1997). "An Algorithm for Automatic Indexing of Oscillation Images using Fourier Analysis," *Journal of Applied Crystallography* 30:1036.1040.
Stermer, B.A. et al. (1994). "Regulation of HMG-CoA Reductase Activity in Plants," *Journal of Lipid Research* 35:1133-1140.
Stevens, D.R. et al. (1997). "Genetic Engineering of Eukaryotic Algae: Progress and Prospects," *J. Phycol.* 33:713-722.
Takagi, M. et al. (Aug. 2000). "A Gene Cluster for the Mevalonate Pathway from *Streptomyces* sp. Strain CL190," *Journal of Bacteriology* 182(15):4153-4157.
Takahashi, S. et al. (Feb. 1999). "Purification, Characterization, and Cloning of a Eubacterial 3-Hydroxy-3-Methylglutaryl Coenzyme A Reductase, a Key Enzyme Involved in Biosynthesis of Terpenoids," *Journal of Bacteriology* 181(4):1256-1263.
Takara Bio Inc. (Feb. 2008). "Chaperon Plasmid Set," Cat. # 3340, pp. 1-8.

Thomas, F. et al. (1988). "Expression of the *rp123*, *rp12* and *rps19* Genes in Spinach Chloroplasts," *Nucleic Acids Research* 16(6):2461-2472.
Thomason, L.C. et al. (2007, e-pub. Apr. 16, 2007). "Multicopy Plasmid Modification with Phage λ Red Recombineering," *Plasmid* 58:148-158.
Thouvenot, B. et al. (2004). "The Strong Efficiency of the *Escherichia coli gapA* P1 Promoter Depends on a Complex Combination of Functional Determinants," *Biochem. J.* 383:371-382.
Timberlake, W.E. (1991). "Cloning and Analysis of Fungal Genes," Chapter 3 in *More Gene Manipulations in Fungi*, Bennett, J.W. et al. eds., Academic Press, San Diego, CA, pp. 70-76.
Tokuriki, N. et al. (2009, e-pub. Sep. 16, 2009). "Stability Effects of Mutations and Protein Evolvability," *Current Opinion in Structural Biology* 19(5):596-604.
Toriyama, K. et al. (1985). "Cell Suspension and Protoplast Culture in Rice," *Plant Science* 41:179-183.
Tsudsuki, T. (Apr. 27, 1998) "Direct submission, bases 1-155939", *Data Processing Center*, Submitted Feb. 27,1998, Aichi-Gakuin University, Aichi, Japan, 12 pages.
UniProt Database Accession No. A2XGY9, last updated Jul. 27, 2011, located at <http://www.uniprot.org/jobs/201109112CDIG8GYZL.txt>, last visited on Sep. 11, 2011, 2 pages.
UniProt Database Accession No. A5AR04, last updated Jul. 27, 2011, located at <http://www.uniprotorg/jobs/20110911315BAWWKZ7.txt>, last visited on Sep. 11, 2011, 1 page.
UniProt Database Accession No. A5AV19, last updated on Oct. 16, 2013, located at http://www.uniprot.org/uniprot/A5AV19, last visited on Oct. 29, 2013, 3 pages.
UniProt Database Accession No. A5B7V4, last updated Jul. 27, 2011, located at <http://www.uniprot.org/jobs/201109115006CWCI3L.txt>, last visited on Sep. 11, 2011, 1 page.
UniProt Database Accession No. A5BKK1, last updated Jul. 27, 2011, located at <http://www.uniprot.org/jobs/20110911315BB1QWK6.txt>, last visited on Sep. 11, 2011, 1 page.
UniProt Database Accession No. A5BLS5, last updated Jul. 27, 2011, located at <http://www.uniprot.org/jobs/201109112CDIFUU28L.txt>, last visited on Sep. 11, 2011, 1 page.
UniProt Database Accession No. A7IZZ1, last updated on Oct. 16, 2013, located at http://www.uniprot.org/uniprot/A7IZZ1, last visited on Oct. 29, 2013, 5 pages.
UniProt Database Accession No. A9PGR5, last updated Jul. 27, 2011, located at <http://www.uniprot.org/jobs/201109112CDIFT06PL.txt>, last visited on Sep. 11, 2011, 1 page.
UniProt Database Accession No. A9Q7C9, last updated on Oct. 16, 2013, located at http://www.uniprot.org/uniprot/A9Q7C9, last visited on Oct. 29, 2013, 3 pages.
UniProt Database Accession No. B1P189, last updated Jul. 27, 2011, located at <http://www.uniprot.org/jobs/201109112CDIFX17BK.txt>, last visited on Sep. 11, 2011, 1 page.
UniProt Database Accession No. B3GEM8, last updated Jul. 27, 2011, located at <http://www.uniprot.org/jobs/20110911315BAG9N17.txt>, last visited on Sep. 11, 2011, 1 page.
UniProt Database Accession No. B3TPQ7, "SubName: Full=Alpha-terpineol synthase." Retrieved from EBI accession No. UniProt:B3TPQ7 (Sep. 2, 2008), last updated on May 16, 2012, located at http://www.uniprot.org/uniprot/B3TPQ7, last visited on Jul. 23, 2012, 5 pages, (XP-002674045, XP-002674053).
UniProt Database Accession No. B6F137, last updated on Oct. 16, 2013, located at http://www.uniprot.org/uniprot/B6F137, last visited on Oct. 29, 2013, 3 pages.
UniProt Database Accession No. B7FLI6, last updated Jul. 27, 2011, located at <http://www.uniprot.org/jobs/20110911315BAXCRQU.txt>, last visited on Sep. 11, 2011, 1 page.
UniProt Database Accession No. B9HE95, last updated Jul. 27, 2011, located at <http://www.uniprot.org/jobs/201109112CDIFY9X6U.txt>, last visited on Sep. 11, 2011, 2 pages.
UniProt Database Accession No. B9MXU1, last updated Jul. 27, 2011, located at <http://www.uniprot.org/jobs/201109112CDIFV8DIC.txt>, last visited on Sep. 11, 2011, 2 pages.
UniProt Database Accession No. B9PAP5, last updated Jul. 27, 2011, located at <http://www.uniprot.org/jobs/201109112CDIG1HNFH.txt>, last visited on Sep. 11, 2011, 2 pages.

(56) References Cited

OTHER PUBLICATIONS

UniProt Database Accession No. B9RPM0, "SubName: Full=(R)-limonene synthase." Retrieved from EBI accession No. UniProt:B9RPM0 (Mar. 24, 2009), last updated on May 16, 2012, located at http://www.uniprot.org/uniprot/B9RPM0, last visited on Jul. 23, 2012, 3 pages.
UniProt Database Accession No. B9T537, last updated Nov. 30, 2010, located at <http://www.uniprot.org/jobs/20110911315BB065GR.txt>, last visited on Sep. 11, 2011, 1 page.
UniProt Database Accession No. B9T825, last updated Jul. 27, 2011, located at <http://www.uniprot.org/jobs/20110911315BALANC9.txt>, last visited on Sep. 11, 2011, 1 page.
UniProt Database Accession No. D7LHH0, last updated on Oct. 16, 2013, located at http://www.uniprot.org/uniprot/D7LHH0, last visited on Oct. 29, 2013, 4 pages.
UniProt Database Accession No. G1JUH1, last updated on Oct. 16, 2013, located at http://www.uniprot.org/uniprot/G1JUH1, last visited on Oct. 29, 2013, 5 pages.
UniProt Database Accession No. Q0PCI3, last updated Jul. 27, 2011, located at <http://www.uniprot.org/jobs/20110911315BAPL92C.txt>, last visited on Sep. 11, 2011, 1 page.
UniProt Database Accession No. Q0PCI4, last updated Jul. 27, 2011, located at <http://www.uniprot.org/jobs/20110911315BAQURQ8.txt>, last visited on Sep. 11, 2011, 1 page.
UniProt Database Accession No. Q50L36, last updated May 31, 2011, located at <http://www.uniprot.org/jobs/201109112CDIGBF1M4.txt>, last visited on Sep. 11, 2011, 2 pages.
UniProt Database Accession No. Q5SBP1, last updated Apr. 5 2011, located at <http://www.uniprot.org/jobs/201109112CDIGFFR1Q.txt>, last visited on Sep. 11, 2011, 2 page.
UniProt Database Accession No. Q5SBP2, last updated Apr. 5, 2011, located at <http://www.uniprot.org/jobs/201109112CDIG4W1U8.txt>, last visited on Sep. 11, 2011, 2 page.
UniProt Database Accession No. Q5SBP4, last updated Jul. 27, 2011, located at <http://www.uniprot.org/jobs/2011091140O0OYGHJF.txt>, last visited on Sep. 11, 2011, 2 pages.
UniProt Database Accession No. Q5UB07, last updated Jul. 27, 2011, located at <http://www.uniprot.org/jobs/201109112CDIFZCWUC.txt>, last visited on Sep. 11, 2011, 1 page.
UniProt Database Accession No. Q672F7, last updated Jul. 27, 2011, located at <http://www.uniprot.org/jobs/201109112CDIFWBP6O.txt>, last visited on Sep. 11, 2011, 1 page.
UniProt Database Accession No. Q6EJ97, last updated Apr. 5, 2011, located at <http://www.uniprot.org/jobs/20110911315BARZM8D.txt>, last visited on Sep. 11, 2011, 2 pages.
UniProt Database Accession No. Q6PWU1, "SubName: Full=(−)-a-terpineol synthase." Retrieved from EBI accession No. UniProt:Q6PWU1 (Jul. 5, 2004), last updated on Jul. 11, 2012, located at http://www.uniprot.org/uniprot/Q6PWU1, last visited on Jul. 23, 2012, 4 pages.
UniProt Database Accession No. Q7Y1V1, last updated Jul. 27, 2011, located at <http://www.uniprot.org/jobs/201109112CDIG0LK2O.txt>, last visited on Sep. 11, 2011, 1 page.
UniProt Database Accession No. Q8L5K1, last updated on Oct. 16, 2013, located at http://www.uniprot.org/uniprot/Q8L5K1, last visited on Oct. 29, 2013, 3 pages.
UniProt Database Accession No. Q93X23, last updated on Oct. 16, 2013, located at http://www.uniprot.org/uniprot/Q93X23, last visited on Oct. 29, 2013, 5 pages.
UniProt Database Accession No. Q941H1, last updated Jul. 27, 2011, located at <http://www.uniprot.org/jobs/201109112CDIG6PW6Y.txt>, last visited on Sep. 11, 2011, 1 page.
UniProt Database Accession No. Q9AR86, last updated May 31, 2011, located at <http://www.uniprot.org/jobs/2011091140O0P1KMN7.txt>, last visited on Sep. 11, 2011, 2 pages.
UniProt Database Accession No. Q9LIA1; Q84UU7, last updated Jul. 27, 2011, located at <http://www.uniprot.org/jobs/20110911315BB4RI8G.txt>, last visited on Sep. 11, 2011, 3 page.
UniProt Database Accession No. Q9LRZ6, "RecName: Full=Beta-myrcene/(E)-beta-ocimene synthase 2, chloroplastic; EC=4.2.3.15; AltName: Full=Terpenoid synthase 24; Short=AtTpS24; Flags: Precursor." Retrieved from EBI accession No. UniProt:Q9LRZ6 (Oct. 1, 2000); last updated on Jul. 11, 2012, located at http://www.uniprot.org/uniprot/Q9LRZ6, last visited on Jul. 23, 2012, 8 pages.
UniProt Database Accession No. Q7XAS7, last updated Apr. 5, 2011, located at <http://www.uniprot.org/jobs/201109112CDIGCK99G.txt>, last visited on Sep. 11, 2011, 2 pages.
UniProt Database Accession No. Q9FQ26, last updated Jul. 27, 2011, located at <http://www.uniprot.org/jobs/20110911315BB3SH2Y.txt>, last visited on Sep. 11, 2011, 1 page.
Vadali, R.V. et al. (2005, e-pub. Sep. 2, 2005). "Enhanced Lycopene Productivity by Manipulation of Carbon Flow to Isopentenyl Diphosphate in *Escherichia coli*," *Biotechnol. Prog.* 21(5):1558-1561.
Vagin, A. et al. (1997). "Molrep: an Automated Program for Molecular Replacement," *Journal of Applied Crystallography* 30:1022-1025.
Vandamme, E.J. et al. (2002, e-pub. 2002). "Bioflavours and Fragrances via Fermentation and Biocatalysis," *Journal of Chemical Technology and Biotechnology* 77:1323-1332.
Van Den Hondel, C.A.M.J.J. et al. (1991). "Heterologous Gene Expression in Filamentous Fungi," Chapter 18 in *More Gene Manipulations in Fungi*, Bennett, J.W. et al. eds., Academic Press, Inc.: San Diego, CA, pp. 396-428.
Van De Walle, M. et al. (Jan. 5, 1998). "Proposed Mechanism of Acetate Accumulation in Two Recombinant *Escherichia coli* Strains During High Density Fermentation," *Biotechnology and Bioengineering* 57(1):71-78.
Van Hylckama, J.E.T. et al. (Apr. 2000). "Characterization of the Gene Cluster Involved in Isoprene Metabolism in *Rhodococcus* sp. Strain AD45," *Journal of Bacteriology* 182(7):1956-1963.
Vane, L.M. (2005, e-pub. Apr. 21, 2005). "A Review of Pervaporation for Product Recovery from Biomass Fermentation Processes," *Journal of Chemical Technology and Biotechnology* 80:603-629.
Velikova, V. et al. (2005). "Consequences of Inhibition of Isoprene Synthesis in *Phragmites australis* Leaves Exposed to Elevated Temperatures," *Agriculture, Ecosystems & Environment* 106:209-217.
Vidal, M. et al. (2006, e-pub. Nov. 23, 2005). "Evaluation of Lower Flammability Limits of Fuel-Air-Diluent Mixtures Using Calculated Adiabatic Flame Temperatures," *Journal of Hazardous Materials* 130:21-27.
Voss, S. et al. (1997). "Mutagenesis of a Flexible Loop in Streptavidin Leads to Higher Affinity for the *Strep*-tag II Peptide and Improved Performance in Recombinant Protein Purification," *Protein Engineering* 10(8):975-982.
Voynova, N.E. et al. (Jan. 2004). "*Staphylococcus aureus* Mevalonate Kinase: Isolation and Characterization of an Enzyme of the Isoprenoid Biosynthetic Pathway," *Journal of Bacteriology* 186(1):61-67.
Wagner, W.P. et al. (Jan. 2000, e-pub. Nov. 18, 1999). "Isoprene Biosynthesis in *Bacillus subtilis* via the Methylerythritol Phosphate Pathway," *J. Nat. Prod.* 63(1):37-40.
Wang, C.-W. et al. (Jan. 20, 1999). "Engineered Isoprenoid Pathway Enhances Astaxanthin Production in *Escherichia coli*," *Biotechnology and Bioengineering* 62(2):235-241.
Ward, M. et al. (Aug. 1993). "Use of *Aspergillus* Overproducing Mutants, Cured for Integrated Plasmid, to Overproduce Heterologous Proteins," *Appl. Microbiol. Biotechnol.* 39(6):738-743.
Whisstock, J.C. et al. (2003). "Prediction of Protein Function from Protein Sequence and Structure," *Quarterly Reviews of Biophysics* 36(3):307-340.
Whittington, D.A. et al. (Nov. 26, 2002). "Bornyl Diphosphate Synthase: Structure and Strategy for Carbocation Manipulation by a Terpenoid Cyclase," *PNAS* 99(24):15375-15380.
Wilde, R.J. et al. (1986). "Transcript Analysis of the Citrate Synthase and Succinate Dehydrogenase Genes of *Escherichia coli* K12," *Journal of General Microbiology* 132:3239-3251.
Wildermuth, M.C. et al. (1998). "Biochemical Characterization of Stromal and Thylakoid-Bound Isoforms of Isoprene Synthase in Willow Leaves," *Plant Physiology* 116:1111-1123.

(56) References Cited

OTHER PUBLICATIONS

Wilding, E.I. et al. (Aug. 2000). "Identification, Evolution, and Essentiality of the Mevalonate Pathway for Isopentenyl Diphosphate Biosynthesis in Gram-Positive Cocci," *Journal of Bacteriology* 182(15):4319-4327.

Williams, D.C. et al. (1998). "Truncation of Limonene Synthase Preprotein Provides a Fully Active 'Pseudomature' Form of This Monoterpene Cyclase and Reveals the Function of the Amino-Terminal Arginine Pair," *Biochemistry* 37(35):12213-12220.

Wishart, M.J. et al. (Nov. 10, 1995). "A Single Mutation Converts a Novel Phosphotyrosine Binding Domain into a Dual-Specificity Phosphatase," *The Journal of Biological Chemistry* 270(45):26782-26785.

Withers, S.T. et al. (Oct. 2007, e-pub. Aug. 10, 2007). "Identification of Isopentenol Biosynthetic Genes from *Bacillus subtilis* by a Screening Method Based on Isoprenoid Precursor Toxicity," *Applied and Environmental Microbiology* 73(19):6277-6283.

Witkowski, A. et al. (1999, e-pub. Aug. 18, 1999). "Conversion of β-Ketoacyl Synthase to a Malonyl Decarboxylase by Replacement of the Active-Site Cysteine with Glutamine," *Biochemistry* 38(36):11643-11650.

Wolfertz, M. et al. (2003). "Biochemical Regulation of Isoprene Emission," *Plant, Cell and Environment* 26:1357-1364.

Wolfertz, M. et al. (Aug. 2004). "Rapid Regulation of the Methylerythritol 4-Phosphate Pathway During Isoprene Synthesis," *Plant Physiology* 135:1939-1945.

Wu, D.Y. et al. (1989). "The Ligation Amplification Reaction (LAR)-Amplification of Specific DNA Sequences Using Sequential Rounds of Template-Dependent Ligation," *Genomics* 4:560-569.

Xia, X.-X. et al. (2008). "Comparison of the Extracellular Proteomes of *Escherichia coli* B and K-12 Strains During High Cell Density Cultivation," *Proteomics* 8:1-15.

Yang, D. et al. (Mar. 15, 2002, published ahead of print Dec. 19, 2001). "Structure of the *Methanococcus jannaschii* Mevalonate Kinase, a Member of the GHMP Kinase Superfamily," *The Journal of Biological Chemistry* 277(11):9462-9467.

Ye, X. et al. (Jan. 14, 2000). "Engineering the Provitamin A (β-Carotene) Biosynthetic Pathway into (Carotenoid-Free) Rice Endosperm," *Science* 287:303-305.

Yelton, M.M. et al. (Mar. 1984). "Transformation of *Aspergillus nidulans* by Using a *trpC* Plasmid," *Proc. Natl. Acad. Sci. USA* 81:1470-1474.

Yoon, S.-H. et al. (2007, e-pub. May 15, 2007). "Increased β-Carotene Production in Recombinant *Escherichia coli* Harboring an Engineered Isoprenoid Precursor Pathway with Mevalonate Addition," *Biotechnol. Prog.* 23(3):599-605.

Yoon, S.-H. et al. (2009). "Combinatorial Expression of Bacterial Whole Mevalonate Pathway for the Production of β-Carotene in *E. coli*," *Journal of Biotechnology* 140:218-226.

International Search Report mailed on Jun. 18, 2009, for PCT Patent Application No. PCT/US08/86869, filed on Dec. 15, 2008, one page.

International Search Report mailed on Dec. 8, 2009, for PCT Application No. PCT/US2009/041581, filed on Apr. 23, 2009, nine pages.

International Search Report mailed on Dec. 30, 2010, for PCT Application No. PCT/US2010/032134, filed on Apr. 22, 2010, 15 pages.

International Search Report mailed on Jul. 24, 2012, for PCT Patent Application No. PCT/US2011/058188, filed on Oct. 27, 2011, ten pages.

Pegg, S.C.-H. et al. (2006). "Leveraging Enzyme Structure-Function Relationships for Functional Inference and Experimental Design: The Structure-Function Linkage Database," *Biochemistry* 45:2545-2555.

Penttila, M. et al. (1987). "A Versatile Transformation System for the Cellulolytic Filamentous Fungus *Trichoderma reesei*," *Gene* 61:155-164.

\* cited by examiner

IDENTIFICATION OF ISOPRENE SYNTHASE VARIANTS WITH IMPROVED PROPERTIES FOR THE PRODUCTION OF ISOPRENE

CROSS-REFERENCE TO RELATED APPLICATIONS

This application claims priority to U.S. Provisional Patent Application No. 61/641,823, filed May 2, 2012, the disclosure of which is incorporated by reference herein in its entirety.

FIELD OF THE INVENTION

The present invention provides methods and compositions comprising isoprene synthase variants. In particular, the present invention provides isoprene synthase variants for increased isoprene production in host cells.

INCORPORATION BY REFERENCE

The content of the following submission of the sequence listing on ASCII text file is incorporated herein by reference in its entirety: a computer readable form (CRF) of the Sequence Listing (file name: 643842004500_Sequence_Listing_XP.txt, date recorded: Aug. 1, 2013, size: 77,597 bytes).

BACKGROUND OF THE INVENTION

Isoprene (2-methyl-1,3-butadiene) is a volatile hydrocarbon that is insoluble in water and soluble in alcohol. Commercially viable quantities of isoprene can be obtained by direct isolation from petroleum C5 cracking fractions or by dehydrogenation of C5 isoalkanes or isoalkenes (Weissermel and Arpe, Industrial Organic Chemistry, 4th ed., Wiley-VCH, pp. 117-122, 2003). The C5 skeleton can also be synthesized from smaller subunits. It would be desirable, however, to have a commercially viable method of producing isoprene that was independent of nonrenewable resources.

Biosynthetic production of isoprene occurs by two distinct metabolic pathways (Julsing et al., Appl Microbiol Biotechnol, 75:1377-1384, 2007). In eukaryotes and archae, isoprene is formed via the mevalonate (MVA) pathway, while some eubacteria and higher plants produce isoprene via the methylerythritol phosphate (MEP) pathway. Isoprene emissions from plants are light and temperature-dependent with increases linked to leaf development. An isoprene-producing enzyme, isoprene synthase, has been identified in Aspen trees (Silver and Fall, *Plant Physiol,* 97:1588-1591, (1991); and Silver and Fall, *J Biol Chem,* 270:13010-13016, (1995)) and is believed to be responsible for the in vivo production of isoprene from whole leaves. Bacterial production of isoprene has also been described (Kuzma et al., *Curr Microbiol,* 30:97-103, (1995); and Wilkins, *Chemosphere,* 32:1427-1434, (1996)), and varies in amount with the phase of bacterial growth and the nutrient content of the culture medium (U.S. Pat. No. 5,849,970 to Fall et al.; and Wagner et al., *J Bacteriol,* 181:4700-4703, (1999)). The levels of isoprene obtainable through bacterial systems of the prior art, however, are insufficient for commercial uses. Thus what the art needs is an efficient, large scale isoprene biological production process to produce isoprene. The invention described herein addresses these problems and provides additional benefits as well.

BRIEF SUMMARY OF THE INVENTION

The invention provides, inter alia, compositions and methods for the increased production of isoprene by using polypeptides having isoprene synthase activity, wherein the polypeptides have one or more amino acid substitution(s) at one or more residues, such that the polypeptides have improved kinetic properties for the production of isoprene.

Accordingly in one aspect, the invention provides for isolated polypeptides having isoprene synthase activity, wherein the polypeptides comprise one or more amino acid substitution(s) at one or more residues corresponding to SEQ ID NO:1 selected from the group consisting of: X323F, X118E, X36W, X22K, X228Y, X448L, X488F, X467H, X443S, X331P, X453I, X71K, X71L, X448I, X71M, X392Y, X448V, X282H, X383Y, X323Y, X511Y, X448E, X376M, X488L, X120E, X461A, X414I, X282W, X071K, X493E, X392S, X448Q, X282Y, X537N, X447Y, X240C, X443Q, X538R, and X510C, and wherein the polypeptides have improved Kcat compared to a parent polypeptide which does not comprise said one or more amino acid substitution(s). In some embodiments, the amino acid substitution is selected from the group consisting of: D323F, A118E, K36W, S22K, M228Y, A448L, E488F, E467H, A443S, C331P, A453I, R71K, R71L, A448I, R71M, W392Y, A448V, S282H, T383Y, D323Y, H511Y, A448E, L376M, E488L, S120E, R461A, K414I, S282W, R071K, S493E, W392S, A448Q, S282Y, E537N, I447Y, T240C, A443Q, P538R, and S510C.

In another aspect, the invention provides for isolated polypeptides having isoprene synthase activity, wherein the polypeptides comprise one or more amino acid substitution(s) at one or more residues corresponding to SEQ ID NO:1 selected from the group consisting of: X389D, X383H, X36E, X436Y, X447V, X392F, X161R, X99D, X99E, X161C, X414S, X537T, X393V, X443G, X510V, X36N, X392A, X161A, X254R, X472C, X161Q, X36Y, X537C, X41Y, X161M, X43L, X120A, X087M, X36S, X36H, X348Y, X467W, X288T, X447T, X025N, and wherein the polypeptides have improved Kcat compared to a parent polypeptide which does not comprise said one or more amino acid substitution(s). In some embodiments, the amino acid substitution is selected from the group consisting of: G389D, T383H, K36E, L436Y, I447V, W392F, K161R, G99D, G99E, K161C, K414S, E537T, K393V, A443G, S510V, K36N, W392A, K161A, H254R, E472C, K161Q, K36Y, E537C, E41Y, K161M, R43L, S120A, G087M, K36S, K36H, K348Y, E467W, S288T, I447T, and D025N.

In another aspect, the invention provides for isolated polypeptides having isoprene synthase activity, wherein the polypeptides comprise one or more amino acid substitution(s) at one or more residues corresponding to SEQ ID NO:1 selected from the group consisting of: X268I, X488M, X480I, X240V, X460A, X071L, X36Q, X118P, X36T, X282I, X409I, X071I, X409T, X436F, X348F, X118Q, X342Y, X74Q, X41P, X437Y, X392T, X89D, X41M, X510E, X36P, X393I, X71I, X381M, X374Y, X58Y, X526Q, X543F, X240M, X111S, X463T, X120M, and X135G, and wherein the polypeptides have improved Kcat compared to a parent polypeptide which does not comprise said one or more amino acid substitution(s). In some embodiments, the amino acid substitution is selected from the group consisting of: V268I, E488M, E480I, T240V, M460A, R071L, K36Q, A118P, K36T, S282I, V409I, R071I, V409T, L436F, K348F, A118Q, I342Y, S74Q, E41P, C437Y, W392T, F89D, E41M, S510E, K36P, K393I, R71I, T381M, K374Y, E58Y, L526Q, E543F, T240M, G111S, K463T, S120M, and E135G.

In another aspect, the invention provides for isolated polypeptides having isoprene synthase activity, wherein the polypeptides comprise one or more amino acid substitution(s) at one or more residues corresponding to SEQ ID NO:1 selected from the group consisting of: X22K, X348F, X392V, X392F, X488C, X22R, X71V, X443R, X234R, X453V, X437Y, X392C, X463F, X538K, X393L, X254C, X436Y, X21R, X437L, X444D, X374Y, X363L, X447V, X444E, X71I, X504F, X488W, X71H, X36P, X381I, X436F, X460A, X443G, X288A, X392T, X537I, X374Y, X242G, X437M, X436I, X376I, X288Y, and X392M, and wherein the polypeptides have improved $K_M$ compared to a parent polypeptide which does not comprise said one or more amino acid substitution(s). In some embodiments, the amino acid substitution is selected from the group consisting of: S22K, K348F, W392V, W392F, E488C, S22R, R71V, A443R, Q234R, A453V, C437Y, W392C, K463F, P538K, K393L, H254C, L436Y, S21R, C437L, S444D, K374Y, A363L, I447V, S444E, R71I, I504F, E488W, R71H, K36P, T381I, L436F, M460A, A443G, S288A, W392T, E537I, K374Y, R242G, C437M, L436I, L376I, S288Y, and W392M.

In another aspect, the invention provides for isolated polypeptides having isoprene synthase activity, wherein the polypeptides comprise one or more amino acid substitution(s) at one or more residues corresponding to SEQ ID NO:1 selected from the group consisting of: X342Y, X414W, X461A, X443S, X392A, X463T, X488T, X526Q, X502F, X502M, X488M, X36Y, X414R, X071I, X36W, X502L, X481Y, X472R, X36H, X36T, X415Y, X415H, X58Y, X381M, X481V, X89E, X480I, X36Q, X89D, X254R, X161N, X071L, X424P, X415V, X22K, X58L, X392S, X268I, X392I, X526E, X537V, and X36D and wherein the polypeptides have improved $K_M$ compared to a parent polypeptide which does not comprise said one or more amino acid substitution(s). In some embodiments, the amino acid substitution is selected from the group consisting of: I342Y, K414W, R461A, A443S, W392A, K463T, E488T, L526Q, T502F, T502M, E488M, K36Y, K414R, R071I, K36W, T502L, T481Y, E472R, K36H, K36T, E415Y, E415H, E58Y, T381M, T481V, F89E, E480I, K36Q, F89D, H254R, K161N, R071L, H424P, E415V, S22K, E58L, W392S, V268I, W392I, L526E, E537V, and K36D.

In another aspect, the invention provides for isolated polypeptides having isoprene synthase activity, wherein the polypeptides comprise one or more amino acid substitution(s) at one or more residues corresponding to SEQ ID NO:1 selected from the group consisting of: X393I, X41M, X025N, X36N, X118Q, X389E, X282W, X348Y, X383L, X510V, X323Y, X323F, X383H, X41P, X288T, X36S, X453I, X447T, X472I, X376M, X161E, X488L, X381L, X071K, X409T, X392Y, X135G, X542L, X228Y, X118P, X543F, and X36E, and wherein the polypeptides have improved $K_M$ compared to a parent polypeptide which does not comprise said one or more amino acid substitution(s). In some embodiments, the amino acid substitution is selected from the group consisting of: K393I, E41M, D025N, K36N, A118Q, G389E, S282W, K348Y, T383L, S510V, D323Y, D323F, T383H, E41P, S288T, K36S, A453I, I447T, E472I, L376M, K161E, E488L, T381L, R071K, V409T, W392Y, E135G, F542L, M228Y, A118P, E543F, and K36E.

In another aspect, the invention provides for isolated polypeptides having isoprene synthase activity, wherein the polypeptides comprise one or more amino acid substitution(s) at one or more residues corresponding to SEQ ID NO:1 selected from the group consisting of: X472R, X389E, X242G, X376I, X161N, X288C, X240V, X481Y, X463F, and X393L, and wherein the polypeptides have improved $K_{iDMAPP}$ compared to a parent polypeptide which does not comprise said one or more amino acid substitution(s). In some embodiments, the amino acid substitution is selected from the group consisting of: E472R, G389E, R242G, L376I, K161N, S288C, T240V, T481Y, K463F, and K393L.

In another aspect, the invention provides for isolated polypeptides having isoprene synthase activity, wherein the polypeptides comprise one or more amino acid substitution(s) at one or more residues corresponding to SEQ ID NO:1 selected from the group consisting of: X120Q, X58L, X240M, and X453V, and wherein the polypeptides have improved $K_{iDMAPP}$ compared to a parent polypeptide which does not comprise said one or more amino acid substitution(s). In some embodiments, the amino acid substitution is selected from the group consisting of: S120Q, E58L, T240M, and A453V.

In another aspect, the invention provides for isolated polypeptides having isoprene synthase activity, wherein the polypeptides comprise one or more amino acid substitution(s) at one or more residues corresponding to SEQ ID NO:1 selected from the group consisting of: X543F, X74Q, X414R, X415H, and X415V, and wherein the polypeptides have improved $K_{iDMAPP}$ compared to a parent polypeptide which does not comprise said one or more amino acid substitution(s). In some embodiments, the amino acid substitution is selected from the group consisting of: E543F, S74Q, K414R, E415H, and E415V.

In another aspect, the invention provides for isolated polypeptides having isoprene synthase activity, wherein the polypeptides comprise one or more amino acid substitution(s) at one or more residues corresponding to SEQ ID NO:1 selected from the group consisting of: X510E, X161M, X120Q, X120E, X161R, X120A, X493E, X448E, X240V, X240M, and X537T, and wherein the polypeptides have improved specific productivity compared to a parent polypeptide which does not comprise said one or more amino acid substitution(s). In some embodiments, the amino acid substitution is selected from the group consisting of: S510E, K161M, S120Q, S120E, K161R, S120A, S493E, A448E, T240V, T240M, and E537T.

In another aspect, the invention provides for isolated polypeptides having isoprene synthase activity, wherein the polypeptides comprise one or more amino acid substitution(s) at one or more residues corresponding to SEQ ID NO:1 selected from the group consisting of: X161N, X447Y, X502M, X537N, X348Y, X543F, X331P, X537C, X120M, X288C, and X161Q, and wherein the polypeptides have improved specific productivity compared to a parent polypeptide which does not comprise said one or more amino acid substitution(s). In some embodiments, the amino acid substitution is selected from the group consisting of: K161N, I447Y, T502M, E537N, K348Y, E543F, C331P, E537C, S120M, S288C, and K161Q.

In another aspect, the invention provides for isolated polypeptides having isoprene synthase activity, wherein the polypeptide comprises one or more amino acid substitution(s) at one or more residues corresponding to SEQ ID NO:1 selected from the group consisting of: X161A, X481V, X087M, X467W, X448V, X502L, and X376M, and wherein the polypeptide has improved specific productivity compared to a parent polypeptide which does not comprise said one or more amino acid substitution(s). In some embodiments, the amino acid substitution is selected from the group consisting of: K161A, T481V, G087M, E467W, A448V, T502L, and L376M.

In any of the aspects and/or embodiments herein, recombinant host cells comprise the polypeptide of any of the above. In some embodiments, the host cell is selected from the group consisting of a bacterial, algal, fungal, yeast, cyanobacterial, or Clostridial cell. In some embodiments, the host cell is a bacterial cell. In some embodiments, the bacterial cell is a gram-positive bacterial cell or gram-negative bacterial cell. In some embodiments, the bacterial cell is selected from the group consisting of *E. coli, L. acidophilus, P. citrea, B. subtilis, B. licheniformis, B. lentus, B. brevis, B. stearothermophilus, B. alkalophilus, B. amyloliquefaciens, B. clausii, B. halodurans, B. megaterium, B. coagulans, B. circulans, B. lautus, B. thuringiensis, S. albus, S. lividans, S. coelicolor, S. griseus, Pseudomonas* sp., *P. alcaligenes, Clostridium* sp., *Corynebacterium* sp., and *C. glutamicum* cells. In some embodiments, the host cell is an algal cell. In some embodiments, the algal cell is selected from the group consisting of green algae, red algae, glaucophytes, chlorarachniophytes, euglenids, chromista, or dinoflagellates. In some embodiments, the host cell is a fungal cell. In some embodiments, the fungal cell is a filamentous fungi. In some embodiments, the host cell is a yeast cell. In some embodiments, the yeast cell is selected from the group consisting of *Saccharomyces* sp., *Schizosaccharomyces* sp., *Pichia* sp., or *Candida* sp. In some embodiments, the yeast cell is a *Saccharomyces cerevisiae* cell.

In any of the aspects and/or embodiments herein, methods for producing isoprene comprise (a) culturing the host cells as described herein, including those described above, under conditions suitable for the production of isoprene and (b) producing isoprene. In some embodiments, the method further comprises recovering the isoprene.

BRIEF DESCRIPTION OF THE DRAWINGS

FIG. 39A shows the correlation of $K_{iDMAPP}$ vs. specific isoprene productivity for isoprene synthase variants. FIG. 39B shows the correlation of $K_M$ vs. specific isoprene productivity for isoprene synthase variants. FIG. 39C shows the correlation of $k_{cat}$ vs. specific isoprene productivity for isoprene synthase variants. All values are normalized to parent molecule performance.

DETAILED DESCRIPTION

Figure 1:
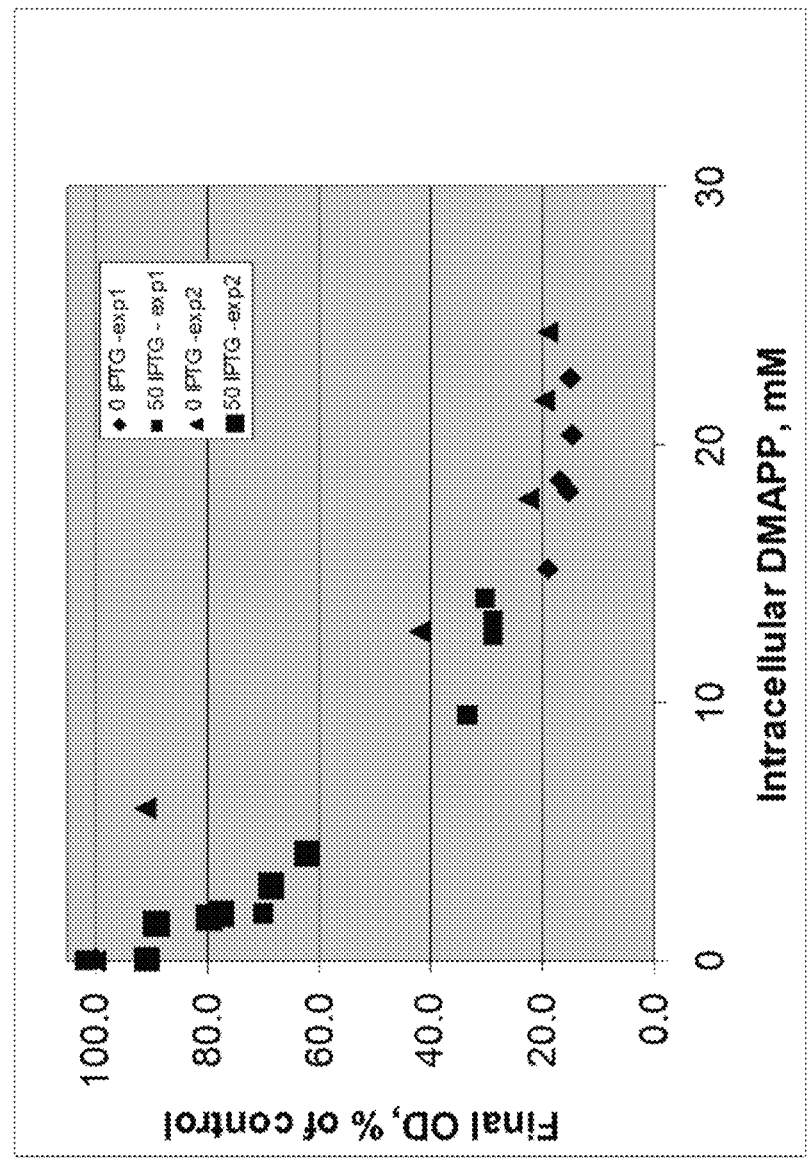
FIG. 1 shows the relationship between growth and DMAPP concentration in assay strain. DW425 was grown in the presence of various concentrations of mevalonate (0, 10, 20, 30, 40, 50 mM mevalonate in exp1, and 0, 2.5, 5, 10, 20 mM mevalonate in expt2) and IPTG (0 µM IPTG and 50 µM IPTG). Cells were harvested and collected for metabolite analysis upon completion of the growth experiment.

The present invention provides for, inter alia, isolated polypeptides having isoprene synthase activity wherein the variant has one or more improved properties, such as 1) kcat (2) KM (3) Ki and (4) specific productivity. The invention also provides for methods and compositions comprising at least one isoprene synthase variant. The variant can include one or more amino acid residue substitution(s) from a parent isoprene synthase polypeptide, wherein the parent isoprene synthase may be a wild type or non-wild type sequence. The invention provides amino acid residue substitutions at particular positions within the polypeptide, wherein the substitution may result in at least one improved property as compared to its parent sequence or a reference sequence. In particular, the present invention provides isoprene synthase variants, host cells and systems for increased isoprene production. Biosynthetically produced isoprene of the present invention finds use in the manufacture of rubber, polymers, and elastomers.

I. GENERAL TECHNIQUES

The practice of the present invention will employ, unless otherwise indicated, conventional techniques of molecular biology (including recombinant techniques), microbiology, cell biology, biochemistry, and immunology, which are within the skill of the art. Such techniques are explained fully in the literature, "*Molecular Cloning: A Laboratory Manual*", second edition (Sambrook et al., 1989); "*Oligonucleotide Synthesis*" (M. J. Gait, ed., 1984); "*Animal Cell Culture*" (R. I. Freshney, ed., 1987); "*Methods in Enzymology*" (Academic Press, Inc.); "*Current Protocols in Molecular Biology*" (F. M. Ausubel et al., eds., 1987, and periodic updates); "*PCR: The Polymerase Chain Reaction*", (Mullis et al., eds., 1994). Singleton et al., "*Dictionary of Microbiology and Molecular Biology*" 2nd ed., J. Wiley & Sons (New York, N.Y. 1994), Baltz et al., "*Manual of Industrial Microbiology and Biotechnology*" $3^{rd}$ ed., (Washington, D.C.: ASM Press, 2010), and March, *Advanced Organic Chemistry Reactions, Mechanisms and Structure* $4^{th}$ ed., John Wiley & Sons (New York, N.Y. 1992) provide one skilled in the art with a general guide to many of the terms used in the present application.

II. DEFINITIONS

Unless defined otherwise herein, all technical and scientific terms used herein have the same meaning as commonly understood by one of ordinary skill in the art to which this invention pertains. Although any methods and materials similar or equivalent to those described herein find use in the practice of the present invention, the preferred methods and materials are described herein. Furthermore, the headings provided herein are not limitations of the various aspects or embodiments of the invention, which can be had by reference to the specification as a whole. Accordingly, the terms defined immediately below are more fully described by reference to the specification as a whole. Nonetheless, in order to facilitate understanding of the invention, a number of terms are defined below.

"X" refers to any amino acid residue. However, when in the context of an amino acid substitution (e.g. "X003C"), it is to be understood that "X" refers to an amino acid residue other than the amino acid residue resulting from the substitution (e.g., X is an amino acid residue other than C).

As used herein, the term "polypeptides" includes polypeptides, proteins, peptides, fragments of polypeptides, and fusion polypeptides.

As used herein, an "isolated polypeptide" is not part of a library of polypeptides, such as a library of 2, 5, 10, 20, 50 or more different polypeptides and is separated from at least one component with which it occurs in nature. An isolated polypeptide can be obtained, for example, by expression of a recombinant nucleic acid encoding the polypeptide.

By "heterologous polypeptide" is meant a polypeptide encoded by a nucleic acid sequence derived from a different organism, species, or strain than the host cell. In some aspects, a heterologous polypeptide is not identical to a wild-type polypeptide that is found in the same host cell in nature.

As used herein, a "nucleic acid" refers to two or more deoxyribonucleotides and/or ribonucleotides covalently joined together in either single or double-stranded form. It is to be understood that mutations, including single nucleotide mutations, can occur within a nucleic acid as defined herein.

By "recombinant nucleic acid" is meant a nucleic acid of interest that is free of one or more nucleic acids (e.g., genes) which, in the genome occurring in nature of the organism from which the nucleic acid of interest is derived, flank the nucleic acid of interest. The term therefore includes, for example, a recombinant DNA which is incorporated into a vector, into an autonomously replicating plasmid or virus, or into the genomic DNA of a prokaryote or eukaryote, or which exists as a separate molecule (e.g., a cDNA, a genomic DNA fragment, or a cDNA fragment produced by PCR or restriction endonuclease digestion) independent of other sequences. A recombinant nucleic acid may be obtained using molecular biology techniques that are known in the art, or part or all of a recombinant nucleic acid may be chemically synthesized.

By "heterologous nucleic acid" is meant a nucleic acid sequence derived from a different organism, species or strain than the host cell. In some aspects, the heterologous nucleic acid is not identical to a wild-type nucleic acid that is found in the same host cell in nature. In some aspects, a heterologous nucleic acid is not identical to a wild-type nucleic acid that is found in the same host cell in nature.

An "endogenous nucleic acid" is a nucleic acid whose nucleic acid sequence is naturally found in the host cell. In some embodiments, an endogenous nucleic acid is identical to a wild-type nucleic acid that is found in the host cell in nature. In some embodiments, one or more copies of endogenous nucleic acids are introduced into a host cell.

A nucleic acid or protein of the invention may be in isolated or purified form. As used herein, "isolated," with respect to nucleic acid or protein, means separated from other components, such as, but not limited to a cell or cell culture. It is preferably in a homogeneous state although it can be in either a dry or aqueous solution. Purity and homogeneity are typically determined using analytical chemistry techniques, such as polyacrylamide gel electrophoresis or high performance liquid chromatography. A protein or nucleic acid that is the predominant species present in a preparation is substantially purified. The term "purified" denotes that a nucleic acid or protein gives rise to essentially one band in an electrophoretic gel. Particularly, "purified" means that when isolated, the isolate contains at least 90%, at least 95%, at least 98%, or more preferably at least 99% of nucleic acid or protein by weight of the isolate.

Purified polypeptides may be obtained by a number of methods including, for example, laboratory synthesis, chromatography, preparative electrophoresis, gel electrophoresis, centrifugation, precipitation, affinity purification, etc. (see, generally, R Scopes, Protein Purification, Springer-Verlag, N.Y. (1982), Deutscher, Methods in Enzymology Vol. 182: Guide to Protein Purification, Academic Press, Inc. N.Y. (1990)).

"Polypeptides" includes polypeptides, proteins, peptides, fragments of polypeptides, and fusion polypeptides. It is also understood that a polypeptide may be coded for by more than one nucleotide sequence due to the degeneracy of the genetic code.

A "heterologous polypeptide" is a polypeptide encoded by a heterologous nucleic acid. In some embodiments, the sequence is not identical to that of another polypeptide encoded by a nucleic acid naturally found in the same host cell. Examples of heterologous proteins include enzymes such as isoprene synthases. In some embodiments, the genes encoding the proteins are naturally occurring genes, while in other embodiments mutated and/or synthetic genes are used.

An "endogenous polypeptide" is a polypeptide whose amino acid sequence is naturally found in the host cell. In some embodiments, an endogenous polypeptide is identical to a wild-type polypeptide that is found in the host cell in nature.

As used herein, an "expression control sequence" means a nucleic acid sequence that directs transcription of a nucleic acid of interest. An expression control sequence can be a promoter, such as a constitutive or an inducible promoter, or an enhancer. An expression control sequence can be "native" or heterologous. A native expression control sequence is derived from the same organism, species, or strain as the gene being expressed. A heterologous expression control sequence is derived from a different organism, species, or strain as the gene being expressed. An "inducible promoter" is a promoter that is active under environmental or developmental regulation.

By "operably linked" is meant a functional linkage between a nucleic acid expression control sequence (such as a promoter) and a second nucleic acid sequence, wherein the expression control sequence directs transcription of the nucleic acid corresponding to the second sequence.

The term "isoprene" refers to 2-methyl-1,3-butadiene (CAS#78-79-5). It can be the direct and final volatile C5 hydrocarbon product from the elimination of pyrophosphate from DMAPP. It may not involve the linking or polymerization of IPP molecules to DMAPP molecules. The term "isoprene" is not generally intended to be limited to its method of production unless indicated otherwise herein.

As used herein, the terms "isoprene synthase," "isoprene synthase variant", and "IspS," refer to enzymes that catalyze the elimination of pyrophosphate from diemethylallyl diphosphate (DMAPP) to form isoprene. An "isoprene synthase" may be a wild type sequence or an isoprene synthase variant.

An "isoprene synthase variant" indicates a non-wild type polypeptide having isoprene synthase activity. One skilled in the art can measure isoprene synthase activity using known methods. See, for example, by GC-MS (see, e.g., WO 2009/132220, Example 3) or Silver et al., J. Biol. Chem. 270: 13010-13016, (1995). Variants may have substitutions, additions, deletions, and/or truncations from a wild type isoprene synthase sequence. Variants may have substitutions, additions, deletions, and/or truncations from a non-wild type isoprene synthase sequence. The variants described herein contain at least one amino acid residue substitution from a parent isoprene synthase polypeptide. In some embodiments, the parent isoprene synthase polypeptide is a wild type sequence. In some embodiments, the parent isoprene synthase polypeptide is a non-wild type sequence. In various embodiments, the variant will have at least about 10%, at least about 20%, at least about 30%, at least about 40%, at least about 50%, at least about 60%, at least about 70%, at least about 80%, at least about 90%, at least about 100%, at least about 110%, at least about 120%, at least about 130%, at least about 140%, at least about 150%, at least about 160%, at least about 170%, at least about 180%, at least about 190%, at least about 200% of the activity of a wild type isoprene synthase. In various embodiments, the variant will have at least about 40%, at least about 50%, at least about 60%, at least about 70%, at least about 80%, at least about 90%, at least about 91%, at least about 92%, at least about 93%, at least about 94%, at least about 95%, at least about 96%, at least about 97%, at least about 98%, at least about 99% sequence identity to a wild type isoprene synthase. In various embodiments, the number of differing amino acid residues between the variant and the wild type may be one or more, e.g. 1, 2, 3, 4, 5, 10, 15, 20, 30, 40, 50, or more amino acid residues. Wild type isoprene synthases can include any isoprene synthases from plants, for example, kudzu isoprene synthases, poplar isoprene synthases, English oak isoprene synthases, and willow isoprene synthases.

As used herein, the term "naturally-occurring" refers to anything (e.g., proteins, amino acids, or nucleic acid sequences) that is found in nature (e.g., has not been manipulated by means of recombinant or chemical methods). As used herein, the term "non-naturally occurring" refers to anything that is not found in nature (e.g., recombinantly produced or chemically synthesized proteins, amino acids, or nucleic acid sequences produced in the laboratory).

As used herein, an amino acid residue of an amino acid sequence of interest that "corresponds to" or is "corresponding to" or in "correspondence with" an amino acid residue of a reference amino acid sequence indicates that the amino acid residue of the sequence of interest is at a location homologous or equivalent to an enumerated residue in the reference amino acid sequence. One skilled in the art can determine whether a particular amino acid residue position in a polypeptide corresponds to that of a homologous reference sequence. For example, the sequence of an isoprene synthase polypeptide may be aligned with that of a reference sequence (e.g. *P. alba* MEA isoprene synthase, SEQ ID NO:1) using known techniques (e.g., basic local alignment search tool (BLAST), ClustalW2, Structure based sequences alignment program (STRAP), or the like). In addition, crystal structure coordinates of a reference sequence may be used as an aid in determining a homologous polypeptide residue's three dimensional structure (see, for example, WO 2010/124146 or US 2011/0076743). In another aspect, equivalent residues may be identified by determining homology at the level of tertiary structure. Using such methods, the amino acid residues of an isoprene synthase polypeptide or isoprene synthase variant may be numbered according to the corresponding amino acid residue position numbering of the reference sequence. For example, the amino acid sequence of SEQ ID NO:1 may be used for determining amino acid residue position numbering of each amino acid residue of an isoprene synthase variant of interest.

The term "identical" in the context of two nucleic acids or polypeptide sequences refers to the residues in the two sequences that are the same when aligned for maximum correspondence, as measured using one of the following sequence comparison or analysis algorithms.

As used herein, "homology" refers to sequence similarity or identity, with identity being preferred. Homology may be determined using standard techniques known in the art (see, e.g., Smith and Waterman, Adv. Appl. Math. 2:482 (1981); Needleman and Wunsch, J. Mol. Biol. 48:443 (1970); Pearson and Lipman, Proc. Natl. Acad. Sci. USA 85:2444 (1988); software programs such as GAP, BESTFIT, FASTA, and TFASTA in the Wisconsin Genetics Software Package (Genetics Computer Group, Madison, Wis.); and Devereux et al., Nucl. Acid Res. 12:387-395 (1984)). One example of a useful algorithm is PILEUP. PILEUP creates a multiple sequence alignment from a group of related sequences using progressive, pair-wise alignments. It can also plot a tree showing the clustering relationships used to create the alignment. PILEUP uses a simplification of the progressive alignment method of Feng and Doolittle (see Feng and Doolittle, J. Mol. Evol. 35:351-360 (1987)). The method is similar to that described by Higgins and Sharp (see Higgins and Sharp, CABIOS 5:151-153 (1989)). Useful PILEUP parameters including a default gap weight of 3.00, a default gap length weight of 0.10, and weighted end gaps. Another example of a useful algorithm is the BLAST algorithm, described by Altschul et al., (see Altschul et al., J. Mol. Biol. 215:403-410 (1990); and Karlin et al. Proc. Natl. Acad. Sci. USA 90:5873-5787 (1993)). A particularly useful BLAST program is the WU-BLAST-2 program (see Altschul et al., Meth. Enzymol. 266: 460-480 (1996)). WU-BLAST-2 uses several search parameters, most of which are set to the default values. The adjustable parameters are set with the following values: overlap span=1, overlap fraction=0.125, word threshold (T)=11. The HSP S and HSP S2 parameters are dynamic values and are established by the program itself depending upon the composition of the particular sequence and composition of the particular database against which the sequence of interest is being searched. However, the values may be adjusted to increase sensitivity.

The percent sequence identity between a reference sequence and a test sequence of interest may be readily determined by one skilled in the art. The percent identity shared by polynucleotide or polypeptide sequences is determined by direct comparison of the sequence information between the molecules by aligning the sequences and determining the identity by methods known in the art. An example of an algorithm that is suitable for determining sequence similarity is the BLAST algorithm, (see Altschul, et al., J. Mol. Biol., 215:403-410 (1990)). Software for performing BLAST analyses is publicly available through the National Center for Biotechnology Information. This algorithm involves first identifying high scoring sequence pairs (HSPs) by identifying short words of length W in the query sequence that either match or satisfy some positive-valued threshold score T when aligned with a word of the same length in a database sequence. These initial neighborhood word hits act as starting points to find longer HSPs containing them. The word hits are expanded in both directions along each of the two sequences being compared for as far as the cumulative alignment score can be increased. Extension of the word hits is stopped when: the cumulative alignment score falls off by the quantity X from a maximum achieved value; the cumulative score goes to zero or below; or the end of either sequence is reached. The BLAST algorithm parameters W, T, and X determine the sensitivity and speed of the alignment. The BLAST program uses as defaults a wordlength (W) of 11, the BLOSUM62 scoring matrix (see Henikoff and Henikoff, Proc. Natl. Acad. Sci. USA 89:10915 (1992)) alignments (B) of 50, expectation (E) of 10, M'5, N'-4, and a comparison of both strands.

The BLAST algorithm then performs a statistical analysis of the similarity between two sequences (see, e.g., Karlin and Altschul, supra). One measure of similarity provided by the BLAST algorithm is the smallest sum probability (P(N)), which provides an indication of the probability by which a match between two nucleotide or amino acid sequences would occur by chance. For example, a nucleic acid is considered similar to a isoprene synthase nucleic acid of this invention if the smallest sum probability in a comparison of the test nucleic acid to a isoprene synthase nucleic acid is less than about 0.1, more preferably less than about 0.01, and most preferably less than about 0.001. Where the test nucleic acid encodes an isoprene synthase polypeptide, it is considered similar to a specified isoprene synthase nucleic acid if the comparison results in a smallest sum probability of less than about 0.5, and more preferably less than about 0.2.

Percent "identical" or "identity" in the context of two or more nucleic acid or polypeptide sequences refers to two or more sequences that are the same or have a specified percentage of nucleic acid residues or amino acid residues, respectively, that are the same, when compared and aligned for maximum similarity, as determined using a sequence comparison algorithm or by visual inspection. "Percent sequence identity" or "% identity" or "% sequence identity or "% amino acid sequence identity" of a subject amino acid sequence to a reference amino acid sequence means that the subject amino acid sequence is identical (i.e., on an amino acid-by-amino acid basis) by a specified percentage to the reference amino acid sequence over a comparison length when the sequences are optimally aligned. Thus, 80% amino acid sequence identity or 80% identity with respect to two amino acid sequences means that 80% of the amino acid residues in two optimally aligned amino acid sequences are identical.

"Percent sequence identity" or "% identity" or "% sequence identity" of a subject nucleic acid sequence to a reference nucleic acid sequence means that the subject nucleic acid sequence is identical (i.e., on a nucleotide-by-nucleotide basis for a polynucleotide sequence) by a specified percentage to the reference sequence over a comparison length when the sequences are optimally aligned. Thus, 80% nucleotide sequence identity or 80% identity with respect to two nucleic acid sequences means that 80% of the nucleotide residues in two optimally aligned nucleic acid sequences are identical.

The "percent sequence identity" or "% sequence identity" or "% identity" of a subject sequence to a reference sequence can be calculated by optimally aligning the two sequences and comparing the two optimally aligned sequences over the comparison length. The number of positions in the optimal alignment at which identical residues occur in both sequences is determined, thereby providing the number of matched positions, and the number of matched positions is then divided by the total number of positions of the comparison length (which, unless otherwise specified, is the length of the reference sequence). The resulting number is multiplied by 100 to yield the percent sequence identity of the subject sequence to the reference sequence.

"Optimal alignment" or "optimally aligned" refers to the alignment of two (or more) sequences giving the highest percent identity score. For example, optimal alignment of two polypeptide sequences can be achieved by manually aligning the sequences such that the maximum number of identical amino acid residues in each sequence are aligned together or by using software programs or procedures described herein or known in the art. Optimal alignment of two nucleic acid sequences can be achieved by manually aligning the sequences such that the maximum number of identical nucleotide residues in each sequence are aligned together or by using software programs or procedures described herein or known in the art.

Two sequences (e.g., polypeptide sequences) may be deemed "optimally aligned" when they are aligned using defined parameters, such as a defined amino acid substitution matrix, gap existence penalty (also termed gap open penalty), and gap extension penalty, so as to achieve the highest similarity score possible for that pair of sequences. The BLOSUM62 scoring matrix (see Henikoff and Henikoff, supra) is often used as a default scoring substitution matrix in polypeptide sequence alignment algorithms (e.g., BLASTP). The gap existence penalty is imposed for the introduction of a single amino acid gap in one of the aligned sequences, and the gap extension penalty is imposed for each residue position in the gap. Exemplary alignment parameters employed are: BLOSUM62 scoring matrix, gap existence penalty=11, and gap extension penalty=1. The alignment score is defined by the amino acid positions of each sequence at which the alignment begins and ends (e.g., the alignment window), and optionally by the insertion of a gap or multiple gaps into one or both sequences, so as to achieve the highest possible similarity score.

Optimal alignment between two or more sequences can be determined manually by visual inspection or by using a computer, such as, but not limited to e.g., the BLASTP program for amino acid sequences and the BLASTN program for nucleic acid sequences (see, e.g., Altschul et al., Nucleic Acids Res. 25(17):3389-3402 (1997); see also the National Center for Biotechnology Information (NCBI) website) or CLUSTALW program.

A polypeptide of interest may be said to be "substantially identical" to a reference polypeptide if the polypeptide of interest comprises an amino acid sequence having at least about 60%, at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, at least about 99%, or at least about 99.5% sequence identity to the amino acid sequence of the reference polypeptide. The percent identity between two such polypeptides can be determined manually by inspection of the two optimally aligned polypeptide sequences or by using software programs or algorithms (e.g., BLAST, ALIGN, CLUSTAL) using standard parameters. One indication that two polypeptides are substantially identical is that the first polypeptide is immunologically cross-reactive with the second polypeptide. Typically, polypeptides that differ by conservative amino acid substitutions are immunologically cross-reactive. Thus, a polypeptide is substantially identical to a second polypeptide, e.g., where the two peptides differ only by a conservative amino acid substitution or one or more conservative amino acid substitutions.

A nucleic acid of interest may be said to be "substantially identical" to a reference nucleic acid if the nucleic acid of interest comprises a nucleotide sequence having at least about 60%, at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, at least about 99%, or at least about 99.5% sequence identity to the nucleotide sequence of the reference nucleic acid. The percent identity between two such nucleic acids can be determined manually by inspection of the two optimally aligned nucleic acid sequences or by using software programs or algorithms (e.g., BLAST, ALIGN, CLUSTAL) using standard parameters. One indication that two nucleic acid sequences are substantially identical is that the two nucleic acid molecules hybridize to each other under stringent conditions (e.g., within a range of medium to high stringency).

As used herein, the term "mass yield" refers to the mass of the product produced by the recombinant (e.g., bacterial) cells divided by the mass of the glucose consumed by the recombinant cells multiplied by 100, or expressed as a percentage.

By "specific productivity," it is meant the mass of the product produced by the recombinant (e.g., bacterial) cell divided by the product of the time for production, the cell density, and the volume of the culture.

By "titer," it is meant the mass of the product produced by the recombinant (e.g., bacterial) cells divided by the volume of the culture.

As used herein, the term "cell productivity index (CPI)" refers to the mass of the product produced by the recombinant (e.g., bacterial) cells divided by the mass of the recombinant cells produced in the culture.

Unless defined otherwise herein, all technical and scientific terms used herein have the same meaning as commonly understood by one of ordinary skill in the art to which this invention pertains.

As used herein, the singular terms "a," "an," and "the" include the plural reference unless the context clearly indicates otherwise.

Unless otherwise indicated, nucleic acids are written left to right in 5' to 3' orientation; amino acid sequences are written left to right in amino to carboxy orientation, respectively.

Reference to "about" a value or parameter herein also includes (and describes) embodiments that are directed to that value or parameter per se.

It is understood that all aspects and embodiments of the invention described herein include "comprising," "consisting," and "consisting essentially of" aspects and embodiments. It is to be understood that methods or compositions "consisting essentially of" the recited elements include only the specified steps or materials and those that do not materially affect the basic and novel characteristics of those methods and compositions.

It is to be understood that this invention is not limited to the particular methodology, protocols, and reagents described, as these may vary, depending upon the context they are used by those of skill in the art.

It is intended that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

Isoprene Synthase Variants with Improved Kinetic Properties

Isoprene (2-methyl-1,3-butadiene) is the monomer of natural rubber and also the critical starting material for a variety of synthetic polymers, most notably synthetic rubbers. Isoprene monomer is employed in the manufacture of polyisoprene and various copolymers (with isobutylene, butadiene, styrene, or other monomers). Building a host cell strain (prokaryotic or eukaryotic) capable of producing commercially viable levels of isoprene requires optimization of the biological pathway, for example isoprene synthase and/or the DXP pathway and/or the MVA pathway. A key enzyme in the pathway is isoprene synthase (IspS), which converts the precursor DMAPP to isoprene. Isoprene synthases (IspS) that have been identified include those from plants such as poplar, English oak and kudzu vine. Some of the plant IspS enzymes identified have been partially characterized in part by expression in E. coli and some of the kinetic parameters of these enzymes have been determined in vitro with purified protein. However, the kinetic parameters ($K_m$, rate, etc.) of the native IspS enzymes are insufficient for commercial production of isoprene in a biological host. Thus, one problem to be solved is the provision of isoprene synthase variants (e.g. with substitutions at specific residues) which have improved properties (e.g., kinetic parameters) such that a greater amount of isoprene can be biologically produced.

As described in more detail herein, the inventors have solved this problem by constructing polypeptides having isoprene synthase activity that are engineered with one or more substitutions (e.g., amino acid substitutions) such that it has one or more improved properties, such as 1) kcat (2) KM (3) Ki and (4) specific productivity. Host cells can be used to express such polypeptides for production of isoprene at a level that is commercially relevant.

As indicated above, optimizing kinetic properties of interest include, but are not limited to: 1) kcat (2) KM (3) Ki and (4) specific productivity. Without wishing to be bound by theory, in one embodiment, isoprene synthase variants that display increased kcat values (e.g., greater than 1 as compared to a reference isoprene synthase, such as P. alba MEA isoprene synthase, SEQ ID NO:1) can catalyze the conversion of DMAPP to isoprene more efficiently. In another embodiment, isoprene synthase variants that display decreased KM values (e.g., lower than 1 as compared to a reference isoprene synthase, such as P. alba MEA isoprene synthase, SEQ ID NO:1) can maintain decreased concentrations of DMAPP. In another embodiment, isoprene synthase variants that display increased $K_{iDMAPP}$ values (e.g., greater than 1 as compared to a reference isoprene synthase, such as P. alba MEA isoprene synthase, SEQ ID NO:1) can catalyze the conversion of DMAPP to isoprene more efficiently. In another embodiment, isoprene synthase variants have increased specific productivity (e.g., greater than 1 as compared to a reference isoprene synthase, such as P. alba isoprene synthase). The sequence of P. alba MEA isoprene synthase is as follows:

```
                                                      (SEQ ID NO: 1)
MEARRSANYEPNSWDYDYLLSSDTDESIEVYKDKAKKLEAEVRREINNEKAEFLTLLELID

NVQRLGLGYRFESDIRGALDRFVSSGGFDAVTKTSLHGTALSFRLLRQHGFEVSQEAFSGF

KDQNGNFLENLKEDIKAILSLYEASFLALEGENILDEAKVFAISHLKELSEEKIGKELAEQVN

HALELPLHRRTQRLEAVWSIEAYRKKEDANQVLLELAILDYNMIQSVYQRDLRETSRWWR

RVGLATKLHFARDRLIESFYWAVGVAFEPQYSDCRNSVAKMFSFVTIIDDIYDVYGTLDEL

ELFTDAVERWDVNAINDLPDYMKLCFLALYNTINEIAYDNLKDKGENILPYLTKAWADLC

NAFLQEAKWLYNKSTPTFDDYFGNAWKSSSGPLQLVFAYFAVVQNIKKEEIENLQKYHDTI

SRPSHIFRLCNDLASASAEIARGETANSVSCYMRTKGISEELATESVMNLIDETWKKMNKE

KLGGSLFAKPFVETAINLARQSHCTYHNGDAHTSPDELTRKRVLSVITEPILPFER.
```

These properties and parameters can be assessed by the conversion of DMAPP to isoprene in vitro with purified or partially purified isoprene synthase or in vivo in the context of a host organism such as *E. coli* expressing the DXP pathway, the MVA pathway, or both. It is contemplated that enzymes having various degrees of stability, solubility, activity, and/or expression level in one or more of test conditions will find use in the present invention for the production of isoprene in a diversity of hosts.

The invention features compositions and methods for the production of increased amounts of isoprene. In particular, these compositions and methods may increase the rate of isoprene production and the total amount of isoprene that is produced. The biosynthetic processes for isoprene production described herein are a desirable alternative to using natural rubber. As discussed further below, the amount of isoprene produced by cells can be greatly increased by introducing a heterologous nucleic acid encoding an isoprene synthase (IspS) variant into the cells.

As exemplified in the Examples section, one of skill in the art can determine in vitro kinetic constants ($k_{cat}$, $K_M$ and $K_{iDMAPP}$) for the ability of the variant isoprene synthases to catalyze the conversion of DMAPP to isoprene by fitting data to the following rate equation:

$$\frac{rate}{[\text{Isoprene synthase}]} = \frac{kcat * [DMAPP]}{KM + [DMAPP]\left(1 + \frac{[DMAPP]}{KiDMAPP}\right)}$$

In one aspect, polypeptides having isoprene synthase activity or isoprene synthase variants with $k_{cat}$ values greater than about 1 with respect to a reference sequence (such as SEQ ID NO:1) are selected. In other aspects, isoprene synthase variants with $k_{cat}$ values greater than about 1.05, 1.1, 1.2, 1.3, 1.4, 1.5, 1.6, 1.7, 1.8, 1.9. 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6. 4.7, 4.8, 4.9, 5.0, 5.1, 5.2, 5.3, 5.4, 5.5, 5.6, 5.7, 5.8. 5.9 or 6.0 are selected. In other aspects, isoprene synthase variants with $k_{cat}$ values greater than about 6.5, 7.0, 7.5, 8.0, 8.5, 9.0, 9.5, or 10 are selected. In some embodiments, the variants have one or more amino acid substitution(s) at one or more residues corresponding to SEQ ID NO:1: X323F, X118E, X36W, X22K, X228Y, X448L, X488F, X467H, X443S, X331P, X453I, X71K, X71L, X448I, X71M, X392Y, X448V, X282H, X383Y, X323Y, X511Y, X448E, X376M, X488L, X120E, X461A, X414I, X282W, X071K, X493E, X3925, X448Q, X282Y, X537N, X447Y, X240C, X443Q, X538R, and X510C. In some embodiments, the polypeptide has improved Kcat compared to a parent polypeptide which does not comprise said one or more amino acid substitution(s). In some embodiments, the variants have one or more amino acid substitution(s) at one or more residues corresponding to SEQ ID NO:1: D323F, A118E, K36W, S22K, M228Y, A448L, E488F, E467H, A443S, C331P, A453I, R71K, R71L, A448I, R71M, W392Y, A448V, S282H, T383Y, D323Y, H511Y, A448E, L376M, E488L, S120E, R461A, K414I, S282W, R071K, S493E, W392S, A448Q, S282Y, E537N, I447Y, T240C, A443Q, P538R, and S510C.

In some embodiments, the variants have one or more amino acid substitution(s) at one or more residues corresponding to SEQ ID NO:1 selected from the group consisting of: X389D, X383H, X36E, X436Y, X447V, X392F, X161R, X99D, X99E, X161C, X414S, X537T, X393V, X443G, X510V, X36N, X392A, X161A, X254R, X472C, X161Q, X36Y, X537C, X41Y, X161M, X43L, X120A, X087M, X36S, X36H, X348Y, X467W, X288T, X447T, X025N. In some embodiments, the polypeptide has improved Kcat compared to a parent polypeptide which does not comprise said one or more amino acid substitution(s). In some embodiments, the variants have one or more amino acid substitution(s) at one or more residues corresponding to SEQ ID NO:1: G389D, T383H, K36E, L436Y, I447V, W392F, K161R, G99D, G99E, K161C, K414S, E537T, K393V, A443G, S510V, K36N, W392A, K161A, H254R, E472C, K161Q, K36Y, E537C, E41Y, K161M, R43L, S120A, G087M, K36S, K36H, K348Y, E467W, S288T, I447T, and D025N.

In some embodiments, the variants have one or more amino acid substitution(s) at one or more residues corresponding to SEQ ID NO:1 selected from the group consisting of: X268I, X488M, X480I, X240V, X460A, X071L, X36Q, X118P, X36T, X282I, X409I, X071I, X409T, X436F, X348F, X118Q, X342Y, X74Q, X41P, X437Y, X392T, X89D, X41M, X510E, X36P, X393I, X71I, X381M, X374Y, X58Y, X526Q, X543F, X240M, X111S, X463T, X120M, and X135G. In some embodiments, the polypeptide has improved Kcat compared to a parent polypeptide which does not comprise said one or more amino acid substitution(s). In some embodiments, the variants have one or more amino acid substitution(s) at one or more residues corresponding to SEQ ID NO:1: V268I, E488M, E480I, T240V, M460A, R071L, K36Q, A118P, K36T, S282I, V409I, R071I, V409T, L436F, K348F, A118Q, I342Y, S74Q, E41P, C437Y, W392T, F89D, E41M, S510E, K36P, K393I, R71I, T381M, K374Y, E58Y, L526Q, E543F, T240M, G111S, K463T, S120M, and E135G.

In another aspect, polypeptides having isoprene synthase activity or isoprene synthase variants with KM values less than about 1 with respect to a reference sequence (such as SEQ ID NO:1) are selected. In other aspects, isoprene synthase variants with KM values less than about 0.95, 0.9, 0.8., 0.7, 0.5, 0.4, 0.3, 0.2 or 0.1 are selected. In some embodiments, the variants have one or more amino acid substitution(s) at one or more residues corresponding to SEQ ID NO:1: X22K, X348F, X392V, X392F, X488C, X22R, X71V, X443R, X234R, X453V, X437Y, X392C, X463F, X538K, X393L, X254C, X436Y, X21R, X437L, X444D, X374Y, X363L, X447V, X444E, X71I, X504F, X488W, X71H, X36P, X381I, X436F, X460A, X443G, X288A, X392T, X537I, X374Y, X242G, X437M, X436I, X376I, X288Y, and X392M. In some embodiments, the polypeptide has improved $K_M$ compared to a parent polypeptide which does not comprise said one or more amino acid substitution(s). In some embodiments, the amino acid substitution is selected from the group consisting of: S22K, K348F, W392V, W392F, E488C, S22R, R71V, A443R, Q234R, A453V, C437Y, W392C, K463F, P538K, K393L, H254C, L436Y, S21R, C437L, S444D, K374Y, A363L, I447V, S444E, R71I, I504F, E488W, R71H, K36P, T381I, L436F, M460A, A443G, S288A, W392T, E537I, K374Y, R242G, C437M, L436I, L376I, S288Y, and W392M.

In some embodiments, the variants have one or more amino acid substitution(s) at one or more residues corresponding to SEQ ID NO:1: X342Y, X414W, X461A, X443S, X392A, X463T, X488T, X526Q, X502F, X502M, X488M, X36Y, X414R, X071I, X36W, X502L, X481Y, X472R, X36H, X36T, X415Y, X415H, X58Y, X381M, X481V, X89E, X480I, X36Q, X89D, X254R, X161N, X071L, X424P, X415V, X22K, X58L, X392S, X268I, X392I, X526E, X537V, and X36D. In some embodiments, the polypeptide has improved $K_M$ compared to a parent polypeptide which does not comprise said one or more amino acid substitution(s). In some embodiments, the amino acid substitution is selected from the group consisting of: I342Y, K414W, R461A, A443S, W392A, K463T, E488T, L526Q, T502F, T502M, E488M, K36Y, K414R, R071I, K36W, T502L, T481I, E472R, K36H, K36T, E415Y, E415H, E58Y, T381M, T481V, F89E, E480I, K36Q, F89D, H254R, K161N, R071L, H424P, E415V, S22K, E58L, W392S, V268I, W392I, L526E, E537V, and K36D.

In some embodiments, the variants have one or more amino acid substitution(s) at one or more residues corresponding to SEQ ID NO:1 selected from the group consisting of: X393I, X41M, X025N, X36N, X118Q, X389E, X282W, X348Y, X383L, X510V, X323Y, X323F, X383H, X41P, X288T, X36S, X453I, X447T, X472I, X376M, X161E, X488L, X381L, X071K, X409T, X392Y, X135G, X542L, X228Y, X118P, X543F, and X36E. In some embodiments, the polypeptide has improved $K_M$ compared to a parent polypeptide which does not comprise said one or more amino acid substitution(s). In some embodiments, the amino acid substitution is selected from the group consisting of: K393I, E41M, D025N, K36N, A118Q, G389E, S282W, K348Y, T383L, S510V, D323Y, D323F, T383H, E41P, S288T, K36S, A453I, I447T, E472I, L376M, K161E, E488L, T381L, R071K, V409T, W392Y, E135G, F542L, M228Y, A118P, E543F, and K36E.

In one aspect, polypeptides having isoprene synthase activity or isoprene synthase variants with $K_{iDMAPP}$ values greater than about 1 with respect to a reference sequence (such as SEQ ID NO:1) are selected. In other aspects, isoprene synthase variants with $K_{iDMAPP}$ values greater than about 1.05, 1.1, 1.2, 1.3, 1.4, 1.5, 1.6, 1.7, 1.8, 1.9. 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6. 4.7, 4.8, 4.9, 5.0, 5.1, 5.2, 5.3, 5.4, 5.5, 5.6, 5.7, 5.8. 5.9 or 6.0 are selected. In other aspects, isoprene synthase variants with $K_{iDMAPP}$ values greater than about 6.5, 7.0, 7.5, 8.0, 8.5, 9.0, 9.5, or 10 are selected. In some embodiments, the variants have one or more amino acid substitution(s) at one or more residues corresponding to SEQ ID NO:1: X472R, X389E, X242G, X376I, X161N, X288C, X240V, X481Y, X463F, and X393L. In some embodiments, the variants have improved $K_{iDMAPP}$ compared to a parent polypeptide which does not comprise said one or more amino acid substitution(s). In some embodiments, the amino acid substitution is selected from the group consisting of: E472R, G389E, R242G, L376I, K161N, S288C, T240V, T481Y, K463F, and K393L.

In another aspect of the invention, the polypeptides have isoprene synthase activity and have one or more amino acid substitution(s) at one or more residues corresponding to SEQ ID NO:1 selected from the group consisting of: X120Q, X58L, X240M, and X453V. In some embodiments, the polypeptide has improved $K_{iDMAPP}$ compared to a parent polypeptide which does not comprise said one or more amino acid substitution(s). In some embodiments, the amino acid substitution is selected from the group consisting of: S120Q, E58L, T240M, and A453V.

In another aspect of the invention, the polypeptides have isoprene synthase activity and have one or more amino acid substitution(s) at one or more residues corresponding to SEQ ID NO:1 selected from the group consisting of: X543F, X74Q, X414R, X415H, and X415V. In some embodiments, the polypeptide has improved $K_{iDMAPP}$ compared to a parent polypeptide which does not comprise said one or more amino acid substitution(s). In some embodiments, the amino acid substitution is selected from the group consisting of: E543F, S74Q, K414R, E415H, and E415V.

In another aspect, polypeptides having isoprene synthase activity or isoprene synthase variants with specific productivity greater than about 1 with respect to a reference sequence (such as SEQ ID NO:1) are selected. In other aspects, isoprene synthase variants with specific productivity greater than about 1.05, 1.1, 1.2, 1.3, 1.4, 1.5, 1.6, 1.7, 1.8, 1.9. 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6. 4.7, 4.8, 4.9, 5.0, 5.1, 5.2, 5.3, 5.4, 5.5, 5.6, 5.7, 5.8. 5.9 or 6.0 are selected. In other aspects, isoprene synthase variants with specific productivity greater than about 6.5, 7.0, 7.5, 8.0, 8.5, 9.0, 9.5, or 10 are selected. In some embodiments, the variants have one or more amino acid substitution(s) at one or more residues corresponding to SEQ ID NO:1: X510E, X161M, X120Q, X120E, X161R, X120A, X493E, X448E, X240V, X240M, and X537T. In some embodiments, the polypeptides have improved specific productivity compared to a parent polypeptide which does not comprise said one or more amino acid substitution(s). In some embodiments, the amino acid substitution is selected from the group consisting of: S510E, K161M, S120Q, S120E, K161R, S120A, S493E, A448E, T240V, T240M, and E537T.

In other aspects, polypeptides have isoprene synthase activity and have one or more amino acid substitution(s) at one or more residues corresponding to SEQ ID NO:1 selected from the group consisting of: X161N, X447Y, X502M, X537N, X348Y, X543F, X331P, X537C, X120M, X288C, and X161Q. In some embodiments, the polypeptide has improved specific productivity compared to a parent polypeptide which does not comprise said one or more amino acid substitution(s). In some embodiments, the amino acid substitution is selected from the group consisting of: K161N, I447Y, T502M, E537N, K348Y, E543F, C331P, E537C, S120M, S288C, and K161Q.

In other aspects, polypeptides have isoprene synthase activity and have one or more amino acid substitution(s) at one or more residues corresponding to SEQ ID NO:1 selected from the group consisting of: X161A, X481V, X087M, X467W, X448V, X502L, and X376M. In some embodiments, the polypeptide has improved specific productivity compared to a parent polypeptide which does not comprise said one or more amino acid substitution(s). In some embodiments, the amino acid substitution is selected from the group consisting of: K161A, T481V, G087M, E467W, A448V, T502L, and L376M.

In some aspects of the invention, polypeptides having isoprene synthase activity or the isoprene synthase variants have increased kcat or decreased KM or increased $K_{iDMAPP}$ or increased specific activity. In another aspect of the invention, the variant has any two of these four properties. In another aspect of the invention, the variant has any three of these four properties. In another aspect of the invention, the variant has all four of these properties.

The invention also contemplates methods for screening for isoprene synthase variants, comprising: (a) contacting a host cell with a medium comprising about 10 μM to about 70 μM IPTG, and about 5 mM to about 20 mM mevalonic acid (MVA), wherein the host cell comprises a nucleic acid encoding an isoprene synthase variant in operable combination with a promoter; and (b) measuring the growth rate of the host cell. The variant growth rate may be compared to that of a reference isoprene synthase (e.g. a parent isoprene synthase, a wild-type isoprene synthase, or MEA *P. alba* isoprene synthase. The methods may be used to screen for variants having a particular property of interest, for example, one or more of the properties described herein. In some embodiments, an increased growth rate indicates an isoprene synthase variant with an increased ability to convert DMAPP to isoprene within the host cell synthase. Growth rates may be analyzed, for example, according to methods known in the art, or as exemplified in the Examples below. In some embodiments, the method further comprises determining a growth index for the variant. In some embodiments, the method further comprises determining a performance index for the variant. Growth rate of the cells in exponential phase and/or final density of the cells may be taken into consideration as factors when selecting variants. As exemplified below, for the variants shown in the examples, the growth rate of the cells in exponential phase was a consideration. In addition, growth rate and final density was also taken into consideration when selecting for variants described herein.

In some embodiments, the IPTG is present in the medium at a concentration from about 10 µM to about 60 µM. In some embodiments, the IPTG is present in the medium at a concentration from about 20 µM to about 60 µM. In some embodiments, the IPTG is present in the medium at a concentration from about 40 µM to about 60 µM. In some embodiments, the IPTG is present in the medium at a concentration of about 50 µM. In some embodiments, the MVA is present in the medium at a concentration of about 5 mM to about 20 mM. In some embodiments, the MVA is present in the medium at a concentration of about 7 mM to about 15 mM. In some embodiments, the MVA is present in the medium at a concentration of about 8 mM to about 12 mM. In some embodiments, the MVA is present in the medium at a concentration of about 10 mM. In some embodiments, the host cell is MD09-170.

Isoprene Synthase Parent Sequences

Isoprene synthase variants may be generated from a parent isoprene synthase, wherein the parent isoprene synthase may be an isoprene synthase as described herein, including wild type and non-wild type isoprene synthases. Exemplary parent isoprene synthase nucleic acids include nucleic acids that encode a polypeptide, fragment of a polypeptide, peptide, or fusion polypeptide that has at least one activity of an isoprene synthase polypeptide. Exemplary parent isoprene synthase polypeptides and nucleic acids include naturally-occurring polypeptides and nucleic acids from any of the source organisms described herein as well as variant polypeptides and nucleic acids derived from any of the source organisms described herein.

In some embodiments, the parent isoprene synthase is from the family Fabaceae, the family Salicaceae, or the family Fagaceae. In some embodiments, the parent isoprene synthase polypeptide or nucleic acid is a naturally-occurring polypeptide or nucleic acid from *Pueraria montana* (kudzu) (Sharkey et al., Plant Physiology 137: 700-712, (2005)), poplar (such as *Populus alba×tremula* AC35696, Miller et al., Planta 213: 483-487, (2001)) or *Populus alba*, aspen (such as *Populus tremuloides*) Silver et al., JBC 270(22): 13010-1316, (1995)), or English Oak (*Quercus robur*) (Zimmer et al., WO 98/02550). Suitable parent isoprene synthases include, but are not limited to, those identified by GenBank Accession Nos. AY341431, AY316691, AB198180, AJ294819.1, EU693027.1, EF638224.1, AM410988.1, EF147555.1, AY279379, AJ457070, and AY182241. Additional parent sequences are described in PCT/US2009/041581 and PCT/US2010/032134.

Figure 38A:
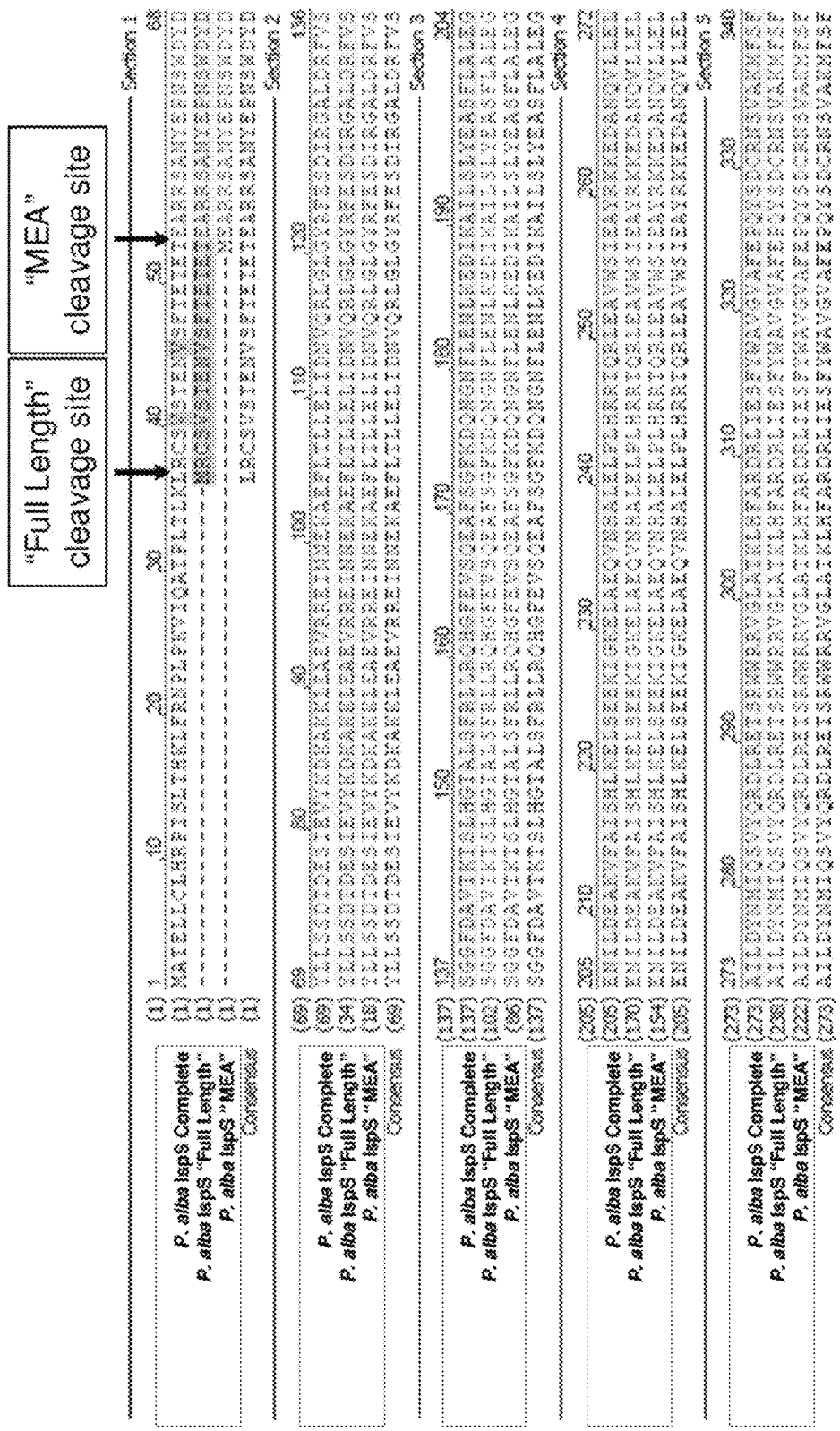
FIG. 38A-B show the alignment of N-terminally cleaved *P. alba* IspS sequences (SEQ ID NOS:31, 32, and 22 respectively).
Figure 38B:
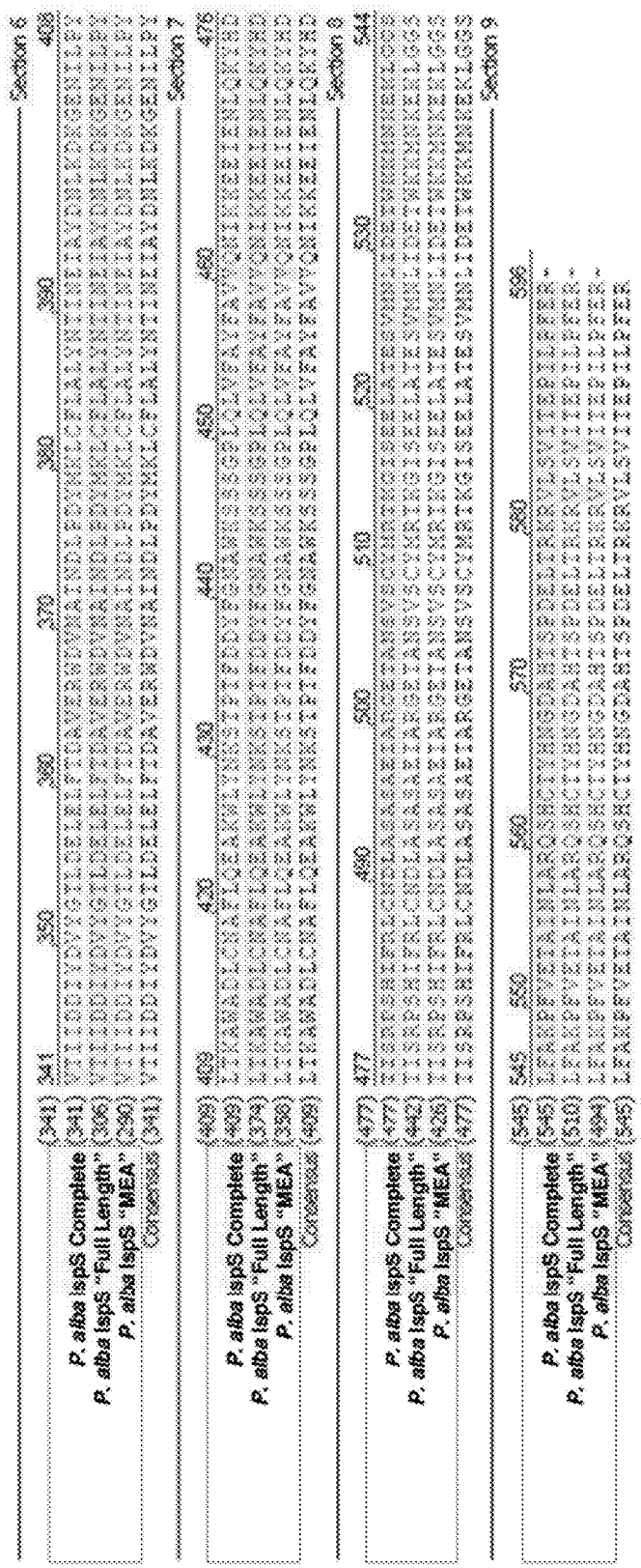

In various embodiments, the parent isoprene synthase has at least about 50%, at least about 60%, at least about 70%, at least about 80%, at least about 90%, at least about 92%, at least about 94%, at least about 96%, at least about 98%, at least about 99% sequence identity with *P. alba* MEA (SEQ ID NO:1). In other embodiments, the parent isoprene synthase has at least about 50%, at least about 60%, at least about 70%, at least about 80%, at least about 90%, at least about 92%, at least about 94%, at least about 96%, at least about 98%, at least about 99% sequence identity with full-length *P. alba* or complete *P. alba* (see, e.g., FIG. 38A-38B).

Several methods are known in the art that are suitable for generating variants of the enzymes of the present invention, including but not limited to site-saturation mutagenesis, scanning mutagenesis, insertional mutagenesis, random mutagenesis, site-directed mutagenesis, and directed-evolution, as well as various other recombinatorial approaches.

Standard methods can be used to determine whether a polypeptide has isoprene synthase polypeptide activity by measuring the ability of the polypeptide to convert DMAPP into isoprene in vitro, in a cell extract, or in vivo. Isoprene synthase polypeptide activity in the cell extract can be measured, for example, as described in Silver et al., J. Biol. Chem. 270:13010-13016, (1995). In one exemplary assay, DMAPP (Sigma) can be evaporated to dryness under a stream of nitrogen and rehydrated to a concentration of 100 mM in 100 mM potassium phosphate buffer pH 8.2 and stored at −20° C. To perform the assay, a solution of 5 µL of 1M $MgCl_2$, 1 mM (250 µg/ml) DMAPP, 65 µL of Plant Extract Buffer (PEB) (50 mM Tris-HCl, pH 8.0, 20 mM $MgCl_2$, 5% glycerol, and 2 mM DTT) can be added to 25 µL of cell extract in a 20 ml Headspace vial with a metal screw cap and teflon coated silicon septum (Agilent Technologies) and cultured at 370 C for 15 minutes with shaking. The reaction can be quenched by adding 200 µL of 250 mM EDTA and quantified by GC/MS.

In some aspects, the isoprene synthase polypeptide is a plant isoprene synthase polypeptide or a variant thereof. In some aspects, the isoprene synthase polypeptide is an isoprene synthase from *Pueraria* or a variant thereof. In some aspects, the isoprene synthase polypeptide is an isoprene synthase from *Populus* or a variant thereof. In some aspects, the isoprene synthase polypeptide is a poplar isoprene synthase polypeptide or a variant thereof. In some aspects, the isoprene synthase polypeptide is a kudzu isoprene synthase polypeptide or a variant thereof. In some aspects, the isoprene synthase polypeptide is a polypeptide from *Pueraria* or *Populus* or a hybrid, *Populus alba×Populus tremula*, or a variant thereof. In some aspects, the isoprene synthase polypeptide is a willow isoprene synthase polypeptide or a variant thereof. In some aspects, the isoprene synthase polypeptide is a eucalyptus isoprene synthase polypeptide or a variant thereof. In some aspects, the isoprene synthase polypeptide is from *Robinia*, *Salix*, or *Melaleuca* or variants thereof.

In some aspects, the isoprene synthase polypeptide or nucleic acid is from the family Fabaceae, such as the Faboideae subfamily. In some aspects, the isoprene synthase polypeptide or nucleic acid is a polypeptide or nucleic acid from *Pueraria montana* (kudzu) (Sharkey et al., Plant Physiology 137: 700-712, (2005)), *Pueraria lobata*, poplar (such as *Populus alba, Populus nigra, Populus trichocarpa*, or *Populus alba×tremula* (CAC35696) (Miller et al., Planta 213: 483-487, (2001)), aspen (such as *Populus tremuloides*) (Silver et al., JBC 270(22):13010-1316, (1995)), English Oak (*Quercus robur*) (Zimmer et al., WO 98/02550), or a variant thereof. In some aspects, the isoprene synthase polypeptide is an isoprene synthase from *Pueraria montana, Pueraria lobata, Populus tremuloides, Populus alba, Populus nigra*, or *Populus trichocarpa* or a variant thereof. In some aspects, the isoprene synthase polypeptide is an isoprene synthase from *Populus alba* or a variant thereof. In some aspects, the isoprene synthase is *Populus balsamifera* (Genbank JN173037), *Populus deltoides* (Genbank JN173039), *Populus fremontii* (Genbank JN173040), *Populus granididenta* (Genbank JN173038), Salix (Genbank JN173043), *Robinia pseudoacacia* (Genbank JN173041), Wisteria (Genbank JN173042),

*Eucalyptus globulus* (Genbank AB266390) or *Melaleuca alterniflora* (Genbank AY279379) or variant thereof. In some aspects, the nucleic acid encoding the isoprene synthase (e.g., isoprene synthase from *Populus alba* or a variant thereof) is codon optimized.

In some aspects, the isoprene synthase nucleic acid or polypeptide is a naturally-occurring polypeptide or nucleic acid (e.g., naturally-occurring polypeptide or nucleic acid from *Populus*). In some aspects, the isoprene synthase nucleic acid or polypeptide is not a wild-type or naturally-occurring polypeptide or nucleic acid. In some aspects, the isoprene synthase nucleic acid or polypeptide is a variant of a wild-type or naturally-occurring polypeptide or nucleic acid (e.g., a variant of a wild-type or naturally-occurring polypeptide or nucleic acid from *Populus*).

In some aspects, the isoprene synthase polypeptide is a variant. In some aspects, the isoprene synthase polypeptide is a variant of a wild-type or naturally occurring isoprene synthase. In some aspects, the variant has improved activity such as improved catalytic activity compared to the wild-type or naturally occurring isoprene synthase. The increase in activity (e.g., catalytic activity) can be at least about any of 10%, 20%, 30%, 40%, 50%, 60%, 70%, 80%, 90%, or 95%. In some aspects, the increase in activity such as catalytic activity is at least about any of 1 fold, 2 folds, 5 folds, 10 folds, 20 folds, 30 folds, 40 folds, 50 folds, 75 folds, or 100 folds. In some aspects, the increase in activity such as catalytic activity is about 10% to about 100 folds (e.g., about 20% to about 100 folds, about 50% to about 50 folds, about 1 fold to about 25 folds, about 2 folds to about 20 folds, or about 5 folds to about 20 folds). In some aspects, the variant has improved solubility compared to the wild-type or naturally occurring isoprene synthase. The increase in solubility can be at least about any of 10%, 20%, 30%, 40%, 50%, 60%, 70%, 80%, 90%, or 95%. The increase in solubility can be at least about any of 1 fold, 2 folds, 5 folds, 10 folds, 20 folds, 30 folds, 40 folds, 50 folds, 75 folds, or 100 folds. In some aspects, the increase in solubility is about 10% to about 100 folds (e.g., about 20% to about 100 folds, about 50% to about 50 folds, about 1 fold to about 25 folds, about 2 folds to about 20 folds, or about 5 folds to about 20 folds). In some aspects, the isoprene synthase polypeptide is a variant of naturally occurring isoprene synthase and has improved stability (such as thermo-stability) compared to the naturally occurring isoprene synthase.

In some aspects, the variant comprises a mutation in the wild-type or naturally occurring isoprene synthase. In some aspects, the variant has at least one amino acid substitution, at least one amino acid insertion, and/or at least one amino acid deletion. In some aspects, the variant has at least one amino acid substitution. In some aspects, the number of differing amino acid residues between the variant and wild-type or naturally occurring isoprene synthase can be one or more, e.g. 1, 2, 3, 4, 5, 10, 15, 20, 30, 40, 50, or more amino acid residues. Naturally occurring isoprene synthases can include any isoprene synthases from plants, for example, kudzu isoprene synthases, poplar isoprene synthases, English oak isoprene synthases, and willow isoprene synthases. In some aspects, the variant is a variant of isoprene synthase from *Populus alba*. In some aspects, the variant of isoprene synthase from *Populus alba* has at least one amino acid substitution, at least one amino acid insertion, and/or at least one amino acid deletion. In some aspects, the variant is a truncated *Populus alba* isoprene synthase. In some aspects, the nucleic acid encoding variant (e.g., variant of isoprene synthase from *Populus alba*) is codon optimized (for example, codon optimized based on host cells where the heterologous isoprene synthase is expressed).

The isoprene synthase polypeptide provided herein can be any of the isoprene synthases or isoprene synthase variants described in WO 2009/132220, WO 2010/124146, and U.S. 2010/0086978, the contents of which are expressly incorporated herein by reference in their entirety with respect to the isoprene synthases and isoprene synthase variants.

Any one of the promoters described herein (e.g., promoters described herein and identified in the Examples of the present disclosure including inducible promoters and constitutive promoters) can be used to drive expression of any of the isoprene synthases described herein.

Suitable isoprene synthases include, but are not limited to, those identified by Genbank Accession Nos. AY341431, AY316691, AY279379, AJ457070, and AY182241. Types of isoprene synthases which can be used in any one of the compositions or methods including methods of making microorganisms encoding isoprene synthase described herein are also described in International Patent Application Publication Nos. WO 2009/076676, WO 2010/003007, WO 2009/132220, WO 2010/031062, WO 2010/031068, WO 2010/031076, WO 2010/013077, WO 2010/031079, WO 2010/148150, WO 2010/124146, WO 2010/078457, and WO 2010/148256.

Nucleic Acids Encoding Isoprene Synthase Variants

The invention also provides for nucleic acids encoding any of the isoprene synthase variants described herein. In various embodiments, the nucleic acid is a recombinant nucleic acid. For instance, in some embodiments, an isoprene synthase variant nucleic acid is operably linked to another nucleic acid encoding all or a portion of another polypeptide such that the recombinant nucleic acid encodes a fusion polypeptide that includes an isoprene synthase variant and all or part of another polypeptide (e.g., a peptide that facilitates purification or detection of the fusion polypeptide, such as a His-tag). In some embodiments, part or all of a recombinant nucleic acid is chemically synthesized. In some aspects, the nucleic acid is a heterologous nucleic acid. By "heterologous nucleic acid" is meant a nucleic acid whose nucleic acid sequence is not identical to that of another nucleic acid naturally found in the same host cell.

In some embodiments, the nucleic acid includes at least or about 50, 100, 150, 200, 300, 400, 500, 600, 700, 800, or more contiguous nucleotides from a naturally-occurring isoprene synthase nucleic acid. In some aspects, the nucleic acid has one or more mutations compared to the sequence of a wild-type (i.e., a sequence occurring in nature) isoprene synthase nucleic acid. In some embodiments, the nucleic acid has one or more mutations (e.g., a silent mutation) that increase the transcription or translation of isoprene synthase nucleic acid. In some embodiments, the nucleic acid is a degenerate variant of any nucleic acid encoding an isoprene synthase polypeptide.

An isoprene synthase nucleic acid can be incorporated into a vector, such as an expression vector, using standard techniques known to one of skill in the art. Methods used to ligate the DNA construct comprising a nucleic acid of interest such as isoprene synthase, a promoter, a terminator, and other sequences and to insert them into a suitable vector are well known in the art. Additionally, vectors can be constructed using known recombination techniques (e.g., Invitrogen Life Technologies, Gateway Technology).

In some embodiments, it may be desirable to over-express isoprene synthase nucleic acids at levels far higher than currently found in naturally-occurring cells. This result may be accomplished by the selective cloning of the nucleic acids encoding those polypeptides into multicopy plasmids or placing those nucleic acids under a strong inducible or constitutive promoter. Methods for over-expressing desired polypeptides are common and well known in the art of molecular biology and examples may be found in Sambrook et al., Molecular Cloning: A Laboratory Manual, 2nd ed., Cold Spring Harbor, (2001).

In other embodiments, the nucleic acids encoding for polypeptides having isoprene synthase activity is integrated into the chromosome of the host cell using molecular biology techniques readily available to one of skill in the art.

Figure 12:
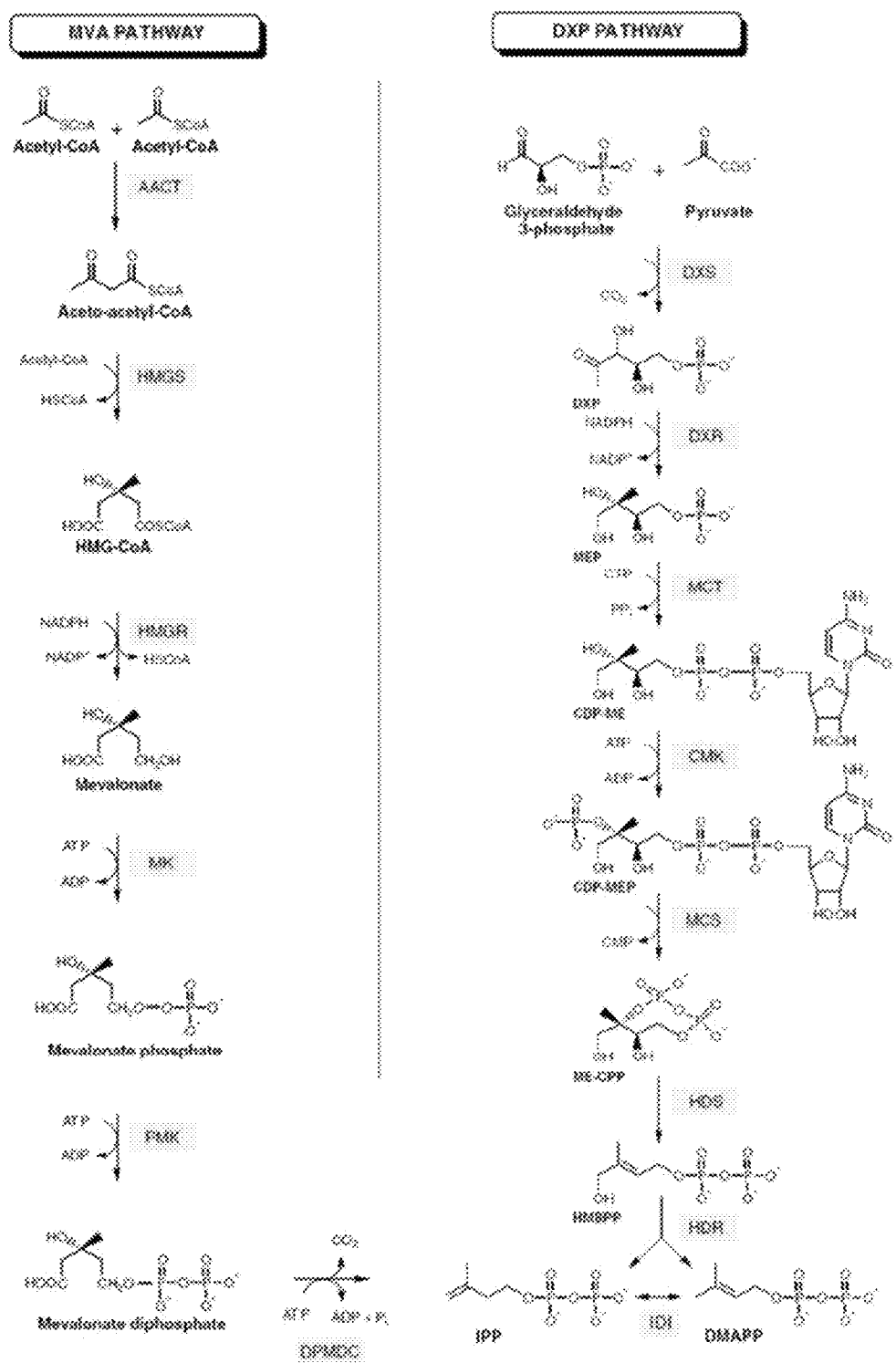
FIG. 12 shows the MVA and DXP metabolic pathways for isoprene (based on F. Bouvier et al., Progress in Lipid Res. 44: 357-429, 2005). The following description includes alternative names for each polypeptide in the pathways and a reference that discloses an assay for measuring the activity of the indicated polypeptide (each of these references are each hereby incorporated by reference in their entireties, particularly with respect to assays for polypeptide activity for polypeptides in the MVA and DXP pathways). Mevalonate Pathway: AACT; Acetyl-CoA acetyltransferase, MvaE, EC 2.3.1.9. Assay: J. Bacteriol., 184: 2116-2122, 2002; HMGS; Hydroxymethylglutaryl-CoA synthase, MvaS, EC 2.3.3.10. Assay: J. Bacteriol., 184: 4065-4070, 2002; HMGR; 3-Hydroxy-3-methylglutaryl-CoA reductase, MvaE, EC 1.1.1.34. Assay: J. Bacteriol., 184: 2116-2122, 2002; MVK; Mevalonate kinase, ERG12, EC 2.7.1.36. Assay: Curr Genet. 19:9-14, 1991. PMK; Phosphomevalonate kinase, ERG8, EC 2.7.4.2, Assay: Mol Cell Biol., 11:620-631, 1991; DPMDC; Diphosphomevalonate decarboxylase, MVD1, EC 4.1.1.33. Assay: Biochemistry, 33:13355-13362, 1994; IDI; Isopentenyl-diphosphate delta-isomerase, IDI1, EC 5.3.3.2 or isopentenyl pyrophosphate. Assay: J. Biol. Chem. 264:19169-19175, 1989. DXP Pathway: DXS; 1-Deoxyxylulose-5-phosphate synthase, dxs, EC 2.2.1.7. Assay: PNAS, 94:12857-62, 1997; DXR; 1-Deoxy-D-xylulose 5-phosphate reductoisomerase, dxr, EC 2.2.1.7. Assay: Eur. J. Biochem. 269:4446-4457, 2002; MCT; 4-Diphosphocytidyl-2C-methyl-D-erythritol synthase, IspD, EC 2.7.7.60. Assay: PNAS, 97: 6451-6456, 2000; CMK; 4-Diphosphocytidyl-2-C-methyl-D-erythritol kinase, IspE, EC 2.7.1.148. Assay: PNAS, 97:1062-1067, 2000; MCS; 2C-Methyl-D-erythritol 2,4-cyclodiphosphate synthase, IspF, EC 4.6.1.12. Assay: PNAS, 96:11758-11763, 1999; HDS; 1-Hydroxy-2-methyl-2-(E)-butenyl 4-diphosphate synthase, ispG, EC 1.17.4.3. Assay: J. Org. Chem., 70:9168-9174, 2005; HDR; 1-Hydroxy-2-methyl-2-(E)-butenyl 4-diphosphate reductase, IspH, EC 1.17.1.2. Assay: JACS, 126:12847-12855, 2004.
Figure 13:
FIG. 13 shows a monomer view of wild type IspS showing the location of sites where substitutions are not tolerated.
Figure 14:
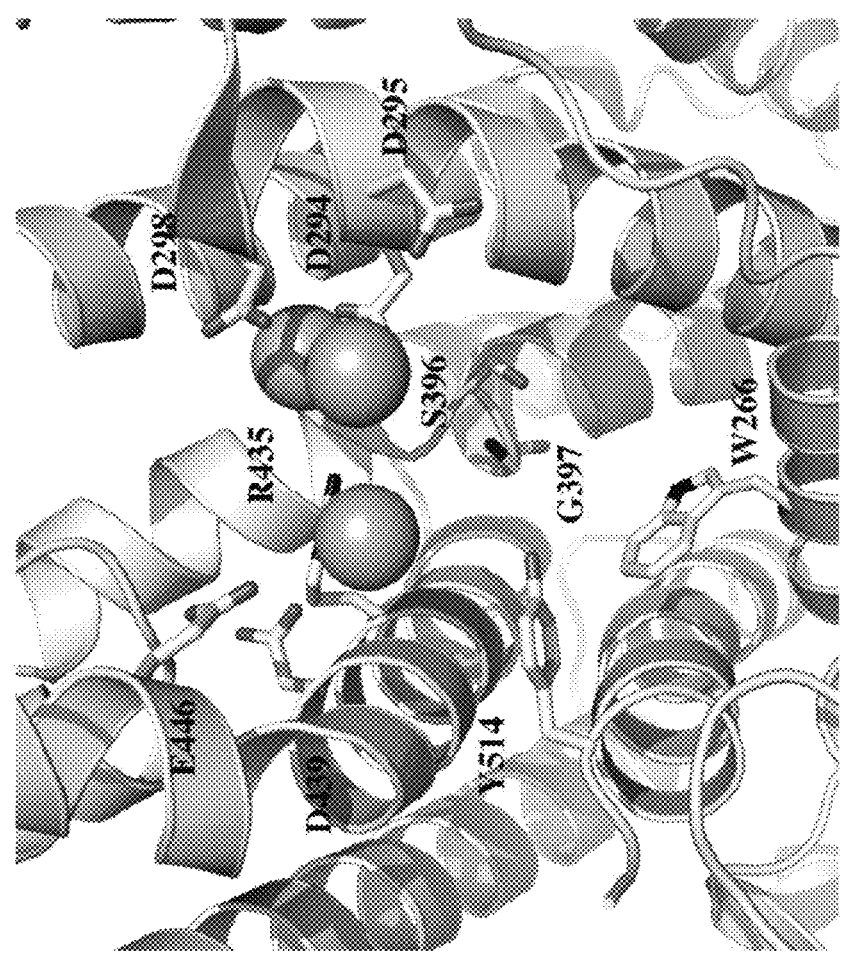
FIG. 14 shows the location of residues in the active site of IspS that do not tolerate substitution. $Mg^{2+}$ (spheres) are placed based on a structural alignment with PDB 1N24.

As is discussed in greater detail below, host cells engineered to contain isoprene synthase variants with improved kinetic properties can also be used in conjunction with one or more MVA pathway polypeptides, one or more DXP pathway polypeptides, IDI, and other components to maximize the isoprene production. Exemplary schematic of the MVA pathway and DXP pathway is shown in FIG. 12.

MVA Pathway Nucleic Acids and Polypeptides

The complete MVA pathway can be subdivided into two groups: an upper and lower pathway. In the upper portion of the MVA pathway, acetyl Co-A produced during cellular metabolism is converted to mevalonate via the actions of polypeptides having either: (a) (i) thiolase activity or (ii) acetoacetyl-CoA synthase activity, (b) HMG-CoA reductase, and (c) HMG-CoA synthase enzymatic activity. First, acetyl Co-A is converted to acetoacetyl CoA via the action of a thiolase or an acetoacetyl-CoA synthase (which utilizes acetyl-CoA and malonyl-CoA). Next, acetoacetyl-CoA is converted to 3-hydroxy-3-methylglutaryl-CoA (HMG-CoA) by the enzymatic action of HMG-CoA synthase. This Co-A derivative is reduced to mevalonate by HMG-CoA reductase. In the lower MVA pathway, mevalonate is then converted into mevalonate-5-phosphate via the action of mevalonate kinase which is subsequently transformed into 5-diphosphomevalonate by the enzymatic activity of phosphomevalonate kinase. Finally, IPP is formed from 5-diphosphomevalonate by the activity of the enzyme mevalonate-5-pyrophosphate decarboxylase. The mevalonate-dependent biosynthetic pathway is particularly important for the production of the isoprenoid precursor molecules dimethylallyl diphosphate (DMAPP) and isopentenyl pyrophosphate (IPP).

Exemplary MVA pathway polypeptides include, but are not limited to: 3-hydroxy-3-methylglutaryl-CoA synthase (HMG-CoA synthase) polypeptides (e.g., an enzyme encoded by mvaS), 3-hydroxy-3-methylglutaryl-CoA reductase (HMG-CoA reductase) polypeptides (e.g., enzyme encoded by mvaR or enzyme encoded by mvaE that has been modified to be thiolase-deficient but still retains its reductase activity), mevalonate kinase (MVK) polypeptides, phosphomevalonate kinase (PMK) polypeptides, diphosphomevalonte decarboxylase (MVD) polypeptides, phosphomevalonate decarboxylase (PMDC) polypeptides, isopentenyl phosphate kinase (IPK) polypeptides, IPP isomerase polypeptides, IDI polypeptides, and polypeptides (e.g., fusion polypeptides) having an activity of two or more MVA pathway polypeptides. In particular, MVA pathway polypeptides include polypeptides, fragments of polypeptides, peptides, and fusions polypeptides that have at least one activity of an MVA pathway polypeptide. Exemplary MVA pathway nucleic acids include nucleic acids that encode a polypeptide, fragment of a polypeptide, peptide, or fusion polypeptide that has at least one activity of an MVA pathway polypeptide. Exemplary MVA pathway polypeptides and nucleic acids include naturally-occurring polypeptides and nucleic acids from any of the source organisms described herein. In addition, variants of MVA pathway polypeptide that confer the result of better isoprene production can also be used as well.

Non-limiting examples of MVA pathway polypeptides which can be used are described in International Patent Application Publication No. WO 2009/076676; WO 2010/003007 and WO 2010/148150.

Nucleic Acids Encoding Polypeptides of the Upper MVA Pathway

The upper portion of the MVA pathway uses acetyl Co-A produced during cellular metabolism as the initial substrate for conversion to mevalonate via the actions of polypeptides having either: (a) (i) thiolase activity or (ii) acetoacetyl-CoA synthase activity, (b) HMG-CoA reductase, and (c) HMG-CoA synthase enzymatic activity. First, acetyl Co-A is converted to acetoacetyl CoA via the action of a thiolase or an acetoacetyl-CoA synthase (which utilizes acetyl-CoA and malonyl-CoA). Next, acetoacetyl-CoA is converted to 3-hydroxy-3-methylglutaryl-CoA (HMG-CoA) by the enzymatic action of HMG-CoA synthase. This Co-A derivative is reduced to mevalonate by HMG-CoA reductase, which is a rate-limiting step of the mevalonate pathway of isoprene production.

Non-limiting examples of upper MVA pathway polypeptides include: acetyl-CoA acetyltransferase (AA-CoA thiolase) polypeptides, acetoacetyl-CoA synthase polypeptides, 3-hydroxy-3-methylglutaryl-CoA synthase (HMG-CoA synthase) polypeptides, 3-hydroxy-3-methylglutaryl-CoA reductase (HMG-CoA reductase) polypeptides. Upper MVA pathway polypeptides can include polypeptides, fragments of polypeptides, peptides, and fusions polypeptides that have at least one activity of an upper MVA pathway polypeptide. Exemplary upper MVA pathway nucleic acids include nucleic acids that encode a polypeptide, fragment of a polypeptide, peptide, or fusion polypeptide that has at least one activity of an upper MVA pathway polypeptide. Exemplary MVA pathway polypeptides and nucleic acids include naturally-occurring polypeptides and nucleic acids from any of the source organisms described herein. Thus, it is contemplated herein that any gene encoding an upper MVA pathway polypeptide can be used in the present invention.

In certain embodiments, various options of mvaE and mvaS genes from *L. grayi, E. faecium, E. gallinarum, E. casseliflavus* and/or *E. faecalis* alone or in combination with one or more other mvaE and mvaS genes encoding proteins from the upper MVA pathway are contemplated within the scope of the invention. In other embodiments, an acetoacetyl-CoA synthase gene is contemplated within the scope of the present invention in combination with one or more other genes encoding: (i) 3-hydroxy-3-methylglutaryl-CoA synthase (HMG-CoA synthase) polypeptides and 3-hydroxy-3-methylglutaryl-CoA reductase (HMG-CoA reductase) polypeptides. Thus, in certain aspects, any of the combinations of genes contemplated herein can be expressed in recombinant cells in any of the ways described herein.

Additional non-limiting examples of upper MVA pathway polypeptides which can be used herein are described in International Patent Application Publication Nos. WO 2009/076676; WO 2010/003007 and WO 2010/148150.

Acetoacetyl-CoA Synthase Nucleic Acids and Polypeptides

The acetoacetyl-CoA synthase gene (aka nphT7) is a gene encoding an enzyme having the activity of synthesizing acetoacetyl-CoA from malonyl-CoA and acetyl-CoA and having minimal activity (e.g., no activity) of synthesizing acetoacetyl-CoA from two acetyl-CoA molecules. See, e.g., Okamura et al., PNAS Vol 107, No. 25, pp. 11265-11270 (2010), the contents of which are expressly incorporated herein for teaching about nphT7. An acetoacetyl-CoA synthase gene from an actinomycete of the genus *Streptomyces* L190 strain was described in JP Patent Publication (Kokai)

No. 2008-61506 A and US 2010/0285549. Acetoacetyl-CoA synthase can also be referred to as acetyl CoA:malonyl CoA acyltransferase. A representative acetoacetyl-CoA synthase (or acetyl CoA:malonyl CoA acyltransferase) that can be used is Genbank AB540131.1.

In one embodiment, acetoacetyl-CoA synthase of the present invention synthesizes acetoacetyl-CoA from malonyl-CoA and acetyl-CoA via an irreversible reaction. The use of acetoacetyl-CoA synthase to generate acetyl-CoA provides an additional advantage in that this reaction is irreversible while acetoacetyl-CoA thiolase enzyme's action of synthesizing acetoacetyl-CoA from two acetyl-CoA molecules is reversible. Consequently, the use of acetoacetyl-CoA synthase to synthesize acetoacetyl-CoA from malonyl-CoA and acetyl-CoA can result in significant improvement in productivity for isoprene compared with using thiolase to generate the end same product.

Furthermore, the use of acetoacetyl-CoA synthase to produce isoprene provides another advantage in that acetoacetyl-CoA synthase can convert malonyl CoA to acetyl CoA via decarboxylation of the malonyl CoA. Thus, stores of starting substrate are not limited by the starting amounts of acetyl CoA. The synthesis of acetoacetyl-CoA by acetoacetyl-CoA synthase can still occur when the starting substrate is only malonyl-CoA. In one embodiment, the pool of starting malonyl-CoA is increased by using host strains that have more malonyl-CoA. Such increased pools can be naturally occurring or be engineered by molecular manipulation. See, for example Fowler, et al., Applied and Environmental Microbiology, Vol. 75, No. 18, pp. 5831-5839 (2009).

In any of the aspects or embodiments described herein, an enzyme that has the ability to synthesize acetoacetyl-CoA from malonyl-CoA and acetyl-CoA can be used. Non-limiting examples of such an enzyme are described herein. In certain embodiments described herein, an acetoacetyl-CoA synthase gene derived from an actinomycete of the genus *Streptomyces* having the activity of synthesizing acetoacetyl-CoA from malonyl-CoA and acetyl-CoA can be used.

An example of such an acetoacetyl-CoA synthase gene is the gene encoding a protein having the amino acid sequence In another aspect, the acetoacetyl-CoA synthase gene encodes a protein having the amino acid sequence of:

As described herein, an acetoacetyl-CoA synthase gene for use in the present invention is not limited to a gene encoding a protein having the amino acid sequence of SEQ ID NO: 2 from an actinomycete of the *Streptomyces* sp. CL190 strain. Any gene encoding a protein having the ability to synthesize acetoacetyl-CoA from malonyl-CoA and acetyl-CoA and which does not synthesize acetoacetyl-CoA from two acetyl-CoA molecules can be used in the presently described methods. In certain embodiments, the acetoacetyl-CoA synthase gene can be a gene encoding a protein having an amino acid sequence with high similarity or substantially identical to the amino acid sequence of SEQ ID NO: 2 and having the function of synthesizing acetoacetyl-CoA from malonyl-CoA and acetyl-CoA. The expression "highly similar" or "substantially identical" refers to, for example, at least about 80% identity, at least about 85%, at least about 90%, at least about 91%, at least about 92%, at least about 93%, at least about 94%, at least about 95%, at least about 96%, at least about 97%, at least about 98%, and at least about 99% identity. As used above, the identity value corresponds to the percentage of identity between amino acid residues in a different amino acid sequence and the amino acid sequence of SEQ ID NO: 2, which is calculated by performing alignment of the amino acid sequence of SEQ ID NO: 2 and the different amino acid sequence with the use of a program for searching for a sequence similarity.

In other embodiments, the acetoacetyl-CoA synthase gene may be a gene encoding a protein having an amino acid sequence derived from the amino acid sequence of SEQ ID NO:2 by substitution, deletion, addition, or insertion of 1 or more amino acid(s) and having the function of synthesizing acetoacetyl-CoA from malonyl-CoA and acetyl-CoA. Herein, the expression "more amino acids" refers to, for example, 2 to 30 amino acids, preferably 2 to 20 amino acids, more preferably 2 to 10 amino acids, and most preferably 2 to 5 amino acids.

In still other embodiments, the acetoacetyl-CoA synthase gene may consist of a polynucleotide capable of hybridizing to a portion or the entirety of a polynucleotide having a nucleotide sequence complementary to the nucleotide sequence encoding the amino acid sequence of SEQ ID NO:2 under stringent conditions and capable of encoding a protein

```
                                                    (SEQ ID NO: 2)
MTDVRFRIIGTGAYVPERIVSNDEVGAPAGVDDDWITRKTGIRQRRWAADDQATSDLATA

AGRAALKAAGITPEQLTVIAVATSTPDRPQPPTAAYVQHHLGATGTAAFDVNAVCSGTVF

ALSSVAGTLVYRGGYALVIGADLYSRILNPADRKTVVLFGDGAGAMVLGPTSTGTGPIVRR

VALHTFGGLTDLIRVPAGGSRQPLDTDGLDAGLQYFAMDGREVRRFVTEHLPQLIKGFLHE

AGVDAADISHFVPHQANGVMLDEVFGELHLPRATMHRTVETYGNTGAASIPITMDAAVRA

GSFRPGELVLLAGFGGGMAASFALIEW.
```

Such a protein having the amino acid sequence of SEQ ID NO: 2 corresponds to an acetoacetyl-CoA synthase having activity of synthesizing acetoacetyl-CoA from malonyl-CoA and acetyl-CoA and having no activity of synthesizing acetoacetyl-CoA from two acetyl-CoA molecules.

In one embodiment, the gene encoding a protein having the amino acid sequence of SEQ ID NO: 2 can be obtained by a nucleic acid amplification method (e.g., PCR) with the use of genomic DNA obtained from an actinomycete of the *Streptomyces* sp. CL190 strain as a template and a pair of primers that can be designed with reference to JP Patent Publication (Kokai) No. 2008-61506A.

having the function of synthesizing acetoacetyl-CoA from malonyl-CoA and acetyl-CoA. Herein, hybridization under stringent conditions corresponds to maintenance of binding under conditions of washing at 60° C. 2×SSC. Hybridization can be carried out by conventionally known methods such as the method described in Sambrook, J. et al. Molecular Cloning, A Laboratory Manual, 3rd Ed., Cold Spring Harbor Laboratory (2001).

As described herein, a gene encoding an acetoacetyl-CoA synthase having an amino acid sequence that differs from the amino acid sequence of SEQ ID NO:2 can be isolated from potentially any organism, for example, an actinomycete that is not obtained from the *Streptomyces* sp. CL190 strain. In addition, acetoacetyl-CoA synthase genes for use herein can be obtained by modifying a polynucleotide encoding the amino acid sequence of SEQ ID NO: 2 by a method known in the art. Mutagenesis of a nucleotide sequence can be carried out by a known method such as the Kunkel method or the gapped duplex method or by a method similar to either thereof. For instance, mutagenesis may be carried out with the use of a mutagenesis kit (e.g., product names; Mutant-K and Mutant-G (TAKARA Bio)) for site-specific mutagenesis, product name; an LA PCR in vitro Mutagenesis series kit (TAKARA Bio), and the like.

The activity of an acetoacetyl-CoA synthase having an amino acid sequence that differs from the amino acid sequence of SEQ ID NO:2 can be evaluated as described below. Specifically, a gene encoding a protein or polypeptide to be evaluated is first introduced into a host cell such that the gene can be expressed therein, followed by purification of the protein by a technique such as chromatography. Malonyl-CoA and acetyl-CoA are added as substrates to a buffer containing the obtained protein to be evaluated, followed by, for example, incubation at a desired temperature (e.g., 10° C. to 60° C.). After the completion of reaction, the amount of substrate lost and/or the amount of product (acetoacetyl-CoA) produced are determined. Thus, it is possible to evaluate whether or not the protein being tested has the function of synthesizing acetoacetyl-CoA from malonyl-CoA and acetyl-CoA and to evaluate the degree of synthesis. In such case, it is possible to examine whether or not the protein has the activity of synthesizing acetoacetyl-CoA from two acetyl-CoA molecules by adding acetyl-CoA alone as a substrate to a buffer containing the obtained protein to be evaluated and determining the amount of substrate lost and/or the amount of product produced in a similar manner.

Genes Encoding mvaE and mvaS Polypeptides

In certain embodiments, various options of mvaE and mvaS genes from *L. grayi, E. faecium, E. gallinarum, E. casseliflavus* and/or *E. faecalis* alone or in combination with one or more other mvaE and mvaS genes encoding proteins from the upper MVA pathway are contemplated within the scope of the invention. In some embodiments, the mvaE gene in *L. grayi, E. faecium, E. gallinarum, E. casseliflavus*, and *E. faecalis* encodes a polypeptide that possesses both thiolase and HMG-CoA reductase activities (Hedl, et al., J. Bacteriol. 184(8):2116-2122 (April 2002)). In fact, the mvaE gene product represented the first bifunctional enzyme of IPP biosynthesis found in eubacteria and the first example of HMG-CoA reductase fused to another protein in nature. The mvaS gene, on the other hand, can encode a polypeptide having an HMG-CoA synthase activity.

Accordingly, recombinant cells (e.g., *E. coli*) can be engineered to express one or more mvaE and mvaS genes from *L. grayi, E. faecium, E. gallinarum, E. casseliflavus* and/or *E. faecalis* to produce isoprene. The one or more mvaE and mvaS genes can be expressed on a multicopy plasmid. The plasmid can be a high copy plasmid, a low copy plasmid, or a medium copy plasmid. Alternatively, the one or more mvaE and mvaS genes can be integrated into the host cell's chromosome. For both heterologous expression of the one or more mvaE and mvaS genes on a plasmid or as an integrated part of the host cell's chromosome, expression of the genes can be driven by either an inducible promoter or a constitutively expressing promoter. The promoter can be a strong driver of expression, it can be a weak driver of expression, or it can be a medium driver of expression of the one or more mvaE and mvaS genes.

Exemplary mvaE Polypeptides and Nucleic Acids

The mvaE gene encodes a polypeptide that possesses both thiolase and HMG-CoA reductase activities. The thiolase activity of the polypeptide encoded by the mvaE gene converts acetyl Co-A to acetoacetyl CoA whereas the HMG-CoA reductase enzymatic activity of the polypeptide converts 3-hydroxy-3-methylglutaryl-CoA to mevalonate. Exemplary mvaE polypeptides and nucleic acids include naturally-occurring polypeptides and nucleic acids from any of the source organisms described herein as well as mutant polypeptides and nucleic acids derived from any of the source organisms described herein that have at least one activity of a mvaE polypeptide.

Mutant mvaE polypeptides include those in which one or more amino acid residues have undergone an amino acid substitution while retaining mvaE polypeptide activity (i.e., the ability to convert acetyl Co-A to acetoacetyl CoA as well as the ability to convert 3-hydroxy-3-methylglutaryl-CoA to mevalonate). The amino acid substitutions can be conservative or non-conservative and such substituted amino acid residues can or cannot be one encoded by the genetic code. The standard twenty amino acid "alphabet" has been divided into chemical families based on similarity of their side chains. Those families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). A "conservative amino acid substitution" is one in which the amino acid residue is replaced with an amino acid residue having a chemically similar side chain (i.e., replacing an amino acid having a basic side chain with another amino acid having a basic side chain). A "non-conservative amino acid substitution" is one in which the amino acid residue is replaced with an amino acid residue having a chemically different side chain (i.e., replacing an amino acid having a basic side chain with another amino acid having an aromatic side chain).

Amino acid substitutions in the mvaE polypeptide can be introduced to improve the functionality of the molecule. For example, amino acid substitutions that increase the binding affinity of the mvaE polypeptide for its substrate, or that improve its ability to convert acetyl Co-A to acetoacetyl CoA and/or the ability to convert 3-hydroxy-3-methylglutaryl-CoA to mevalonate can be introduced into the mvaE polypeptide. In some aspects, the mutant mvaE polypeptides contain one or more conservative amino acid substitutions.

In one aspect, mvaE proteins that are not degraded or less prone to degradation can be used for the production of isoprene. Examples of gene products of mvaEs that are not degraded or less prone to degradation which can be used include, but are not limited to, those from the organisms *E. faecium, E. gallinarum, E. casseliflavus, E. faecalis*, and *L. grayi*. One of skill in the art can express mvaE protein in *E. coli* BL21 (DE3) and look for absence of fragments by any standard molecular biology techniques. For example, absence of fragments can be identified on Safestain stained SDS-PAGE gels following His-tag mediated purification or when expressed in isoprene-producing *E. coli* BL21 using the methods of detection described herein.

Standard methods, such as those described in Hedl et al. J. Bacteriol. 184(8): 2116-2122 (April 2002)) can be used to determine whether a polypeptide has mvaE activity, by measuring acetoacetyl-CoA thiolase as well as HMG-CoA reductase activity. In an exemplary assay, acetoacetyl-CoA thiolase activity is measured by spectrophotometer to monitor the change in absorbance at 302 nm that accompanies the formation or thiolysis of acetoacetyl-CoA. Standard assay conditions for each reaction to determine synthesis of acetoacetyl-CoA, are 1 mM acetyl-CoA, 10 mM $MgCl_2$, 50 mM Tris, pH 10.5 and the reaction is initiated by addition of enzyme. Assays can employ a final volume of 200 µl. For the assay, 1 enzyme unit (eu) represents the synthesis or thiolysis in 1 min of 1 µmol of acetoacetyl-CoA. In another exemplary assay, of HMG-CoA reductase activity can be monitored by spectrophotometer by the appearance or disappearance of NADP(H) at 340 nm. Standard assay conditions for each reaction measured to show reductive deacylation of HMG-CoA to mevalonate are 0.4 mM NADPH, 1.0 mM (R,S)-HMG-CoA, 100 mM KCl, and 100 mM $K_xPO_4$, pH 6.5. Assays employ a final volume of 200 µl. Reactions are initiated by adding the enzyme. For the assay, 1 eu represents the turnover, in 1 min, of 1 µmol of NADP(H). This corresponds to the turnover of 0.5 µmol of HMG-CoA or mevalonate.

Exemplary mvaE nucleic acids include nucleic acids that encode a polypeptide, fragment of a polypeptide, peptide, or fusion polypeptide that has at least one activity of a mvaE polypeptide. Exemplary mvaE polypeptides and nucleic acids include naturally-occurring polypeptides and nucleic acids from any of the source organisms described herein as well as mutant polypeptides and nucleic acids derived from any of the source organisms described herein. Exemplary mvaE nucleic acids include, for example, mvaE nucleic acids isolated from *Listeria grayi*_DSM 20601, *Enterococcus faecium*, *Enterococcus gallinarum* EG2, *Enterococcus faecalis*, and/or *Enterococcus casseliflavus*. The mvaE nucleic acid encoded by the *Listeria grayi*_DSM 20601 mvaE gene can have at least about 99%, 98%, 97%, 96%, 95%, 95%, 93%, 92%, 91%, 90%, 89%, 88%, 87%, 86%, or 85% sequence identity to SEQ ID NO:7. The mvaE nucleic acid encoded by the *Enterococcus faecium* mvaE gene can have at least about 99%, 98%, 97%, 96%, 95%, 95%, 93%, 92%, 91%, 90%, 89%, 88%, 87%, 86%, or 85% sequence identity to SEQ ID NO:8. The mvaE nucleic acid encoded by the *Enterococcus gallinarum* EG2 mvaE gene can have at least about 99%, 98%, 97%, 96%, 95%, 95%, 93%, 92%, 91%, 90%, 89%, 88%, 87%, 86%, or 85% sequence identity to SEQ ID NO:9. The mvaE nucleic acid encoded by the *Enterococcus casseliflavus* mvaE gene can have at least about 99%, 98%, 97%, 96%, 95%, 95%, 93%, 92%, 91%, 90%, 89%, 88%, 87%, 86%, or 85% sequence identity to SEQ ID NO:10. The mvaE nucleic acid encoded by the *Enterococcus faecalis* mvaE gene can have at least about 99%, 98%, 97%, 96%, 95%, 95%, 93%, 92%, 91%, 90%, 89%, 88%, 87%, 86%, or 85% sequence identity to the mvaE gene previously disclosed in *E. coli* to produce mevalonate (see US 2005/0287655 A1; Tabata, K. and Hashimoto, S.-I. Biotechnology Letters 26:1487-1491, (2004)). The mvaE nucleic acid can be expressed in a recombinant cell on a multicopy plasmid. The plasmid can be a high copy plasmid, a low copy plasmid, or a medium copy plasmid. Alternatively, the mvaE nucleic acid can be integrated into the host cell's chromosome. For both heterologous expression of an mvaE nucleic acid on a plasmid or as an integrated part of the host cell's chromosome, expression of the nucleic acid can be driven by either an inducible promoter or a constitutively expressing promoter. The promoter can be a strong driver of expression, it can be a weak driver of expression, or it can be a medium driver of expression of the mvaE nucleic acid.

```
Sequence of Listeria grayi DSM 20601 mvaE
                                                                                                  (SEQ ID NO: 7)
atggttaaagacattgtaataattgatgccctccgtactcccatcggtaagtaccgcggtcagctctcaaagatgacggcggtggaattgggaacc gcagttacaaaggctctgttcgagaagaacgaccaggtcaaagaccatgtagaacaagtcattttttggcaacgttttacaggcagggaacggcc agaatcccgcccgtcagatcgcccttaattctggcctgtccgcagagataccggcttcgactattaaccaggtgtgtggttctggcctgaaagcaa taagcatggcgcgccaacagatcctactcggagaagcggaagtaatagtagcaggaggtatcgaatccatgacgaatgcgccgagtattacat attataataaagaagaagacaccctctcaaagcctgttcctacgatgaccttcgatggtctgaccgacgcgtttagcggaaagattatgggtttaac agccgaaaatgttgccgaacagtacggcgtatcacgtgaggcccaggacgcctttgcgtatggatcgcagatgaaagcagcaaaggcccaag aacagggcattttcgcagctgaaatactgcctcttgaaataggggacgaagttattactcaggacgagggggttcgtcaagagaccaccctcga aaaattaagtctgcttcggaccatttttaaagaagatggtactgttacagcgggcaacgcctcaacgatcaatgatggcgcctcagccgtgatcatt gcatcaaaggagtttgctgagacaaaccagattccctaccttgcgatcgtacatgatattacagagataggcattgatccatcaataatgggcattg ctcccgtgagtgcgatcaataaactgatcgatcgtaaccaaattagcatggaagaaatcgatctctttgaaattaatgaggcatttgcagcatcctc ggtggtagttcaaaaagagttaagcattcccgatgaaaagatcaatattggcggttccggtattgcactaggccatcctcttggcgcacaggagc gcgcattgtaaccaccctagcgcaccagttgaaacgtacacacgacgctatggtattgcctccctgtgcattggcggtggccttggcctagcaa tattaatagaagtgcctcaggaagatcagccggttaaaaaatttttatcaattggcccgtgaggaccgtctggctagacttcaggagcaagccgtga tcagcccagctacaaaacatgtactggcagaaatgacacttcctgaagatattgccgacaatctgatcgaaaatcaaatatctgaaatggaaatcc ctcttggtgtggctttgaatctgagggtcaatgataagagttataccatcccactagcaactgaggaaccgagtgtaatcgctgcctgtaataatggt gcaaaaatggcaaaccacctgggcggttttcagtcagaattaaaagatggtttcctgcgtgggcaaattgtacttatgaacgtcaaagaacccgca actatcgagcatacgatcacggcagagaaagcggcaattttcgtgccgcagcgcagtcacatccatcgattgtgaaacgaggtgggggtctaa aagagatagtagtgcgtacgttcgatgatgatccgacgttcctgtctattgatctgatagttgatactaaagacgcaatgggcgctaacatcattaac accattctcgagggtgtagccggctttctgagggaaatccttaccgaagaaattctgttctctattttatctaattacgcaaccgaatcaattgtgacc
```

```
gccagctgtcgcataccttacgaagcactgagtaaaaaggtgatggtaaacgaatcgctgaaaaagtggctgctgcatctaaatttgcccagtta
gatccttatcgagctgcaacccacaacaaaggtattatgaatggtattgaggccgtcgttttggcctcaggaaatgacacacgggcggtcgcggc
agccgcacatgcgtatgcttcacgcgatcagcactatcggggcttaagccagtggcaggttgcagaaggcgcgttacacggggagatcagtct
accacttgcactcggcagcgttggcggtgcaattgaggtcttgcctaaagcgaaggcggcattcgaaatcatggggatcacagaggcgaagga
gctggcagaagtcacagctgcggtagggctggcgcaaaacctggcggcgttaagagcgcttgttagtgaaggaatacagcaaggtcacatgtc
gctccaggctcgctctcttgcattatcggtaggtgctacaggcaaggaagttgaaatcctggccgaaaaattacagggctctcgtatgaatcaggc
gaacgctcagaccatactcgcagagatcagatcgcaaaaagttgaattgtga
```

Sequence of *Enterococcus faecium* mvaE (SEQ ID NO: 8)

```
atgaccatgaacgttggaatcgataaaatgtcattctttgttccaccttactttgtggacatgactgatctggcagtagcacgggatgtcgatcccaat
aagtttctgattggtattggccaggaccagatggcagttaatccgaaaacgcaggatattgtgacatttgccacaaatgctgccaaaaacatactgt
cagctgaggaccttgataaaattgatatggtcatagtcggcaccgagagtggaatcgatgaatccaaagcgagtgccgtagtgcttcacaggttg
ctcggtatccagaagtttgctcgctcctttgaaatcaaagaagcctgttatgggggtaccgcggctttacagttcgctgtaaaccacattaggaatc
atcctgaatcaaaggttcttgtagttgcatcagatatcgcgaaatacggcctggcttctggaggtgaaccaacgcaaggtgcaggcgctgtggct
atgctcgtctcaactgaccctaagatcattgctttcaacgacgatagcctcgcgcttacacaagatatctatgacttctggcgaccagttggacatga
ctatcctatggtcgacgggcctcttagtacagagacctacatccagtcatttcagaccgtatggcaggaatacacaaaacggtcgcagcatgcac
tggcagactttgctgcccttagcttctatccgtatctaaaatgggcaaaaggcgctgcttgcaatcttgaaggcgaatcagaggaggctc
agaaccgtatactagcaaaatatgaaaagagtatagcctactccagaaaggcgggtaacctgtataccggtagcctgtatctaggacttatttcact
tctggaaaatgcagaagaccttaaagctggtgatttaataggcctctttttcttacggttccggtgctgttgcggagtttttctcaggaaggctggttga
ggactatcaggaacagctacttaaaacaaaacatgccgaacagctggcccatagaaagcaactgacaatcgaggagtacgaaacgatgttctc
cgatcgcttggacgtggacaaagacgccgaatacgaagacacattagcttatagcatttcgtcagtccgaaacaccgtacgtgagtacaggagtt
ga
```

Sequence of *Enterococcus gallinarum* EG2 mvaE (SEQ ID NO: 9)

```
atgaaagaagtggttatgattgatgcggctcgcacacccattgggaaatacagaggtagtcttagtccttttacagcggtggagctggggacact
ggtcacgaaagggctgctggataaaacaaagcttaagaaagacaagatagaccaagtgatattcggcaatgtgcttcaggcaggaaacggaca
aaacgttgcaagacaaatagccctgaacagtggcttaccagttgacgtgccggcgatgactattaacgaagtttgcgggtccggaatgaaagcg
gtgattttagcccgccagttaatacagttaggggaggcagagttggtcattgcaggggtacggagtcaatgtcacaagcacccatgctgaaac
cttaccagtcagagaccaacgaatacggagagccgatatcatcaatggttaatgacgggctgacggatgcgttttccaatgctcacatgggtctta
ctgccgaaaaggtggcgacccagttttcagtgtcgcgcgaggaacaagaccggtacgcattgtccagccaattgaaagcagcgcacgcggttg
aagcggggtgttctcagaagagattattccggttaagattagcgacgaggatgtcttgagtgaagacgaggcagtaagaggcaacagcacttt
ggaaaaactgggcaccttgcggacggtgttttctgaagagggcacggttaccgctggcaatgcttcaccgctgaatgacggcgctagtgtcgtg
attcttgcatcaaaagaatacgcgaaaacaataatctgccttacctggcgacgataaaggaggttgcggaagttggtatcgatccttctatcatgg
gtattgccccaataaaggccattcaaaagttaacagatcggtcgggcatgaacctgtccacgattgatctgttcgaaattaatgaagcattcgcgg
catctagcattgttgtttctcaagagctgcaattggacgaagaaaaagtgaatatctatggcggggcgatagctttaggccatcaatcggcgcaa
gcggagcccggatactgacaaccttagcatacggcctcctgcgtgagcaaaagcgttatggtattgcgtcattatgtatcggcggtggtcttggtc
tggccgtgctgttagaagctaatatggagcagacccacaaagacgttcagaagaaaaagttttaccagcttaccccctccgagcggagatcgca
gcttatcgagaagaacgttctgactcaagaaacggcacttattttccaggagcagacgttgtccgaagaactgtccgatcacatgattgagaatca
ggtctccgaagtggaaattccaatgggaattgcacaaaattttcagattaatggcaagaaaaatggattcctatgcgactgaagaaccttcagt
aatagcggcagcatcgaacggcgccaaaatctgcgggaacatttgcgcggaaacgcctcagcggcttatgcgcgggcagattgtcctgtctgg
caaatcagaatatcaagccgtgataaatgccgtgaatcatcgcaaagaagaactgattcttttgcgcaaacgagtcgtacccgagtattgttaaacg
cgggggaggtgttcaggatatttctacgcgggagtttatgggttcttttcacgcgtatttatcaatcgactttctggtggacgtcaaggacgcaatgg
```

-continued

```
gggcaaacatgatcaactctattctcgaaagcgttgcaaataaactgcgtgaatggttcccggaagaggaaatactgttctccatcctgtcaaactt cgctacggagtccctggcatctgcatgttgcgagattccttttgaaagacttggtcgtaacaaagaaattggtgaacagatcgccaagaaaattca acaggcaggggaatatgctaagcttgacccttaccgcgcggcaacccataacaaggggattatgaacggtatcgaagccgtcgttgccgcaac gggaaacgacacacgggctgtttccgcttctattcacgcatacgccgcccgtaatggcttgtaccaaggtttaacggattggcagatcaagggcg ataaactggttggtaaattaacagtcccactggctgtggcgactgtcggtggcgcgtcgaacatattaccaaaagccaaagcttccctcgccatgc tggatattgattccgcaaaagaactggcccaagtgatcgccgcggtaggtttagcacagaatctggcggcgttacgtgcattagtgacagaagg cattcagaaaggacacatgggcttgcaagcacgttctttagcgatttcgataggtgccatcggtgaggagatagagcaagtcgcgaaaaaactg cgtgaagctgaaaaaatgaatcagcaaacggcaatacagattttagaaaaaattcgcgagaaatga
```

Sequence of *Enterococcus casseliflavus* mvaE (SEQ ID NO: 10)
```
atgaaaatcggtattgaccgtctgtccttcttcatcccgaatttgtatttggacatgactgagctggcagaatcacgcggggatgatccagctaaata tcatattggaatcggacaagatcagatggcagtgaatcgcgcaaacgaggacatcataacactgggtgcaaacgctgcgagtaagatcgtgac agagaaagaccgcgagttgattgatatggtaatcgttggcacggaatcaggaattgaccactccaaagcaagcgccgtgattattcaccatctcct taaaattcagtcgttcgcccgttctttcgaggtaaaagaagcttgctatggcggaactgctgccctgcacatggcgaaggagtatgtcaaaaatcat ccggagcgtaaggtcttggtaattgcgtcagacatcgcgcgttatggtttggccagcggaggagaagttactcaaggcgtgggggccgtagcc atgatgattacacaaaaccccggattctttcgattgaagacgatagtgttttctcacagaggatatctatgatttctggcggcctgattactccgagt tccctgtagtggacgggccctttcaaactcaacgtatatagagagttttcagaaagtttggaaccggcacaaggaattgtccggaagagggctg gaagattatcaagctattgcttttcacatacctatacgaagatgggtaagaaagcgctccagagtgttttagaccaaaccgatgaagataaccag gagcgcttaatggctagatatgaggagtctattcgctatagccggagaattggtaacctgtacacaggcagcttgtaccttggtcttacaagcttgtt ggaaaactctaaaagtttacaaccgggagatcggatcggcctcttttcctatggcagtggtgcggtgtccgagttctttaccgggtatttagaagaa aattaccaagagtacctgttcgctcaaagccatcaagaaatgctggatagccggactcggattacggtcgatgaatacgagaccatcttttcagag actctgccagaacatggtgaatgcgccgaatacgagcgacgtccccttttctataaccaagattgagaacgacattcgttattataaaatctga
```

Exemplary mvaS Polypeptides and Nucleic Acids

The mvaS gene encodes a polypeptide that possesses HMG-CoA synthase activity. This polypeptide can convert acetoacetyl CoA to 3-hydroxy-3-methylglutaryl-CoA (HMG-CoA). Exemplary mvaS polypeptides and nucleic acids include naturally-occurring polypeptides and nucleic acids from any of the source organisms described herein as well as mutant polypeptides and nucleic acids derived from any of the source organisms described herein that have at least one activity of a mvaS polypeptide.

Mutant mvaS polypeptides include those in which one or more amino acid residues have undergone an amino acid substitution while retaining mvaS polypeptide activity (i.e., the ability to convert acetoacetyl CoA to 3-hydroxy-3-methylglutaryl-CoA). Amino acid substitutions in the mvaS polypeptide can be introduced to improve the functionality of the molecule. For example, amino acid substitutions that increase the binding affinity of the mvaS polypeptide for its substrate, or that improve its ability to convert acetoacetyl CoA to 3-hydroxy-3-methylglutaryl-CoA can be introduced into the mvaS polypeptide. In some aspects, the mutant mvaS polypeptides contain one or more conservative amino acid substitutions.

Standard methods, such as those described in Quant et al. (Biochem J., 262:159-164 (1989)), can be used to determine whether a polypeptide has mvaS activity, by measuring HMG-CoA synthase activity. In an exemplary assay, HMG-CoA synthase activity can be assayed by spectrophotometrically measuring the disappearance of the enol form of acetoacetyl-CoA by monitoring the change of absorbance at 303 nm. A standard 1 ml assay system containing 50 mm-Tris/HCl, pH 8.0, 10 mM-MgCl2 and 0.2 mM-dithiothreitol at 30° C.; 5 mM-acetyl phosphate, 10 µM-acetoacetyl-CoA and 5 µl samples of extracts can be added, followed by simultaneous addition of acetyl-CoA (100 µM) and 10 units of PTA. HMG-CoA synthase activity is then measured as the difference in the rate before and after acetyl-CoA addition. The absorption coefficient of acetoacetyl-CoA under the conditions used (pH 8.0, 10 mM-MgCl$_2$), is $12.2 \times 10^3$ $M^{-1}$ $cm^{-1}$. By definition, 1 unit of enzyme activity causes 1 µmol of acetoacetyl-CoA to be transformed per minute.

Alternatively, production of mevalonate in recombinant cells can be measured by, without limitation, gas chromatography (see U.S. Patent Application Publication No.: US 2005/0287655 A1) or HPLC (See U.S. Patent Application Publication No.: 2011/0159557 A1). As an exemplary assay, cultures can be inoculated in shake tubes containing LB broth supplemented with one or more antibiotics and incubated for 14 h at 34° C. at 250 rpm. Next, cultures can be diluted into well plates containing TM3 media supplemented with 1% Glucose, 0.1% yeast extract, and 200 µM IPTG to final OD of 0.2. The plate are then sealed with a Breath Easier membrane (Diversified Biotech) and incubated at 34° C. in a shaker/incubator at 600 rpm for 24 hours. 1 mL of each culture is then centrifuged at 3,000×g for 5 min. Supernatant is then added to 20% sulfuric acid and incubated on ice for 5 min. The mixture is then centrifuged for 5 min at 3000×g and the supernatant was collected for HPLC analysis. The concentration of mevalonate in samples is determined by comparison to a standard curve of mevalonate (Sigma). The glucose concentration can additionally be measured by performing a glucose oxidase assay according to any method known in the art. Using HPLC, levels of mevalonate can be quantified by comparing the refractive index response of each sample versus a calibration curve generated by running various mevonate containing solutions of known concentration.

Exemplary mvaS nucleic acids include nucleic acids that encode a polypeptide, fragment of a polypeptide, peptide, or fusion polypeptide that has at least one activity of a mvaS polypeptide. Exemplary mvaS polypeptides and nucleic acids include naturally-occurring polypeptides and nucleic acids from any of the source organisms described herein as well as mutant polypeptides and nucleic acids derived from any of the source organisms described herein. Exemplary mvaS nucleic acids include, for example, mvaS nucleic acids isolated from *Listeria grayi*_DSM 20601, *Enterococcus faecium*, *Enterococcus gallinarum* EG2, *Enterococcus faecalis*, and/or *Enterococcus casseliflavus*. The mvaS nucleic acid encoded by the *Listeria grayi*_DSM20601 mvaS gene can have at least about 99%, 98%, 97%, 96%, 95%, 95%, 93%, 92%, 91%, 90%, 89%, 88%, 87%, 86%, or 85% sequence identity to SEQ ID NO:11. The mvaS nucleic acid encoded by the *Enterococcus faecium* mvaS gene can have at least about 99%, 98%, 97%, 96%, 95%, 95%, 93%, 92%, 91%, 90%, 89%, 88%, 87%, 86%, or 85% sequence identity to SEQ ID NO:12. The mvaS nucleic acid encoded by the *Enterococcus gallinarum* EG2 mvaS gene can have at least about 99%, 98%, 97%, 96%, 95%, 95%, 93%, 92%, 91%, 90%, 89%, 88%, 87%, 86%, or 85% sequence identity to SEQ ID NO:13. The mvaS nucleic acid encoded by the *Enterococcus casseliflavus* mvaS gene can have at least about 99%, 98%, 97%, 96%, 95%, 95%, 93%, 92%, 91%, 90%, 89%, 88%, 87%, 86%, or 85% sequence identity to SEQ ID NO:14. The mvaS nucleic acid encoded by the *Enterococcus faecalis* mvaS gene can have at least about 99%, 98%, 97%, 96%, 95%, 95%, 93%, 92%, 91%, 90%, 89%, 88%, 87%, 86%, or 85% sequence identity to the mvaE gene previously disclosed in *E. coli* to produce mevalonate (see US 2005/0287655 A1; Tabata, K. and Hashimoto, S.-I. Biotechnology Letters 26: 1487-1491, (2004)).

```
Sequence of Listeria grayi DSM 20601 mvaS
                                                                                (SEQ ID NO: 11)
atggaagaagtggtaattatagatgcacgtcggactccgattggtaaatatcacgggtcgttgaagaagttttcagcggtggcgctggggacggc cgtggctaaagacatgttcgaacgcaaccagaaaatcaaagaggagatcgcgcaggtcataattggtaatgtcttgcaggcaggaaatggcca gaaccccgcgcggcaagttgctcttcaatcaggggttgtccgttgacattcccgcttctacaattaacgagggtttgtgggtctggtttgaaagctatctt gatgggcatggaacaaatccaactcggcaaagcgcaagtagtgctggcaggcggcattgaatcaatgacaaatgcgccaagcctgtcccacta taacaaggcggaggatacgtatagtgtcccagtgtcgagcatgacactggatggtctgacagacgcattttctagtaaacctatgggattaacagc ggaaaacgtcgcacagcgctacggtatctcccgtgaggcgcaagatcaattcgcatatcaatctcagatgaaagcagcaaaagcgcaggcag aaaacaaattcgctaaggaaattgtgccactggcgggtgaaactaaaaccatcacagctgacgaagggatcagatcccaaacaacgatggaga aactggcaagtctcaaacctgttttttaaaaccgatggcactgtaaccgcagggaatgctagcaccattaatgacggggccgcccttgtgctgcttg ctagcaaaacttactgcgaaactaatgacataccgtaccttgcgacaatcaaagaaattgttgaagttggaatcgatccggagattatgggcatctc tccgataaaagcgatacaaacattgttacaaaatcaaaaagttagcctcgaagatattggagttttttgaaataaatgaagcctttgccgcaagtagc atagtggttgaatctgagttgggattagatccggctaaagttaaccgttatggggtggtatatccttaggtcatgcaattggggcaaccggcgctc gcctggccacttcactggtgtatcaaatgcaggagatacaagcacgttatggtattgcgagcctgtgcgttggtggtggacttggactggcaatgc ttttagaacgtccaactattgagaaggctaaaccgacagacaaaaagttctatgaattgtcaccagctgaacggttgcaagagctggaaaatcaac agaaaatcagttctgaaactaaacagcagttatctcagatgatgcttgccgaggacactgcaaaccatttgatagaaaatcaaatatcagagattga actcccaatgggcgtcgggatgaacctgaaggttgatgggaaagcctatgttgtgccaatggcgacggaagagccgtccgtcatcgcggccat gtctaatggtgccaaaatggccggcgaaattcacactcagtcgaaagaacggctgctcagaggtcagattgttttcagcgcgaagaatccgaat gaaatcgaacagagaatagctgagaaccaagctttgattttcgaacgtgccgaacagtcctatccttccattgtgaaaagagagggaggtctccg ccgcattgcacttcgtcattttcctgccgattctcagcaggagtctgcggaccagtccacatttttatcagtggacctttttgtagatgtgaaagacgc gatggggcaaatatcataaatgcaatacttgagggcgtcgcagccctgtttcgcgaatggttccccaatgaggaaattcttttttctattctctcgaa cttggctacggagagcttagtcacggctgtttgtgaagtcccatttagtgcacttagcaagagaggtggtgcaacggtggcccagaaaattgtgc aggcgtcgctcttcgcaaagacagacccataccgcgcagtgacccacaacaaagggattatgaacggtgtagaggctgttatgcttgccacag gcaacgacacgcgcgcagtctcagccgcttgtcatggatacgcagcgcgcaccggtagctatcagggtctgactaactggacgattgagtcgg atcgcctggtaggcgagataacactgccgctggccatcgctacagttggaggcgctaccaaagtgttgcccaaagctcaagcggcactggaga ttagtgatgttcactcttctcaagagcttgcagccttagcggcgtcagtaggtttagtacaaaatctcgcggccctgcgcgcactggtttccgaagg tatacaaaaagggcacatgtccatgcaagcccggtctctcgcaatcgcggtcggtgctgaaaaagccgagatcgagcaggtcgccgaaaagtt gcggcagaacccgccaatgaatcagcagcaggcgctccgttttcttggcgagatccgcgaacaatga
```

Sequence of *Enterococcus faecium* mvaS (SEQ ID NO: 12)

atgaacgtcggcattgacaaaattaattttttcgttccaccgtattatctggatatggtcgacctggcccacgcacgcgaagtggacccgaacaaat ttacaattggaattggacaggatcagatggctgtgagcaaaaagacgcacgatatcgtaacattcgcggctagtgccgcgaaggaaattttagaa cctgaggacttgcaagctatagacatggttatagttggtaccgaatcgggcattgacgagagcaaagcatccgcggtcgttttacatcgtttgttgg gcgtacaacctttcgctcgcagttttgaaattaaagaagcctgttacggggcaaccgcaggcattcagtttgccaagactcatatacaagcgaacc cggagagcaaggtcctggtaattgcaagcgatatagctcggtatggtcttcggtcaggtggagcccacacaaggcgcaggggcagttgcta tgcttctcacggcaaatcccagaatcctgaccttcgaaaacgacaatctgatgttaacgcaggatatttatgacttctggagaccacttggtcacgct taccctatggtagatggccaccttccaatcaagtctatattgacagttttaagaaggtctggcaagcacattgcgaacgcaatcaagcttctatatc cgactatgccgcgattagttttcatattccgtatacaaaaatgggtaagaaagccctgctcgctgtttttgcagatgaagtggaaactgaacaggaa cgcgttatggcacggtatgaagagtctatcgtatattcacgccggatcggcaacttgtatacgggatcattgtacctggggctgatatccttattgga aaacagttctcacctgtcggcgggcgaccggataggattgtttagttatgggagtggcgctgtcagcgaatttttctccggtcgtttagtggcaggc tatgaaaatcaattgaacaaagaggcgcatacccagctcctggatcagcgtcagaagcttttccatcgaagagtatgaggcgatttttacagattcct tagaaattgatcaggatgcagcgttctcggatgacctgccatattccatccgcgagataaaaaacacgattcggtactataaggagagctga Sequence of *Enterococcus gallinarum* EG2 mvaS (SEQ ID NO: 13)

atggaagaagttgtcatcattgacgcactgcgtactccaataggaaagtaccacggttcgctgaaagattacacagctgttgaactggggacagt agcagcaaaggcgttgctggcacgaaatcagcaagcaaaagaacacatagcgcaagttattattggcaacgtcctgcaagccggaagtgggc agaatccaggccgacaagtcagtttacagtcaggattgtcttctgatatccccgctagcacgatcaatgaagtgtgtggctcgggtatgaaagcga ttctgatgggtatggagcaaattcagctgaacaaagcctctgtggtcttaacaggcggaattgaaagcatgaccaacgcgccgctgtttagttatta caacaaggctgaggatcaatattcggcgccggttagcacaatgatgcacgatggtctaacagatgctttcagttccaaaccaatgggcttaaccg cagagaccgtcgctgagagatatggaattacgcgtaaggaacaagatgaatttgcttatcactctcaaatgaaggcggcaaaagcccaggcgg cgaaaaagtttgatcaggaaattgtaccctgacggaaaaatccggaacggttctccaggacgaaggcatcagagccgcgacaacagtcgag aagctagctgagcttaaaacggtgttcaaaaaagacggaacagttacagcgggtaacgcctctacgataaatgatgcgctgctatggtattaat agcatcaaaatcttattgcgaagaacaccagattccttatctggccgttataaaggagatcgttgaggtgggttttgccccgaaataatgggtatt tccccccattaaggctatagacaccctgctgaaaaatcaagcactgaccatagaggatataggaatatttgagattaatgaagcctttgctgcgagttc gattgtggtagaacgcgagttgggcctggaccccaaaaaagttaatcgctatggcggtggtatatcactcggccacgcaattggggcgacggg agctcgcattgcgacgaccgttgcttatcagctgaaagatacccaggagcgctacggtatagcttccttatgcgttggtgggggtcttggattggc gatgcttctggaaaacccatcggccactgcctcacaaactaattttttgatgaggaatctgcttccgaaaaaactgagaagaagaagtttatgcgcta gctcctaacgaacgcttagcgttttttggaagcccaaggcgctattaccgctgctgaaaccctggtcttccaggagatgaccttaaacaaagagac agccaatcacttaatcgaaaaccaaatcagcgaagttgaaattcctttaggcgtgggcctgaacttacaggtgaatgggaaagcgtataatgttcc tctggccacggaggaaccgtccgttatcgctgcgatgtcgaatgcgccaaaatggctggtcctattacaacaacaagtcaggagaggctgtta cggggtcagattgtcttcatggacgtacaggacccagaagcaatattagcgaaagttgaatccgagcaagctaccattttcgcggtggcaaatga aacatacccgtctatcgtgaaaagaggaggaggtctgcgtagagtcattggcaggaatttcagtccggccgaaagtgacttagccacggcgtat gtatcaattgacctgatggtagatgttaaggatgcaatgggtgctaatatcatcaatagtatcctagaaggtgttgcggaattgtttagaaaatggttc ccagaagaagaaatcctgttctcaattctctccaatctcgcgacagaaagtctggtaacggcgacgtgctcagttccgtttgataaattgtccaaaa ctgggaatggtcgacaagtagctggtaaaatagtgcacgcggcgactttgctaagatagatccatacagagctgccacacacaataaaggtatt atgaatggcgttgaagcgttaatcttagccaccggtaatgacacccgtgcggtgtcggctgcatgccacggttacgcggcacgcaatgggcgaa tgcaagggcttacctcttggacgattatcgaagatcggctgataggctctatcacattacctttggctattgcgacagtggggggtgccacaaaaat cttgccaaaagcacaggccgccctggcgctaactggcgttgagacggcgtcggaactggccagcctggcggcgagtgtgggattagttcaaa atttggccgctttacgagcactagtgagcgagggcattcagcaagggcacatgagtatgcaagctagatccctggccattagcgtaggtgcgaa -continued

```
aggtactgaaatagagcaactagctgcgaagctgagggcagcgacgcaaatgaatcaggagcaggctcgtaaatttctgaccgaaataagaaa
ttaa
```

Sequence of Enterococcus casseliflavus mvaS (SEQ ID NO: 14)

```
atgaacgttggaattgataaaatcaattttttcgttccgccctatttcattgatatggtggatctcgctcatgcaagagaagttgacccccaacaagttca
ctataggaataggccaagatcagatggcagtaaacaagaaaacgcaagatatcgtaacgttcgcgatgcacgccgcgaaggatattctgactaa
ggaagatttacaggccatagatatggtaatagtggggactgagtctgggatcgacgagagcaaggcaagtgctgtcgtattgcatcggcttttag
gtattcagccttttgcgcgctcctttgaaattaaggaggcatgctatggggccactgccggccttcagtttgcaaaagctcatgtgcaggctaatcc
ccagagcaaggtcctggtggtagcttccgatatagcacgctacggactggcatccggaggagaaccgactcaaggtgtaggtgctgtggcaat
gttgatttccgctgatccagctatcttgcagttagaaaatgataatctcatgttgacccaagatatatacgattttttggcgcccggtcgggcatcaatat
cctatggtagacggccatctgtctaatgccgtctatatagacagctttaaacaagtctggcaagcacattgcgagaaaaaccaacggactgctaaa
gattatgctgcattgtcgttccatattccgtacacgaaaatgggtaagaaagctctgttagcggtttttgcggaggaagatgagacagaacaaaag
cggttaatggcacgttatgaagaatcaattgtatacagtcgtcggactggaaatctgtatactggctcactctatctgggcctgatttccttactggag
aatagtagcagtttacaggcgaacgatcgcataggtctgtttagctatggttcaggggccgttgcggaattttttcagtggcctcttggtaccgggtta
cgagaaacaattagcgcaagctgcccatcaagctcttctggacgaccggcaaaaactgactatcgcagagtacgaagccatgtttaatgaaacc
attgatattgatcaggaccagtcatttgaggatgacttactgtactccatcagagagatcaaaaacactattcgctactataacgaggagaatgaataa
```

The mvaS nucleic acid can be expressed in a recombinant cell on a multicopy plasmid. The plasmid can be a high copy plasmid, a low copy plasmid, or a medium copy plasmid. Alternatively, the mvaS nucleic acid can be integrated into the host cell's chromosome. For both heterologous expression of an mvaS nucleic acid on a plasmid or as an integrated part of the host cell's chromosome, expression of the nucleic acid can be driven by either an inducible promoter or a constitutively expressing promoter. The promoter can be a strong driver of expression, it can be a weak driver of expression, or it can be a medium driver of expression of the mvaS nucleic acid.

Compositions of recombinant cells as described herein are contemplated within the scope of the invention as well. It is understood that recombinant cells also encompass progeny cells as well.

Nucleic Acids Encoding Polypeptides of the Lower MVA Pathway

In some aspects of the invention, the cells described in any of the compositions or methods described herein further comprise one or more nucleic acids encoding a lower mevalonate (MVA) pathway polypeptide(s). In some aspects, the lower MVA pathway polypeptide is an endogenous polypeptide. In some aspects, the endogenous nucleic acid encoding a lower MVA pathway polypeptide is operably linked to a constitutive promoter. In some aspects, the endogenous nucleic acid encoding a lower MVA pathway polypeptide is operably linked to an inducible promoter. In some aspects, the endogenous nucleic acid encoding a lower MVA pathway polypeptide is operably linked to a strong promoter. In a particular aspect, the cells are engineered to over-express the endogenous lower MVA pathway polypeptide relative to wild-type cells. In some aspects, the endogenous nucleic acid encoding a lower MVA pathway polypeptide is operably linked to a weak promoter.

The lower mevalonate biosynthetic pathway comprises mevalonate kinase (MVK), phosphomevalonate kinase (PMK), and diphosphomevalonte decarboxylase (MVD). In some aspects, the lower MVA pathway can further comprise isopentenyl diphosphate isomerase (IDI). Cells provided herein can comprise at least one nucleic acid encoding isoprene synthase, one or more upper MVA pathway polypeptides, and/or one or more lower MVA pathway polypeptides. Polypeptides of the lower MVA pathway can be any enzyme (a) that phosphorylates mevalonate to mevalonate 5-phosphate; (b) that converts mevalonate 5-phosphate to mevalonate 5-pyrophosphate; and (c) that converts mevalonate 5-pyrophosphate to isopentenyl pyrophosphate. More particularly, the enzyme that phosphorylates mevalonate to mevalonate 5-phosphate can be from the group consisting of *M. mazei* mevalonate kinase, *Lactobacillus* mevalonate kinase polypeptide, *Lactobacillus sakei* mevalonate kinase polypeptide, yeast mevalonate kinase polypeptide, *Saccharomyces cerevisiae* mevalonate kinase polypeptide, *Streptococcus* mevalonate kinase polypeptide, *Streptococcus pneumoniae* mevalonate kinase polypeptide, *Streptomyces* mevalonate kinase polypeptide, and *Streptomyces* L190 mevalonate kinase polypeptide. In another aspect, the enzyme that phosphorylates mevalonate to mevalonate 5-phosphate is *M. mazei* mevalonate kinase.

In some aspects, the lower MVA pathway polypeptide is a heterologous polypeptide. In some aspects, the cells comprise more than one copy of a heterologous nucleic acid encoding a lower MVA pathway polypeptide. In some aspects, the heterologous nucleic acid encoding a lower MVA pathway polypeptide is operably linked to a constitutive promoter. In some aspects, the heterologous nucleic acid encoding a lower MVA pathway polypeptide is operably linked to an inducible promoter. In some aspects, the heterologous nucleic acid encoding a lower MVA pathway polypeptide is operably linked to a strong promoter. In some aspects, the heterologous nucleic acid encoding a lower MVA pathway polypeptide is operably linked to a weak promoter. In some aspects, the heterologous lower MVA pathway polypeptide is a polypeptide from *Saccharomyces cerevisiae*, *Enterococcus faecalis*, or *Methanosarcina mazei*.

The nucleic acids encoding a lower MVA pathway polypeptide(s) can be integrated into a genome of the cells or can be stably expressed in the cells. The nucleic acids encoding a lower MVA pathway polypeptide(s) can additionally be on a vector.

Exemplary lower MVA pathway polypeptides are also provided below: (i) mevalonate kinase (MVK); (ii) phosphomevalonate kinase (PMK); (iii) diphosphomevalonate decarboxylase (MVD); and (iv) isopentenyl diphosphate isomerase (IDI). In particular, the lower MVK polypeptide can be from the genus *Methanosarcina* and, more specifically, the lower MVK polypeptide can be from *Methanosarcina mazei*. Additional examples of lower MVA pathway polypeptides can be found in U.S. Patent Application Publication 2010/0086978 the contents of which are expressly incorporated herein by reference in their entirety with respect to lower MVK pathway polypeptides and lower MVK pathway polypeptide variants.

Lower MVA pathway polypeptides include polypeptides, fragments of polypeptides, peptides, and fusions polypeptides that have at least one activity of a lower MVA pathway polypeptide. Exemplary lower MVA pathway nucleic acids include nucleic acids that encode a polypeptide, fragment of a polypeptide, peptide, or fusion polypeptide that has at least one activity of a lower MVA pathway polypeptide. Exemplary lower MVA pathway polypeptides and nucleic acids include naturally-occurring polypeptides and nucleic acids from any of the source organisms described herein. In addition, variants of lower MVA pathway polypeptides that confer the result of better isoprene production can also be used as well.

In some aspects, the lower MVA pathway polypeptide is a polypeptide from *Saccharomyces cerevisiae, Enterococcus faecalis*, or *Methanosarcina mazei*. In some aspects, the MVK polypeptide is selected from the group consisting of *Lactobacillus* mevalonate kinase polypeptide, *Lactobacillus sakei* mevalonate kinase polypeptide, yeast mevalonate kinase polypeptide, *Saccharomyces cerevisiae* mevalonate kinase polypeptide, *Streptococcus* mevalonate kinase polypeptide, *Streptococcus pneumoniae* mevalonate kinase polypeptide, *Streptomyces* mevalonate kinase polypeptide, *Streptomyces* L190 mevalonate kinase polypeptide, *Methanosarcina mazei* mevalonate kinase polypeptide, and *M. burtonii* mevalonate kinase polypeptide. Any one of the promoters described herein (e.g., promoters described herein and identified in the Examples of the present disclosure including inducible promoters and constitutive promoters) can be used to drive expression of any of the MVA polypeptides described herein.

Any one of the cells described herein can comprise IDI nucleic acid(s) (e.g., endogenous or heterologous nucleic acid(s) encoding IDI). Isopentenyl diphosphate isomerase polypeptides (isopentenyl-diphosphate delta-isomerase or IDI) catalyzes the interconversion of isopentenyl diphosphate (IPP) and dimethylallyl diphosphate (DMAPP) (e.g., converting IPP into DMAPP and/or converting DMAPP into IPP). Exemplary IDI polypeptides include polypeptides, fragments of polypeptides, peptides, and fusions polypeptides that have at least one activity of an IDI polypeptide. Standard methods (such as those described herein) can be used to determine whether a polypeptide has IDI polypeptide activity by measuring the ability of the polypeptide to interconvert IPP and DMAPP in vitro, in a cell extract, or in vivo. Exemplary IDI nucleic acids include nucleic acids that encode a polypeptide, fragment of a polypeptide, peptide, or fusion polypeptide that has at least one activity of an IDI polypeptide. Exemplary IDI polypeptides and nucleic acids include naturally-occurring polypeptides and nucleic acids from any of the source organisms described herein as well as mutant polypeptides and nucleic acids derived from any of the source organisms described herein.

DXP Pathway Nucleic Acids and Polypeptides

In some aspects of the invention, the recombinant cells described in any of the compositions or methods described herein (including host cells that have been modified as described herein) further comprise one or more heterologous nucleic acids encoding a DXS polypeptide and/or other DXP pathway polypeptides. In some aspects, the cells further comprise a chromosomal copy of an endogenous nucleic acid encoding a DXS polypeptide and/or other DXP pathway polypeptides. In some aspects, the *E. coli* cells further comprise one or more nucleic acids encoding an IDI polypeptide and a DXS polypeptide and/or other DXP pathway polypeptides. In some aspects, one nucleic acid encodes the isoprene synthase polypeptide, IDI polypeptide, and DXS polypeptide and/or other DXP pathway polypeptides. In some aspects, one plasmid encodes the isoprene synthase polypeptide, IDI polypeptide, and DXS polypeptide and/or other DXP pathway polypeptides. In some aspects, multiple plasmids encode the isoprene synthase polypeptide, IDI polypeptide, and DXS polypeptide or other DXP pathway polypeptides.

Exemplary DXS polypeptides include polypeptides, fragments of polypeptides, peptides, and fusions polypeptides that have at least one activity of a DXS polypeptide. Standard methods (such as those described herein) can be used to determine whether a polypeptide has DXS polypeptide activity by measuring the ability of the polypeptide to convert pyruvate and D-glyceraldehyde-3-phosphate into 1-deoxy-D-xylulose-5-phosphate in vitro, in a cell extract, or in vivo. Exemplary DXS polypeptides and nucleic acids and methods of measuring DXS activity are described in more detail in International Publication No. WO 2009/076676, U.S. patent application Ser. No. 12/335,071 (US Publ. No. 2009/0203102), WO 2010/003007, US Publ. No. 2010/0048964, WO 2009/132220, and US Publ. No. 2010/0003716.

Exemplary DXP pathways polypeptides include, but are not limited to any of the following polypeptides: DXS polypeptides, DXR polypeptides, MCT polypeptides, CMK polypeptides, MCS polypeptides, HDS polypeptides, HDR polypeptides, and polypeptides (e.g., fusion polypeptides) having an activity of one, two, or more of the DXP pathway polypeptides. In particular, DXP pathway polypeptides include polypeptides, fragments of polypeptides, peptides, and fusions polypeptides that have at least one activity of a DXP pathway polypeptide. Exemplary DXP pathway nucleic acids include nucleic acids that encode a polypeptide, fragment of a polypeptide, peptide, or fusion polypeptide that has at least one activity of a DXP pathway polypeptide. Exemplary DXP pathway polypeptides and nucleic acids include naturally-occurring polypeptides and nucleic acids from any of the source organisms described herein as well as mutant polypeptides and nucleic acids derived from any of the source organisms described herein. Exemplary DXP pathway polypeptides and nucleic acids and methods of measuring DXP pathway polypeptide activity are described in more detail in International Publication No.: WO 2010/148150.

Exemplary DXS polypeptides include polypeptides, fragments of polypeptides, peptides, and fusions polypeptides that have at least one activity of a DXS polypeptide. Standard methods (such as those described herein) can be used to determine whether a polypeptide has DXS polypeptide activity by measuring the ability of the polypeptide to convert pyruvate and D-glyceraldehyde-3-phosphate into 1-deoxy-D-xylulose-5-phosphate in vitro, in a cell extract, or in vivo. Exemplary DXS polypeptides and nucleic acids and methods of measuring DXS activity are described in more detail in International Publication No. WO 2009/076676, U.S. patent application Ser. No. 12/335,071 (US Publ. No. 2009/

0203102), WO 2010/003007, US Publ. No. 2010/0048964, WO 2009/132220, and US Publ. No. 2010/0003716.

In particular, DXS polypeptides convert pyruvate and D-glyceraldehyde 3-phosphate into 1-deoxy-D-xylulose 5-phosphate (DXP). Standard methods can be used to determine whether a polypeptide has DXS polypeptide activity by measuring the ability of the polypeptide to convert pyruvate and D-glyceraldehyde 3-phosphate in vitro, in a cell extract, or in vivo.

DXR polypeptides convert 1-deoxy-D-xylulose 5-phosphate (DXP) into 2-C-methyl-D-erythritol 4-phosphate (MEP). Standard methods can be used to determine whether a polypeptide has DXR polypeptides activity by measuring the ability of the polypeptide to convert DXP in vitro, in a cell extract, or in vivo.

MCT polypeptides convert 2-C-methyl-D-erythritol 4-phosphate (MEP) into 4-(cytidine 5'-diphospho)-2-methyl-D-erythritol (CDP-ME). Standard methods can be used to determine whether a polypeptide has MCT polypeptides activity by measuring the ability of the polypeptide to convert MEP in vitro, in a cell extract, or in vivo.

CMK polypeptides convert 4-(cytidine 5'-diphospho)-2-C-methyl-D-erythritol (CDP-ME) into 2-phospho-4-(cytidine 5'-diphospho)-2-C-methyl-D-erythritol (CDP-MEP). Standard methods can be used to determine whether a polypeptide has CMK polypeptides activity by measuring the ability of the polypeptide to convert CDP-ME in vitro, in a cell extract, or in vivo.

MCS polypeptides convert 2-phospho-4-(cytidine 5'-diphospho)-2-C-methyl-D-erythritol (CDP-MEP) into 2-C-methyl-D-erythritol 2,4-cyclodiphosphate (ME-CPP or cMEPP). Standard methods can be used to determine whether a polypeptide has MCS polypeptides activity by measuring the ability of the polypeptide to convert CDP-MEP in vitro, in a cell extract, or in vivo.

HDS polypeptides convert 2-C-methyl-D-erythritol 2,4-cyclodiphosphate into (E)-4-hydroxy-3-methylbut-2-en-1-yl diphosphate (HMBPP or HDMAPP). Standard methods can be used to determine whether a polypeptide has HDS polypeptides activity by measuring the ability of the polypeptide to convert ME-CPP in vitro, in a cell extract, or in vivo.

HDR polypeptides convert (E)-4-hydroxy-3-methylbut-2-en-1-yl diphosphate into isopentenyl diphosphate (IPP) and dimethylallyl diphosphate (DMAPP). In one embodiment, the ispH gene can be used to encode for HDR polypeptides. IspH is also known as 1-hydroxy-2-methyl-2-(E)-butenyl 4-diphosphate reductase, 4Fe-4S protein, ECK0030, JW0027, lytB, yaaE, and b0029. Standard methods can be used to determine whether a polypeptide has HDR polypeptides activity by measuring the ability of the polypeptide to convert HMBPP in vitro, in a cell extract, or in vivo.

Source Organisms for Isoprene Synthase, MVA Pathway, DXP Pathway and IDI Polypeptides Isoprene synthase, IDI, DXP pathway, and/or MVA pathway nucleic acids (and their encoded polypeptides) can be obtained from any organism that naturally contains isoprene synthase, IDI, DXP pathway, and/or MVA pathway nucleic acids. Isoprene is formed naturally by a variety of organisms, such as bacteria, yeast, plants, and animals. Some organisms contain the MVA pathway for producing isoprene. Isoprene synthase nucleic acids can be obtained, e.g., from any organism that contains an isoprene synthase. MVA pathway nucleic acids can be obtained, e.g., from any organism that contains the MVA pathway. IDI and DXP pathway nucleic acids can be obtained, e.g., from any organism that contains the IDI and DXP pathway.

The nucleic acid sequence of the isoprene synthase, DXP pathway, IDI, and/or MVA pathway nucleic acids can be isolated from a bacterium, fungus, plant, algae, or cyanobacterium. Exemplary source organisms include, for example, yeasts, such as species of *Saccharomyces* (e.g., *S. cerevisiae*), bacteria, such as species of *Escherichia* (e.g., *E. coli*), or species of *Methanosarcina* (e.g., *Methanosarcina mazei*), *M. burtonii*, plants, such as kudzu or poplar (e.g., *Populus alba* or *Populus alba×tremula* AC35696) or aspen (e.g., *Populus tremuloides*). Exemplary sources for isoprene synthases, IDI, and/or MVA pathway polypeptides which can be used are also described in International Patent Application Publication Nos. WO 2009/076676, WO 2010/003007, WO 2009/132220, WO 2010/031062, WO 2010/031068, WO 2010/031076, WO 2010/013077, WO 2010/031079, WO 2010/148150, WO 2010/078457, and WO 2010/148256.

In some aspects, the source organism is a yeast, such as *Saccharomyces* sp., *Schizosaccharomyces* sp., *Pichia* sp., or *Candida* sp.

In some aspects, the source organism is a bacterium, such as strains of *Bacillus* such as *B. lichenformis* or *B. subtilis*, strains of *Pantoea* such as *P. citrea*, strains of *Pseudomonas* such as *P. alcaligenes*, strains of *Streptomyces* such as *S. lividans* or *S. rubiginosus*, strains of *Escherichia* such as *E. coli*, strains of *Enterobacter*, strains of *Streptococcus*, or strains of *Archaea* such as *Methanosarcina mazei*.

As used herein, "the genus *Bacillus*" includes all species within the genus "*Bacillus*," as known to those of skill in the art, including but not limited to *B. subtilis*, *B. licheniformis*, *B. lentus*, *B. brevis*, *B. stearothermophilus*, *B. alkalophilus*, *B. amyloliquefaciens*, *B. clausii*, *B. halodurans*, *B. megaterium*, *B. coagulans*, *B. circulans*, *B. lautus*, and *B. thuringiensis*. It is recognized that the genus *Bacillus* continues to undergo taxonomical reorganization. Thus, it is intended that the genus include species that have been reclassified, including but not limited to such organisms as *B. stearothermophilus*, which is now named "*Geobacillus stearothermophilus*." The production of resistant endospores in the presence of oxygen is considered the defining feature of the genus *Bacillus*, although this characteristic also applies to the recently named *Alicyclobacillus, Amphibacillus, Aneurinibacillus, Anoxybacillus, Brevibacillus, Filobacillus, Gracilibacillus, Halobacillus, Paenibacillus, Salibacillus, Thermobacillus, Ureibacillus,* and *Virgibacillus*.

In some aspects, the source organism is a gram-positive bacterium. Non-limiting examples include strains of *Streptomyces* (e.g., *S. lividans, S. coelicolor,* or *S. griseus*) and *Bacillus*. In some aspects, the source organism is a gram-negative bacterium, such as *E. coli* or *Pseudomonas* sp. In some aspects, the source organism is *L. acidophilus*.

In some aspects, the source organism is a plant, such as a plant from the family Fabaceae, such as the Faboideae subfamily. In some aspects, the source organism is kudzu, poplar (such as *Populus alba×tremula* AC35696), aspen (such as *Populus tremuloides*), or *Quercus robur*.

In some aspects, the source organism is an algae, such as a green algae, red algae, glaucophytes, chlorarachniophytes, euglenids, chromista, or dinoflagellates.

In some aspects, the source organism is a cyanobacteria, such as cyanobacteria classified into any of the following groups based on morphology: *Chroococcales, Pleurocapsales, Oscillatoriales, Nostocales,* or *Stigonematales*.

Phosphoketolase Nucleic Acids and Polypeptides

Phosphoketolase enzymes catalyze the conversion of xylulose 5-phosphate to glyceraldehyde 3-phosphate and acetyl phosphate and/or the conversion of fructose 6-phosphate to erythrose 4-phosphate and acetyl phosphate. In certain embodiments, the phosphoketolase enzyme is capable of catalyzing the conversion of xylulose 5-phosphate to glyceraldehyde 3-phosphate and acetyl phosphate. In other embodiments, the phosphoketolase enzyme is capable of catalyzing the conversion of fructose 6-phosphate to erythrose 4-phosphate and acetyl phosphate. In further embodiments, the phosphoketolase polypeptide catalyzes the conversion of sedoheptulose-7-phosphate to a product (e.g., ribose-5-phosphate) and acetyl phosphate. Thus, without being bound by theory, the expression of phosphoketolase as set forth herein can result in an increase in the amount of acetyl phosphate produced from a carbohydrate or carbon source. This acetyl phosphate can be converted into acetyl-CoA which can then be utilized by the enzymatic activities of the MVA pathway to produces isoprene. Thus the amount of these compounds produced from a carbohydrate substrate may be increased. Alternatively, production of Acetyl-P and AcCoA can be increased without the increase being reflected in higher intracellular concentration. In certain embodiments, intracellular acetyl-P or acetyl-CoA concentrations will remain unchanged or even decrease, even though the phosphoketolase reaction is taking place.

In some aspects of the invention, the recombinant cells described in any of the compositions or methods described herein further comprise one or more nucleic acids encoding a phosphoketolase polypeptide or a polypeptide having phosphoketolase activity. In some aspects, the phosphoketolase polypeptide is an endogenous polypeptide. In some aspects, the endogenous nucleic acid encoding a phosphoketolase polypeptide is operably linked to a constitutive promoter. In some aspects, the endogenous nucleic acid encoding a phosphoketolase polypeptide is operably linked to an inducible promoter. In some aspects, the endogenous nucleic acid encoding a phosphoketolase polypeptide is operably linked to a strong promoter. In some aspects, more than one endogenous nucleic acid encoding a phosphoketolase polypeptide is used (e.g, 2, 3, 4, or more copies of an endogenous nucleic acid encoding a phosphoketolase polypeptide). In a particular aspect, the cells are engineered to overexpress the endogenous phosphoketolase polypeptide relative to wild-type cells. In some aspects, the endogenous nucleic acid encoding a phosphoketolase polypeptide is operably linked to a weak promoter.

Exemplary phosphoketolase nucleic acids include nucleic acids that encode a polypeptide, fragment of a polypeptide, peptide, or fusion polypeptide that has at least one activity of a phosphoketolase polypeptide. Exemplary phosphoketolase polypeptides and nucleic acids include naturally-occurring polypeptides and nucleic acids from any of the source organisms described herein as well as mutant polypeptides and nucleic acids derived from any of the source organisms described herein. In some aspects, a nucleic acid encoding a phosphoketolase is from *Clostridium acetobutylicum, Lactobacillus reuteri, Lactobacillus plantarum, Lactobacillus paraplantarum, Bifidobacterium longum, Bifidobacterium animalis, Bifidobacterium breve, Enterococcus gallinarum, Gardnerella vaginalis, Ferrimonas balearica, Mucilaginibacter paludis, Nostoc punctiforme, Nostoc punctiforme PCC 73102, Pantoea, Pedobacter saltans, Rahnella aquatilis, Rhodopseudomonas palustris, Streptomyces griseus, Streptomyces avermitilis, Nocardiopsis dassonvillei*, and/or *Thermobifida furca*. Additional examples of phosphoketolase enzymes which can be used herein are described in U.S. Pat. No. 7,785,858 and International Patent Application Publication No. WO 2011/159853 which are incorporated by reference herein.

Standard methods can be used to determine whether a polypeptide has phosphoketolase peptide activity by measuring the ability of the peptide to convert D-fructose 6-phosphate or D-xylulose 5-phosphate into acetyl-P. Acetyl-P can then be converted into ferryl acetyl hydroxamate, which can be detected spectrophotometrically (Meile et al., J. Bact. 183: 2929-2936, (2001)). Any polypeptide identified as having phosphoketolase peptide activity as described herein is suitable for use in the present invention.

In any of the embodiments herein, the recombinant cells can be further engineered to increase the activity of one or more of the following genes selected from the group consisting of ribose-5-phosphate isomerase (rpiA and/or rpiB), D-ribulose-5-phosphate 3-epimerase (rpe), transketolase (tktA and/or tktB), transaldolase B (tal B), phosphate acetyltransferase (pta and/or eutD). In another embodiment, the recombinant cells can be further engineered to decrease the activity of one or more genes of the following genes including glucose-6-phosphate dehydrogenase (zwf), 6-phosphofructokinase-1 (pfkA and/or pfkB), fructose bisphosphate aldolase (ffia, fbaA, fbaB, and/or fbaC), glyceraldehyde-3-phosphate dehydrogenase (gapA and/or gapB), acetate kinase (ackA), citrate synthase (gltA), EI (ptsI), EIICB$^{Glc}$ (ptsG), EIIA$^{Glc}$ (crr), and/or HPr (ptsH).

Recombinant Cells Capable of Producing Isoprene

Isoprene (2-methyl-1,3-butadiene) is an important organic compound used in a wide array of applications. For instance, isoprene is employed as an intermediate or a starting material in the synthesis of numerous chemical compositions and polymers, including in the production of synthetic rubber. Isoprene is also an important biological material that is synthesized naturally by many plants and animals.

As described herein, the present invention provides recombinant cells capable of producing of isoprene, wherein the cells comprise one or more nucleic acids encoding one or more polypeptides of the MVA pathway, and a heterologous nucleic acid encoding an isoprene synthase polypeptide, wherein culturing the cells in a suitable media provides for the production of isoprene. In a further embodiment, the recombinant cells further comprise one or more nucleic acids encoding an isopentenyl diphosphate isomerase (IDI) polypeptide. In certain embodiments, the present invention provides recombinant cells capable of isoprene production, wherein the cells comprise one or more nucleic acids encoding one or more polypeptides of the MVA pathway, and a heterologous nucleic acid encoding an isoprene synthase polypeptide, wherein the cells produce increased amounts of isoprene compared to isoprene-producing cells that do not comprise a nucleic acid encoding a polypeptide having phosphomevalonate decarboxylase activity and/or a nucleic acid encoding a polypeptide having isopentenyl kinase activity. In a further embodiment, the recombinant cells further comprise one or more nucleic acids encoding an isopentenyl diphosphate isomerase (IDI) polypeptide.

Production of isoprene can also be made by using any of the recombinant host cells described herein further comprising one or more of the enzymatic pathways manipulations wherein enzyme activity is modulated to increase carbon flow towards mevalonate production. The recombinant cells described herein that have various enzymatic pathways manipulated for increased carbon flow to mevalonate production can be used to produce isoprene. In one embodiment, the recombinant cells further comprise a nucleic acid encoding a phosphoketolase. In another embodiment, the recombinant cells can be further engineered to incease the activity of one or more of the following genes selected from the group consisting of rribose-5-phosphate isomerase (rpiA and/or rpiB), D-ribulose-5-phosphate 3-epimerase (rpe), transketolase (tktA and/or tktB), transaldolase B (tal B), phosphate acetyltransferase (pta and/or eutD). In another embodiment, these recombinant cells can be further engineered to decrease the activity of one or more genes of the following genes including glucose-6-phosphate dehydrogenase (zwf), 6-phosphofructokinase-1 (pfkA and/or pfkB), fructose bisphosphate aldolase (fba, fbaA, fbaB, and/or fbaC), glyceraldehyde-3-phosphate dehydrogenase (gapA and/or gapB), acetate kinase (ackA), citrate synthase (gltA), EI (ptsI), EIICB$^{Glc}$ (ptsG), EIIA$^{Glc}$ (crr), and/or HPr (ptsH).

Isoprene Synthase Nucleic Acids and Polypeptides

In some aspects of the invention, the cells described in any of the compositions or methods described herein (including host cells that have been modified as described herein) further comprise one or more nucleic acids encoding an isoprene synthase polypeptide or a polypeptide having isoprene synthase activity. In some aspects, the isoprene synthase polypeptide is an endogenous polypeptide. In some aspects, the endogenous nucleic acid encoding an isoprene synthase polypeptide is operably linked to a constitutive promoter. In some aspects, the endogenous nucleic acid encoding an isoprene synthase polypeptide is operably linked to an inducible promoter. In some aspects, the endogenous nucleic acid encoding an isoprene synthase polypeptide is operably linked to a strong promoter. In a particular aspect, the cells are engineered to overexpress the endogenous isoprene synthase pathway polypeptide relative to wild-type cells. In some aspects, the endogenous nucleic acid encoding an isoprene synthase polypeptide is operably linked to a weak promoter.

In some aspects, the isoprene synthase polypeptide is a heterologous polypeptide. In some aspects, the cells comprise more than one copy of a heterologous nucleic acid encoding an isoprene synthase polypeptide. In some aspects, the heterologous nucleic acid encoding an isoprene synthase polypeptide is operably linked to a constitutive promoter. In some aspects, the heterologous nucleic acid encoding an isoprene synthase polypeptide is operably linked to an inducible promoter. In some aspects, the heterologous nucleic acid encoding an isoprene synthase polypeptide is operably linked to a strong promoter. In some aspects, the heterologous nucleic acid encoding an isoprene synthase polypeptide is operably linked to a weak promoter. In some aspects, the isoprene synthase polypeptide is a polypeptide or variant thereof from *Pueraria* or *Populus* or a hybrid such as *Populus alba×Populus tremula*. In some aspects, the isoprene synthase polypeptide is a polypeptide or variant thereof from *Pueraria montana* or *Pueraria lobata, Populus tremuloides, Populus alba, Populus nigra*, and *Populus trichocarpa*. In some aspects, the isoprene synthase polypeptide is from *Eucalyptus*.

The nucleic acids encoding an isoprene synthase polypeptide(s) can be integrated into a genome of the host cells or can be stably expressed in the cells. The nucleic acids encoding an isoprene synthase polypeptide(s) can additionally be on a vector.

Exemplary isoprene synthase nucleic acids include nucleic acids that encode a polypeptide, fragment of a polypeptide, peptide, or fusion polypeptide that has at least one activity of an isoprene synthase polypeptide. Isoprene synthase polypeptides convert dimethylallyl diphosphate (DMAPP) into isoprene. Exemplary isoprene synthase polypeptides include polypeptides, fragments of polypeptides, peptides, and fusions polypeptides that have at least one activity of an isoprene synthase polypeptide. Exemplary isoprene synthase polypeptides and nucleic acids include naturally-occurring polypeptides and nucleic acids from any of the source organisms described herein. In addition, variants of isoprene synthase can possess improved activity such as improved enzymatic activity. In some aspects, an isoprene synthase variant has other improved properties, such as improved stability (e.g., thermo-stability), and/or improved solubility.

Pathways Involving the Entner-Doudoroff Pathway

The Entner-Doudoroff (ED) pathway is an alternative to the Emden-Meyerhoff-Parnass (EMP—glycolysis) pathway. Some organisms, like *E. coli*, harbor both the ED and EMP pathways, while others have only one or the other. *Bacillus subtilis* has only the EMP pathway, while *Zymomonas mobilis* has only the ED pathway (Peekhaus and Conway. J. Bact. 180:3495-3502 (1998); Stulke and Hillen. Annu. Rev. Microbiol. 54, 849-880 (2000); Dawes et al. Biochem. J. 98:795-803 (1966)). Fructose bisphophate aldolase (fba, fbaA, fbaB, and/or fbaC) interacts with the Entner-Doudoroff pathway and reversibly catalyzes the conversion of fructose 1,6-bisphosphate into dihydroxyacetone phosphate (DHAP) and glyceraldehyde 3-phosphate (GAP) (Baldwin S. A., et. al., Biochem J. 169(3):633-41 (1978)).

Phosphogluconate dehydratase (edd) removes one molecule of $H_2O$ from 6-phospho-D-gluconate to form 2-dehydro-3-deoxy-D-gluconate 6-phosphate, while 2-keto-3-deoxygluconate 6-phosphate aldolase (eda) catalyzes an aldol cleavage (Egan et al. J. Bact. 174:4638-4646 (1992)). The two genes are in an operon.

Metabolites that can be directed into the phosphoketolase pathway can also be diverted into the ED pathway. To avoid metabolite loss to the ED-pathway, phosphogluconate dehydratase gene (e.g., the endogenous phosphogluconate dehydratase gene) and/or an 2-keto-3-deoxygluconate 6-phosphate aldolase gene (e.g., the endogenous 2-keto-3-deoxygluconate 6-phosphate aldolase gene) activity is attenuated. One way of achieving attenuation is by deleting phosphogluconate dehydratase (edd) and/or 2-keto-3-deoxygluconate 6-phosphate aldolase (eda). This can be accomplished by replacing one or both genes with a chloramphenicol or kanamycin cassette followed by looping out of the cassette. Without these enzymatic activities, more carbon can flux through the phosphoketolase enzyme, thus increasing the yield of isoprene.

The activity of phosphogluconate dehydratase (edd) and/or 2-keto-3-deoxygluconate 6-phosphate aldolase (eda) can also be decreased by other molecular manipulations of the enzymes. The decrease of enzyme activity can be any amount of reduction of specific activity or total activity as compared to when no manipulation has been effectuated. In some instances, the decrease of enzyme activity is decreased by at least about 1%, 2%, 3%, 4%, 5%, 6%, 7%, 8%, 9%, 10%, 15%, 20%, 25%, 30%, 35%, 35%, 40%, 45%, 50%, 55%, 60%, 65%, 70%, 75%, 80%, 85%, 90%, 95%, 96%, 97%, 98%, or 99%.

In some cases, attenuating the activity of the endogenous phosphogluconate dehydratase gene and/or the endogenous 2-keto-3-deoxygluconate 6-phosphate aldolase gene results in more carbon flux into the mevalonate dependent biosynthetic pathway in comparison to cells that do not have attenuated endogenous phosphogluconate dehydratase gene and/or endogenous acetate kinase2-keto-3-deoxygluconate 6-phosphate aldolase gene expression.

Pathways Involving the Oxidative Branch of the Pentose Phosphate Pathway

*E. coli* uses the pentose phosphate pathway to break down hexoses and pentoses and to provide cells with intermediates for various anabolic pathways. It is also a major producer of NADPH. The pentose phosphate pathway is composed from an oxidative branch (with enzymes like glucose 6-phosphate 1-dehydrogenase (zwf), 6-phosphogluconolactonase (pgl) or 6-phosphogluconate dehydrogenase (gnd)) and a non-oxidative branch (with enzymes such as transketolase (tktA), transaldolase (talA or talB), ribulose-5-phosphate-epimerase and (or) ribose-5-phosphate epimerase) (Sprenger. Arch. Microbiol. 164:324-330 (1995)).

In order to direct carbon towards the phosphoketolase enzyme, the non-oxidative branch of the pentose phosphate pathway (transketolase, transaldolase, ribulose-5-phosphate-epimerase and (or) ribose-5-phosphate epimerase) expression can be modulated (e.g., increase enzyme activity) to allow more carbon to flux towards fructose 6-phosphate and xylulose 5-phosphate, thereby increasing the eventual production of isoprene. Increase of transketolase, transaldolase, ribulose-5-phosphate-epimerase and (or) ribose-5-phosphate epimerase activity can be any amount of increase of specific activity or total activity as compared to when no manipulation has been effectuated. In some instances, the enzyme activity is increased by at least about 1%, 2%, 3%, 4%, 5%, 6%, 7%, 8%, 9%, 10%, 15%, 20%, 25%, 30%, 35%, 35%, 40%, 45%, 50%, 55%, 60%, 65%, 70%, 75%, 80%, 85%, 90%, 95%, 96%, 97%, 98%, 99%, or 100%. In some aspects, the activity of transketolase, transaldolase, ribulose-5-phosphate-epimerase and (or) ribose-5-phosphate epimerase is modulated by increasing the activity of an endogenous transketolase, transaldolase, ribulose-5-phosphate-epimerase and (or) ribose-5-phosphate epimerase. This can be accomplished by replacing the endogenous transketolase, transaldolase, ribulose-5-phosphate-epimerase and (or) ribose-5-phosphate epimerase gene promoter with a synthetic constitutively high expressing promoter. The genes encoding transketolase, transaldolase, ribulose-5-phosphate-epimerase and (or) ribose-5-phosphate epimerase can also be cloned on a plasmid behind an appropriate promoter. The increase of the activity of transketolase, transaldolase, ribulose-5-phosphate-epimerase and (or) ribose-5-phosphate epimerase can result in more carbon flux into the mevalonate dependent biosynthetic pathway in comparison to cells that do not have increased expression of transketolase, transaldolase, ribulose-5-phosphate-epimerase and (or) ribose-5-phosphate epimerase.

Pathways Involving Phosphofructokinase

Phosphofructokinase is a crucial enzyme of glycolysis which catalyzes the phosphorylation of fructose 6-phosphate. *E. coli* has two isozymes encoded by pfkA and pfkB. Most of the phosphofructokinase activity in the cell is due to pfkA (Kotlarz et al. Biochim. Biophys. Acta 381:257-268 (1975)).

In order to direct carbon towards the phosphoketolase enzyme, phosphofructokinase expression can be modulated (e.g., decrease enzyme activity) to allow more carbon to flux towards fructose 6-phosphate and xylulose 5-phosphate, thereby increasing the eventual production of isoprene. Decrease of phosphofructokinase activity can be any amount of reduction of specific activity or total activity as compared to when no manipulation has been effectuated. In some instances, the decrease of enzyme activity is decreased by at least about 1%, 2%, 3%, 4%, 5%, 6%, 7%, 8%, 9%, 10%, 15%, 20%, 25%, 30%, 35%, 35%, 40%, 45%, 50%, 55%, 60%, 65%, 70%, 75%, 80%, 85%, 90%, 95%, 96%, 97%, 98%, 99%, or 100%. In some aspects, the activity of phosphofructokinase is modulated by decreasing the activity of an endogenous phosphofructokinase. This can be accomplished by replacing the endogenous phosphofructokinase gene promoter with a synthetic constitutively low expressing promoter. The gene encoding phosphofructokinase can also be deleted. The decrease of the activity of phosphofructokinase can result in more carbon flux into the mevalonate dependent biosynthetic pathway in comparison to cells that do not have decreased expression of phosphofructokinase.

Vectors

Suitable vectors can be used for any of the compositions and methods described herein. For example, suitable vectors can be used to optimize the expression of one or more copies of a gene encoding an isoprene synthase, an acetoacetyl co-A synthase, an MVA pathway enzyme, a DXP pathway enzyme, a phosphoketolase, and/or a polyprenyl pyrophosphate synthase, in a cell. In some aspects, the vector contains a selective marker. Examples of selectable markers include, but are not limited to, antibiotic resistance nucleic acids (e.g., kanamycin, ampicillin, carbenicillin, gentamicin, hygromycin, phleomycin, bleomycin, neomycin, or chloramphenicol) and/or nucleic acids that confer a metabolic advantage, such as a nutritional advantage on the host cell. In some aspects, one or more copies of an isoprene synthase, an acetoacetyl co-A synthase, an MVA pathway enzyme, a DXP pathway enzyme, a phosphoketolase, and/or a polyprenyl pyrophosphate synthases nucleic acid(s) integrate into the genome of host cells without a selective marker.

Any one of the vectors characterized herein or used in the Examples of the present disclosure can be used in the present invention.

Exemplary Host Cells

One of skill in the art will recognize that expression vectors are designed to contain certain components which optimize gene expression for certain host strains. Such optimization components include, but are not limited to origin of replication, promoters, and enhancers. The vectors and components referenced herein are described for exemplary purposes and are not meant to narrow the scope of the invention.

Any microorganism or progeny thereof that can be used to heterologously express genes can be used to express one or more copies of a nucleic acid encoding an isoprene synthase, acetoacetyl co-A synthase, MVA pathway enzyme, DXP pathway enzyme, phosphoketolase, and/or a polyprenyl pyrophosphate synthase polypeptides in a cell. Exemplary host cells include, for example, yeasts, such as species of *Saccharomyces* (e.g., *S. cerevisiae*), bacteria, such as species of *Escherichia* (e.g., *E. coli*), archaea, such as species of *Methanosarcina* (e.g., *Methanosarcina mazei*), plants, such as kudzu or poplar (e.g., *Populus alba* or *Populus alba*× *tremula AC35696*) or aspen (e.g., *Populus tremuloides*).

Bacteria cells, including gram positive or gram negative bacteria can be used to express any of the nucleic acids or polypeptides described above. In some embodiments, the host cell is a gram-positive bacterium. Non-limiting examples include strains of *Streptomyces* (e.g., *S. lividans*, *S. coelicolor*, *S. rubiginosus*, or *S. griseus*), *Streptococcus*, *Bacillus* (e.g., *B. lichenformis* or *B. subtilis*), *Listeria* (e.g., *L. monocytogenes*), *Corynebacteria*, or *Lactobacillus* (e.g., L. spp). In some embodiments, the source organism is a gram-negative bacterium. Non-limiting examples include strains of *Escherichia* (e.g., *E. coli*), *Pseudomonas* (e.g., *P. alcaligenes*), *Pantoea* (e.g., *P. citrea*), *Enterobacter*, or *Helicobacter* (*H. pylori*). In particular, one or more copies of a nucleic acid encoding an isoprene synthase, acetoacetyl co-A synthase, MVA pathway enzyme, DXP pathway enzyme, phosphoketolase, and/or a polyprenyl pyrophosphate synthase polypeptides can be expressed in any one of *P. citrea*, *B. subtilis*, *B. licheniformis*, *B. lentus*, *B. brevis*, *B. stearothermophilus*, *B. alkalophilus*, *B. amyloliquefaciens*, *B. clausii*, *B. halodurans*, *B. megaterium*, *B. coagulans*, *B. circulans*, *B. lautus*, *B. thuringiensis*, *S. albus*, *S. lividans*, *S. coelicolor*, *S. griseus*, *Pseudomonas* sp., and *P. alcaligenes* cells.

There are numerous types of anaerobic cells that can be used as host cells in the compositions and methods of the present invention. In one aspect of the invention, the cells described in any of the compositions or methods described herein are obligate anaerobic cells and progeny thereof. Obligate anaerobes typically do not grow well, if at all, in conditions where oxygen is present. It is to be understood that a small amount of oxygen may be present, that is, there is some tolerance level that obligate anaerobes have for a low level of oxygen. In one aspect, obligate anaerobes engineered to produce isoprene can serve as host cells for any of the methods and/or compositions described herein and are grown under substantially oxygen-free conditions, wherein the amount of oxygen present is not harmful to the growth, maintenance, and/or fermentation of the anaerobes.

In another aspect of the invention, the host cells described and/or used in any of the compositions or methods described herein are facultative anaerobic cells and progeny thereof. Facultative anaerobes can generate cellular ATP by aerobic respiration (e.g., utilization of the TCA cycle) if oxygen is present. However, facultative anaerobes can also grow in the absence of oxygen. This is in contrast to obligate anaerobes which die or grow poorly in the presence of greater amounts of oxygen. In one aspect, therefore, facultative anaerobes can serve as host cells for any of the compositions and/or methods provided herein and can be engineered to produce isoprene. Facultative anaerobic host cells can be grown under substantially oxygen-free conditions, wherein the amount of oxygen present is not harmful to the growth, maintenance, and/or fermentation of the anaerobes, or can be alternatively grown in the presence of greater amounts of oxygen.

The host cell can additionally be a filamentous fungal cell and progeny thereof. (See, e.g., Berka & Barnett, Biotechnology Advances, 7(2):127-154 (1989)). In some aspects, the filamentous fungal cell can be any of *Trichoderma longibrachiatum, T. viride, T. koningii, T. harzianum, Penicillium* sp., *Humicola insolens, H. lanuginose, H. grisea, Chrysosporium* sp., *C. lucknowense, Gliocladium* sp., *Aspergillus* sp., such as *A. oryzae, A. niger, A sojae, A. japonicus, A. nidulans,* or *A. awamori, Fusarium* sp., such as *F. roseum, F. graminum F. cerealis, F. oxysporuim,* or *F. venenatum, Neurospora* sp., such as *N. crassa, Hypocrea* sp., *Mucor* sp., such as *M. miehei, Rhizopus* sp. or *Emericella* sp. In some aspects, the fungus is *A. nidulans, A. awamori, A. oryzae, A. aculeatus, A. niger, A. japonicus, T. reesei, T. viride, F. oxysporum,* or *F. solani*. In certain embodiments, plasmids or plasmid components for use herein include those described in U.S. Patent Pub. No. US 2011/0045563.

The host cell can also be a yeast, such as *Saccharomyces* sp., *Schizosaccharomyces* sp., *Pichia* sp., or *Candida* sp. In some aspects, the *Saccharomyces* sp. is *Saccharomyces cerevisiae* (See, e.g., Romanos et al., Yeast, 8(6):423-488 (1992)). In certain embodiments, plasmids or plasmid components for use herein include those described in U.S. Pat. No. 7,659,097 and U.S. Patent Pub. No. US 2011/0045563.

The host cell can also be a species of plant, such as a plant from the family Fabaceae, such as the Faboideae subfamily. In some aspects, the host cell is kudzu, poplar (such as *Populus alba×tremula* CAC35696), aspen (such as *Populus tremuloides*), or *Quercus robur*.

The host cell can additionally be a species of algae, such as a green algae, red algae, glaucophytes, chlorarachniophytes, euglenids, chromista, or dinoflagellates. (See, e.g., Saunders & Warmbrodt, "*Gene Expression in Algae and Fungi, Including Yeast*," (1993), National Agricultural Library, Beltsville, Md.). In certain embodiments, plasmids or plasmid components for use herein include those described in U.S. Patent Pub. No. US 2011/0045563. In some aspects, the host cell is a cyanobacterium, such as cyanobacterium classified into any of the following groups based on morphology: *Chlorococcales, Pleurocapsales, Oscillatoriales, Nostocales,* or *Stigonematales* (See, e.g., Lindberg et al., Metab. Eng., 12(1): 70-79 (2010)). In certain embodiments, plasmids or plasmid components for use herein include those described in U.S. Patent Pub. No.: US 2010/0297749; US 2009/0282545 and PCT Pat. Appl. No. WO 2011/034863.

*E. coli* host cells can be used to express one or more isoprene synthase (which would also include variants), acetoacetyl co-A synthase, MVA pathway enzyme, DXP pathway enzyme, phosphoketolase, and/or a polyprenyl pyrophosphate synthase polypeptides in the compositions and methods described herein. In one aspect, the host cell is a recombinant cell of an *Escherichia coli (E. coli)* strain, or progeny thereof, capable of producing isoprene that expresses one or more nucleic acids encoding isoprene synthase variant, acetoacetyl co-A synthase, MVA pathway enzyme, DXP pathway enzyme, phosphoketolase, and/or IDI polypeptides. The *E. coli* host cells can produce isoprene, in amounts, peak titers, and cell productivities greater than that of the same cells lacking one or more heterologously expressed nucleic acids encoding isoprene synthase, acetoacetyl co-A synthase, MVA pathway enzyme, DXP pathway enzyme, phosphoketolase, and/or IDI polypeptides. In addition, the one or more heterologously expressed nucleic acids encoding isoprene synthase, acetoacetyl co-A synthase, MVA pathway enzyme, DXP pathway enzyme, phosphoketolase, and/or IDI polypeptides in *E. coli* can be chromosomal copies (e.g., integrated into the *E. coli* chromosome). In other aspects, the *E. coli* cells are in culture.

In other aspects, the host cell can be a species of yeast other than *S. cerevisiae* such as, but not limited to, a *Pichia* spp., a *Candida* spp., a *Hansenula* spp., a *Kluyveromyces* spp., a *Kluyveromyces* spp., or a *Schizosaccharomyces* spp. In still other aspects, the host cell can be a species of bacterium including, but not limited to, an *Arthrobacter* spp., a *Zymomonas* spp., a *Brevibacterium* spp., a *Clostridium* spp., an *Aerococcus* spp., a *Bacillus* spp., an *Actinobacillus* spp. (such as, but not limited to, *A. succinogens*), a *Carbobacterium* spp., a *Corynebacterium* spp., an *Enterococcus* spp., an *Erysipelothrix* spp., a *Gemella* spp., a *Geobacillus* spp., a *Globicatella* spp., a *Lactobacillus* spp. (such as, but not limited to, *L. lactis* and *L. rhammosus*), a *Lactococcus* spp., a *Leuconostoc* spp., a *Pediococcus* spp., a *Streptococcus* spp., a *Tetragenococcus* spp., an *Actinobacillus* spp., or a *Vagococcus* spp., In other aspects, the fermenting organism can be a fungus such as, but not limited to, a *Rhizopus* spp.

In other aspects, the host cell can be a lactic acid bacteria, such as those of the genera *Aerococcus, Bacillus, Carbobacterium, Enterococcus, Erysipelothrix, Gemella, Globicatella, Lactobacillus, Lactococcus, Leuconostoc, Pediococcus, Streptococcus, Tetragenococcus* and *Vagococcus*. For example, other bacteria of the genus *Lactobacillus* which may be substituted include, but are not limited to, *L. heiveticus, L. delbrueckii, L. casei, L, acidophilus, L. amylovorus, L. leichmanii* or *L. bulgaricus. L. amylovorus,* and *L. pentosus*.

Additional Host Cell Mutations

The invention also contemplates additional host cell mutations that increase carbon flux through the MVA pathway. By increasing the carbon flow, more isoprene can be produced. The recombinant cells comprising acetoacetyl-CoA synthase as described herein can also be engineered for increased carbon flux towards mevalonate production wherein the activity of one or more enzymes from the group consisting of: (a) citrate synthase, (b) phosphotransacetylase; (c) acetate kinase; (d) lactate dehydrogenase; (e) NADP-dependent malic enzyme; (f) pyruvate dehydrogenase; (g) 6-phosphogluconolactonase; (h) phosphoenolpyruvate carboxylase; (i)

the inhibitor of RssB activity during magnesium starvation protein; (j) the acrA component of the multidrug efflux pump acrAB-TolC; and (k) the fumarate and nitrate reduction sRNA (FNR) is modulated.

Citrate Synthase Pathway

Citrate synthase catalyzes the condensation of oxaloacetate and acetyl-CoA to form citrate, a metabolite of the Tricarboxylic acid (TCA) cycle (Ner, S. et al. Biochemistry 22: 5243-5249 (1983); Bhayana, V. and Duckworth, H., Biochemistry 23: 2900-2905 (1984)). In $E.$ $coli$, this enzyme, encoded by gltA, behaves like a trimer of dimeric subunits. The hexameric form allows the enzyme to be allosterically regulated by NADH. This enzyme has been widely studied (Wiegand, G., and Remington, S. Annual Rev. Biophysics Biophys. Chem. 15: 97-117 (1986); Duckworth et al. Biochem Soc Symp. 54:83-92 (1987); Stockell, D. et al. J. Biol. Chem. 278: 35435-35443 (2003); Maurus, R. et al. Biochemistry. 42:5555-5565 (2003)). To avoid allosteric inhibition by NADH, replacement by or supplementation with the $Bacillus$ $subtilis$ NADH-insensitive citrate synthase has been considered (Underwood et al. Appl. Environ. Microbiol. 68:1071-1081 (2002); Sanchez et al. Met. Eng. 7:229-239 (2005)).

The reaction catalyzed by citrate synthase is directly competing with the thiolase catalyzing the first step of the mevalonate pathway, as they both have acetyl-CoA as a substrate (Hedl et al. J. Bact. 184:2116-2122 (2002)). Therefore, one of skill in the art can modulate citrate synthase expression (e.g., decrease enzyme activity) to allow more carbon to flux into the mevalonate pathway, thereby increasing the eventual production of mevalonate and isoprene. Decrease of citrate synthase activity can be any amount of reduction of specific activity or total activity as compared to when no manipulation has been effectuated. In some instances, the decrease of enzyme activity is decreased by at least about 1%, 2%, 3%, 4%, 5%, 6%, 7%, 8%, 9%, 10%, 15%, 20%, 25%, 30%, 35%, 35%, 40%, 45%, 50%, 55%, 60%, 65%, 70%, 75%, 80%, 85%, 90%, 95%, 96%, 97%, 98%, or 99% or 100%. In some aspects, the activity of citrate synthase is modulated by decreasing the activity of an endogenous citrate synthase gene. This can be accomplished by chromosomal replacement of an endogenous citrate synthase gene with a transgene encoding an NADH-insensitive citrate synthase or by using a transgene encoding an NADH-insensitive citrate synthase that is derived from $Bacillus$ $subtilis$. The activity of citrate synthase can also be modulated (e.g., decreased) by replacing the endogenous citrate synthase gene promoter with a synthetic constitutively low expressing promoter. The gene encoding citrate synthase can also be deleted. The decrease of the activity of citrate synthase can result in more carbon flux into the mevalonate dependent biosynthetic pathway in comparison to microorganisms that do not have decreased expression of citrate synthase.

Pathways Involving Phosphotransacetylase and/or Acetate Kinase

Phosphotransacetylase (encoded in $E.$ $coli$ by (i) (pta) (Shimizu et al. Biochim. Biophys. Acta 191: 550-558 (1969)) or (ii) (eutD) (Bologna et al. J. Microbiology 48:629-636 (2010)) catalyzes the reversible conversion between acetyl-CoA and acetylphosphate (acetyl-P), while acetate kinase (encoded in $E.$ $coli$ by ackA) (Kakuda, H. et al. J. Biochem. 11:916-922 (1994)) uses acetyl-P to form acetate. These genes can be transcribed as an operon in $E.$ $coli$. Together, they catalyze the dissimilation of acetate, with the release of ATP. Thus, one of skill in the art can increase the amount of available acetyl Co-A by attenuating the activity of phosphotransacetylase gene (e.g., the endogenous phosphotransacetylase gene) and/or an acetate kinase gene (e.g., the endogenous acetate kinase gene). In certain embodiments, enhancement is achieved by placing an upregulated promoter upstream of the gene in the chromosome, or to place a copy of the gene behind an adequate promoter on a plasmid. One way of achieving attenuation is by deleting phosphotransacetylase (pta) and/or acetate kinase (ackA). This can be accomplished by replacing one or both genes with a chloramphenicol cassette followed by looping out of the cassette. In some aspects, the activity of acetate kinase is modulated by decreasing the activity of an endogenous acetate kinase. This can be accomplished by replacing the endogenous acetate kinase gene promoter with a synthetic constitutively low expressing promoter. In certain embodiments, the attenuation of the acetate kinase gene disrupts the expression of the phosphotransacetylase (pta) gene. Acetate is produced by $E.$ $coli$ for a variety of reasons (Wolfe, A. Microb. Mol. Biol. Rev. 69:12-50 (2005)). Without being bound by theory, since ackA-pta use acetyl-CoA, deleting those genes might allow carbon not to be diverted into acetate and to increase the yield of mevalonate and/or isoprene.

In some aspects, the recombinant microorganism produces decreased amounts of acetate in comparison to microorganisms that do not have attenuated endogenous phosphotransacetylase gene and/or endogenous acetate kinase gene expression. Decrease in the amount of acetate produced can be measured by routine assays known to one of skill in the art. The amount of acetate reduction is at least about 1%, 2%, 3%, 4%, 5%, 6%, 7%, 8%, 9%, 10%, 15%, 20%, 25%, 30%, 35%, 35%, 40%, 45%, 50%, 55%, 60%, 65%, 70%, 75%, 80%, 85%, 90%, 95%, 96%, 97%, 98%, or 99% as compared when no molecular manipulations are done.

The activity of phosphotransacetylase (pta and/or eutD) can be increased by other molecular manipulations of the enzymes. The increase of enzyme activity can be and increase in any amount of specific activity or total activity as compared to when no manipulation has been effectuated. In some instances, the increase of enzyme activity is increased by at least about 1%, 2%, 3%, 4%, 5%, 6%, 7%, 8%, 9%, 10%, 15%, 20%, 25%, 30%, 35%, 35%, 40%, 45%, 50%, 55%, 60%, 65%, 70%, 75%, 80%, 85%, 90%, 95%, 96%, 97%, 98%, or 99%. In one embodiment the activity of pta is increased by altering the promoter and/or rbs on the chromosome, or by expressing it from a plasmid. In any aspects of the invention, provided herein are recombinant cells comprising one or more heterologously expressed nucleic acids encoding monophosphate decarboxylase and/or isopentenyl kinase polypeptides as disclosed herein and further engineered to increase the activity of phosphotransacetylase (pta and/or eutD). Activity modulation (e.g., increased) of phosphotransacetylase isozymes is also contemplated herein. In any aspects of the invention, provided herein are recombinant cells comprising one or more expressed nucleic acids encoding monophosphate decarboxylase and/or isopentenyl kinase polypeptides as disclosed herein and further engineered to increase the activity of a phosphotransacetylase (pta and/or eutD) isozyme.

The activity of phosphotransacetylase (pta) and/or acetate kinase (ackA) can also be decreased by other molecular manipulation of the enzymes. The decrease of enzyme activity can be any amount of reduction of specific activity or total activity as compared to when no manipulation has been effectuated. In some instances, the decrease of enzyme activity is decreased by at least about 1%, 2%, 3%, 4%, 5%, 6%, 7%, 8%, 9%, 10%, 15%, 20%, 25%, 30%, 35%, 35%, 40%, 45%, 50%, 55%, 60%, 65%, 70%, 75%, 80%, 85%, 90%, 95%, 96%, 97%, 98%, or 99%. In any aspects of the invention, provided herein are recombinant cells comprising one or more heterologously expressed nucleic acids encoding phosphoketolase polypeptides as disclosed herein and further engineered to decrease the activity of acetate kinase (ackA). Activity modulation (e.g., decreased) of acetate kinase isozymes is also contemplated herein. In any aspects of the invention, provided herein are recombinant cells comprising one or more expressed nucleic acids encoding monophosphate decarboxylase and/or isopentenyl kinase polypeptides as disclosed herein and further engineered to decrease the activity of a acetate kinase isozyme.

In some cases, attenuating the activity of the endogenous phosphotransacetylase gene and/or the endogenous acetate kinase gene results in more carbon flux into the mevalonate dependent biosynthetic pathway in comparison to microorganisms that do not have attenuated endogenous phosphotransacetylase gene and/or endogenous acetate kinase gene expression.

Pathways Involving Glyceraldehyde 3-Phosphate

Glyceraldehyde 3-phosphate dehydrogenase (gapA and/or gapB) is a crucial enzyme of glycolysis catalyzes the conversion of glyceraldehyde 3-phosphate into 1,3-biphospho-D-glycerate (Branlant G. and Branlant C. Eur. J. Biochem. 150: 61-66 (1985)).

In certain aspects, recombinant cells comprising one or more expressed nucleic acids encoding monophosphate decarboxylase and/or isopentenyl kinase polypeptides as disclosed herein further comprise one more nucleic acids encoding a phosphoketolase polypeptide. In order to direct carbon towards the phosphoketolase enzyme, glyceraldehyde 3-phosphate dehydrogenase expression can be modulated (e.g., decrease enzyme activity) to allow more carbon to flux towards fructose 6-phosphate and xylulose 5-phosphate, thereby increasing the eventual production of isoprene. Decrease of glyceraldehyde 3-phosphate dehydrogenase activity can be any amount of reduction of specific activity or total activity as compared to when no manipulation has been effectuated. In some instances, the decrease of enzyme activity is decreased by at least about 1%, 2%, 3%, 4%, 5%, 6%, 7%, 8%, 9%, 10%, 15%, 20%, 25%, 30%, 35%, 35%, 40%, 45%, 50%, 55%, 60%, 65%, 70%, 75%, 80%, 85%, 90%, 95%, 96%, 97%, 98%, 99%. Or 100%. In some aspects, the activity of glyceraldehyde 3-phosphate dehydrogenase is modulated by decreasing the activity of an endogenous glyceraldehyde 3-phosphate dehydrogenase. This can be accomplished by replacing the endogenous glyceraldehyde 3-phosphate dehydrogenase gene promoter with a synthetic constitutively low expressing promoter. The gene encoding glyceraldehyde 3-phosphate dehydrogenase can also be deleted. The gene encoding glyceraldehyde 3-phosphate dehydrogenase can also be replaced by a *Bacillus* enzyme catalyzing the same reaction but producing NADPH rather than NADH. The decrease of the activity of glyceraldehyde 3-phosphate dehydrogenase can result in more carbon flux into the mevalonate-dependent biosynthetic pathway in comparison to cells that do not have decreased expression of glyceraldehyde 3-phosphate dehydrogenase. In any aspects of the invention, provided herein are recombinant cells comprising one or more expressed nucleic acids encoding monophosphate decarboxylase and/or isopentenyl kinase polypeptides as disclosed herein and further engineered to decrease the activity of glyceraldehyde 3-phosphate dehydrogenase (gapA and/or gapB). Activity modulation (e.g., decreased) of glyceraldehyde 3-phosphate dehydrogenase isozymes is also contemplated herein. In any aspects of the invention, provided herein are recom binant cells comprising one or more heterologously expressed nucleic acids encoding monophosphate decarboxylase and/or isopentenyl kinase polypeptides as disclosed herein and further engineered to decrease the activity of a glyceraldehyde 3-phosphate dehydrogenase (gapA and/or gapB) isozyme.

Pathways Involving Lactate Dehydrogenase

In *E. coli*, D-Lactate is produced from pyruvate through the enzyme lactate dehydrogenase (ldhA) (Bunch, P. et al. Microbiol. 143:187-195 (1997)). Production of lactate is accompanied with oxidation of NADH, hence lactate is produced when oxygen is limited and cannot accommodate all the reducing equivalents. Thus, production of lactate could be a source for carbon consumption. As such, to improve carbon flow through to mevalonate production (and isoprene production, if desired), one of skill in the art can modulate the activity of lactate dehydrogenase, such as by decreasing the activity of the enzyme.

Accordingly, in one aspect, the activity of lactate dehydrogenase can be modulated by attenuating the activity of an endogenous lactate dehydrogenase gene. Such attenuation can be achieved by deletion of the endogenous lactate dehydrogenase gene. Other ways of attenuating the activity of lactate dehydrogenase gene known to one of skill in the art may also be used. By manipulating the pathway that involves lactate dehydrogenase, the recombinant microorganism produces decreased amounts of lactate in comparison to microorganisms that do not have attenuated endogenous lactate dehydrogenase gene expression. Decrease in the amount of lactate produced can be measured by routine assays known to one of skill in the art. The amount of lactate reduction is at least about 1%, 2%, 3%, 4%, 5%, 6%, 7%, 8%, 9%, 10%, 15%, 20%, 25%, 30%, 35%, 35%, 40%, 45%, 50%, 55%, 60%, 65%, 70%, 75%, 80%, 85%, 90%, 95%, 96%, 97%, 98%, or 99% as compared when no molecular manipulations are done.

The activity of lactate dehydrogenase can also be decreased by other molecular manipulations of the enzyme. The decrease of enzyme activity can be any amount of reduction of specific activity or total activity as compared to when no manipulation has been effectuated. In some instances, the decrease of enzyme activity is decreased by at least about 1%, 2%, 3%, 4%, 5%, 6%, 7%, 8%, 9%, 10%, 15%, 20%, 25%, 30%, 35%, 35%, 40%, 45%, 50%, 55%, 60%, 65%, 70%, 75%, 80%, 85%, 90%, 95%, 96%, 97%, 98%, or 99%.

Accordingly, in some cases, attenuation of the activity of the endogenous lactate dehydrogenase gene results in more carbon flux into the mevalonate dependent biosynthetic pathway in comparison to microorganisms that do not have attenuated endogenous lactate dehydrogenase gene expression.

Pathways Involving Malic Enzyme

Malic enzyme (in *E. coli* sfcA and maeB) is an anaplerotic enzyme that catalyzes the conversion of malate into pyruvate (using NAD+ or NADP+) by the equation below:

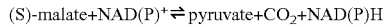

$$(S)\text{-malate} + NAD(P)^+ \rightleftharpoons pyruvate + CO_2 + NAD(P)H$$

Thus, the two substrates of this enzyme are (S)-malate and $NAD(P)^+$, whereas its 3 products are pyruvate, $CO_2$, and NADPH.

Expression of the NADP-dependent malic enzyme (maeB) (Iwikura, M. et al. J. Biochem. 85: 1355-1365 (1979)) can help increase mevalonate and/or isoprene yield by 1) bringing carbon from the TCA cycle back to pyruvate, direct precursor of acetyl-CoA, itself direct precursor of the mevalonate pathway and 2) producing extra NADPH which could be used in the HMG-CoA reductase reaction (Oh, M. K. et al. J. Biol. Chem. 277: 13175-13183 (2002); Bologna, F. et al. J. Bact. 189:5937-5946 (2007)).

As such, more starting substrate (pyruvate or acetyl-CoA) for the downstream production of mevalonate and/or isoprene can be achieved by modulating, such as increasing, the activity and/or expression of malic enzyme. The NADP-dependent malic enzyme gene can be an endogenous gene. One non-limiting way to accomplish this is by replacing the endogenous NADP-dependent malic enzyme gene promoter with a synthetic constitutively expressing promoter. Another non-limiting way to increase enzyme activity is by using one or more heterologous nucleic acids encoding an NADP-dependent malic enzyme polypeptide. One of skill in the art can monitor the expression of maeB RNA during fermentation or culturing using readily available molecular biology techniques.

Accordingly, in some embodiments, the recombinant microorganism produces increased amounts of pyruvate in comparison to microorganisms that do not have increased expression of an NADP-dependent malic enzyme gene. In some aspects, increasing the activity of an NADP-dependent malic enzyme gene results in more carbon flux into the mevalonate dependent biosynthetic pathway in comparison to microorganisms that do not have increased NADP-dependent malic enzyme gene expression.

Increase in the amount of pyruvate produced can be measured by routine assays known to one of skill in the art. The amount of pyruvate increase can be at least about 1%, 2%, 3%, 4%, 5%, 6%, 7%, 8%, 9%, 10%, 15%, 20%, 25%, 30%, 35%, 35%, 40%, 45%, 50%, 55%, 60%, 65%, 70%, 75%, 80%, 85%, 90%, 95%, 96%, 97%, 98%, or 99% as compared when no molecular manipulations are done.

The activity of malic enzyme can also be increased by other molecular manipulations of the enzyme. The increase of enzyme activity can be any amount of increase of specific activity or total activity as compared to when no manipulation has been effectuated. In some instances, the increase of enzyme activity is at least about 1%, 2%, 3%, 4%, 5%, 6%, 7%, 8%, 9%, 10%, 15%, 20%, 25%, 30%, 35%, 35%, 40%, 45%, 50%, 55%, 60%, 65%, 70%, 75%, 80%, 85%, 90%, 95%, 96%, 97%, 98%, or 99%.

Pathways Involving Pyruvate Dehydrogenase Complex

The pyruvate dehydrogenase complex, which catalyzes the decarboxylation of pyruvate into acetyl-CoA, is composed of the proteins encoded by the genes aceE, aceF and lpdA. Transcription of those genes is regulated by several regulators. Thus, one of skill in the art can increase acetyl-CoA by modulating the activity of the pyruvate dehydrogenase complex. Modulation can be to increase the activity and/or expression (e.g., constant expression) of the pyruvate dehydrogenase complex. This can be accomplished by different ways, for example, by placing a strong constitutive promoter, like PL.6 (aattcatataaaaaacatacagataaccatctgcggtgataaattatctctggcg-gtgttgacataaataccactggcggtgatactgagcacatca gcaggacgcactgaccaccatgaaggtg (SEQ ID NO:3) lambda promoter, GenBank NC_001416), in front of the operon or using one or more synthetic constitutively expressing promoters.

Accordingly, in one aspect, the activity of pyruvate dehydrogenase is modulated by increasing the activity of one or more genes of the pyruvate dehydrogenase complex consisting of (a) pyruvate dehydrogenase (E1), (b) dihydrolipoyl transacetylase, and (c) dihydrolipoyl dehydrogenase. It is understood that any one, two or three of these genes can be manipulated for increasing activity of pyruvate dehydrogenase. In another aspect, the activity of the pyruvate dehydrogenase complex can be modulated by attenuating the activity of an endogenous pyruvate dehydrogenase complex repressor gene, further detailed below. The activity of an endogenous pyruvate dehydrogenase complex repressor can be attenuated by deletion of the endogenous pyruvate dehydrogenase complex repressor gene.

In some cases, one or more genes of the pyruvate dehydrogenase complex are endogenous genes. Another way to increase the activity of the pyruvate dehydrogenase complex is by introducing into the microorganism one or more heterologous nucleic acids encoding one or more polypeptides from the group consisting of (a) pyruvate dehydrogenase (E1), (b) dihydrolipoyl transacetylase, and (c) dihydrolipoyl dehydrogenase.

By using any of these methods, the recombinant microorganism can produce increased amounts of acetyl Co-A in comparison to microorganisms wherein the activity of pyruvate dehydrogenase is not modulated. Modulating the activity of pyruvate dehydrogenase can result in more carbon flux into the mevalonate dependent biosynthetic pathway in comparison to microorganisms that do not have modulated pyruvate dehydrogenase expression.

Combinations of Mutations

It is understood that for any of the enzymes and/or enzyme pathways described herein, molecular manipulations that modulate any combination (two, three, four, five or six) of the enzymes and/or enzyme pathways described herein is expressly contemplated. For ease of the recitation of the combinations, citrate synthase (gltA) is designated as A, phosphotransacetylase (ptaB) is designated as B, acetate kinase (ackA) is designated as C, lactate dehydrogenase (ldhA) is designated as D, malic enzyme (sfcA or maeB) is designated as E, pyruvate decarboxylase (aceE, aceF, and/or lpdA) is designated as F, 6-phosphogluconolactonase (ybhE) is designated as G, and phosphoenolpyruvate carboxylase (ppl) is designated as H. As discussed above, aceE, aceF, and/or lpdA enzymes of the pyruvate decarboxylase complex can be used singly, or two of three enzymes, or three of three enzymes for increasing pyruvate decarboxylase activity.

Accordingly, for combinations of any two of the enzymes A-H, non-limiting combinations that can be used are: AB, AC, AD, AE, AF, AG, AH, BC, BD, BE, BF, BG, BH, CD, CE, CF, CG, CH, DE, DF, DG, DH, EF, EG, EH, and GH. For combinations of any three of the enzymes A-H, non-limiting combinations that can be used are: ABC, ABD, ABE, ABF, ABG, ABH, BCD, BCE, BCF, BCG, BCH, CDE, CDF, CDG, CDH, DEF, DEH, ACD, ACE, ACF, ACG, ACH, ADE, ADF, ADG, ADH, AEF, AEG, AEH, BDE, BDF, BDG, BDH, BEF, BEG, BEH, CEF, CEG, CEH, CFG, CFH, and CGH. For combinations of any four of the enzymes A-H, non-limiting combinations that can be used are: ABCD, ABCE, ABCF, ABCG, ABCH, ABDE, ABDF, ABDG, ABDH, ABEF, ABEG, ABEH, BCDE, BCDF, BCDG, BCDH, CDEF, CDEG, CDEH, ACDE, ACDF, ACDG, ACDH, ACEF, ACEG, ACEH, BCEF, BDEF, BGEF, BHEF, ADEF. For combinations of any five of the enzymes A-H, non-limiting combinations that can be used are: ABCDE, ABCDF, ABCDG, ABCDH, ABDEF, ABDEG, ABDEH, BCDEF, BCDEG, BCDEH, ACDEF, ACDEG, ACEDH, ABCEF, ABCEG, and ABCEH. For combinations of any six of the enzymes A-H, non-limiting combinations that can be used are: ABCDEF, ABCDEG, ABCDEH, BCDEFG, BCDEFH, and CDEFGH. For combinations of any seven of the enzymes A-H, non-limiting combinations that can be used are: ABCDEFG, ABCDEFH, BCDEFGH. In another aspect, all eight enzyme combinations are used ABCDEFGH.

Accordingly, the recombinant microorganism as described herein can achieve increased mevalonate production that is increased compared to microorganisms that are not grown under conditions of tri-carboxylic acid (TCA) cycle activity, wherein metabolic carbon flux in the recombinant microorganism is directed towards mevalonate production by modulating the activity of one or more enzymes from the group consisting of (a) citrate synthase, (b) phosphotransacetylase; (c) acetate kinase; (d) lactate dehydrogenase; (e) NADP-dependent malic enzyme; (f) pyruvate dehydrogenase; (g) 6-phosphogluconolactonase; and (h) phosphoenolpyruvate carboxylase.

Other Regulators and Factors for Increased Isoprene Production

Other molecular manipulations can be used to increase the flow of carbon towards isoprene production. One method is to reduce, decrease or eliminate the effects of negative regulators for pathways that feed into the mevalonate pathway. For example, in some cases, the genes aceEF-lpdA are in an operon, with a fourth gene upstream pdhR. pdhR is a negative regulator of the transcription of its operon. In the absence of pyruvate, it binds its target promoter and represses transcription. It also regulates ndh and cyoABCD in the same way (Ogasawara, H. et al. J. Bact. 189:5534-5541 (2007)). In one aspect, deletion of pdhR regulator can improve the supply of pyruvate, and hence the production mevalonate and/or isoprene.

In other embodiments, any of the resultant strains described above can be further engineered to modulate the activity of the Entner-Doudoroff pathway. The gene coding for phosphogluconate dehydratase or aldolase can be attenuated or deleted. In other embodiments, any of the resultant strains described above may also be engineered to decrease or remove the activity of acetate kinase or citrate synthase. In other embodiments, any of the strains the resultant strain may also be engineered to decrease or remove the activity of phosphofructokinase. In other embodiments, any of the resultant strains described above may also be engineered to modulate the activity of glyceraldehyde-3-phosphate dehydrogenase. The activity of glyceraldehyde-3-phosphate dehydrogenase can be modulated by decreasing its activity. In other embodiments, the enzymes from the non-oxidative branch of the pentose phosphate pathway, such as transketolase, transaldolase, ribulose-5-phosphate-epimerase and (or) ribose-5-phosphate epimerase can be overexpressed.

In other aspects, the host cells can be further engineered to increase intracellular acetyl-phospate concentrations by introducing heterologous nucleic acids encoding sedoheptulose-1,7-bisphosphatase/fructose-1,6-bisphosphate aldolase and sedoheptulose-1,7-bisphosphatase/fructose-1,6-bisphosphate phosphatase. In certain embodiments, the host cells having these molecular manipulations can be combined with attenuated or deleted transaldolase (talB) and phosphofructokinase (pfkA and/or pfkB) genes, thereby allowing faster conversion of erythrose 4-phosphate, dihydroxyacetone phosphate, and glyceraldehyde 3-phosphate into sedoheptulose 7-phosphate and fructose 1-phosphate.

In other aspects, the introduction of 6-phosphogluconolactonase (PGL) into microorganisms (such as various E. coli strains) which lack PGL can be used to improve production of mevalonate and/or isoprene. PGL may be introduced using chromosomal integration or extrachromosomal vehicles, such as plasmids. In other aspects, PGL may be deleted from the genome of microorganisms (such as various E. coli strains) which express an endogenous PGL to improve production of mevalonate and/or isoprene. In some aspects, deletion of PGL results in any of about 10%, 20%, 30%, 40%, 50%, 60%, 70%, 80%, 90%, or 100%, inclusive, including any values in between these percentages, higher percent yield of isoprene in comparison to microorganisms that express PGL. In other aspects, deletion of PGL results in any of about 10%, 20%, 30%, 40%, 50%, 60%, 70%, 80%, 90%, or 100%, inclusive, including any values in between these percentages, higher instantaneous percent yield of isoprene in comparison to microorganisms that express PGL. In other aspects, deletion of PGL results in any of about 10%, 20%, 30%, 40%, 50%, 60%, 70%, 80%, 90%, or 100%, inclusive, including any values in between these percentages, higher cell productivity index for isoprene in comparison to microorganisms that express PGL. In other aspects, deletion of PGL results in any of about 10%, 20%, 30%, 40%, 50%, 60%, 70%, 80%, 90%, or 100%, inclusive, including any values in between these percentages, higher volumetric productivity of isoprene in comparison to microorganisms that express PGL. In other aspects, deletion of PGL results in any of about 10%, 20%, 30%, 40%, 50%, 60%, 70%, 80%, 90%, or 100%, inclusive, including any values in between these percentages, higher peak specific productivity of isoprene in comparison to microorganisms that express PGL. In some aspects the deletion of PGL results in peak specific productivity being maintained for a longer period of time in comparison to microorganisms that express PGL.

Exemplary Transformation Methods

Isoprene synthase, DXS, IDI, and/or MVA pathway nucleic acids or vectors containing them can be inserted into a host cell (e.g., a plant cell, a fungal cell, a yeast cell, or a bacterial cell described herein) using standard techniques for expression of the encoded isoprene synthase, DXS, IDI, and/or MVA pathway polypeptide. Introduction of a DNA construct or vector into a host cell can be performed using techniques such as transformation, electroporation, nuclear microinjection, transduction, transfection (e.g., lipofection mediated or DEAE-Dextrin mediated transfection or transfection using a recombinant phage virus), incubation with calcium phosphate DNA precipitate, high velocity bombardment with DNA-coated microprojectiles, and protoplast fusion. General transformation techniques are known in the art (see, e.g., Current Protocols in Molecular Biology F. M. Ausubel et al. (eds) Chapter 9, (1987); Sambrook et al., Molecular Cloning: A Laboratory Manual, 3rd ed., Cold Spring Harbor, (2001); and Campbell et al., Curr Genet, 16:53-56, (1989), which are each hereby incorporated by reference in their entireties, particularly with respect to transformation methods). The introduced nucleic acids may be integrated into chromosomal DNA or maintained as extrachromosomal replicating sequences. Transformants can be selected by any method known in the art. Suitable methods for selecting transformants are described in International Publication No. WO 2009/076676, U.S. Patent Publ. No. 2009/0203102, WO 2010/003007, US Publ. No. 2010/0048964, WO 2009/132220, and US Publ. No. 2010/0003716.

Other exemplary transformation methods that can be used are described in US Pub. 2009/0203102, WO 2009/076676, WO 2010/003007, WO 2009/132220, WO 2010/031062, WO 2010/031068, WO 2010/031076, WO 2010/031077, and WO 2010/031079.

Exemplary Cell Culture Media

As used herein, the terms "minimal medium" or "minimal media" refer to growth media containing the minimum nutrients possible for cell growth, generally, but not always, without the presence of one or more amino acids (e.g., 1, 2, 3, 4, 5, 6, 7, 8, 9, 10, or more amino acids). Minimal medium typically contains: (1) a carbon source for host cell (e.g., bacterial cell) growth; (2) various salts, which can vary among host cell species and growing conditions; and (3) water. The carbon source can vary significantly, from simple sugars like glucose to more complex hydrolysates of other biomass, such as yeast extract, as discussed in more detail below. The salts generally provide essential elements such as magnesium, nitrogen, phosphorus, and sulfur to allow the cells to synthesize proteins and nucleic acids. Minimal medium can also be supplemented with selective agents, such as antibiotics, to select for the maintenance of certain plasmids and the like. For example, if a microorganism is resistant to a certain antibiotic, such as ampicillin or tetracycline, then that antibiotic can be added to the medium in order to prevent cells lacking the resistance from growing. Medium can be supplemented with other compounds as necessary to select for desired physiological or biochemical characteristics, such as particular amino acids and the like.

Any minimal medium formulation can be used to cultivate the host cells. Exemplary minimal medium formulations include, for example, M9 minimal medium and TM3 minimal medium. Each liter of M9 minimal medium contains (1) 200 ml sterile M9 salts (64 g $Na_2HPO_4$-$7H_2O$, 15 g $KH_2PO_4$, 2.5 g NaCl, and 5.0 g $NH_4Cl$ per liter); (2) 2 ml of 1 M $MgSO_4$ (sterile); (3) 20 ml of 20% (w/v) glucose (or other carbon source); and (4) 100 µl of 1 M $CaCl_2$ (sterile). Each liter of TM3 minimal medium contains (1) 13.6 g $K_2HPO_4$; (2) 13.6 g $KH_2PO_4$; (3) 2 g $MgSO_4$*$7H_2O$; (4) 2 g Citric Acid Monohydrate; (5) 0.3 g Ferric Ammonium Citrate; (6) 3.2 g $(NH_4)_2SO_4$; (7) 0.2 g yeast extract; and (8) 1 ml of 1000× Trace Elements solution; pH is adjusted to ~6.8 and the solution is filter sterilized. Each liter of 1000× Trace Elements contains: (1) 40 g Citric Acid Monohydrate; (2) 30 g $MnSO_4$*$H_2O$; (3) 10 g NaCl; (4) 1 g $FeSO_4$*$7H_2O$; (4)1 g $CoCl_2$*$6H_2O$; (5) 1 g $ZnSO_4$*$7H_2O$; (6) 100 mg $CuSO_4$*$5H_2O$; (7) 100 mg $H_3BO_3$; and (8) 100 mg $NaMoO_4$*$2H_2O$; pH is adjusted to ~3.0.

An additional exemplary minimal media includes (1) potassium phosphate $K_2HPO_4$, (2) Magnesium Sulfate $MgSO_4$*$7H_2O$, (3) citric acid monohydrate $C_6H_8O_7$*$H_2O$, (4) ferric ammonium citrate $NH_4FeC_6H_5O_7$, (5) yeast extract (from biospringer), (6) 1000× Modified Trace Metal Solution, (7) sulfuric acid 50% w/v, (8) foamblast 882 (Emerald Performance Materials), and (9) Macro Salts Solution 3.36 ml. All of the components are added together and dissolved in deionized $H_2O$ and then heat sterilized. Following cooling to room temperature, the pH is adjusted to 7.0 with ammonium hydroxide (28%) and q.s. to volume. Vitamin Solution and spectinomycin are added after sterilization and pH adjustment.

Any carbon source can be used to cultivate the host cells. The term "carbon source" refers to one or more carbon-containing compounds capable of being metabolized by a host cell or organism. For example, the cell medium used to cultivate the host cells may include any carbon source suitable for maintaining the viability or growing the host cells.

In some embodiments, the carbon source is a carbohydrate (such as monosaccharide, disaccharide, oligosaccharide, or polysaccharides), invert sugar (e.g., enzymatically treated sucrose syrup), glycerol, glycerine (e.g., a glycerine byproduct of a biodiesel or soap-making process), dihydroxyacetone, one-carbon source, fatty acid (e.g., a saturated fatty acid, unsaturated fatty acid, or polyunsaturated fatty acid), lipid, phospholipid, glycerolipid, monoglyceride, diglyceride, triglyceride, polypeptide (e.g., a microbial or plant protein or peptide), renewable carbon source (e.g., a biomass carbon source such as a hydrolyzed biomass carbon source; beet sugar or cane sugar molasses), yeast extract, component from a yeast extract, polymer, acid, alcohol, aldehyde, ketone, amino acid, succinate, lactate, acetate, ethanol, or any combination of two or more of the foregoing. In some embodiments, the carbon source is a product of photosynthesis, including, but not limited to, glucose.

Exemplary monosaccharides include glucose and fructose; exemplary oligosaccharides include lactose and sucrose, and exemplary polysaccharides include starch and cellulose. Exemplary carbohydrates include C6 sugars (e.g., fructose, mannose, galactose, or glucose) and C5 sugars (e.g., xylose or arabinose). In some embodiments, the cell medium includes a carbohydrate as well as a carbon source other than a carbohydrate (e.g., glycerol, glycerine, dihydroxyacetone, one-carbon source, fatty acid, lipid, phospholipid, glycerolipid, monoglyceride, diglyceride, triglyceride, renewable carbon source, or a component from a yeast extract). In some embodiments, the cell medium includes a carbohydrate as well as a polypeptide (e.g., a microbial or plant protein or peptide). In some embodiments, the microbial polypeptide is a polypeptide from yeast or bacteria. In some embodiments, the plant polypeptide is a polypeptide from soy, corn, canola, jatropha, palm, peanut, sunflower, coconut, mustard, rapeseed, cottonseed, palm kernel, olive, safflower, sesame, or linseed.

In some embodiments, the concentration of the carbohydrate is at least or about 5 grams per liter of broth (g/L, wherein the volume of broth includes both the volume of the cell medium and the volume of the cells), such as at least or about 10, 15, 20, 30, 40, 50, 60, 80, 100, 150, 200, 300, 400, or more g/L. In some embodiments, the concentration of the carbohydrate is between about 50 and about 400 g/L, such as between about 100 and about 360 g/L, between about 120 and about 360 g/L, or between about 200 and about 300 g/L. In some embodiments, this concentration of carbohydrate includes the total amount of carbohydrate that is added before and/or during the culturing of the host cells.

Exemplary lipids are any substance containing one or more fatty acids that are C4 and above fatty acids that are saturated, unsaturated, or branched.

Exemplary fatty acids include compounds of the formula R—COOH, where "R" is a hydrocarbon. Exemplary unsaturated fatty acids include compounds where "R" includes at least one carbon-carbon double bond. Exemplary unsaturated fatty acids include, but are not limited to, oleic acid, vaccenic acid, linoleic acid, palmitelaidic acid, and arachidonic acid. Exemplary polyunsaturated fatty acids include compounds where "R" includes a plurality of carbon-carbon double bonds. Exemplary saturated fatty acids include compounds where "R" is a saturated aliphatic group. In some embodiments, the carbon source includes one or more C12-C22 fatty acids, such as a C12 saturated fatty acid, a C14 saturated fatty acid, a C16 saturated fatty acid, a C18 saturated fatty acid, a C20 saturated fatty acid, or a C22 saturated fatty acid. In an exemplary embodiment, the fatty acid is palmitic acid. In some embodiments, the carbon source is a salt of a fatty acid (e.g., an unsaturated fatty acid), a derivative of a fatty acid (e.g., an unsaturated fatty acid), or a salt of a derivative of fatty acid (e.g., an unsaturated fatty acid). Suitable salts include, but are not limited to, lithium salts, potassium salts, sodium salts, and the like. Di- and triglycerols are fatty acid esters of glycerol.

In some embodiments, the concentration of the lipid, fatty acid, monoglyceride, diglyceride, or triglyceride is at least or about 1 gram per liter of broth (g/L, wherein the volume of broth includes both the volume of the cell medium and the volume of the cells), such as at least or about 5, 10, 15, 20, 30, 40, 50, 60, 80, 100, 150, 200, 300, 400, or more g/L. In some embodiments, the concentration of the lipid, fatty acid, monoglyceride, diglyceride, or triglyceride is between about 10 and about 400 g/L, such as between about 25 and about 300 g/L, between about 60 and about 180 g/L, or between about 75 and about 150 g/L. In some embodiments, the concentration includes the total amount of the lipid, fatty acid, monoglyceride, diglyceride, or triglyceride that is added before and/or during the culturing of the host cells. In some embodiments, the carbon source includes both (i) a lipid, fatty acid, monoglyceride, diglyceride, or triglyceride and (ii) a carbohydrate, such as glucose. In some embodiments, the ratio of the lipid, fatty acid, monoglyceride, diglyceride, or triglyceride to the carbohydrate is about 1:1 on a carbon basis (i.e., one carbon in the lipid, fatty acid, monoglyceride, diglyceride, or triglyceride per carbohydrate carbon). In particular embodiments, the amount of the lipid, fatty acid, monoglyceride, diglyceride, or triglyceride is between about 60 and 180 g/L, and the amount of the carbohydrate is between about 120 and 360 g/L.

Exemplary microbial polypeptide carbon sources include one or more polypeptides from yeast or bacteria. Exemplary plant polypeptide carbon sources include one or more polypeptides from soy, corn, canola, jatropha, palm, peanut, sunflower, coconut, mustard, rapeseed, cottonseed, palm kernel, olive, safflower, sesame, or linseed.

Exemplary renewable carbon sources include cheese whey permeate, cornsteep liquor, sugar beet molasses, barley malt, and components from any of the foregoing. Exemplary renewable carbon sources also include glucose, hexose, pentose and xylose present in biomass, such as corn, switchgrass, sugar cane, cell waste of fermentation processes, and protein by-product from the milling of soy, corn, or wheat. In some embodiments, the biomass carbon source is a lignocellulosic, hemicellulosic, or cellulosic material such as, but are not limited to, a grass, wheat, wheat straw, bagasse, sugar cane bagasse, soft wood pulp, corn, corn cob or husk, corn kernel, fiber from corn kernels, corn stover, switch grass, rice hull product, or a by-product from wet or dry milling of grains (e.g., corn, sorghum, rye, triticate, barley, wheat, and/or distillers grains). Exemplary cellulosic materials include wood, paper and pulp waste, herbaceous plants, and fruit pulp. In some embodiments, the carbon source includes any plant part, such as stems, grains, roots, or tubers. In some embodiments, all or part of any of the following plants are used as a carbon source: corn, wheat, rye, sorghum, triticate, rice, millet, barley, cassava, legumes, such as beans and peas, potatoes, sweet potatoes, bananas, sugarcane, and/or tapioca. In some embodiments, the carbon source is a biomass hydrolysate, such as a biomass hydrolysate that includes both xylose and glucose or that includes both sucrose and glucose.

In some embodiments, the renewable carbon source (such as biomass) is pretreated before it is added to the cell culture medium. In some embodiments, the pretreatment includes enzymatic pretreatment, chemical pretreatment, or a combination of both enzymatic and chemical pretreatment (see, for example, Farzaneh et al., Bioresource Technology 96 (18): 2014-2018, (2005); U.S. Pat. No. 6,176,176; U.S. Pat. No. 6,106,888). In some embodiments, the renewable carbon source is partially or completely hydrolyzed before it is added to the cell culture medium.

In some embodiments, the renewable carbon source (such as corn stover) undergoes ammonia fiber expansion (AFEX) pretreatment before it is added to the cell culture medium (see, for example, Farzaneh et al., Bioresource Technology 96 (18): 2014-2018, (2005)). During AFEX pretreatment, a renewable carbon source is treated with liquid anhydrous ammonia at moderate temperatures (such as about 60 to about 100° C.) and high pressure (such as about 250 to about 300 psi) for about 5 minutes. Then, the pressure is rapidly released. In this process, the combined chemical and physical effects of lignin solubilization, hemicellulose hydrolysis, cellulose decrystallization, and increased surface area enables near complete enzymatic conversion of cellulose and hemicellulose to fermentable sugars. AFEX pretreatment has the advantage that nearly all of the ammonia can be recovered and reused, while the remaining serves as nitrogen source for microbes in downstream processes. Also, a wash stream is not required for AFEX pretreatment. Thus, dry matter recovery following the AFEX treatment is essentially 100%. AFEX is basically a dry-to-dry process. The treated renewable carbon source is stable for long periods and can be fed at very high solid loadings in enzymatic hydrolysis or fermentation processes. Cellulose and hemicellulose are well preserved in the AFEX process, with little or no degradation. There is no need for neutralization prior to the enzymatic hydrolysis of a renewable carbon source that has undergone AFEX pretreatment. Enzymatic hydrolysis of AFEX-treated carbon sources produces clean sugar streams for subsequent fermentation use.

In some embodiments, the concentration of the carbon source (e.g., a renewable carbon source) is equivalent to at least or about 0.1, 0.5, 1, 1.5 2, 3, 4, 5, 10, 15, 20, 30, 40, or 50% glucose (w/v). The equivalent amount of glucose can be determined by using standard HPLC methods with glucose as a reference to measure the amount of glucose generated from the carbon source. In some embodiments, the concentration of the carbon source (e.g., a renewable carbon source) is equivalent to between about 0.1 and about 20% glucose, such as between about 0.1 and about 10% glucose, between about 0.5 and about 10% glucose, between about 1 and about 10% glucose, between about 1 and about 5% glucose, or between about 1 and about 2% glucose.

In some embodiments, the carbon source includes yeast extract or one or more components of yeast extract. In some aspects, the concentration of yeast extract is 0.1% (w/v), 0.09% (w/v), 0.08% (w/v), 0.07% (w/v), 0.06% (w/v), 0.05% (w/v), 0.04% (w/v), 0.03% (w/v), 0.02% (w/v), or 0.01% (w/v) yeast extract. In some embodiments, the concentration of yeast extract is at least 1 gram of yeast extract per liter of broth (g/L, wherein the volume of broth includes both the volume of the cell medium and the volume of the cells), such at least or about 5, 10, 15, 20, 30, 40, 50, 60, 80, 100, 150, 200, 300, or more g/L. In some embodiments, the concentration of yeast extract is between about 1 and about 300 g/L, such as between about 1 and about 200 g/L, between about 5 and about 200 g/L, between about 5 and about 100 g/L, or between about 5 and about 60 g/L. In some embodiments, the concentration includes the total amount of yeast extract that is added before and/or during the culturing of the host cells. In some embodiments, the carbon source includes both yeast extract (or one or more components thereof) and another carbon source, such as glucose. In some embodiments, the ratio of yeast extract to the other carbon source is about 1:5, about 1:10, or about 1:20 (w/w).

Additionally the carbon source may also be one-carbon substrates such as carbon dioxide, or methanol. Glycerol production from single carbon sources (e.g., methanol, formaldehyde, or formate) has been reported in methylotrophic yeasts (Yamada et al., Agric. Biol. Chem., 53(2):541-543, (1989)) and in bacteria (Hunter et. al., Biochemistry, 24:4148-4155, (1985)). These organisms can assimilate single carbon compounds, ranging in oxidation state from methane to formate, and produce glycerol. The pathway of carbon assimilation can be through ribulose monophosphate, through serine, or through xylulose-momophosphate (Gottschalk, Bacterial Metabolism, Second Edition, Springer-Verlag: New York, (1986), which is hereby incorporated by reference in its entirety, particularly with respect to carbon sources). The ribulose monophosphate pathway involves the condensation of formate with ribulose-5-phosphate to form a six carbon sugar that becomes fructose and eventually the three carbon product glyceraldehyde-3-phosphate. Likewise, the serine pathway assimilates the one-carbon compound into the glycolytic pathway via methylenetetrahydrofolate.

In addition to one and two carbon substrates, methylotrophic organisms are also known to utilize a number of other carbon containing compounds such as methylamine, glucosamine and a variety of amino acids for metabolic activity. For example, methylotrophic yeast is known to utilize the carbon from methylamine to form trehalose or glycerol (Bellion et al., Microb. Growth Cl Compd., Int. Symp., 7th ed., 415-432., Murrell et al. (eds), Intercept, Andover, UK, (1993)). Similarly, various species of Candida metabolize alanine or oleic acid (Sulter et al., Arch. Microbiol. 153(5), 485-9, (1990)).

In some embodiments, cells are cultured in a standard medium containing physiological salts and nutrients (see, e.g., Pourquie, J. et al., Biochemistry and Genetics of Cellulose Degradation, Aubert et al. (eds), Academic Press, pp. 71-86, (1988); and Ilmen et al., Appl. Environ. Microbiol. 63:1298-1306, (1997)). Exemplary growth media are common commercially prepared media such as Luria Bertani (LB) broth, Sabouraud Dextrose (SD) broth, or Yeast medium (YM) broth. One skilled in the art of microbiology or fermentation science would know other defined or synthetic growth media that may also be used, and the appropriate medium for growth of particular host cells.

In some aspects, the cells described herein are capable of using syngas as a source of energy and/or carbon. In some embodiments, the syngas includes at least carbon monoxide and hydrogen. In some embodiments, the syngas further additionally includes one or more of carbon dioxide, water, or nitrogen. In some embodiments, the molar ratio of hydrogen to carbon monoxide in the syngas is 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 3.0, 4.0, 5.0, or 10.0. In some embodiments, the syngas comprises 10, 20, 30, 40, 50, 60, 70, 80, or 90% by volume carbon monoxide. In some embodiments, the syngas comprises 10, 20, 30, 40, 50, 60, 70, 80, or 90% by volume hydrogen. In some embodiments, the syngas comprises 10, 20, 30, 40, 50, 60, 70, 80, or 90% by volume carbon dioxide. In some embodiments, the syngas comprises 10, 20, 30, 40, 50, 60, 70, 80, or 90% by volume water. In some embodiments, the syngas comprises 10, 20, 30, 40, 50, 60, 70, 80, or 90% by volume nitrogen.

Synthesis gas may be derived from natural or synthetic sources. The source from which the syngas is derived is referred to as a "feedstock." In some embodiments, the syngas is derived from biomass (e.g., wood, switch grass, agriculture waste, municipal waste) or carbohydrates (e.g., sugars). In other embodiments, the syngas is derived from coal, petroleum, kerogen, tar sands, oil shale, or natural gas. In other embodiments, the syngas is derived from rubber, such as from rubber tires.

Syngas can be derived from a feedstock by a variety of processes, including methane reforming, coal liquefaction, co-firing, fermentative reactions, enzymatic reactions, and biomass gasification. Biomass gasification is accomplished by subjecting biomass to partial oxidation in a reactor at temperatures above about 700° C. in the presence of less than a stoichiometric amount of oxygen. The oxygen is introduced into the bioreactor in the form of air, pure oxygen, or steam. Gasification can occur in three main steps: 1) initial heating to dry out any moisture embedded in the biomass; 2) pyrolysis, in which the biomass is heated to 300-500° C. in the absence of oxidizing agents to yield gas, tars, oils and solid char residue; and 3) gasification of solid char, tars and gas to yield the primary components of syngas. Co-firing is accomplished by gasification of a coal/biomass mixture. The composition of the syngas, such as the identity and molar ratios of the components of the syngas, can vary depending on the feedstock from which it is derived and the method by which the feedstock is converted to syngas.

Synthesis gas can contain impurities, the nature and amount of which vary according to both the feedstock and the process used in production. Fermentations may be tolerant to some impurities, but there remains the need to remove from the syngas materials such as tars and particulates that might foul the fermentor and associated equipment. It is also advisable to remove compounds that might contaminate the isoprene product such as volatile organic compounds, acid gases, methane, benzene, toluene, ethylbenzene, xylenes, $H_2S$, COS, $CS_2$, HCl, $O_3$, organosulfur compounds, ammonia, nitrogen oxides, nitrogen-containing organic compounds, and heavy metal vapors. Removal of impurities from syngas can be achieved by one of several means, including gas scrubbing, treatment with solid-phase adsorbents, and purification using gas-permeable membranes.

In addition to an appropriate carbon source, the cell medium desirably contains suitable minerals, salts, cofactors, buffers, and other components known to those skilled in the art suitable for the growth of the cultures or the enhancement of isoprene production (see, for example, WO 2004/033646 and references cited therein and WO 96/35796 and references cited therein). In some embodiments where an isoprene synthase, DXS, IDI, and/or MVA pathway nucleic acid is under the control of an inducible promoter, the inducing agent (e.g., a sugar, metal salt or antimicrobial), is desirably added to the medium at a concentration effective to induce expression of an isoprene synthase, DXS, IDI, and/or MVA pathway polypeptide. In some embodiments, cell medium has an antibiotic (such as kanamycin) that corresponds to the antibiotic resistance nucleic acid (such as a kanamycin resistance nucleic acid) on a vector that has one or more DXS, IDI, or MVA pathway nucleic acids.

Other exemplary cell culture media that can be used are described in US Pub. 2009/0203102, WO 2009/076676, WO 2010/003007, WO 2009/132220, WO 2010/031062, WO 2010/031068, WO 2010/031076, WO 2010/031077, and WO 2010/031079.

Methods for the Production of Isoprene

Provided herein are methods of producing isoprene by culturing any of the recombinant cells described herein under conditions suitable for production of isoprene. In one aspect, isoprene can be produced by culturing recombinant cells expressing one or more nucleic acids encoding: (a) polypeptide having isoprene synthase activity and improved kinetic properties, wherein polypeptide is encoded by a heterologous nucleic acid; and (b) one or more mevalonate (MVA) pathway polypeptides in culture media. In one aspect, one or more heterologous nucleic acids encoding a thiolase, a HMG-CoA reductase, a lower MVA pathway polypeptide, and an isoprene synthase polypeptide can be used. In another aspect, isoprene can be produced by culturing recombinant cells comprising one or more heterologous nucleic acids encoding a thiolase, a HMG-CoA reductase and HMG-CoA synthase, a lower MVA pathway polypeptide, and an isoprene synthase polypeptide. In yet another aspect, one or more heterologous nucleic acids encoding one or more upper MVA pathway polypeptides, one or more lower MVA pathway polypeptides, and/or one or more DXP pathway polypeptides can be used. In some aspects, the recombinant cells described herein exhibit any of about 10%, 15%, 20%, 25%, 30%, 35%, 40%, 45%, 50%, 55%, 60%, 65%, 70%, 75%, 80%, 95%, or 100%, inclusive, including any value in between these percentages, increased isoprene production in comparison to cells which do not comprise one or more heterologous nucleic acids encoding an isoprene synthase polypeptide and one or more MVA pathway polypeptides. The isoprene can be produced from any of the cells described herein and according to any of the methods described herein. Any of the cells can be used for the purpose of producing isoprene using the fermentable sugar feedstocks produced by any of the methods described herein as a carbon source.

The cells can further express one or more nucleic acid molecules encoding the lower MVA pathway polypeptide(s) described above (e.g., MVK, PMK, MVD, and/or IDI), any of the upper MVA pathways polypeptide(s) described above (e.g., a thiolase, an acetoacetyl-CoA synthase, an HMG-CoA reductase, and/or an HMG-CoA synthase) and/or any of the isoprene synthase polypeptide(s) described above (e.g. P. alba isoprene synthase). In some aspects, the recombinant (e.g., bacterial) cells can be any of the cells described herein. Any of the isoprene synthases or variants thereof described herein, any of the bacterial strains described herein, any of the promoters described herein, and/or any of the vectors described herein can also be used to produce isoprene. In some aspects, the method of producing isoprene further comprises a step of recovering the isoprene.

In some aspects, the amount of isoprene produced is measured at a productivity time point. In some aspects, the productivity for the cells is about any of the amounts of isoprene disclosed herein. In some aspects, the cumulative, total amount of isoprene produced is measured. In some aspects, the cumulative total productivity for the cells is about any of the amounts of isoprene disclosed herein.

In some aspects, any of the cells described herein (for examples the cells in culture) produce isoprene at greater than about any of or about any of 1, 10, 25, 50, 100, 150, 200, 250, 300, 400, 500, 600, 700, 800, 900, 1,000, 1,250, 1,500, 1,750, 2,000, 2,500, 3,000, 4,000, 5,000, or more nmole of isoprene/gram of cells for the wet weight of the cells/hour (nmole/$g_{wcm}$/hr). In some aspects, the amount of isoprene is between about 2 to about 5,000 nmole/$g_{wcm}$/hr, such as between about 2 to about 100 nmole/$g_{wcm}$/hr, about 100 to about 500 nmole/$g_{wcm}$/hr, about 150 to about 500 nmole/$g_{wcm}$/hr, about 500 to about 1,000 nmole/$g_{wcm}$/hr, about 1,000 to about 2,000 nmole/$g_{wcm}$/hr, or about 2,000 to about 5,000 nmole/$g_{wcm}$/hr. In some aspects, the amount of isoprene is between about 20 to about 5,000 nmole/$g_{wcm}$/hr, about 100 to about 5,000 nmole/$g_{wcm}$/hr, about 200 to about 2,000 nmole/$g_{wcm}$/hr, about 200 to about 1,000 nmole/$g_{wcm}$/hr, about 300 to about 1,000 nmole/$g_{wcm}$/hr, or about 400 to about 1,000 nmole/$g_{wcm}$/hr.

In some aspects, the cells in culture produce isoprene at greater than or about 1, 10, 25, 50, 100, 150, 200, 250, 300, 400, 500, 600, 700, 800, 900, 1,000, 1,250, 1,500, 1,750, 2,000, 2,500, 3,000, 4,000, 5,000, 10,000, 100,000, or more ng of isoprene/gram of cells for the wet weight of the cells/hr (ng/$g_{wcm}$/h). In some aspects, the amount of isoprene is between about 2 to about 5,000 ng/$g_{wcm}$/h, such as between about 2 to about 100 ng/$g_{wcm}$/h, about 100 to about 500 ng/$g_{wcm}$/h, about 500 to about 1,000 ng/$g_{wcm}$/h, about 1,000 to about 2,000 ng/$g_{wcm}$/h, or about 2,000 to about 5,000 ng/$g_{wcm}$/h. In some aspects, the amount of isoprene is between about 20 to about 5,000 ng/$g_{wcm}$/h, about 100 to about 5,000 ng/$g_{wcm}$/h, about 200 to about 2,000 ng/$g_{wcm}$/h, about 200 to about 1,000 ng/$g_{wcm}$/h, about 300 to about 1,000 ng/$g_{wcm}$/h, or about 400 to about 1,000 ng/$g_{wcm}$/h.

In some aspects, the cells in culture produce a cumulative titer (total amount) of isoprene at greater than about any of or about any of 1, 10, 25, 50, 100, 150, 200, 250, 300, 400, 500, 600, 700, 800, 900, 1,000, 1,250, 1,500, 1,750, 2,000, 2,500, 3,000, 4,000, 5,000, 10,000, 50,000, 100,000, or more mg of isoprene/L of broth (mg/$L_{broth}$, wherein the volume of broth includes the volume of the cells and the cell medium). In some aspects, the amount of isoprene is between about 2 to about 5,000 mg/$L_{broth}$, such as between about 2 to about 100 mg/$L_{broth}$, about 100 to about 500 mg/$L_{broth}$, about 500 to about 1,000 mg/$L_{broth}$, about 1,000 to about 2,000 mg/$L_{broth}$, or about 2,000 to about 5,000 mg/$L_{broth}$. In some aspects, the amount of isoprene is between about 20 to about 5,000 mg/$L_{broth}$, about 100 to about 5,000 mg/$L_{broth}$, about 200 to about 2,000 mg/$L_{broth}$, about 200 to about 1,000 mg/$L_{broth}$, about 300 to about 1,000 mg/$L_{broth}$, or about 400 to about 1,000 mg/$L_{broth}$.

In some aspects, the isoprene produced by the cells in culture (such as any of the recombinant cells described herein) comprises at least about 1, 2, 5, 10, 15, 20, or 25% by volume of the fermentation offgas. In some aspects, the isoprene comprises between about 1 to about 25% by volume of the offgas, such as between about 5 to about 15%, about 15 to about 25%, about 10 to about 20%, or about 1 to about 10%.

In some aspects, any of the methods described herein further include a step of recovering isoprene produced by any of the recombinant cells disclosed herein. In some aspects, the isoprene is recovered by absorption stripping (See, e.g., U.S. Patent Application Publication No. 2011/0178261 A1). Other purification methods which can be used are described in more detail in U.S. Patent Application Publication No. US2010/0196977 A1.

Exemplary Production of Isoprene

In some embodiments, the cells are cultured in a culture medium under conditions permitting the production of isoprene by the cells. In some embodiments, the cells in culture produce isoprene at greater than or about 1, 10, 25, 50, 100, 150, 200, 250, 300, 400, 500, 600, 700, 800, 900, 1,000, 1,250, 1,500, 1,750, 2,000, 2,500, 3,000, 4,000, 5,000, or more nmole of isoprene/gram of cells for the wet weight of the cells/hour (nmole/gwcm/hr). In some embodiments, the amount of isoprene is between about 2 to about 5,000 nmole/gwcm/hr, such as between about 2 to about 100 nmole/gwcm/hr, about 100 to about 500 nmole/gwcm/hr, about 150 to about 500 nmole/gwcm/hr, about 500 to about 1,000 nmole/gwcm/hr, about 1,000 to about 2,000 nmole/gwcm/hr, or about 2,000 to about 5,000 nmole/gwcm/hr. The amount of isoprene in units of nmole/gwcm/hr can be measured as disclosed in U.S. Pat. No. 5,849,970. For example, two mL of headspace (e.g., headspace from a culture such as 2 mL of culture cultured in sealed vials at 32° C. with shaking at 200 rpm for approximately 3 hours) are analyzed for isoprene using a standard gas chromatography system, such as a system operated isothermally (85° C.) with an n-octane/porasil C column (Alltech Associates, Inc., Deerfield, Ill.) and coupled to a RGD2 mercuric oxide reduction gas detector (Trace Analytical, Menlo Park, Calif.) (see, e.g., Greenberg et al, Atmos. Environ. 27A: 2689-2692, (1993); Silver et al., Plant Physiol. 97:1588-1591, (1991)). The gas chromatography area units are converted to nmol isoprene via a standard isoprene concentration calibration curve. In some embodiments, the value for the grams of cells for the wet weight of the cells is calculated by obtaining the $A_{600}$ value for a sample of the cell culture, and then converting the $A_{600}$ value to grams of cells based on a calibration curve of wet weights for cell cultures with a known $A_{600}$ value. In some embodiments, the grams of the cells is estimated by assuming that one liter of broth (including cell medium and cells) with an $A_{600}$ value of 1 has a wet cell weight of 1 gram. The value is also divided by the number of hours the culture has been incubating for, such as three hours.

In some embodiments, the cells in culture produce isoprene at greater than or about 1, 10, 25, 50, 100, 150, 200, 250, 300, 400, 500, 600, 700, 800, 900, 1,000, 1,250, 1,500, 1,750, 2,000, 2,500, 3,000, 4,000, 5,000, 10,000, 100,000, or more ng of isoprene/gram of cells for the wet weight of the cells/hr (ng/gwcm/h). In some embodiments, the amount of isoprene is between about 2 to about 5,000 ng/gwcm/h, such as between about 2 to about 100 ng/gwcm/h, about 100 to about 500 ng/gwcm/h, about 500 to about 1,000 ng/gwcm/h, about 1,000 to about 2,000 ng/gwcm/h, or about 2,000 to about 5,000 ng/gwcm/h. The amount of isoprene in ng/gwcm/h can be calculated by multiplying the value for isoprene production in the units of nmole/gwcm/hr discussed above by 68.1 (as described in Equation 5 below).

In some embodiments, the cells in culture produce a cumulative titer (total amount) of isoprene at greater than or about 1, 10, 25, 50, 100, 150, 200, 250, 300, 400, 500, 600, 700, 800, 900, 1,000, 1,250, 1,500, 1,750, 2,000, 2,500, 3,000, 4,000, 5,000, 10,000, 50,000, 100,000, or more mg of isoprene/L of broth (mg/L broth, wherein the volume of broth includes the volume of the cells and the cell medium). In some embodiments, the amount of isoprene is between about 2 to about 5,000 mg/L broth, such as between about 2 to about 100 mg/L broth, about 100 to about 500 mg/L broth, about 500 to about 1,000 mg/L broth, about 1,000 to about 2,000 mg/L broth, or about 2,000 to about 5,000 mg/L broth. The specific productivity of isoprene in mg of isoprene/L of headspace from shake flask or similar cultures can be measured by taking a 1 ml sample from the cell culture at an $OD_{600}$ value of approximately 1.0, putting it in a 20 mL vial, incubating for 30 minutes, and then measuring the amount of isoprene in the headspace. If the $OD_{600}$ value is not 1.0, then the measurement can be normalized to an $OD_{600}$ value of 1.0 by dividing by the $OD_{600}$ value. The value of mg isoprene/L headspace can be converted to mg/Lbroth/hr/$OD_{600}$ of culture broth by multiplying by a factor of 38. The value in units of mg/Lbroth/hr/$OD_{600}$ can be multiplied by the number of hours and the $OD_{600}$ value to obtain the cumulative titer in units of mg of isoprene/L of broth.

The instantaneous isoprene production rate in mg/L broth/hr in a fermentor can be measured by taking a sample of the fermentor off-gas, analyzing it for the amount of isoprene (in units such as mg of isoprene per L of gas), and multiplying this value by the rate at which off-gas is passed though each liter of broth (e.g., at 1 vvm (volume of air/volume of broth/minute) this is 60 Lgas per hour). Thus, an off-gas level of 1 mg/Lgas corresponds to an instantaneous production rate of 60 mg/Lbroth/hr at air flow of 1 vvm. If desired, the value in the units mg/Lbroth/hr can be divided by the $OD_{600}$ value to obtain the specific rate in units of mg/Lbroth/hr/OD. The average value of mg isoprene/Lgas can be converted to the total product productivity (grams of isoprene per liter of fermentation broth, mg/Lbroth) by multiplying this average off-gas isoprene concentration by the total amount of off-gas sparged per liter of fermentation broth during the fermentation. Thus, an average off-gas isoprene concentration of 0.5 mg/Lbroth/hr over 10 hours at 1 vvm corresponds to a total product concentration of 300 mg isoprene/Lbroth.

In some embodiments, the cells in culture convert greater than or about 0.0015, 0.002, 0.005, 0.01, 0.02, 0.05, 0.1, 0.12, 0.14, 0.16, 0.2, 0.3, 0.4, 0.5, 0.6, 0.7, 0.8, 0.9, 1.0, 1.2, 1.4, or 1.6% of the carbon in the cell culture medium into isoprene. In some embodiments, the percent conversion of carbon into isoprene is between about 0.002 to about 1.6%, such as about 0.002 to about 0.005%, about 0.005 to about 0.01%, about 0.01 to about 0.05%, about 0.05 to about 0.15%, 0.15 to about 0.2%, about 0.2 to about 0.3%, about 0.3 to about 0.5%, about 0.5 to about 0.8%, about 0.8 to about 1.0%, or about 1.0 to about 1.6%. The percent conversion of carbon into isoprene (also referred to as "% carbon yield") can be measured by dividing the moles carbon in the isoprene produced by the moles carbon in the carbon source (such as the moles of carbon in batched and fed glucose and yeast extract). This number is multiplied by 100% to give a percentage value (as indicated in Equation 1).

% Carbon Yield=(moles carbon in isoprene produced)/(moles carbon in carbon source)*100       Equation 1

For this calculation, yeast extract can be assumed to contain 50% w/w carbon.

% Carbon Yield=(39.1 g isoprene*1/68.1 mol/g*5 C/mol)/[(181221 g glucose*1/180 mol/g*6 C/mol)+(17780 g yeast extract*0.5*1/12 mol/g)] *100=0.042%       Equation 2

One skilled in the art can readily convert the rates of isoprene production or amount of isoprene produced into any other units. Exemplary equations are listed below for interconverting between units.

Units for Rate of Isoprene production (total and specific)

1 g isoprene/$L_{broth}$/hr=14.7 mmol isoprene/$L_{broth}$/hr (total volumetric rate)       Equation 3

1 nmol isoprene/$g_{wcm}$/hr=1 nmol isoprene/$L_{broth}$/hr/$OD_{600}$ (This conversion assumes that one liter of broth with an $OD_{600}$ value of 1 has a wet cell weight of 1 gram.)       Equation 4

1 nmol isoprene/$g_{wcm}$/hr=68.1 ng isoprene/$g_{wcm}$/hr (given the molecular weight of isoprene)       Equation 5

1 nmol isoprene/$L_{gas}O_2$/hr=90 nmol isoprene/$L_{broth}$/hr (at an $O_2$ flow rate of 90 L/hr per L of culture broth)       Equation 6

1 µg isoprene/$L_{gas}$ isoprene in off-gas=60 µg isoprene/$L_{broth}$/hr at a flow rate of 60 $L_{gas}$ per $L_{broth}$ (1 vvm)       Equation 7

Units for Titer (total and specific)

1 nmol isoprene/mg cell protein=150 nmol isoprene/$L_{broth}$/$OD_{600}$ (This conversion assumes that one liter of broth with an $OD_{600}$ value of 1 has a total cell protein of approximately 150 mg) (specific productivity)       Equation 8

1 g isoprene/$L_{broth}$=14.7 mmol isoprene/$L_{broth}$ (total titer)       Equation 9

If desired, Equation 10 can be used to convert any of the units that include the wet weight of the cells into the corresponding units that include the dry weight of the cells.

Dry weight of cells=(wet weight of cells)/3.3       Equation 10

In some embodiments encompassed by the invention, a cell comprising a heterologous nucleic acid encoding an isoprene synthase variant polypeptide produces an amount of isoprene that is at least or about 2-fold, 3-fold, 5-fold, 10-fold, 25-fold, 50-fold, 100-fold, 150-fold, 200-fold, 400-fold, or greater than the amount of isoprene produced from a corresponding cell grown under essentially the same conditions without the heterologous nucleic acid encoding the isoprene synthase variant polypeptide.

In some embodiments encompassed by the invention, a cell comprising a heterologous nucleic acid encoding an isoprene synthase variant polypeptide and one or more heterologous nucleic acids encoding a DXS, IDI, and/or MVA pathway polypeptide produces an amount of isoprene that is at least or about 2-fold, 3-fold, 5-fold, 10-fold, 25-fold, 50-fold, 100-fold, 150-fold, 200-fold, 400-fold, or greater than the amount of isoprene produced from a corresponding cell grown under essentially the same conditions without the heterologous nucleic acids.

Exemplary Isoprene Purification Methods

In some embodiments, any of the methods described herein further include recovering the isoprene. For example, the isoprene produced using the compositions and methods of the invention can be recovered using standard techniques, such as gas stripping, membrane enhanced separation, fractionation, adsorption/desorption, pervaporation, thermal or vacuum desorption of isoprene from a solid phase, or extraction of isoprene immobilized or absorbed to a solid phase with a solvent (see, for example, U.S. Pat. Nos. 4,703,007 and 4,570,029, which are each hereby incorporated by reference in their entireties, particularly with respect to isoprene recovery and purification methods). In one aspect, the isoprene is recovered by absorption stripping (see, e.g., US Pub. No. 2011/0178261). In particular aspects, extractive distillation with an alcohol (such as ethanol, methanol, propanol, or a combination thereof) is used to recover the isoprene. In some embodiments, the recovery of isoprene involves the isolation of isoprene in a liquid form (such as a neat solution of isoprene or a solution of isoprene in a solvent). Gas stripping involves the removal of isoprene vapor from the fermentation off-gas stream in a continuous manner. Such removal can be achieved in several different ways including, but not limited to, adsorption to a solid phase, partition into a liquid phase, or direct condensation. In some embodiments, membrane enrichment of a dilute isoprene vapor stream above the dew point of the vapor resulting in the condensation of liquid isoprene. In some embodiments, the recovery is performed as described in U.S. 2011/0178261, which is incorporated by reference, in particular for the teaching for purification and/or recovery of isoprene.

The recovery of isoprene may involve one step or multiple steps. In some embodiments, the removal of isoprene vapor from the fermentation off-gas and the conversion of isoprene to a liquid phase are performed simultaneously. For example, isoprene can be directly condensed from the off-gas stream to form a liquid. In some embodiments, the removal of isoprene vapor from the fermentation off-gas and the conversion of isoprene to a liquid phase are performed sequentially. For example, isoprene may be adsorbed to a solid phase and then extracted from the solid phase with a solvent. In one aspect, the isoprene is recovered by using absorption stripping as described in U.S. application Ser. No. 12/969,440 (US Publ. No. 2011/0178261).

In some embodiments, any of the methods described herein further include purifying the isoprene. For example, the isoprene produced using the compositions and methods of the invention can be purified using standard techniques. Purification refers to a process through which isoprene is separated from one or more components that are present when the isoprene is produced. In some embodiments, the isoprene is obtained as a substantially pure liquid. Examples of purification methods include (i) distillation from a solution in a liquid extractant and (ii) chromatography. As used herein, "purified isoprene" means isoprene that has been separated from one or more components that are present when the isoprene is produced. See, e.g. U.S. Patent Application Publication No. 2009/0203102, PCT Publication No. WO 2009/076676 and U.S. patent application Ser. No. 12/496,573. In some embodiments, the isoprene is at least about 20%, by weight, free from other components that are present when the isoprene is produced. In various embodiments, the isoprene is at least or about 25%, 30%, 40%, 50%, 60%, 70%, 75%, 80%, 90%, 95%, or 99%, by weight, pure. Purity can be assayed by any appropriate method, e.g., by column chromatography, HPLC analysis, or GC-MS analysis. Suitable purification methods are described in more detail in U.S. Patent Application Publication 2010/0196977 A1.

Throughout this specification, various patents, patent applications and other types of publications (e.g., journal articles, nucleotide and protein sequence database accession numbers) are referenced. The disclosure of all patents, patent applications, sequences and publications cited herein are hereby incorporated by reference in their entirety for all purposes.

The invention can be further understood by reference to the following examples, which are provided by way of illustration and are not meant to be limiting.

EXAMPLES

Various modifications and variations of the described composition, method and/or system of the invention will be apparent to those skilled in the art without departing from the scope and spirit of the invention. Although the invention has been described in connection with specific embodiments or aspects, it should be understood that the invention as claimed should not be unduly limited to such specific embodiments. It is also to be understood that one, some, or all of the properties of the various embodiments described herein may be combined to form other embodiments of the present invention. These and other aspects of the invention will become apparent to one of skill in the art.

In the experimental disclosure which follows, the following abbreviations apply: ° C. (degrees Centigrade); rpm (revolutions per minute); $H_2O$ (water); $diH_2O$ (deionized water); aa and AA (amino acid); by (base pair); kb (kilobase pair); kD (kilodaltons); gm (grams); μg and ug (micrograms); mg (milligrams); ng (nanograms); μl and ul (microliters); ml (milliliters); mm (millimeters); qs (quantity sufficient); nm (nanometers); μm and um (micrometer); M (molar); mM (millimolar); μM and uM (micromolar); pM (picomolar); U (units); MW (molecular weight); sec (seconds); min (minute/minutes); hr (hour/hours); $OD_{600}$ (optical density at 600 nm); BSA (bovine serum albumin); DMAPP (dimethylallyl diphosphate); DTT (dithiothreitol); EtOH (ethanol); IPTG (isopropyl-beta-D-thiogalactopyranoside); isoprene (2-methyl-1,3-butadiene); IspS (isoprene synthase); PAGE (polyacrylamide gel electrophoresis); PBS (phosphate buffered saline [150 mM NaCl, 10 mM sodium phosphate buffer, pH 7.2]); and SDS (sodium dodecyl sulfate).

The following abbreviations apply to companies whose products or services may have been referred to in the experimental examples: Agilent (Agilent Technologies, Santa Clara, Calif.); Becton Coulter (Becton Coulter, Inc., Fullerton, Calif.); Bio-Rad (Bio-Rad Laboratories, Hercules, Calif.); Cayman Chemical (Cayman Chemical Co., Ann Arbor, Mich.); CTC Analytics (CTC Analytics A.G., Zwingen, Switzerland); EMS (Electron Microscopy Supply, Hatfield, Pa.); Epicentre (Epicentre Biotechnologies, Madison, Wis.); Integrated DNA Technologies (Integrated DNA Technologies, Coralville, Iowa); Invitrogen (Invitrogen Corp., Carlsbad, Calif.); Molecular Dynamics (Molecular Dynamics, Sunnyvale, Calif.); Novagen (Novagen, Inc., Madison, Wis.); Perkin Elmer (Perkin Elmer, Waltham, Mass.); Roche (Roche Applied Science, Indianapolis, Ind.); Sigma (Sigma- Aldrich, St. Louis, Mo.); Stratagene (Stratagene Cloning Systems, La Jolla, Calif.); Qiagen (Qiagen, Inc., Valencia, Calif.); Takara (Takara Bio USA, Madison, Wis.); Thomson Instrument (Thomson Instrument Co., Oceanside, Calif.); V&P Scientific (V&P Scientific, Inc., San Diego, Calif.); and Zinsser (Zinsser North America, Northridge, Calif.).

Example 1

Isoprene Synthase Growth Screen: Validation, Optimization and Limitations

This Example describes the development of an in vivo screen to select improved variants of isoprene synthase. The inventors have found that the in vivo screen can be used to select cells that contain less isoprene synthase activity than a control (in our case, an isoprene synthase MEA-Poplar Alba). In addition, the in vivo screen can be used to select cells that contain more isoprene synthase activity than a control (in our case, an isoprene synthase MEA-Poplar Alba).
Methods
Strains: The screening strain contained a constitutively expressed lower pathway and variants of isoprene synthase expressed from a pET plasmid. The screening strains were DW425-positive control.

Assay conditions: Strains were grown overnight in LB medium containing 50 uM kanamycin at 34° C. The overnight cultures were diluted to approximately 0.2 $OD_{600}$ in TM3 media containing 1% glucose, 0.1% yeast extract, 8 mM $MgSO_4$ and one of the following concentrations of IPTG: 0, 10, 20, 30, 40, 50, 60, or 70 uM. Cells were grown for approximately 2 hours post-induction and transferred to a 96-well clear bottom microtiter plate containing various concentrations of mevalonate (0, 5, 7.5, 10, 15, 20 mM) and the same media used in the day culture to a final $OD_{600}$ of 0.2-0.3. The plates were monitored in kinetic mode on a Spectramax UV-Vis spectrophotometer. The experiment was monitored at 34 C for 3 hours with shaking for 1 minute prior to each measurement (taken every 5 minutes).

Data analysis: All data were transferred to Excel. The absorbance measurements were converted to their natural log. A line was then fit to the series using the function "LINEST" to yield the exponential growth constant (growth rate).

Metabolite analysis was performed by using the following protocol for methanol/water extraction of metabolites at small-scale (MVA, DXP):
1. Samples from small-scale experiment was quenched; commonly 1 ml sample was spun down, the supernatant was discarded, 100 μl pure methanol was loaded onto the pellet, and the samples was stored at −80 C until there was time for metabolite extraction and analysis.
2. Samples were taken from storage in −80 C; pellets were resuspended (recommended to break pellet with glass capillary tubes).
3. The sample was spun down in a refrigerated microcentrifuge at 14000 g (rfc) for 4 min.
4. The supernatant was placed into clean 1.5 mL Eppendorf tubes.
5. The pellet was resuspended in 100 μl 6:1 MeOH/5 mM $NH_4OAc$ pH 8.0. Centrifuge at 14000 g (rfc) for 4 min. The samples may be extracted in 6:1 MeOH/5 mM $NH_4OAc$ pH 7.0 if the metabolites of interest are not stable at pH 8.0 (for example, DXP metabolites, or CoA-containing metabolites).
6. The supernatant was combined with the supernatant from step 4.
7. Steps 5-6 were repeated, extracting with 100 μl 1:1 MeOH/5 mM $NH_4OAc$ pH 8.0 (or pH 7.0, see above). Sample pellets can be discarded after taking the supernatant. 1.5 ml Eppendorf tubes containing accumulated supernatant fractions were closed and extract was mixed by vortexing.
8. In order to remove suspended debris, 1.5 ml Eppendorf tubes were centrifuged at 14000 g (rfc) for 4 min.
9. ~200 μl extract were placed into LC/MS vials containing conical inserts. The remaining extracts were stored at −20° C.

Without being bound by theory, it is recommended to use repeat pipettors for dispensing 2% formic acid (for fast pipetting and consistent volumes). Repeat pipettors significantly improve time efficiency over standard pipettors, and because they are technically positive displacement pipettes, they are quite precise (and accurate, assuming good calibration and proper maintenance). Further recommendations include, but are not limited to: keep Eppendorf tubes on ice (at 0° C.) whenever possible, the microcentrifuge should be set at −9° C.; allow ~20 min. for the centrifuge to cool, for resuspending pellets, the use of the glass capillary tubes is recommended. Mechanical breaking of the cell pellet is usually very fast with just a little physical assistance. It is not recommended to vortex the resuspended pellets, as the cell mass ends up on the sides of the tubes very easily, potentially causing significant experimental error due to the low volumes of the samples.

Without being bound by theory, the following recommendations are given for conducting LC/MS analysis:
1. The LC/MS vials should be kept on the tray at 4° C. during the analysis. The column should be at room temperature. The tray/column temperatures will be set automatically after starting the sequence in Xcalibur, but it is better to set the tray temperature in advance.
2. Use standards prepared as in the attached spreadsheet for calibration. Record standard preparation date as labeled on each tube.
3. LC/MS method for isoprenoids and MVA pathway metabolites (currently on new TSQ Quantum Access)—Method file: IPS_BioBasic100_090316 (or similar, see latest date extension); HPLC column: Macherey-Nagel Nucleodex beta-OH EC 2 mm×100 mm (particle size 5 μm, pore size 100 Å), C/N 720351.20; Guard column: 721460.40 (2 mm guard column not currently available). LC/MS method for DXP pathway metabolites: Method development C 18-ion pair\Metabolites_18_TBAip_11, with tributylammonium acetate as an ion-pair reagent; HPLC column: C18 Phenomenex Synergi 4μ. Hydro-RP 80A 150×2.0 mm, C/N 00E-4375-B0; Guard column: Security Guard Cartridges AQ C18 4×2.0 mm, C/N AJ0-7510. For LC/MS method for detection of CoA-containing metabolites, see "Protocol for acidic extraction of metabolites at small-scale (CoAs, etc.)."
4. After analysis, samples should be stored at −20° C.; standards should be stored at −80° C.
5. Metabolite quantitation can be determined using LCQuan software package. After back-calculation of all dilutions (including initial methanol quench), concentrations should be normalized to OD and converted to intracellular concentrations, utilizing the assumption that the intracellular volume of 1 L of fermentation broth at 2000D is ~50 mL.
Results A system has previously been developed to select DMAPP utilizing enzymes from pools of plasmids that express unknown proteins (Appl Environ Microbiol. 2007 October; 73(19): 6277-6283). The inventors have refined and optimized the screening protocol to enable selection cells that contain isoprene synthase activity. The screen is based on experimental results concluding that the concentration of DMAPP in E. coli correlates with cell growth rate (FIG. 1). Therefore, without being bound by theory, the growth rate of these cells can be thought of as a biosensor for intracellular DMAPP concentrations. Without being bound by theory, the underlying rationale of this screen was that the concentration of DMAPP in a cell can be decreased by increasing the enzyme activity of DMAPP consuming enzymes (isoprene synthase) and, thus, would result in increased growth rate.

Figure 2:
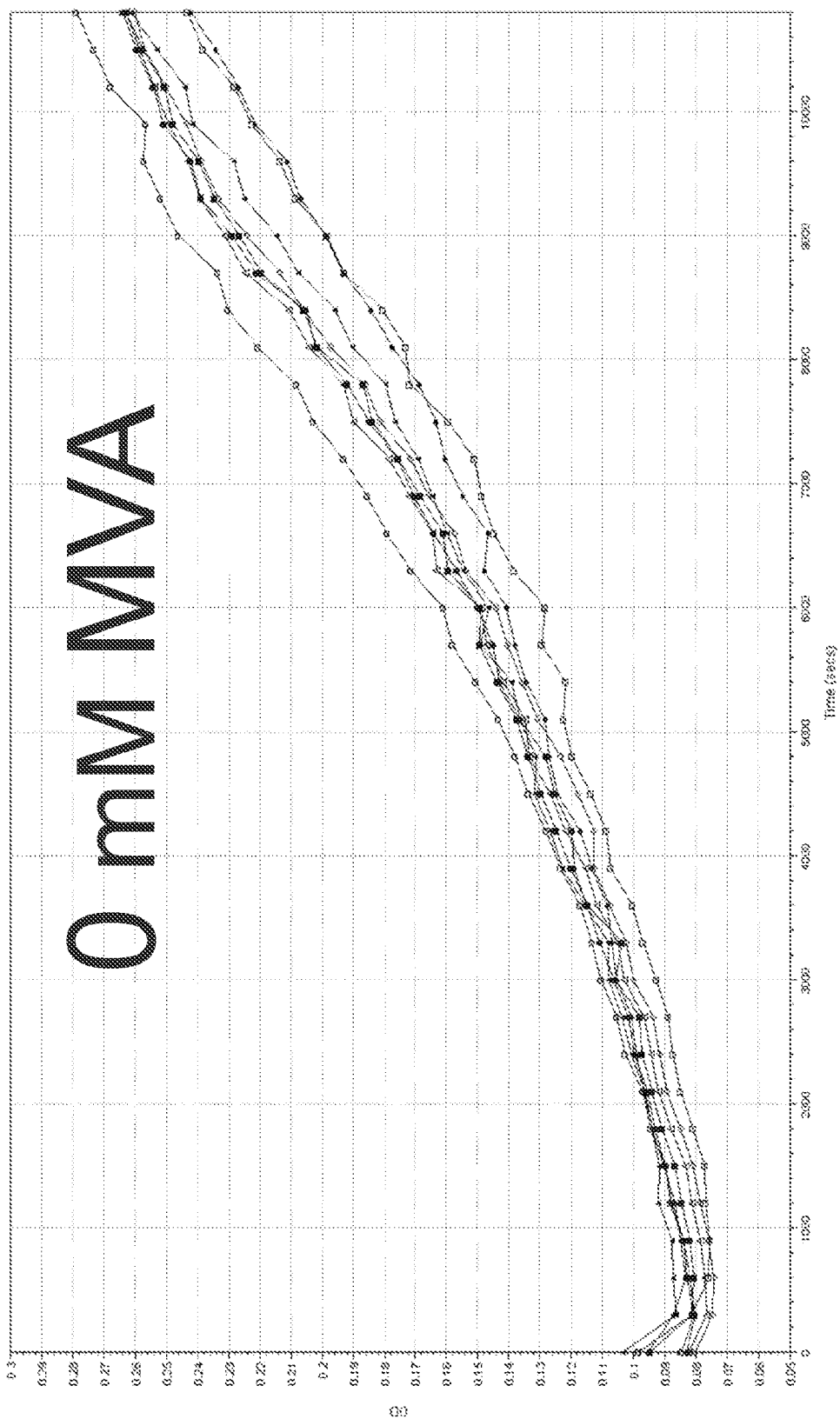
FIG. 2 shows DW425 growth in the presence of varying concentrations of IPTG (0, 10, 20, 30, 40, 50, 60, and 70 µM) and mevalonate (0, 5, 7.5, 10, 15, 20 mM).
Figure 2:
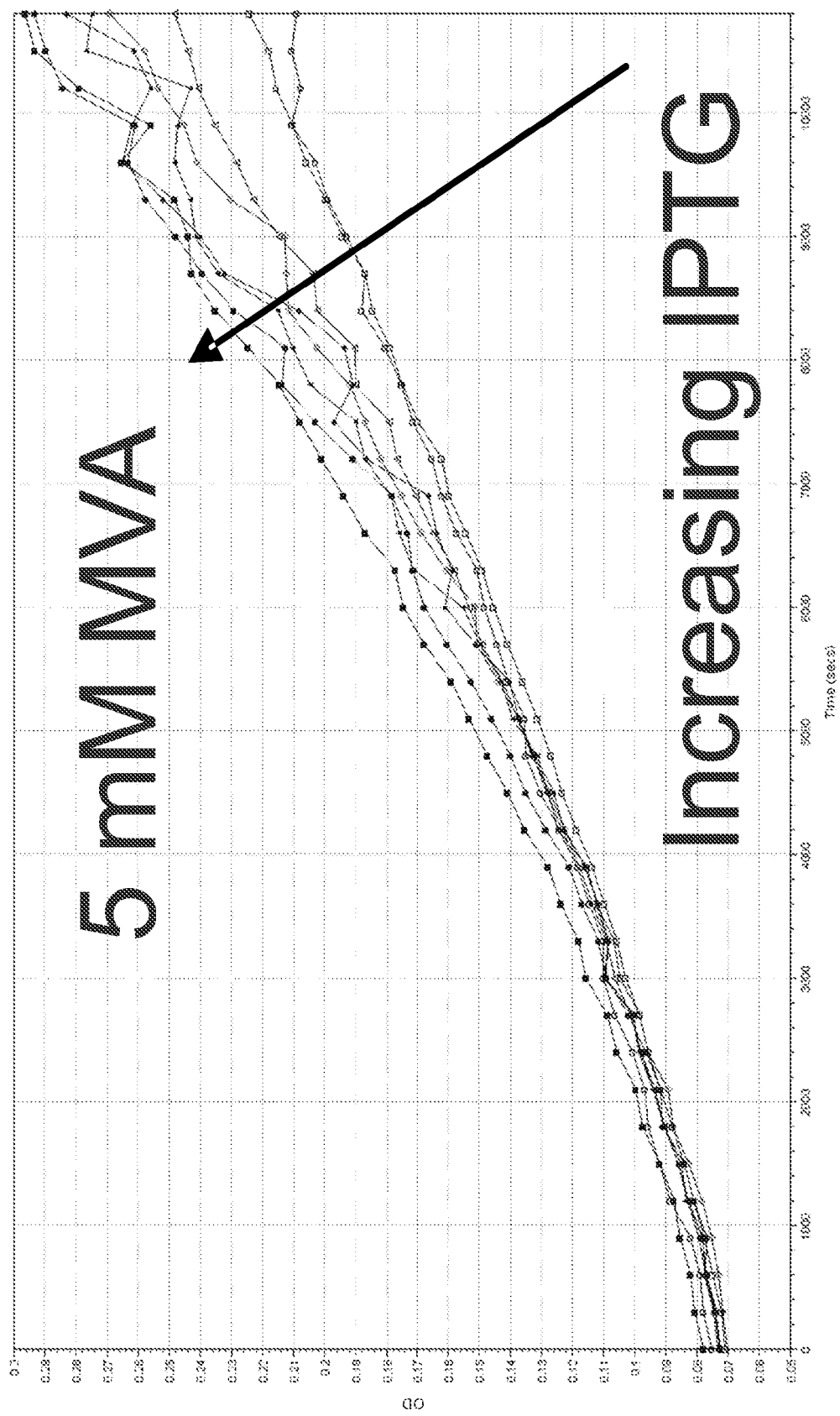
Figure 2:
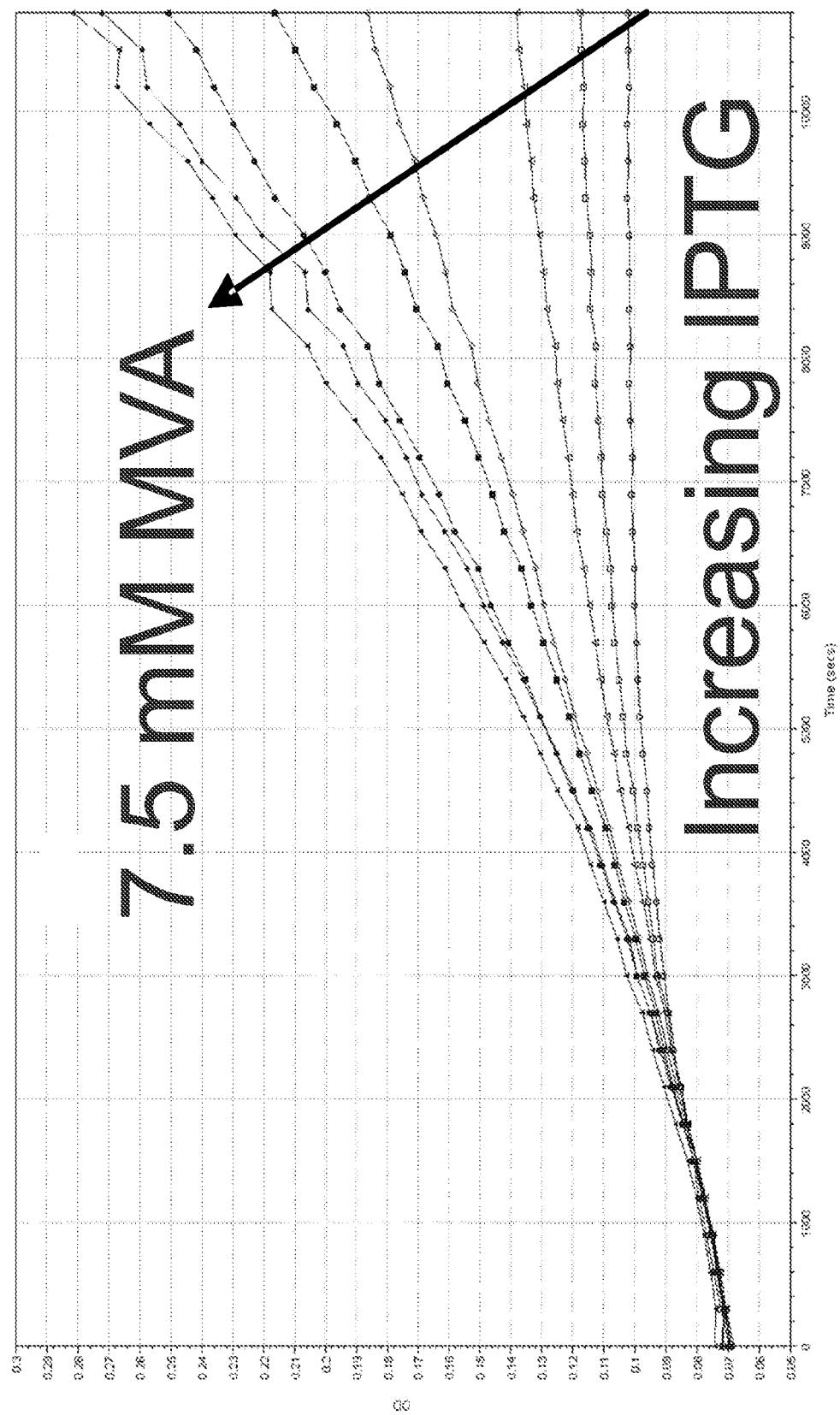
Figure 2:
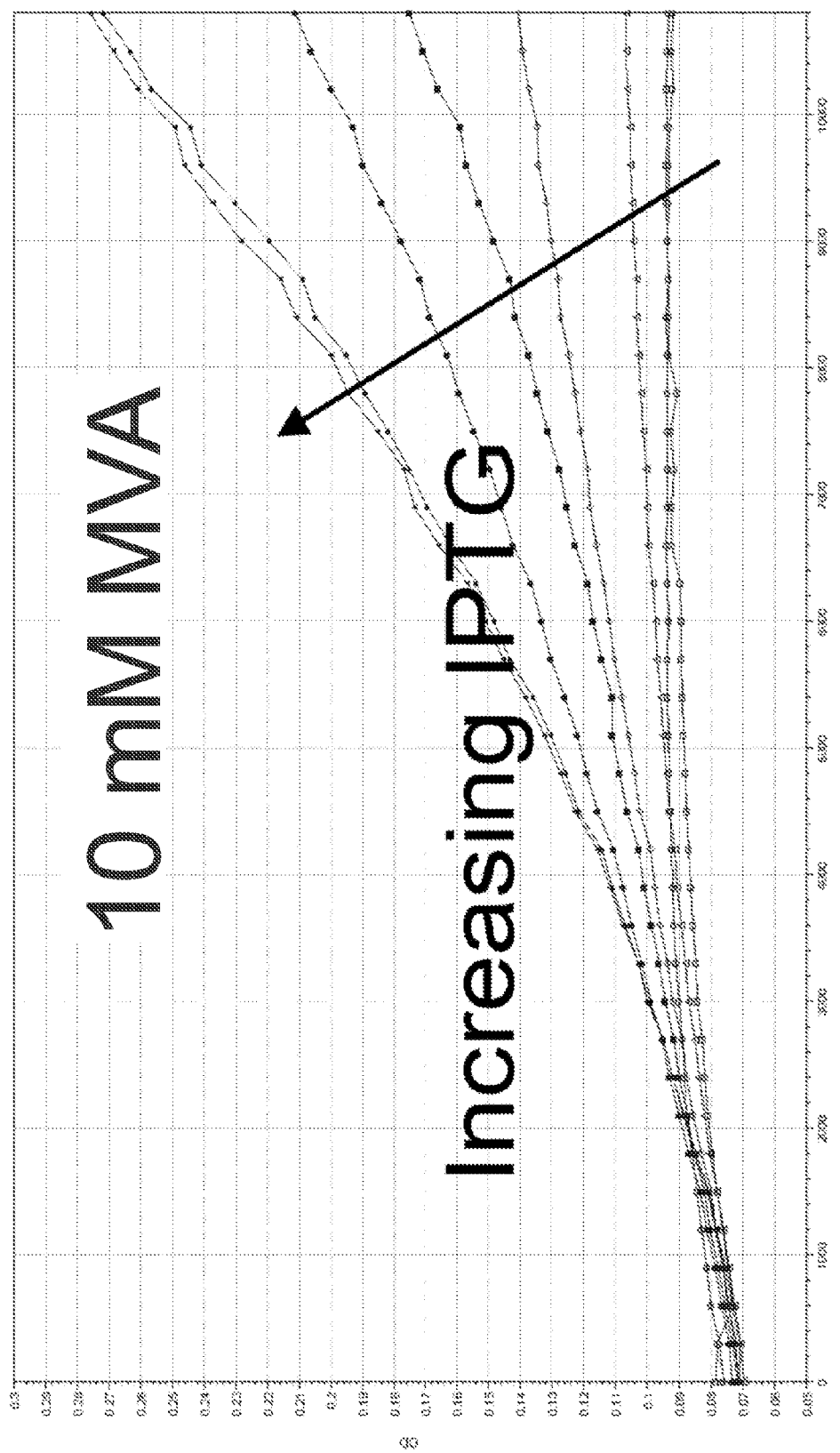
Figure 2:
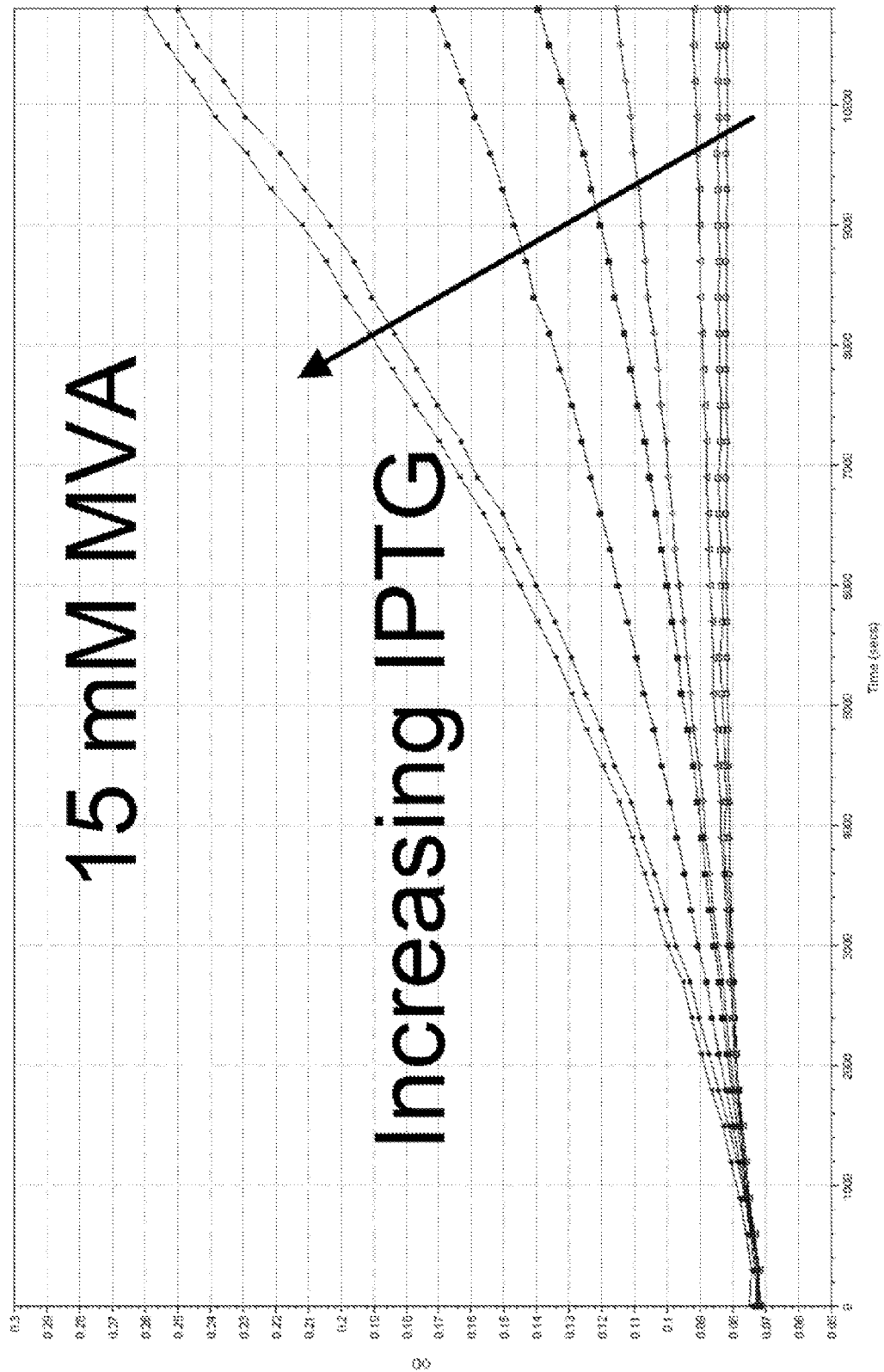
Figure 2:
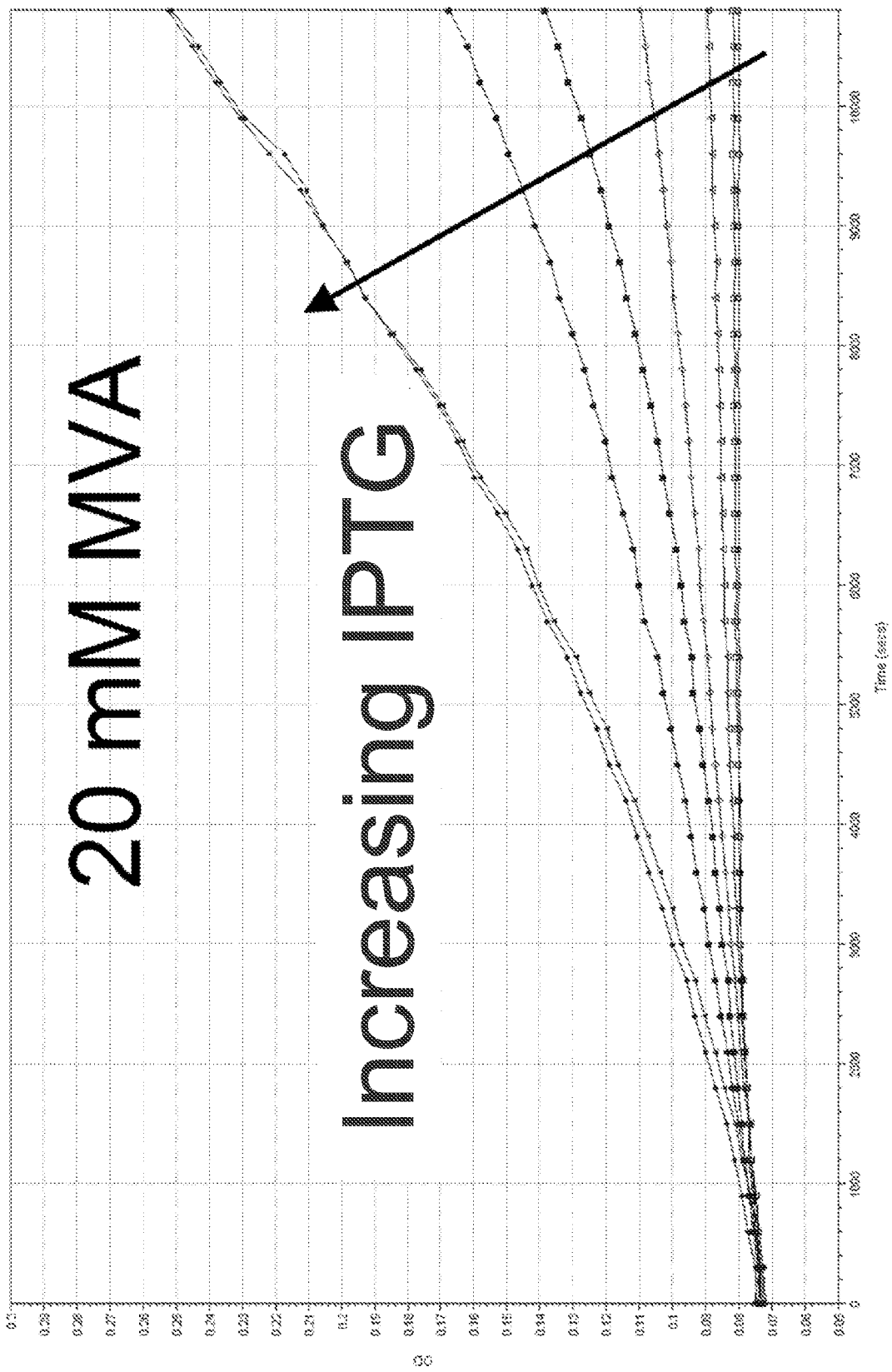
Figure 3:
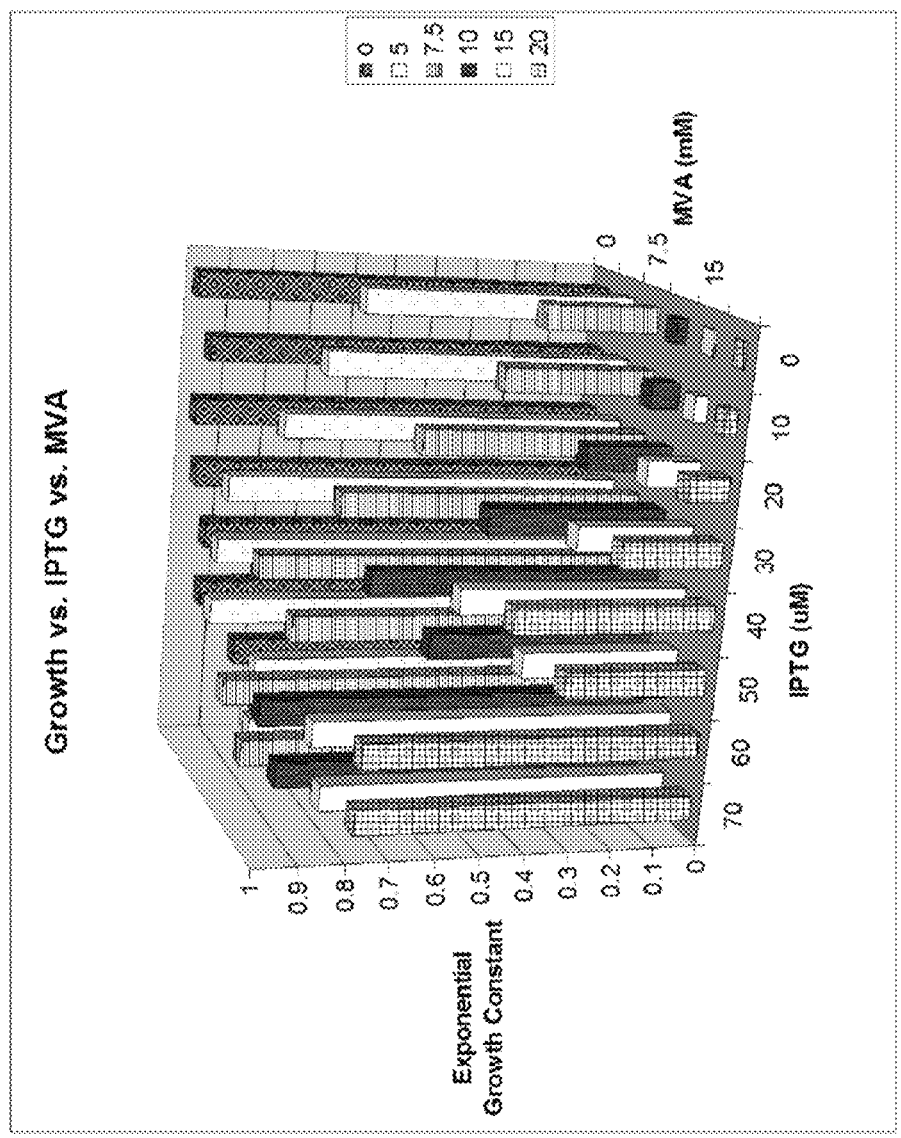
FIG. 3 shows growth as a function of [IPTG] and [mevalonate].

To test this hypothesis, DW425 cells were grown in media containing a matrix of IPTG and mevalonate concentrations (FIG. 2 and FIG. 3). Cells grown in the presence of 60 uM IPTG, and greater, resulted in impared growth without addition of mevalonate (compared to non-induced cells). At IPTG concentrations of 0-50 μM IPTG, growth was unimpaired, compared to non-induced cells. Cell growth was inhibited with all concentrations of mevalonate in uninduced cells. Increasing the concentration of IPTG resulted in increased growth rate for any given mevalonate concentration screened (FIG. 2 and FIG. 3). Earlier studies were performed to determine that the concentration of enzyme expressed in the cells correlates with the concentration of IPTG present. Therefore, increased isoprene synthase expression/activity in these strains results in improved growth.

Example 2

Analysis of *P. alba* Isoprene Synthase SELs by DMAPP Toxicity Relief

There is a strong correlation between increased intracellular DMAPP levels and growth inhibition of *E. coli*, which can be alleviated by the expression of *P. alba* isoprene synthase (IspS). Without being bound by theory, increased levels of IspS activity should therefore allow for better growth due to more rapid conversion of DMAPP to isoprene. By monitoring the growth rates of *E. coli* expressing variants of IspS under these conditions, the inventors can identify mutant IspS enzymes that display increased ability to convert DMAPP to isoprene within the cell.

Figure 4:
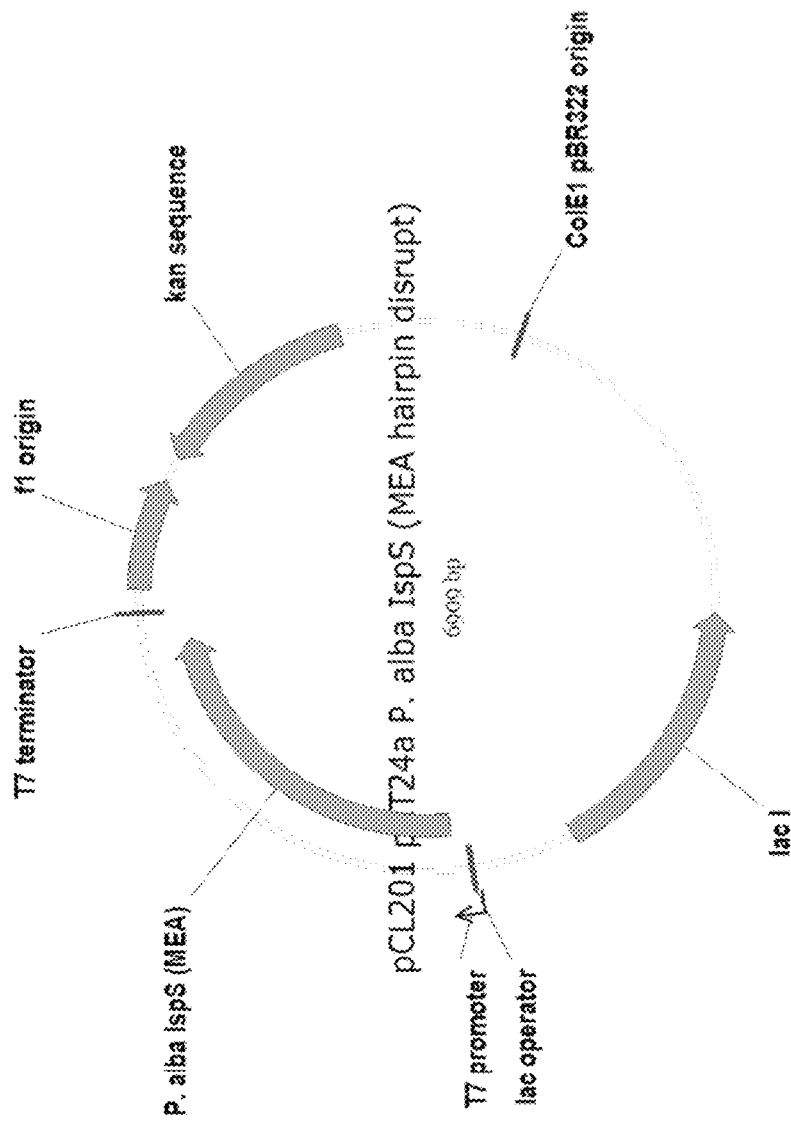
FIG. 4 shows a map of pCL201.
Figure 5:
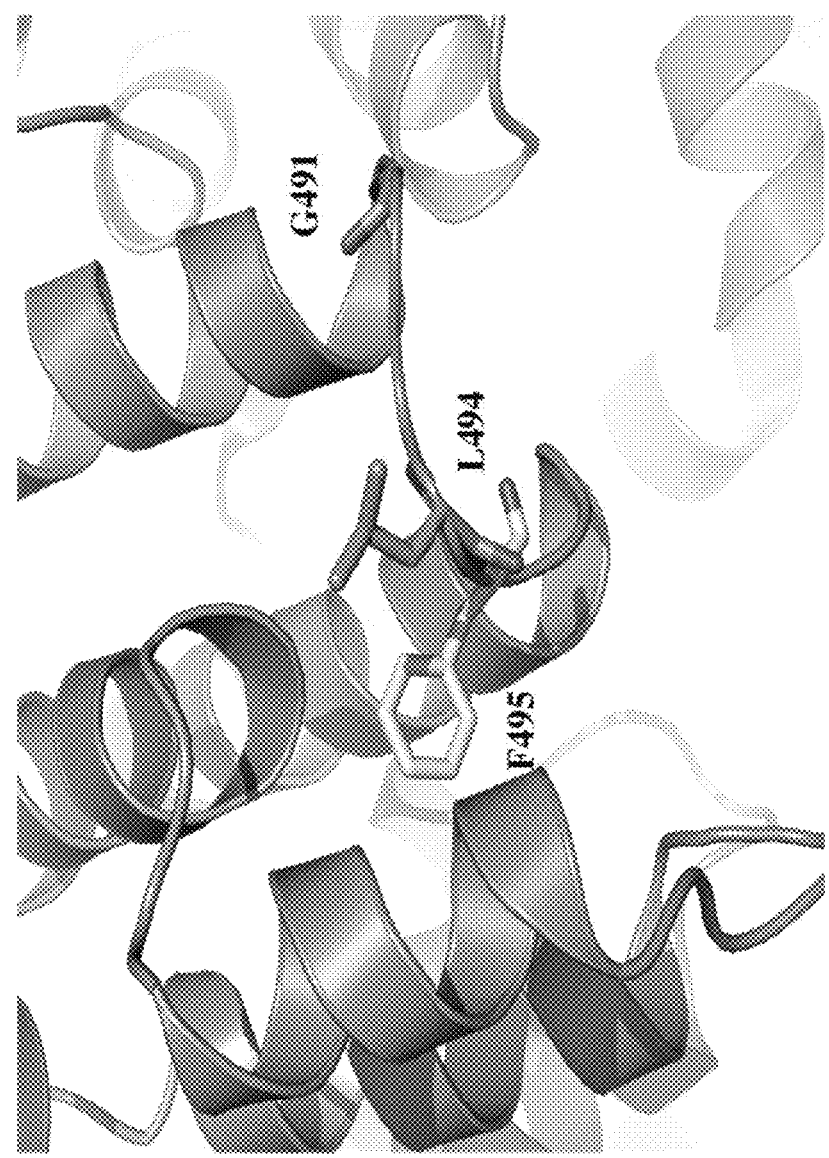
FIG. 5 shows a view of Wild Type IspS showing the location of Phe495 with respect to Gly491 and Leu494, all in stick representation.
Figure 6:
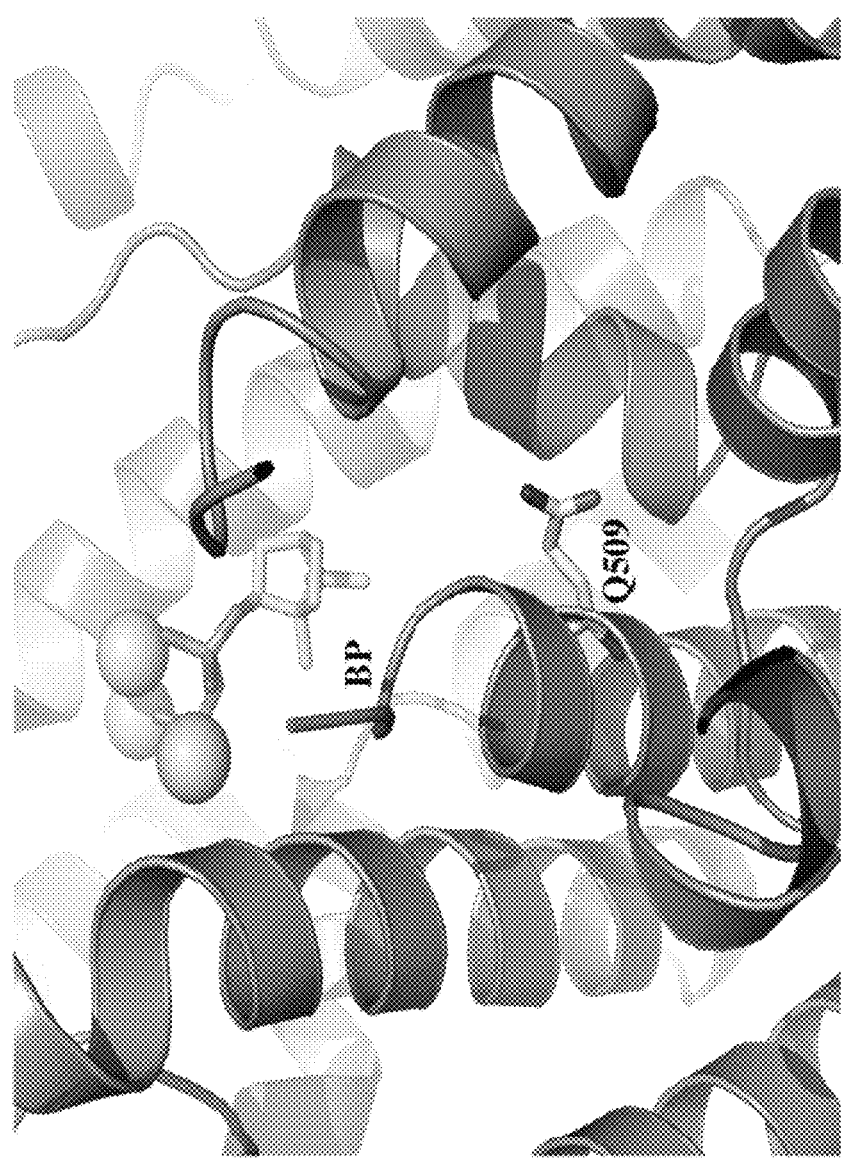
FIG. 6 shows a view of Wild Type IspS showing the location of Gln509, in stick representation, with respect to the active site. The magnesium ions and (+)-bornyl diphosphate in the active site are modeled based on a structural alignment with PDB 1N24.

Methods:

1) Plasmid and Strain Construction:

SEL Plasmid Backbone—The plasmid backbone used to generate SELs was constructed by QuikChange (Stratagene) PCR on the template pDu39 (see Table 1 for primer sequences). The PCR product was treated with 1 μl DpnI (Roche) for 3 hours, and then 1 μl of the entire reaction was transformed into chemically competent *E. coli* Top10 cells (Invitrogen) according to the manufacturer's recommended protocol. Cells were recovered and plated on LB medium containing 50 μg/ml kanamycin. The next day, positive colonies were chosen for growth, plasmid purification (Qiagen) and sequencing (Quintara Biosciences). Plasmids which harbored the correct base changes were selected for sequencing of the entire open reading frame to confirm the integrity of the coding sequence. One of these plasmids, pCL201 (see FIG. 4), was selected as the backbone for construction of SELs (by Verdezyne and DNA2.0).

TABLE 1

| QuikChange and Sequencing Primers | | |
|---|---|---|
| MEA Hairpin Disrupt (pET) F | ggagatatacatatggaagcacgt cgctctgcgaactacgaacctaa | (SEQ ID NO: 4) |
| MEA Hairpin Disrupt (pET) R | ttaggttcgtagttcgcagagcga cgtgcttccatatgtatatctcc | (SEQ ID NO: 5) |
| T7 Forward | taatacgactcactataggg | (SEQ ID NO: 6) |
| T7 Reverse | gctagttattgctcagcgg | (SEQ ID NO: 15) |
| EL-1000 | gcactgtctttccgtctgctgc | (SEQ ID NO: 16) |
| QB1493 | cttcggcaacgcatggaaat | (SEQ ID NO: 17) |
| A-rev | ctcgtacaggctcaggatag | (SEQ ID NO: 18) |
| A-rev2 | ttacgtcccaacgctcaact | (SEQ ID NO: 19) |

PCR and Cycling Parameters:
QuikChange PCR:
1 ul pDu39
5 ul 10×PfuUltra HF buffer
1 ul dNTPs
1 ul (50 uM) MEA Hairpin Disrupt (pET) F
1 ul (50 uM) MEA Hairpin Disrupt (pET) R
2 ul DMSO
39 ul diH2O
1 ul PfuUltra HF Polymerase (Stratagene)
PCR Cycling Parameters for QuikChange:
1. 95° C. 1 min.
2. 95° C. 50 sec.
3. 60° C. 50 sec.
4. 68° C. 7 min.
5. Go to step 2-18 cycles
6. 68° C. 7 min Sequence of pCL201:

(SEQ ID NO: 21)

tggcgaatgggacgcgccctgtagcggcgcattaagcgcggcgggtgtggtggttacgcgcagcgtgaccgctacacttgccagcgccctag cgcccgctcctttcgctttcttcccttcctttctcgccacgttcgccggctttccccgtcaagctctaaatcgggggctcccttagggttccgatttag tgctttacggcacctcgaccccaaaaaacttgattagggtgatggttcacgtagtgggccatcgccctgatagacggttttcgccctttgacgttg gagtccacgttctttaatagtggactcttgttccaaactggaacaacactcaaccctatctcggtctattcttttgatttataagggattttgccgatttcg gcctattggttaaaaaatgagctgatttaacaaaaatttaacgcgaattttaacaaaatattaacgtttacaatttcaggtggcacttttcggggaaatg tgcgcggaacccctatttgtttatttttctaaatacattcaaatatgtatccgctcatgaattaattcttagaaaaactcatcgagcatcaaatgaaactg caatttattcatatcaggattatcaataccatatttttgaaaaagccgtttctgtaatgaaggagaaaactcaccgaggcagttccataggatggcaa gatcctggtatcggtctgcgattccgactcgtccaacatcaatacaacctattaatttcccctcgtcaaaaataaggttatcaagtgagaaatcacca -continued

```
tgagtgacgactgaatccggtgagaatggcaaaagtttatgcatttctttccagacttgttcaacaggccagccattacgctcgtcatcaaaatcact
cgcatcaaccaaaccgttattcattcgtgattgcgcctgagcgagacgaaatacgcgatcgctgttaaaaggacaattaaacaggaatcgaat
gcaaccggcgcaggaacactgccagcgcatcaacaatattttcacctgaatcaggatattcttctaatacctggaatgctgttttcccggggatcgc
agtggtgagtaaccatgcatcatcaggagtacggataaaatgcttgatggtcggaagaggcataaattccgtcagccagtttagtctgaccatctc
atctgtaacatcattggcaacgctacctttgccatgtttcagaaacaactctggcgcatcgggcttcccatacaatcgatagattgtcgcacctgatt
gcccgacattatcgcgagcccatttatacccatataaatcagcatccatgttggaatttaatcgcggcctagagcaagacgtttcccgttgaatatg
gctcataacaccccttgtattactgtttatgtaagcagacagttttattgttcatgaccaaaatcccttaacgtgagttttcgttccactgagcgtcagac
cccgtagaaaagatcaaaggatcttcttgagatcctttttttctgcgcgtaatctgctgcttgcaaacaaaaaaaccaccgctaccagcggtggtttg
tttgccggatcaagagctaccaactctttttccgaaggtaactggcttcagcagagcgcagataccaaatactgtccttctagtgtagccgtagttag
gccaccacttcaagaactctgtagcaccgcctacatacctcgctctgctaatcctgttaccagtggctgctgccagtggcgataagtcgtgtcttac
cgggttggactcaagacgatagttaccggataaggcgcagcggtcgggctgaacggggggttcgtgcacacagcccagcttggagcgaacg
acctacaccgaactgagatacctacagcgtgagctatgagaaagcgccacgcttcccgaaggggagaaaggcggacaggtatccggtaagcg
gcagggtcggaacaggagagcgcacgagggagcttccaggggaaacgcctggtatctttatagtcctgtcgggtttcgccacctctgacttga
gcgtcgatttttgtgatgctcgtcagggggcggagcctatggaaaaacgccagcaacgcggcctttttacggttcctggccttttgctggccttttt
gctcacatgttctttcctgcgttatcccctgattctgtggataaccgtattaccgcctttgagtgagctgataccgctcgccgcagccgaacgaccga
gcgcagcgagtcagtgagcgaggaagcggaagagcgcctgatgcggtattttctccttacgcatctgtgcggtatttcacaccgcatatatggtg
cactctcagtacaatctgctctgatgccgcatagttaagccagtatacactccgctatcgctacgtgactgggtcatggctgcgccccgacacccg
ccaacacccgctgacgcgccctgacgggcttgtctgctcccggcatccgcttacagacaagctgtgaccgtctccgggagctgcatgtgtcaga
ggttttcaccgtcatcaccgaaacgcgcgaggcagctgcggtaaagctcatcagcgtggtcgtgaagcgattcacagatgtctgcctgttcatcc
gcgtccagctcgttgagtttctccagaagcgttaatgtctggcttctgataaagcgggccatgttaagggcggttttttcctgtttggtcactgatgcc
tccgtgtaagggggatttctgttcatgggggtaatgataccgatgaaacgagagaggatgctcacgatacggttactgatgatgaacatgcccg
gttactggaacgttgtgagggtaaacaactggcggtatggatgcggcgggaccagagaaaaatcactcagggtcaatgccagcgcttcgttaat
acagatgtaggtgttccacagggtagccagcagcatcctgcgatgcagatccggaacataatggtgcagggcgctgacttccgcgtttccagac
tttacgaaacacggaaaccgaagaccattcatgttgttgctcaggtcgcagacgttttgcagcagcagtcgcttcacgttcgctcgcgtatcggtg
attcattctgctaaccagtaaggcaaccccgccagcctagccgggtcctcaacgacaggagcacgatcatgcgcacccgtggggccgccatg
ccggcgataatggcctgcttctcgccgaaacgtttggtggcgggaccagtgacgaaggcttgagcgagggcgtgcaagattccgaataccgca
agcgacaggccgatcatcgtcgcgctccagcgaaagcggtcctcgccgaaaatgacccagagcgctgccggcacctgtcctacgagttgcat
gataaagaagacagtcataagtgcggcgacgatagtcatgccccgcgcccaccggaaggagctgactgggttgaaggctctcaagggcatcg
gtcgagatcccggtgcctaatgagtgagctaacttacattaattgcgttgcgctcactgcccgctttccagtcgggaaacctgtcgtgccagctgc
attaatgaatcggccaacgcgcggggagaggcggtttgcgtattgggcgccagggtggtttttcttttcaccagtgagacgggcaacagctgatt
gcccttcaccgcctggccctgagagagttgcagcaagcggtccacgctggtttgccccagcaggcgaaaatcctgtttgatggtggttaacggc
gggatataacatgagctgtcttcggtatcgtcgtatcccactaccgagatatccgcaccaacgcgcagcccggactcggtaatggcgcgcattgc
gcccagcgccatctgatcgttggcaaccagcatcgcagtgggaacgatgccctcattcagcatttgcatggtttgttgaaaaccggacatggcac
tccagtcgccttcccgttccgctatcggctgaatttgattgcgagtgagatatttatgccagccagccagacgcagacgcgccgagacagaactt
aatgggcccgctaacagcgcgatttgctggtgacccaatgcgaccagatgctccacgcccagtcgcgtaccgtcttcatgggagaaaataatac
tgttgatgggtgtctggtcagagacatcaagaaataacgccggaacattagtgcaggcagcttccacagcaatggcatcctggtcatccagcgg
atagttaatgatcagcccactgacgcgttgcgcgagaagattgtgcaccgccgctttacaggcttcgacgccgcttcgttctaccatcgacaccac
cacgctggcacccagttgatcggcgcgagatttaatcgccgcgacaatttgcgacggcgcgtgcagggccagactggaggtggcaacgccaa
tcagcaacgactgtttgcccgccagttgttgtgccacgcggttgggaatgtaattcagctccgccatcgccgcttccactttttcccgcgttttcgca
gaaacgtggctggcctggttcaccacgcgggaaacggtctgataagagacaccggcatactctgcgacatcgtataacgttactggtttcacatt
caccaccctgaattgactctcttccgggcgctatcatgccataccgcgaaaggttttgcgccattcgatggtgtccgggatctcgacgctctcccttt
```

-continued

```
atgcgactcctgcattaggaagcagcccagtagtaggttgaggccgttgagcaccgccgccgcaaggaatggtgcatgcaaggagatggcgc
ccaacagtcccccggccacggggcctgccaccatacccacgccgaaacaagcgctcatgagcccgaagtggcgagcccgatcttccccatc
ggtgatgtcggcgatataggcgccagcaaccgcacctgtggcgccggtgatgccggccacgatgcgtccggcgtagaggatcgagatctcga
tcccgcgaaattaatacgactcactatagggaattgtgagcggataacaattcccctctagaaataattttgtttaactttaagaaggagatatacat
atggaagcacgtcgctctgcgaactacgaacctaacagctgggactatgattacctgctgtcctccgacacggacgagtccatcgaagtatacaa
agacaaagcgaaaaagctggaagccgaagttcgtcgcgagattaataacgaaaaagcagaatttctgaccctgctggaactgattgacaacgtc
cagcgcctgggcctgggttaccgtttcgagtctgatatccgtggtgcgctggatcgcttcgtttcctccggcggcttcgatgcggtaaccaagactt
ccctgcacggtacggcactgtcttccgtctgctgcgtcaacacggttttgaggtttctcaggaagcgttcagcggcttcaaagaccaaaacggca
acttcctggagaacctgaaggaagatatcaaagctatcctgagcctgtacgaggccagcttcctggctctggaaggcgaaaacatcctggacga
ggcgaaggttttcgcaatctctcatctgaaagaactgtctgaagaaaagatcggtaaagagctggcagaacaggtgaaccatgcactggaactg
ccactgcatcgccgtactcagcgtctggaagcagtatggtctatcgaggcctaccgtaaaaaggaggacgcgaatcaggttctgctggagctgg
caattctggattacaacatgatccagtctgtataccagcgtgatctgcgtgaaacgtcccgttggtggcgtcgtgtgggtctggcgaccaaactgc
actttgctcgtgaccgcctgattgagagcttctactgggccgtgggtgtagcattcgaaccgcaatactccgactgccgtaactccgtcgcaaaaa
tgttttctttcgtaaccattatcgacgatatctacgatgtatacggcaccctggacgaactggagctgtttactgatgcagttgagcgttgggacgtaa
acgccatcaacgacctgccggattacatgaaactgtgcttctggctctgtataacactattaacgaaatcgcctacgacaacctgaaagataaag
gtgagaacatcctgccgtatctgaccaaagcctgggctgacctgtgcaacgcttcctgcaagaagccaagtggctgtacaacaaatctactccg
acctttgacgactacttcggcaacgcatggaaatcctcttctggcccgctgcaactggtgttcgcttacttcgctgtcgtgcagaacattaaaaagg
aagagatcgaaaacctgcaaaaataccatgacaccatctctcgtccttcccatatcttccgtctgtgcaatgacctggctagcgcgtctgcggaaat
tgcgcgtggtgaaaccgcaaatagcgtttcttgttacatgcgcactaaaggtatctccgaagaactggctaccgaaagcgtgatgaatctgatcga
tgaaacctggaaaaagatgaacaaggaaaaactgggtggtagcctgttcgcgaaaccgttcgtggaaaccgcgatcaacctggcacgtcaatc
tcactgcacttatcataacggcgacgcgcatacctctccggatgagctgacccgcaaacgcgttctgtctgtaatcactgaaccgattctgccgttt
gaacgctaaggatccgaattcgagctccgtcgacaagcttgcggccgcactcgagcaccaccaccaccaccactgagatccggctgctaaca
aagcccgaaaggaagctgagttggctgctgccaccgctgagcaataactagcataaccccttggggcctctaaacgggtcttgaggggttttttg
ctgaaaggaggaactatatccggat
```

Amino Acid Sequence of P. alba IspS: (SEQ ID NO: 22)

MEARRSANYEPNSWDYDYLLSSDTDESIEVYKDKAKKLEAEVRREINNEKAEFLTLLELID
NVQRLGLGYRFESDIRGALDRFVSSGGFDAVTKTSLHGTALSFRLLRQHGFEVSQEAFSGF
KDQNGNFLENLKEDIKAILSLYEASFLALEGENILDEAKVFAISHLKELSEEKIGKELAEQVN
HALELPLHRRTQRLEAVWSIEAYRKKEDANQVLLELAILDYNMIQSVYQRDLRETSRWWR
RVGLATKLHFARDRLIESFYWAVGVAFEPQYSDCRNSVAKMFSFVTIIDDIYDVYGTLDEL
ELFTDAVERWDVNAINDLPDYMKLCFLALYNTINEIAYDNLKDKGENILPYLTKAWADLC
NAFLQEAKWLYNKSTPTFDDYFGNAWKSSSGPLQLVFAYFAVVQNIKKEEIENLQKYHDTI
SRPSHIFRLCNDLASASAEIARGETANSVSCYMRTKGISEELATESVMNLIDETWKKMNKE
KLGGSLFAKPFVETAINLARQSHCTYHNGDAHTSPDELTRKRVLSVITEPILPFER

SEL Expression Host—A P1 lysate of MCM521 (described herein) was made and transduced into BL21(DE3) according to standard molecular biology techniques (Miller, A Short Course in Bacterial Genetics). Transductants were selected on LB medium plates containing 20 μg/ml of kanamycin. Positive colonies were further verified by PCR to confirm the presence of PL.2-mKKDyI in the BL21 DE3 strain. 1 μl of pCP20 plasmid was then transformed into this strain and positive colonies were selected for on LB containing 50 μg/ml carbenicillin and incubated overnight at 30° C. Positive transformants were streaked on an LB plate and incubated at 37° C. to induce loss of the pCP20 plasmid. To confirm the loss of the neomycin (kanamycin) resistance marker, colonies that grew at 37° C. were patched onto LB medium containing either 20 μg/ml of kanamycin, 50 μg/ml of carbenicillin, or no antibiotics. The strains with integrated PL.2 mKKDyI without the kanamycin resistance marker that have lost pCP20 should be sensitive to kanamycin and carbenicillin. Four colonies sensitive to kanamycin and carbenicillin were checked by PCR for the presence of mKKDyI in BL21(DE3) with the parental BL21(DE3) strain as a control. The resulting strain, MD09-170, was used for expression of IspS variants in the growth assay on SELs described below. Control strains for the growth assay harbored either the empty pET24a+ vector or pCL201 as negative and positive controls for IspS expression, respectively (see Table 2).

TABLE 2

Strains

| Strain | Plasmid | Description |
| --- | --- | --- |
| MD09-170 | | BL21 (DE3) PL.2-mKKDyI |
| DW424 | pET24a+ | BL21 (DE3) PL.2-mKKDyI + vector (negative control) |
| DW425 | pCL201 | BL21 (DE3) PL.2-mKKDyI + P. alba IspS (wild type control) |

2) Construction of SELs:

25 Site Evaluation Libraries (SELs) of IspS were analyzed previously for specific activity. Table 3 lists the residues included in these libraries. For the growth assay, plasmids harboring variant IspS enzymes in these libraries were purified and transformed into the expression host MD09-170: Original libraries were replicated directly from glycerol stocks and grown at 30° C. overnight in LB containing 50 µg/ml kanamycin in 96 deep-well plates (VWR). Cells from the overnight growth were harvested by centrifugation (Eppendorf 5804R), and supernatants were discarded. Plasmid purification was performed on cell pellets using a Hamilton Microlab STAR robot using the Nucleospin Multi-96 Plus Plasmid purification kit (Macherey Nagel) according to the manufacturers' recommended protocols. 3 µl of the resulting plasmid DNA for each variant was transformed into chemically competent MD09-170 cells in a flat-bottom 96-well polystyrene plate (Falcon) using an Eppendorf Thermomixer R set to 42° C. Cells were recovered for 2 hours in LB medium, and then diluted and incubated overnight in LB medium containing 50 µg/ml kanamycin. Glycerol stocks of plates containing MD09-170 cells with variants from all 25 original libraries were made and stored at −80° C. prior to analysis by growth assay.

A second set of 80 SELs was ordered and manufactured by DNA2.0. These libraries were transformed directly into the screening host MD09-170. Table 4 lists all 80 residues that were chosen for this set. Sites were picked primarily based upon their location in the recently solved crystal structure of P. alba IspS. Strains DW425 and DW424 (see Table 2) were seeded back into 96-well plates for the wild type and negative controls, respectively.

TABLE 3

Sites selected for 25 SELs

| Description | Sites |
| --- | --- |
| Surface hydrophobic residues | I28, V30, L130, G153, V299, L303, L469, L494 |
| Hinge region | R198, I229, L260 |
| Negatively charged area | D311, D323 |
| Flexible loops | A443, A453, N454, H515, A519, E525 |
| Active site | F388, N438, E451 |
| Miscellaneous | D345, R528, T536 |

TABLE 4

Sites selected for 80 SELs

| Position | Residue | Selection Criteria |
| --- | --- | --- |
| 3 | A | surface hydrophobic |
| 7 | A | symmetry contact |
| 9 | Y | symmetry contact |
| 12 | N | conservation |
| 13 | S | conservation |
| 16 | Y | N-terminal loop |
| 18 | Y | N-terminal loop |
| 20 | L | conservation |
| 23 | D | conservation |
| 25 | D | surface hydrophilic |
| 26 | E | symmetry contact |
| 27 | S | surface hydrophilic |
| 33 | D | symmetry contact |
| 36 | K | symmetry contact |
| 44 | R | symmetry contact |
| 50 | K | surface hydrophilic |
| 53 | F | conservation |
| 59 | L | surface hydrophobic |
| 69 | G | conservation |
| 74 | S | surface hydrophilic |
| 78 | G | conservation |
| 81 | D | surface hydrophilic |
| 87 | G | surface hydrophobic |
| 99 | G | conservation |
| 116 | Q | conservation |
| 117 | E | symmetry contact |
| 120 | S | surface hydrophilic |
| 121 | G | surface loop |
| 125 | Q | surface hydrophilic |
| 127 | G | conservation |
| 139 | A | conservation |
| 165 | I | surface hydrophobic |
| 173 | E | surface hydrophilic |
| 174 | E | symmetry contact |
| 177 | G | conservation |
| 179 | E | surface hydrophilic |
| 194 | R | conservation |
| 197 | Q | conservation |
| 202 | V | conservation |
| 216 | Q | conservation |
| 240 | T | conservation |
| 246 | R | symmetry contact |
| 251 | T | surface hydrophilic |
| 254 | H | conservation |
| 287 | F | active site |
| 290 | V | active site |
| 308 | L | surface hydrophobic |
| 376 | L | flexible loops |
| 377 | Y | symmetry contact |
| 379 | K | conservation |
| 389 | G | conservation |
| 397 | G | active site |
| 400 | Q | hydrophobic pocket |
| 403 | F | active site |
| 421 | Q | conservation |
| 426 | T | conservation |
| 430 | P | misc |
| 434 | F | active site |
| 445 | A | surface hydrophobic |
| 448 | A | conservation |
| 457 | S | flexible loops |
| 462 | T | conservation |
| 476 | N | surface hydrophilic |
| 487 | K | surface loop |
| 488 | E | surface loop |
| 489 | K | surface loop |
| 490 | L | surface loop |
| 491 | G | surface loop |
| 492 | G | surface loop |
| 493 | S | surface loop |
| 495 | F | surface loop |
| 496 | A | surface loop |
| 497 | K | surface loop |
| 498 | P | conservation |
| 509 | Q | conservation |
| 514 | Y | active site |

TABLE 4-continued

Sites selected for 80 SELs

| Position | Residue | Selection Criteria |
|---|---|---|
| 521 | T | conservation |
| 539 | I | C-terminal |
| 540 | L | surface hydrophobic |
| 544 | R | conservation |

3) Growth Assay for Increased IspS Activity

For the growth assay, glycerol stocks of SELs were inoculated into 200 µl LB medium containing 50 µg/ml kanamycin in flat bottom microtiter plates (Cellstar) and grown overnight at 30° C. using the System Duetz (Enzyscreen BV). For pre-induction, 7 µl of the overnight culture from each well was inoculated into 100 µl of TM3 medium containing 50 µM IPTG and 50 µg/ml kanamycin, and plates were grown for 2 hours at 30° C. Pre-induced cultures were then diluted 1:10 into TM3 medium containing 11 mM mevalonic acid, 50 µM IPTG and 50 µg/ml kanamycin in glass-bottom 96 square-well microtiter plates (Matrical). Cultures were grown at 34° C. and shaken at 225 rpm for approximately 10 hours in a Growth Profiler 1152 (Enzyscreen). Growth curves were generated for each IspS variant according to the manufacturer's recommended protocol. Negative controls were strains harboring the empty pET24a+ vector (DW424), and positive controls were strains expressing wild type *P. alba* IspS (DW425) grown either with or without MVA.

For data analysis, the relative growth rate of each variant over a given period of time was measured against wild type controls. Specifically, a line was fit to the series using the "LINEST" function in Microsoft Excel to yield the exponential growth constant (growth rate). These values were then divided by the average of 4 (in most cases) growth constants from the positive controls to yield a "Growth Index" number for each variant. The Growth Index values for variants in all 105 SEL libraries are listed in Table 5. In some cases, a particular variant was either absent from the glycerol stock, did not grow in the overnight LB culture, or was not transferred to the final plate for growth assay. Values for these particular wells are listed as ND (Not Determined). In the instances where a particular variant was not generated in initial mutagenesis of *P. alba* IspS, the wild type residue was substituted.

TABLE 5

| Variant | GI |
|---|---|
| Growth Index Ranking for Plate 001. | |
| V30L | 1.61 |
| V30K | 1.52 |
| I28T | 1.46 |
| V30Y | 1.45 |
| V30W | 1.39 |
| I28S | 1.38 |
| G153W | 1.34 |
| I28R | 1.31 |
| L130Y | 1.29 |
| V30S | 1.26 |
| V30V | 1.25 |
| V30F | 1.22 |
| L130L | 1.20 |
| L130K | 1.17 |
| I28I | 1.15 |
| L130G | 1.15 |
| L130I | 1.14 |
| V30R | 1.13 |
| G153Y | 1.12 |
| L130L | 1.12 |
| V30I | 1.11 |
| I28Y | 1.10 |
| L130V | 1.09 |
| L130L | 1.09 |
| V30P | 1.08 |
| V30E | 1.07 |
| G153G | 1.07 |
| L130R | 1.05 |
| V30T | 1.05 |
| L130L | 1.04 |
| V30Q | 1.04 |
| I28P | 1.03 |
| G153S | 1.02 |
| G153R | 1.01 |
| G153C | 1.00 |
| L130D | 0.97 |
| G153G | 0.97 |
| L130E | 0.96 |
| G153A | 0.96 |
| V30V | 0.95 |
| V30M | 0.94 |
| I28I | 0.92 |
| G153G | 0.92 |
| L130L | 0.91 |
| G153T | 0.90 |
| V30G | 0.89 |
| L130W | 0.88 |
| L130Q | 0.88 |
| G153Q | 0.86 |
| G153G | 0.86 |
| G153M | 0.83 |
| G153N | 0.83 |
| G153D | 0.81 |
| L130P | 0.76 |
| V30N | 0.60 |
| I28I | 0.57 |
| I28I | 0.55 |
| I28L | 0.52 |
| I28W | 0.42 |
| I28D | 0.38 |
| G153K | 0.32 |
| G153L | 0.32 |
| G153P | 0.32 |
| V30C | 0.31 |
| G153V | 0.31 |
| I28E | 0.29 |
| L130A | 0.28 |
| I28G | 0.28 |
| I28F | 0.27 |
| V30A | 0.26 |
| I28A | ND |
| L130M | 0.22 |
| I28M | 0.15 |
| L130C | 0.15 |
| I28N | 0.14 |
| I28C | 0.10 |
| I28V | ND |
| V30D | ND |
| L130S | ND |
| G153H | ND |
| Growth Index Ranking for Plate 002. | |
| R198R | 1.11 |
| R198R | 1.08 |
| I229L | 1.00 |
| R198R | 0.98 |
| I229C | 0.94 |
| L260L | 0.89 |
| L260L | 0.88 |
| R198R | 0.87 |
| I229I | 0.86 |
| R198K | 0.84 |
| V299V | 0.82 |
| I229T | 0.80 |
| I229V | 0.78 |
| I229M | 0.78 |
| L260M | 0.77 |

TABLE 5-continued

| Variant | GI |
|---|---|
| L260L | 0.75 |
| L260W | 0.74 |
| R198C | 0.74 |
| V299L | 0.72 |
| V299V | 0.69 |
| R198M | 0.68 |
| L260Y | 0.66 |
| R198V | 0.64 |
| R198A | 0.62 |
| I229A | 0.62 |
| V299V | 0.62 |
| L260Q | 0.61 |
| V299V | 0.60 |
| I229H | 0.57 |
| L260I | 0.54 |
| R198I | 0.52 |
| I229N | 0.49 |
| I229F | 0.45 |
| I229S | 0.45 |
| L260H | 0.45 |
| R198T | 0.42 |
| L260P | 0.40 |
| L260V | 0.38 |
| I229G | 0.36 |
| I229Q | 0.35 |
| R198S | 0.35 |
| L260G | 0.34 |
| V299T | 0.29 |
| L260C | 0.25 |
| V299A | 0.25 |
| R198G | 0.24 |
| R198N | 0.23 |
| L260A | 0.22 |
| V299M | 0.22 |
| L260S | ND |
| V299S | 0.15 |
| L260D | 0.15 |
| V299N | 0.14 |
| L260E | 0.11 |
| I229Y | 0.11 |
| V299R | 0.10 |
| R198L | 0.10 |
| I229K | 0.09 |
| R198F | 0.08 |
| I229W | 0.08 |
| R198H | 0.07 |
| V299E | 0.05 |
| V299K | 0.03 |
| R198Y | 0.03 |
| V299W | 0.02 |
| R198D | 0.02 |
| I229D | 0.02 |
| I229R | 0.01 |
| V299Y | 0.01 |
| V299G | 0.01 |
| I229E | 0.01 |
| L260R | 0.01 |
| R198P | ND |
| L260K | 0.00 |
| L260T | 0.00 |
| V299I | ND |
| I229P | −0.02 |
| V299H | −0.03 |
| V299P | −0.04 |
| V299D | −0.05 |

Growth Index Ranking for Plate 003.

| Variant | GI |
|---|---|
| L303L | 1.10 |
| L303L | 1.10 |
| D311D | 1.08 |
| L303L | 1.06 |
| L303L | 0.99 |
| D311W | 0.99 |
| D311L | 0.98 |
| D311K | 0.98 |
| L303W | 0.96 |
| D311F | 0.93 |
| D311S | 0.92 |
| D311G | 0.90 |
| D323K | 0.89 |
| L303T | 0.88 |
| D311R | 0.87 |
| L303R | 0.85 |
| D311T | 0.84 |
| D311V | 0.82 |
| L303L | 0.81 |
| L303V | 0.81 |
| L303I | 0.80 |
| D311D | 0.80 |
| D311A | 0.80 |
| L303S | 0.79 |
| D311I | 0.78 |
| L303M | 0.77 |
| D323L | 0.77 |
| D323R | 0.75 |
| D311D | 0.75 |
| L303E | 0.74 |
| D323Y | 0.74 |
| L303C | 0.74 |
| D323S | 0.74 |
| D345L | 0.73 |
| D311Q | 0.73 |
| L303G | 0.72 |
| D323G | 0.71 |
| D311D | 0.71 |
| D345G | 0.70 |
| D323T | 0.69 |
| D311E | 0.69 |
| D323M | 0.69 |
| D323N | 0.68 |
| D345W | 0.68 |
| D311D | 0.67 |
| L303Q | 0.67 |
| D345D | 0.66 |
| L303A | 0.66 |
| D323E | 0.66 |
| L303P | 0.66 |
| D323A | 0.66 |
| D345M | 0.66 |
| D345A | 0.65 |
| D323D | 0.64 |
| D323V | 0.63 |
| D323C | 0.62 |
| L303H | 0.62 |
| L303D | 0.62 |
| D323F | 0.61 |
| D345S | 0.61 |
| D323I | 0.61 |
| D345V | 0.59 |
| D323Q | 0.58 |
| D345T | 0.58 |
| D323W | 0.57 |
| D345Y | 0.57 |
| D345R | 0.56 |
| D345N | 0.55 |
| D345K | 0.53 |
| D345Q | 0.53 |
| D345I | 0.53 |
| D345D | 0.53 |
| D345E | 0.52 |
| D345C | 0.51 |
| D345D | 0.41 |
| D345P | 0.37 |
| D311M | ND |
| D323P | ND |
| D323H | ND |
| D311P | −0.02 |

Growth Index Ranking for Plate 004.

| Variant | GI |
|---|---|
| E451E | 1.48 |
| A443A | 1.36 |
| A443A | 1.34 |
| A443A | 1.29 |
| F388F | 1.28 |
| N438N | 1.27 |
| A443A | 1.20 |

TABLE 5-continued

| Variant | GI |
|---|---|
| F388V | 1.20 |
| A443A | 1.17 |
| A443A | 1.15 |
| A443A | 1.13 |
| E451E | 1.13 |
| A443A | 1.12 |
| F388Q | 0.96 |
| F388T | 0.89 |
| F388F | 0.89 |
| A443S | 0.86 |
| A443H | 0.85 |
| A443L | 0.84 |
| A443N | 0.82 |
| F388R | 0.74 |
| F388S | 0.68 |
| A443Q | 0.66 |
| A443I | 0.63 |
| A443G | 0.50 |
| A443R | 0.44 |
| F388D | 0.42 |
| A443V | 0.40 |
| A443F | 0.28 |
| A443P | 0.06 |
| E451Q | 0.06 |
| A443T | 0.03 |
| F388H | ND |
| F388L | 0.00 |
| F388F | −0.01 |
| F388F | −0.01 |
| E451W | −0.01 |
| E451K | −0.01 |
| F388A | −0.02 |
| N438A | −0.02 |
| E451G | −0.02 |
| E451H | −0.02 |
| F388P | −0.02 |
| E451D | −0.02 |
| E451R | −0.03 |
| F388Y | ND |
| F388K | −0.03 |
| E451Y | −0.03 |
| E451F | −0.03 |
| F388C | −0.03 |
| E451I | −0.03 |
| N438F | −0.04 |
| E451V | −0.04 |
| N438H | −0.04 |
| E451A | −0.04 |
| E451C | −0.04 |
| E451T | −0.04 |
| N438T | −0.04 |
| N438D | −0.04 |
| N438E | −0.04 |
| E451L | −0.05 |
| N438I | −0.05 |
| N438W | ND |
| E451P | −0.05 |
| N438V | −0.05 |
| F388F | −0.05 |
| N438M | −0.05 |
| N438L | −0.05 |
| N438C | −0.05 |
| N438K | −0.06 |
| E451S | −0.06 |
| F388F | −0.06 |
| E451N | −0.06 |
| N438R | −0.06 |
| N438Y | −0.06 |
| N438Q | −0.06 |
| N438P | −0.06 |
| N438G | −0.07 |
| F388G | −0.08 |
| N438S | −0.09 |

Growth Index Ranking for Plate 005.

| Variant | GI |
|---|---|
| N454N | 1.10 |
| L494L | 1.06 |
| L469W | 1.06 |
| L494K | 1.03 |
| L469L | 1.00 |
| L469R | 0.98 |
| L469L | 0.98 |
| L494L | 0.98 |
| L494W | 0.97 |
| L494Y | 0.95 |
| L469V | 0.95 |
| L494G | 0.94 |
| L469F | 0.93 |
| L494I | 0.93 |
| L469I | 0.92 |
| A453T | 0.91 |
| A453A | 0.90 |
| L494V | 0.90 |
| L494R | 0.89 |
| A453W | 0.88 |
| L469N | 0.88 |
| A453C | 0.88 |
| L469T | 0.88 |
| L469S | 0.87 |
| L469H | 0.87 |
| N454N | 0.86 |
| L494C | 0.86 |
| L494D | 0.86 |
| L494E | 0.86 |
| L469C | 0.85 |
| A453S | 0.85 |
| A453A | 0.85 |
| N454S | 0.84 |
| A453A | 0.84 |
| L469P | 0.83 |
| L494S | 0.83 |
| N454G | 0.83 |
| A453N | 0.83 |
| L494H | 0.83 |
| L469A | 0.83 |
| L469L | 0.82 |
| L494N | 0.81 |
| L469Q | 0.79 |
| L494L | 0.78 |
| A453E | 0.77 |
| L469L | 0.77 |
| N454H | 0.76 |
| A453L | 0.76 |
| A453H | 0.75 |
| L469G | 0.75 |
| L494Q | 0.74 |
| N454A | 0.73 |
| L494P | 0.73 |
| N454T | 0.73 |
| L469L | 0.73 |
| N454E | 0.72 |
| A453I | 0.70 |
| L494A | 0.69 |
| N454Y | 0.67 |
| N454W | 0.66 |
| A453V | 0.64 |
| N454V | 0.63 |
| A453F | 0.62 |
| N454Q | 0.62 |
| N454L | 0.61 |
| A453R | 0.59 |
| N454D | 0.56 |
| A453D | 0.54 |
| N454C | 0.53 |
| N454F | 0.49 |
| A453K | 0.45 |
| L494T | 0.42 |
| N454I | 0.31 |
| A453G | 0.26 |
| N454M | 0.22 |
| L469Y | 0.19 |
| A453P | 0.02 |
| N454P | 0.00 |
| A453Y | ND |
| N454R | −0.03 |

TABLE 5-continued

| Variant | GI |
|---|---|
| Growth Index Ranking for Plate 006. | |
| A519W | 1.27 |
| E525K | 1.13 |
| H515Y | 1.07 |
| R528K | 1.05 |
| E525E | 1.01 |
| A519K | 0.99 |
| H515K | 0.98 |
| H515W | 0.97 |
| H515R | 0.96 |
| E525W | 0.94 |
| R528R | 0.92 |
| R528R | 0.92 |
| A519A | 0.91 |
| E525L | 0.89 |
| A519R | 0.89 |
| A519A | 0.87 |
| R528V | 0.85 |
| A519A | 0.85 |
| E525V | 0.85 |
| A519G | 0.85 |
| H515G | 0.85 |
| A519A | 0.85 |
| R528R | 0.85 |
| E525R | 0.83 |
| E525E | 0.83 |
| E525D | 0.83 |
| E525T | 0.82 |
| E525C | 0.81 |
| E525G | 0.80 |
| E525M | 0.79 |
| H515F | 0.78 |
| H515M | 0.78 |
| H515V | 0.78 |
| E525F | 0.77 |
| A519H | 0.76 |
| A519F | 0.76 |
| H515Q | 0.73 |
| A519Y | 0.73 |
| H515T | 0.73 |
| E525H | 0.73 |
| E525N | 0.73 |
| E525Q | 0.72 |
| R528M | 0.70 |
| H515N | 0.70 |
| E525A | 0.69 |
| R528F | 0.69 |
| E525E | 0.67 |
| R528H | 0.67 |
| A519S | 0.66 |
| A519L | 0.66 |
| H515E | 0.66 |
| E525S | 0.64 |
| H515S | 0.63 |
| A519T | 0.61 |
| R528Y | 0.61 |
| R528T | 0.60 |
| R528L | 0.59 |
| H515A | 0.58 |
| A519C | 0.50 |
| R528A | 0.49 |
| A519V | 0.45 |
| A519Q | 0.44 |
| R528S | 0.43 |
| A519E | 0.39 |
| E525P | 0.37 |
| R528N | 0.35 |
| R528E | 0.34 |
| A519D | 0.33 |
| R528G | 0.33 |
| R528C | 0.31 |
| R528W | 0.30 |
| H515L | 0.15 |
| R528D | 0.08 |
| A519P | 0.00 |
| H515H | −0.01 |
| H515H | ND |
| H515P | −0.02 |
| R528P | −0.02 |
| H515H | ND |
| H515H | ND |
| Growth Index Ranking for Plate 007. | |
| T536L | 0.62 |
| T536T | 0.59 |
| T536Y | 0.58 |
| T536I | 0.49 |
| T536H | 0.46 |
| T536F | 0.45 |
| T536G | 0.42 |
| T536T | 0.40 |
| T536V | 0.38 |
| T536S | 0.36 |
| T536K | 0.31 |
| T536T | 0.30 |
| T536M | 0.29 |
| T536N | 0.29 |
| T536C | 0.27 |
| T536A | 0.26 |
| T536D | 0.18 |
| T536R | 0.15 |
| T536E | 0.14 |
| T536P | 0.01 |
| Growth Index Ranking for Plate 008. | |
| G78L | 1.33 |
| G78Y | 1.31 |
| G78W | 1.27 |
| G78I | 1.26 |
| S74K | 1.24 |
| K36L | 1.23 |
| S74W | 1.22 |
| S74I | 1.20 |
| K36K | 1.20 |
| K36I | 1.19 |
| G78V | 1.19 |
| K36V | 1.19 |
| G78H | 1.18 |
| G78T | 1.18 |
| S74V | 1.17 |
| K36Y | 1.17 |
| S74L | 1.14 |
| S74T | 1.14 |
| S74Y | 1.13 |
| G78K | 1.13 |
| K36R | 1.11 |
| S74H | 1.10 |
| K36T | 1.07 |
| G78F | 1.01 |
| K36W | 1.01 |
| S74G | 0.98 |
| K36S | 0.98 |
| G78R | 0.97 |
| S74R | 0.97 |
| K36H | 0.97 |
| K36F | 0.95 |
| S74S | 0.94 |
| G78G | 0.91 |
| G78S | 0.91 |
| S74F | 0.86 |
| G78C | 0.84 |
| K36G | 0.83 |
| S74C | 0.78 |
| K36M | 0.77 |
| A7G | 0.77 |
| S74Q | 0.77 |
| G78P | 0.76 |
| S74P | 0.76 |
| G78E | 0.74 |
| S74N | 0.72 |
| G78D | 0.72 |
| K36N | 0.72 |
| S74E | 0.72 |
| S74D | 0.70 |
| S74A | 0.70 |

TABLE 5-continued

| Variant | GI |
|---|---|
| G78M | 0.70 |
| A7A | 0.69 |
| K36C | 0.69 |
| G78N | 0.68 |
| G78Q | 0.68 |
| G78A | 0.66 |
| S74M | 0.65 |
| K36Q | 0.65 |
| K36P | 0.61 |
| K36D | 0.58 |
| K36A | 0.56 |
| K36E | 0.54 |
| A7W | 0.50 |
| A7V | 0.39 |
| A7C | 0.34 |
| A7H | 0.31 |
| A7P | 0.31 |
| A7Y | 0.30 |
| A7S | 0.30 |
| A7T | 0.29 |
| A7I | 0.29 |
| A7F | 0.20 |
| A7Q | 0.19 |
| A7E | 0.17 |
| A7N | 0.16 |
| A7L | 0.09 |
| A7D | 0.07 |
| A7R | 0.07 |
| A7M | 0.06 |
| A7K | −0.02 |

Growth Index Ranking for Plate 009.

| Variant | GI |
|---|---|
| R44H | 1.30 |
| R44T | 1.27 |
| R44F | 1.21 |
| G121I | 1.17 |
| R44V | 1.17 |
| G121L | 1.15 |
| G121H | 1.14 |
| R44Y | 1.13 |
| R44I | 1.10 |
| G121F | 1.09 |
| G121T | 1.07 |
| G121Y | 1.07 |
| R44K | 1.04 |
| G121V | 1.03 |
| G121K | 1.02 |
| G121W | 1.00 |
| R44C | 1.00 |
| R44A | 1.00 |
| Q216H | 0.99 |
| R44M | 0.99 |
| R44L | 0.99 |
| R44D | 0.96 |
| R44N | 0.96 |
| R44S | 0.95 |
| Q216I | 0.94 |
| G121A | 0.94 |
| Q216T | 0.92 |
| G121G | 0.91 |
| Q216V | 0.90 |
| G121M | 0.90 |
| Q216K | 0.89 |
| G121C | 0.88 |
| E488I | 0.88 |
| Q216F | 0.87 |
| Q216L | 0.87 |
| G121R | 0.87 |
| Q216W | 0.86 |
| Q216Y | 0.84 |
| Q216A | 0.83 |
| G121P | 0.83 |
| R44E | 0.82 |
| Q216C | 0.81 |
| R44Q | 0.80 |
| R44W | 0.79 |
| R44P | 0.78 |
| Q216G | 0.78 |
| R44R | 0.78 |
| E488A | 0.77 |
| E488L | 0.76 |
| G121D | 0.75 |
| Q216E | 0.75 |
| G121S | 0.74 |
| Q216S | 0.74 |
| G121N | 0.74 |
| G121Q | 0.72 |
| E488V | 0.72 |
| Q216M | 0.72 |
| Q216N | 0.71 |
| G121E | 0.71 |
| E488W | 0.70 |
| Q216D | 0.70 |
| Q216Q | 0.68 |
| E488F | 0.67 |
| E488C | 0.66 |
| E488E | 0.66 |
| E488G | 0.66 |
| E488D | 0.65 |
| E488T | 0.65 |
| E488H | 0.64 |
| E488Q | 0.61 |
| Q216P | 0.60 |
| Q216R | 0.60 |
| E488R | 0.54 |
| R44G | 0.53 |
| E488M | 0.52 |
| E488Y | 0.44 |
| E488S | 0.43 |
| E488K | 0.32 |
| E488N | 0.25 |
| E488P | 0.17 |

Growth Index Ranking for Plate 010.

| Variant | GI |
|---|---|
| E179L | 1.46 |
| E179I | 1.40 |
| T251T | 1.36 |
| E179K | 1.35 |
| E179H | 1.33 |
| E179W | 1.26 |
| G177V | 1.26 |
| G177T | 1.25 |
| E179T | 1.23 |
| G177L | 1.22 |
| E179V | 1.22 |
| G177I | 1.18 |
| R246R | 1.17 |
| E179Y | 1.14 |
| G177H | 1.14 |
| G177K | 1.13 |
| R246K | 1.13 |
| E179F | 1.11 |
| G177P | 1.11 |
| T251N | 1.10 |
| T251Y | 1.09 |
| E179S | 1.07 |
| E179G | 1.05 |
| T251H | 1.04 |
| R246T | 1.04 |
| G177Y | 1.03 |
| R246H | 1.03 |
| G177A | 1.03 |
| T251K | 1.01 |
| G177M | 1.01 |
| E179M | 1.01 |
| G177W | 1.00 |
| T251S | 1.00 |
| E179A | 0.96 |
| T251R | 0.94 |
| E179R | 0.94 |
| E179C | 0.94 |
| R246G | 0.94 |
| G177G | 0.93 |
| G177N | 0.93 |
| T251G | 0.92 |
| G177S | 0.92 |

TABLE 5-continued

| Variant | GI |
|---|---|
| T251Q | 0.91 |
| G177R | 0.90 |
| R246S | 0.90 |
| G177C | 0.88 |
| R246N | 0.87 |
| R246Q | 0.85 |
| E179D | 0.84 |
| E179P | 0.82 |
| G177F | 0.81 |
| R246E | 0.80 |
| E179N | 0.79 |
| T251E | 0.79 |
| R246D | 0.79 |
| G177D | 0.79 |
| T251D | 0.78 |
| T251C | 0.77 |
| T251M | 0.76 |
| R246A | 0.75 |
| E179Q | 0.74 |
| G177E | 0.74 |
| T251A | 0.74 |
| T251W | 0.73 |
| T251V | 0.71 |
| T251F | 0.71 |
| T251L | 0.69 |
| R246M | 0.65 |
| R246Y | 0.61 |
| R246C | 0.61 |
| R246L | 0.54 |
| R246V | 0.53 |
| R246W | 0.53 |
| T251I | 0.52 |
| G177Q | 0.44 |
| R246I | 0.40 |
| T251P | 0.37 |
| R246F | 0.30 |
| R246P | 0.01 |
| E179E | 0.00 |
| Growth Index Ranking for Plate 011. | |
| H254H | 1.32 |
| H254K | 1.20 |
| L308H | 1.19 |
| L308I | 1.18 |
| H254F | 1.17 |
| H254V | 1.16 |
| H254W | 1.15 |
| H254I | 1.12 |
| H254T | 1.11 |
| H254R | 1.07 |
| L308W | 1.07 |
| L308L | 1.05 |
| H254Y | 0.97 |
| L308R | 0.94 |
| V290I | 0.92 |
| L308Y | 0.92 |
| V290V | 0.89 |
| H254G | 0.89 |
| H254L | 0.88 |
| H254S | 0.87 |
| L308C | 0.85 |
| H254D | 0.85 |
| L308G | 0.84 |
| H254E | 0.81 |
| H254A | 0.80 |
| H254C | 0.78 |
| L308D | 0.76 |
| F287F | 0.74 |
| L308N | 0.71 |
| L308E | 0.71 |
| L308S | 0.69 |
| H254M | 0.68 |
| H254Q | 0.68 |
| L308Q | 0.65 |
| L308V | 0.59 |
| H254N | 0.59 |
| V290T | 0.59 |
| V290L | 0.48 |
| F287W | 0.42 |
| F287L | 0.39 |
| F287M | 0.26 |
| F287V | 0.21 |
| L308P | 0.20 |
| L308A | 0.19 |
| F287Y | 0.19 |
| V290C | 0.18 |
| L308T | 0.17 |
| V290A | 0.17 |
| V290S | 0.16 |
| V290G | 0.15 |
| L308K | 0.15 |
| F287A | 0.10 |
| F287H | 0.09 |
| F287K | 0.08 |
| L308F | 0.06 |
| V290H | 0.04 |
| F287T | 0.04 |
| V290K | 0.04 |
| F287Q | 0.03 |
| V290W | 0.03 |
| F287S | 0.02 |
| V290Y | 0.02 |
| L308M | 0.02 |
| F287G | 0.02 |
| F287I | 0.01 |
| F287N | 0.01 |
| F287R | 0.01 |
| V290R | 0.00 |
| H254P | ND |
| V290F | 0.00 |
| F287C | 0.00 |
| F287P | −0.01 |
| V290M | −0.01 |
| V290Q | −0.02 |
| F287D | −0.02 |
| V290E | −0.02 |
| F287E | −0.02 |
| V290N | −0.03 |
| V290D | −0.03 |
| V290P | −0.03 |
| Growth Index Ranking for Plate 012. | |
| Q421R | 1.39 |
| Q421H | 1.26 |
| Q421E | 1.24 |
| T426I | 1.19 |
| Q421G | 1.16 |
| Q421V | 1.13 |
| Q421K | 1.12 |
| P430S | 1.10 |
| P430T | 1.10 |
| Q421I | 1.09 |
| Q421T | 1.08 |
| Q421Q | 1.08 |
| P430V | 1.06 |
| T426V | 1.05 |
| Q421W | 1.05 |
| Q421L | 1.05 |
| Q421M | 0.92 |
| Q421A | 0.91 |
| Q421Y | 0.91 |
| T426S | 0.86 |
| T426G | 0.86 |
| Q421D | 0.86 |
| T426H | 0.86 |
| Q421S | 0.83 |
| T426F | 0.82 |
| T426L | 0.82 |
| P430A | 0.78 |
| Q421N | 0.77 |
| T426C | 0.76 |
| Q421P | 0.74 |
| T426W | 0.73 |
| P430C | 0.72 |
| T426A | 0.68 |
| T426M | 0.66 |

TABLE 5-continued

| Variant | GI |
|---|---|
| T426D | 0.66 |
| T426N | 0.60 |
| T426Q | 0.59 |
| T426E | 0.59 |
| F434I | 0.55 |
| F434L | 0.48 |
| T426Y | 0.48 |
| T426P | 0.46 |
| F434V | 0.46 |
| F434M | 0.45 |
| F434T | 0.44 |
| T426K | 0.40 |
| T426R | 0.38 |
| P430G | 0.30 |
| F434F | 0.24 |
| F434C | 0.23 |
| F434A | 0.17 |
| F434Y | 0.14 |
| F434S | 0.10 |
| F434H | 0.09 |
| F434K | 0.05 |
| F434N | 0.05 |
| T426T | 0.04 |
| F434Q | 0.04 |
| F434G | 0.03 |
| P430H | 0.02 |
| P430I | 0.02 |
| P430W | 0.02 |
| F434P | 0.01 |
| P430K | 0.01 |
| P430Q | 0.01 |
| Q421F | 0.01 |
| F434E | 0.01 |
| F434D | 0.01 |
| F434W | 0.01 |
| Q421C | 0.00 |
| P430R | 0.00 |
| F434R | 0.00 |
| P430M | 0.00 |
| P430D | 0.00 |
| P430E | 0.00 |
| P430F | 0.00 |
| P430P | 0.00 |
| P430L | 0.00 |
| P430Y | 0.00 |
| P430N | −0.01 |
| Growth Index Ranking for Plate 013. | |
| A445H | 1.18 |
| F403V | 1.06 |
| G397G | 1.05 |
| F403T | 1.03 |
| F403I | 0.93 |
| A445S | 0.92 |
| F403Y | 0.91 |
| F403L | 0.91 |
| A445K | 0.86 |
| F403S | 0.81 |
| F403H | 0.78 |
| F403F | 0.76 |
| A445Q | 0.74 |
| Q400Q | 0.74 |
| F403A | 0.72 |
| F403G | 0.71 |
| F403M | 0.70 |
| A445T | 0.70 |
| A445R | 0.68 |
| A445A | 0.68 |
| F403C | 0.67 |
| A445E | 0.67 |
| A445C | 0.65 |
| A445N | 0.64 |
| A445G | 0.62 |
| A445D | 0.62 |
| A445F | 0.61 |
| Q400L | 0.61 |
| A445M | 0.60 |
| F403N | 0.58 |
| A445L | 0.53 |
| A445Y | 0.53 |
| A445P | 0.52 |
| Q400H | 0.52 |
| A445V | 0.51 |
| Q400T | 0.51 |
| Q400C | 0.46 |
| A445W | 0.44 |
| Q400N | 0.43 |
| Q400M | 0.43 |
| A445I | 0.42 |
| G397A | 0.40 |
| F403Q | 0.38 |
| Q400S | 0.27 |
| Q400V | 0.20 |
| F403E | 0.18 |
| G397V | 0.16 |
| G397I | 0.09 |
| Q400G | 0.09 |
| G397M | 0.08 |
| F403W | 0.05 |
| G397C | 0.05 |
| Q400E | 0.02 |
| Q400A | 0.01 |
| F403D | 0.01 |
| Q400P | 0.01 |
| Q400I | 0.00 |
| G397Q | 0.00 |
| G397R | 0.00 |
| G397P | 0.00 |
| G397S | 0.00 |
| G397Y | 0.00 |
| G397N | 0.00 |
| F403P | −0.01 |
| F403K | −0.01 |
| G397L | −0.01 |
| Q400R | −0.01 |
| Q400F | −0.01 |
| Q400K | −0.02 |
| G397E | −0.02 |
| Q400D | −0.02 |
| G397F | −0.02 |
| G397H | −0.02 |
| F403R | −0.02 |
| Q400Y | −0.02 |
| G397D | −0.02 |
| Q400W | −0.03 |
| G397K | −0.03 |
| G397W | −0.03 |
| G397T | −0.03 |
| Growth Index Ranking for Plate 014. | |
| D33T | 1.49 |
| D33V | 1.46 |
| F53L | 1.44 |
| G99T | 1.43 |
| D33Y | 1.39 |
| K50K | 1.35 |
| F53T | 1.34 |
| K50I | 1.33 |
| K50L | 1.33 |
| G99V | 1.32 |
| D33W | 1.30 |
| F53W | 1.27 |
| G99I | 1.27 |
| F53V | 1.26 |
| F53I | 1.26 |
| D33H | 1.26 |
| G99K | 1.24 |
| F53Y | 1.24 |
| D33I | 1.23 |
| G99Y | 1.23 |
| G99L | 1.23 |
| D33S | 1.22 |
| K50W | 1.22 |
| D33K | 1.21 |
| D33R | 1.18 |
| K50H | 1.18 |

TABLE 5-continued

| Variant | GI |
|---|---|
| K50Y | 1.17 |
| F53R | 1.17 |
| K50T | 1.14 |
| D33L | 1.13 |
| F53S | 1.12 |
| K50V | 1.11 |
| G99S | 1.11 |
| G99R | 1.09 |
| F53K | 1.08 |
| D33Q | 1.07 |
| D33F | 1.07 |
| F53F | 1.06 |
| F53H | 1.05 |
| F53G | 1.05 |
| G99W | 1.03 |
| G99F | 1.02 |
| D33G | 0.97 |
| F53Q | 0.96 |
| G99Q | 0.94 |
| K50S | 0.91 |
| F53E | 0.90 |
| F53P | 0.87 |
| D33E | 0.83 |
| K50E | 0.83 |
| D33P | 0.82 |
| D33D | 0.81 |
| G99P | 0.80 |
| G99E | 0.78 |
| K50G | 0.77 |
| K50Q | 0.74 |
| F53D | 0.71 |
| K50P | 0.70 |
| G99D | 0.70 |
| K50D | 0.68 |
| D33N | 0.64 |
| G99N | 0.57 |
| D33C | 0.50 |
| G99C | 0.46 |
| F53C | 0.44 |
| F53N | 0.43 |
| K50C | 0.43 |
| G99M | 0.43 |
| K50N | 0.35 |
| G99H | ND |
| K50A | 0.27 |
| G99A | 0.22 |
| F53A | 0.16 |
| K50M | 0.11 |
| D33A | 0.04 |
| K50R | ND |
| G99G | ND |
| K50F | ND |
| D33M | −0.03 |
| F53M | −0.07 |
| Growth Index Ranking for Plate 015. | |
| D23H | 1.04 |
| D23V | 0.96 |
| D23T | 0.94 |
| E26G | 0.93 |
| D81T | 0.93 |
| D23F | 0.92 |
| D23S | 0.91 |
| D23I | 0.89 |
| D23K | 0.88 |
| D23W | 0.88 |
| D23E | 0.86 |
| D81V | 0.85 |
| D81H | 0.85 |
| D81L | 0.84 |
| D81F | 0.83 |
| D23G | 0.82 |
| D23L | 0.82 |
| D23D | 0.82 |
| D23R | 0.81 |
| D81A | 0.81 |
| D23C | 0.81 |
| D81S | 0.80 |

TABLE 5-continued

| Variant | GI |
|---|---|
| S27H | 0.80 |
| D81Y | 0.80 |
| D81G | 0.80 |
| S27L | 0.78 |
| D23P | 0.78 |
| D23M | 0.77 |
| D23N | 0.76 |
| D23Y | 0.75 |
| S27Q | 0.73 |
| D81C | 0.71 |
| D81M | 0.70 |
| D81N | 0.69 |
| D81I | 0.69 |
| E26H | 0.68 |
| S27K | 0.67 |
| S27I | 0.67 |
| D23Q | 0.66 |
| E26I | 0.65 |
| E26V | 0.65 |
| E26K | 0.64 |
| S27T | 0.64 |
| D81Q | 0.63 |
| S27M | 0.63 |
| D81W | 0.62 |
| D81R | 0.62 |
| D81K | 0.61 |
| S27G | 0.59 |
| S27C | 0.59 |
| S27V | 0.58 |
| E26L | 0.58 |
| E26T | 0.55 |
| E26Q | 0.55 |
| E26E | 0.54 |
| S27N | 0.54 |
| S27S | 0.54 |
| S27R | 0.54 |
| D23A | 0.53 |
| E26S | 0.52 |
| S27E | 0.51 |
| D81E | 0.51 |
| S27A | 0.49 |
| E26N | 0.49 |
| E26P | 0.49 |
| E26D | 0.47 |
| E26M | 0.46 |
| S27F | 0.46 |
| E26R | 0.46 |
| E26C | 0.45 |
| S27D | 0.44 |
| D81P | 0.42 |
| S27P | 0.41 |
| S27Y | 0.38 |
| E26W | 0.34 |
| E26F | 0.33 |
| S27W | 0.30 |
| E26Y | 0.29 |
| E26A | 0.24 |
| D81D | 0.01 |
| Growth Index Ranking for Plate 016. | |
| G69S | 1.21 |
| G69M | 1.16 |
| L20M | 1.14 |
| G69G | 1.13 |
| G69K | 1.12 |
| G69T | 1.11 |
| G69I | 1.10 |
| G69L | 1.10 |
| Y16M | 1.09 |
| Y16I | 1.09 |
| L20V | 1.08 |
| G69V | 1.08 |
| L20S | 1.08 |
| G69H | 1.08 |
| G69R | 1.06 |
| G69Q | 1.05 |
| Y16L | 1.05 |
| G69N | 1.04 |

TABLE 5-continued

| Variant | GI |
|---|---|
| Y18G | 1.03 |
| L20Y | 1.03 |
| G69A | 1.03 |
| L20L | 1.03 |
| Y16Y | 1.01 |
| L20T | 1.01 |
| Y18C | 1.00 |
| L20W | 1.00 |
| G69E | 1.00 |
| G69C | 0.99 |
| Y18H | 0.97 |
| L20F | 0.97 |
| L20I | 0.96 |
| G69F | 0.96 |
| Y18N | 0.96 |
| Y18Y | 0.95 |
| L20A | 0.95 |
| G69Y | 0.94 |
| G69W | 0.92 |
| Y18I | 0.91 |
| Y18W | 0.91 |
| Y16V | 0.91 |
| Y16H | 0.86 |
| Y16F | 0.85 |
| G69D | 0.84 |
| Y18R | 0.83 |
| Y18F | 0.82 |
| Y18T | 0.80 |
| Y18V | 0.78 |
| Y16T | 0.77 |
| L20H | 0.77 |
| Y18M | 0.76 |
| L20N | 0.76 |
| Y18L | 0.75 |
| L20G | 0.75 |
| L20Q | 0.75 |
| Y18Q | 0.74 |
| L20C | 0.74 |
| Y16W | 0.73 |
| Y18S | 0.72 |
| G69P | 0.72 |
| Y18D | 0.67 |
| L20E | 0.66 |
| Y18K | 0.65 |
| Y18E | 0.61 |
| Y16E | 0.53 |
| L20R | 0.53 |
| Y16C | 0.50 |
| Y18P | 0.49 |
| Y16Q | 0.48 |
| Y16P | 0.48 |
| Y18A | 0.45 |
| L20D | 0.45 |
| Y16S | 0.44 |
| Y16N | 0.41 |
| Y16D | 0.40 |
| Y16K | 0.39 |
| L20K | 0.36 |
| L20P | 0.36 |
| Y16G | 0.36 |
| Y16A | 0.34 |
| Y16R | 0.21 |
| Growth Index Ranking for Plate 017. | |
| A3T | 1.39 |
| A3H | 1.21 |
| A3K | 1.13 |
| A3F | 1.10 |
| A3Y | 1.09 |
| A3I | 1.05 |
| S13L | 1.04 |
| A3R | 1.04 |
| A3Q | 0.97 |
| A3E | 0.94 |
| S13T | 0.90 |
| A3N | 0.89 |
| S13H | 0.87 |
| S13K | 0.85 |

TABLE 5-continued

| Variant | GI |
|---|---|
| Y9F | 0.84 |
| N12S | 0.83 |
| A3L | 0.83 |
| S13I | 0.82 |
| S13V | 0.81 |
| A3D | 0.79 |
| N12T | 0.79 |
| A3G | 0.78 |
| S13R | 0.76 |
| S13G | 0.76 |
| A3P | 0.76 |
| N12C | 0.73 |
| A3A | 0.73 |
| S13Y | 0.72 |
| N12A | 0.72 |
| A3W | 0.70 |
| S13M | 0.69 |
| S13S | 0.68 |
| A3C | 0.68 |
| N12N | 0.68 |
| S13N | 0.67 |
| S13F | 0.67 |
| S13W | 0.64 |
| S13Q | 0.62 |
| N12M | 0.61 |
| N12V | 0.59 |
| S13A | 0.57 |
| Y9W | 0.56 |
| S13C | 0.56 |
| A3S | 0.51 |
| S13E | 0.50 |
| N12H | 0.48 |
| N12I | 0.44 |
| N12P | 0.43 |
| N12R | 0.41 |
| N12Q | 0.38 |
| S13D | 0.35 |
| N12G | 0.33 |
| Y9H | 0.31 |
| N12K | 0.29 |
| N12D | 0.27 |
| N12L | 0.25 |
| N12F | 0.25 |
| Y9I | 0.22 |
| Y9V | 0.20 |
| S13P | 0.18 |
| A3M | 0.16 |
| Y9T | 0.15 |
| N12E | 0.15 |
| A3V | 0.14 |
| N12W | 0.14 |
| Y9R | 0.11 |
| Y9P | 0.10 |
| Y9L | 0.09 |
| Y9A | 0.09 |
| Y9S | 0.08 |
| Y9C | 0.05 |
| Y9N | 0.04 |
| Y9Y | 0.04 |
| Y9K | 0.03 |
| Y9Q | 0.03 |
| Y9M | 0.02 |
| Y9G | 0.01 |
| Y9D | −0.01 |
| Y9E | −0.01 |
| N12Y | −0.01 |
| Growth Index Ranking for Plate 018. | |
| A139T | 1.29 |
| Q197T | 1.19 |
| G127T | 1.19 |
| R194H | 1.16 |
| Q197V | 1.15 |
| G127H | 1.13 |
| G127F | 1.08 |
| A139P | 1.07 |
| A139H | 1.07 |
| A139S | 1.07 |

TABLE 5-continued

| Variant | GI |
| --- | --- |
| A139V | 1.07 |
| G127V | 1.05 |
| Q197H | 1.04 |
| A139I | 1.04 |
| Q197I | 1.04 |
| A139C | 1.03 |
| G127I | 1.03 |
| G127L | 1.03 |
| Q197M | 1.01 |
| G127Y | 1.01 |
| Q197F | 0.99 |
| A139Q | 0.98 |
| A139G | 0.97 |
| Q197Y | 0.97 |
| Q197S | 0.97 |
| G127S | 0.96 |
| Q197E | 0.95 |
| A139E | 0.95 |
| R194R | 0.93 |
| R194Y | 0.92 |
| Q197L | 0.91 |
| Q197N | 0.90 |
| Q197K | 0.90 |
| Q197D | 0.89 |
| A139L | 0.88 |
| G127E | 0.88 |
| A139D | 0.87 |
| G127P | 0.87 |
| G127C | 0.87 |
| R194L | 0.87 |
| Q197C | 0.87 |
| G127W | 0.86 |
| Q197R | 0.86 |
| G127D | 0.85 |
| A139M | 0.84 |
| R194W | 0.84 |
| Q197G | 0.83 |
| Q197A | 0.83 |
| A139A | 0.83 |
| A139N | 0.83 |
| Q197W | 0.83 |
| R194F | 0.82 |
| Q197P | 0.82 |
| A139F | 0.82 |
| R194K | 0.81 |
| G127M | 0.80 |
| A139W | 0.80 |
| Q197Q | 0.75 |
| G127N | 0.74 |
| R194C | 0.72 |
| G127Q | 0.71 |
| G127A | 0.70 |
| R194M | 0.68 |
| R194I | 0.65 |
| R194Q | 0.61 |
| G127R | 0.59 |
| G127K | 0.58 |
| A139Y | 0.56 |
| R194V | 0.43 |
| A139R | 0.30 |
| A139K | 0.30 |
| R194A | 0.27 |
| R194N | 0.18 |
| R194T | 0.15 |
| R194S | 0.08 |
| R194E | 0.03 |
| R194D | 0.02 |
| G127G | 0.00 |
| R194P | −0.01 |
| R194G | −0.03 |
| Growth Index Ranking for Plate 019. | |
| L59H | 1.96 |
| L59K | 1.49 |
| Q116V | 1.47 |
| L59I | 1.46 |
| E117I | 1.42 |
| L59R | 1.41 |
| Q116W | 1.36 |
| Q116T | 1.36 |
| Q116Y | 1.32 |
| E117L | 1.29 |
| L59G | 1.28 |
| E117W | 1.27 |
| L59F | 1.26 |
| L59A | 1.25 |
| Q116I | 1.22 |
| L59M | 1.22 |
| E117F | 1.21 |
| L59C | 1.21 |
| Q116F | 1.20 |
| L59E | 1.19 |
| L59T | 1.18 |
| L59D | 1.12 |
| Q116L | 1.12 |
| Q116K | 1.09 |
| L59L | 1.09 |
| E117H | 1.08 |
| Q125M | 1.06 |
| L59W | 1.06 |
| Q125I | 1.05 |
| L59N | 1.05 |
| Q125W | 1.05 |
| L59V | 1.05 |
| L59Q | 1.04 |
| Q125H | 1.02 |
| Q116S | 1.02 |
| Q125Y | 1.01 |
| Q125T | 1.01 |
| Q116A | 1.01 |
| E117M | 1.00 |
| Q116C | 0.99 |
| Q125P | 0.99 |
| E117V | 0.99 |
| L59Y | 0.97 |
| Q125N | 0.97 |
| Q116D | 0.97 |
| Q125V | 0.96 |
| E117A | 0.95 |
| E117Y | 0.94 |
| Q125A | 0.93 |
| Q125L | 0.93 |
| Q116E | 0.92 |
| Q116H | 0.92 |
| Q125F | 0.92 |
| Q116P | 0.91 |
| Q116R | 0.91 |
| E117C | 0.90 |
| Q125C | 0.90 |
| Q125R | 0.89 |
| Q125K | 0.89 |
| Q116G | 0.86 |
| E117T | 0.86 |
| Q125S | 0.85 |
| Q125D | 0.83 |
| E117N | 0.82 |
| Q125G | 0.82 |
| Q116Q | 0.81 |
| Q116N | 0.80 |
| E117R | 0.80 |
| E117S | 0.80 |
| Q116M | 0.76 |
| L59S | 0.74 |
| Q125E | 0.73 |
| E117G | 0.70 |
| E117D | 0.70 |
| Q125Q | 0.69 |
| E117Q | 0.66 |
| E117K | 0.55 |
| E117P | 0.44 |
| E117E | 0.26 |
| L59P | 0.03 |
| Growth Index Ranking for Plate 020. | |
| Y377W | 1.26 |
| G389K | 1.24 |

TABLE 5-continued

| Variant | GI |
|---|---|
| L376L | 1.24 |
| Y377Y | 1.23 |
| L376I | 1.20 |
| G389T | 1.18 |
| Y377V | 1.17 |
| G389L | 1.16 |
| G389H | 1.13 |
| G389V | 1.12 |
| K379R | 1.12 |
| Y377H | 1.12 |
| Y377L | 1.10 |
| K379V | 1.10 |
| L376Y | 1.09 |
| K379T | 1.09 |
| G389R | 1.06 |
| K379H | 1.04 |
| G389I | 1.03 |
| Y377I | 1.03 |
| G389Y | 1.01 |
| G389M | 1.01 |
| G389S | 1.01 |
| Y377T | 0.98 |
| G389N | 0.96 |
| Y377F | 0.95 |
| K379L | 0.95 |
| G389G | 0.94 |
| K379G | 0.93 |
| L376F | 0.92 |
| K379W | 0.92 |
| G389F | 0.88 |
| K379S | 0.88 |
| G389W | 0.87 |
| K379I | 0.86 |
| K379A | 0.86 |
| K379P | 0.83 |
| G389C | 0.83 |
| G389P | 0.82 |
| K379Q | 0.81 |
| G389Q | 0.80 |
| K379N | 0.79 |
| K379C | 0.78 |
| K379M | 0.77 |
| K379E | 0.77 |
| Y377S | 0.77 |
| G389E | 0.77 |
| G389A | 0.75 |
| G389D | 0.73 |
| K379D | 0.70 |
| Y377G | 0.69 |
| K379F | 0.69 |
| L376M | 0.65 |
| Y377P | 0.61 |
| Y377K | 0.60 |
| L376V | 0.60 |
| Y377M | 0.59 |
| Y377D | 0.58 |
| L376W | 0.57 |
| Y377N | 0.57 |
| Y377E | 0.56 |
| Y377C | 0.55 |
| Y377A | 0.54 |
| Y377Q | 0.49 |
| L376H | 0.49 |
| L376T | 0.48 |
| L376Q | 0.48 |
| L376C | 0.43 |
| L376A | 0.23 |
| Y377R | 0.23 |
| L376K | 0.22 |
| L376S | 0.17 |
| L376N | 0.16 |
| L376G | 0.14 |
| L376R | 0.12 |
| L376P | 0.11 |
| L376D | 0.08 |
| L376E | 0.08 |
| K379Y | 0.00 |
| K379K | −0.01 |

TABLE 5-continued

| Variant | GI |
|---|---|
| Growth Index Ranking for Plate 021. | |
| I165Y | 1.46 |
| E173H | 1.25 |
| V202H | 1.24 |
| I165H | 1.24 |
| E173W | 1.23 |
| E174I | 1.23 |
| E173T | 1.23 |
| E173V | 1.20 |
| E174H | 1.20 |
| E173L | 1.19 |
| E173I | 1.19 |
| V202T | 1.18 |
| E173Y | 1.18 |
| V202R | 1.16 |
| E174L | 1.16 |
| I165K | 1.16 |
| E174V | 1.15 |
| V202I | 1.15 |
| E174T | 1.14 |
| I165T | 1.14 |
| E173F | 1.14 |
| E174K | 1.13 |
| E173K | 1.12 |
| I165F | 1.11 |
| E174F | 1.11 |
| V202K | 1.09 |
| E173R | 1.08 |
| E173G | 1.08 |
| E174R | 1.07 |
| E174W | 1.05 |
| I165R | 1.05 |
| I165I | 1.04 |
| I165D | 1.03 |
| I165A | 1.02 |
| V202F | 1.02 |
| V202Y | 1.02 |
| E173M | 1.01 |
| E173S | 1.01 |
| I165L | 1.00 |
| E174Y | 1.00 |
| I165G | 0.99 |
| V202W | 0.98 |
| I165W | 0.98 |
| I165S | 0.95 |
| I165N | 0.95 |
| E174M | 0.94 |
| E174A | 0.94 |
| E173A | 0.94 |
| V202C | 0.93 |
| V202L | 0.93 |
| V202M | 0.93 |
| V202A | 0.92 |
| I165M | 0.91 |
| E173Q | 0.90 |
| I165Q | 0.90 |
| V202Q | 0.90 |
| E174G | 0.90 |
| E173N | 0.88 |
| V202N | 0.88 |
| E174S | 0.87 |
| E174N | 0.86 |
| E173P | 0.86 |
| V202S | 0.85 |
| V202E | 0.85 |
| V202D | 0.84 |
| E173C | 0.83 |
| E174C | 0.83 |
| I165E | 0.83 |
| E173E | 0.81 |
| V202G | 0.81 |
| I165C | 0.79 |
| E174Q | 0.72 |
| E174D | 0.70 |
| E174E | 0.69 |
| E174P | 0.68 |
| I165P | 0.67 |

TABLE 5-continued

| Variant | GI |
|---|---|
| E173D | 0.65 |
| I165V | 0.61 |
| V202P | 0.35 |
| V202V | 0.32 |
| Growth Index Ranking for Plate 022. | |
| K489K | 1.65 |
| G491I | 1.57 |
| L490I | 1.52 |
| L490H | 1.46 |
| G491H | 1.41 |
| L490V | 1.41 |
| I539V | 1.40 |
| G491V | 1.36 |
| G491L | 1.36 |
| K489W | 1.35 |
| L490W | 1.34 |
| G491W | 1.33 |
| G491T | 1.33 |
| G491Y | 1.31 |
| G491K | 1.29 |
| I539T | 1.26 |
| L490L | 1.25 |
| K489R | 1.24 |
| L490T | 1.21 |
| K489I | 1.21 |
| I539L | 1.21 |
| K489T | 1.20 |
| I539I | 1.17 |
| G491R | 1.16 |
| G491M | 1.14 |
| K489V | 1.14 |
| L490F | 1.14 |
| G491F | 1.13 |
| K489H | 1.08 |
| G491A | 1.08 |
| G491C | 1.05 |
| K489L | 1.05 |
| L490M | 1.04 |
| G491S | 1.03 |
| I539K | 1.00 |
| G491N | 1.00 |
| L490S | 0.98 |
| G491D | 0.96 |
| I539M | 0.96 |
| L490N | 0.95 |
| K489A | 0.94 |
| L490K | 0.94 |
| G491E | 0.94 |
| G491Q | 0.93 |
| K489F | 0.93 |
| G491G | 0.91 |
| L490R | 0.90 |
| L490A | 0.90 |
| I539S | 0.90 |
| I539H | 0.89 |
| I539C | 0.88 |
| L490C | 0.88 |
| K489S | 0.88 |
| L490G | 0.86 |
| K489G | 0.84 |
| K489Y | 0.83 |
| L490D | 0.78 |
| I539A | 0.77 |
| L490E | 0.75 |
| K489C | 0.68 |
| I539Y | 0.67 |
| K489Q | 0.66 |
| I539F | 0.65 |
| I539R | 0.64 |
| I539W | 0.64 |
| I539Q | 0.64 |
| L490Q | 0.62 |
| K489D | 0.62 |
| K489N | 0.61 |
| K489E | 0.58 |
| I539P | 0.53 |
| K489P | 0.50 |
| I539E | 0.36 |
| I539N | 0.32 |
| I539G | 0.28 |
| K489M | 0.23 |
| G491P | 0.21 |
| L490P | 0.17 |
| I539D | −0.01 |
| L490Y | −0.01 |
| Growth Index Ranking for Plate 023. | |
| Q509T | 1.49 |
| K487T | 1.39 |
| Q509V | 1.34 |
| Q509I | 1.30 |
| K487H | 1.19 |
| K487K | 1.18 |
| K487V | 1.12 |
| K487L | 1.11 |
| Y514Y | 1.08 |
| K487C | 1.06 |
| K487W | 1.05 |
| Q509S | 1.03 |
| K487R | 1.03 |
| K487F | 1.03 |
| K487A | 0.99 |
| K487G | 0.97 |
| K487S | 0.93 |
| Q509G | 0.91 |
| Q509Q | 0.90 |
| K487E | 0.90 |
| Q509C | 0.90 |
| K487I | 0.90 |
| K487M | 0.87 |
| Q509A | 0.86 |
| K487Q | 0.81 |
| Q509M | 0.80 |
| T521G | 0.77 |
| T521E | 0.77 |
| Q509N | 0.74 |
| T521S | 0.73 |
| K487D | 0.69 |
| K487Y | 0.61 |
| T521L | 0.60 |
| Q509H | 0.53 |
| T521Q | 0.51 |
| K487N | 0.44 |
| Q509E | 0.40 |
| T521V | 0.36 |
| Q509D | 0.28 |
| Q509K | 0.26 |
| Q509L | 0.16 |
| K487P | 0.15 |
| T521M | 0.13 |
| T521H | 0.02 |
| Y514H | 0.01 |
| Y514T | 0.01 |
| Q509F | 0.01 |
| Y514V | 0.00 |
| T521T | 0.00 |
| Q509Y | 0.00 |
| T521A | −0.01 |
| Y514I | −0.01 |
| Y514W | −0.01 |
| T521N | −0.01 |
| Q509R | −0.01 |
| Y514D | −0.02 |
| Y514S | −0.02 |
| T521F | −0.02 |
| T521C | −0.02 |
| Q509P | −0.02 |
| T521Y | −0.02 |
| Y514P | −0.02 |
| T521K | −0.02 |
| Y514R | −0.02 |
| Y514A | −0.02 |
| Y514L | −0.02 |
| Y514N | −0.03 |
| T521I | −0.03 |

TABLE 5-continued

| Variant | GI |
|---|---|
| T521R | −0.03 |
| Q509W | −0.03 |
| Y514Q | −0.03 |
| T521P | −0.03 |
| Y514E | −0.03 |
| Y514K | −0.03 |
| Y514C | −0.03 |
| T521W | −0.03 |
| T521D | −0.03 |
| Y514F | −0.04 |
| Y514G | −0.04 |
| Y514M | −0.04 |
| Growth Index Ranking for Plate 024. | |
| L540V | 1.73 |
| L540T | 1.58 |
| T462T | 1.43 |
| A448T | 1.35 |
| L540H | 1.34 |
| R544T | 1.33 |
| T462V | 1.31 |
| L540I | 1.31 |
| R544W | 1.28 |
| L540K | 1.28 |
| A448H | 1.26 |
| T462K | 1.26 |
| T462H | 1.26 |
| R544V | 1.26 |
| R544S | 1.23 |
| A448V | 1.23 |
| L540Y | 1.20 |
| R544K | 1.19 |
| T462I | 1.18 |
| L540W | 1.18 |
| A448R | 1.15 |
| T462W | 1.14 |
| T462Y | 1.14 |
| L540R | 1.14 |
| L540S | 1.12 |
| L540L | 1.12 |
| R544H | 1.11 |
| A448S | 1.11 |
| L540Q | 1.09 |
| L540M | 1.09 |
| T462F | 1.08 |
| T462S | 1.06 |
| L540G | 1.05 |
| R544I | 1.05 |
| R544C | 1.04 |
| T462L | 1.04 |
| L540F | 1.03 |
| R544L | 1.02 |
| T462G | 1.02 |
| A448I | 1.01 |
| L540E | 1.01 |
| L540A | 1.00 |
| R544M | 0.98 |
| L540N | 0.98 |
| L540P | 0.96 |
| R544F | 0.95 |
| R544P | 0.95 |
| T462R | 0.94 |
| L540D | 0.93 |
| T462A | 0.93 |
| R544G | 0.91 |
| L540C | 0.90 |
| T462M | 0.89 |
| A448K | 0.89 |
| R544N | 0.89 |
| A448Y | 0.88 |
| A448G | 0.87 |
| R544R | 0.86 |
| R544Q | 0.86 |
| A448L | 0.85 |
| T462C | 0.84 |
| R544E | 0.84 |
| T462D | 0.84 |
| R544A | 0.83 |

TABLE 5-continued

| Variant | GI |
|---|---|
| R544D | 0.83 |
| T462Q | 0.83 |
| A448C | 0.83 |
| A448Q | 0.82 |
| T462N | 0.81 |
| A448N | 0.79 |
| A448M | 0.78 |
| A448F | 0.78 |
| A448A | 0.77 |
| A448D | 0.74 |
| A448W | 0.72 |
| A448E | 0.72 |
| A448P | 0.70 |
| T462P | 0.60 |
| R544Y | 0.50 |
| T462E | −0.08 |
| Growth Index Ranking for Plate 025. | |
| P498H | 1.26 |
| S457S | 1.23 |
| A496H | 1.20 |
| A496T | 1.17 |
| S457H | 1.16 |
| P498T | 1.16 |
| A496I | 1.14 |
| K497T | 1.13 |
| K497V | 1.12 |
| P498R | 1.12 |
| K497K | 1.12 |
| P498I | 1.11 |
| P498K | 1.11 |
| P498V | 1.10 |
| S457R | 1.10 |
| P498Y | 1.10 |
| P498L | 1.09 |
| S457T | 1.09 |
| A496L | 1.06 |
| A496R | 1.06 |
| S457Q | 1.06 |
| A496V | 1.04 |
| K497H | 1.04 |
| P498S | 1.03 |
| A496K | 1.03 |
| K497L | 1.03 |
| K497I | 1.02 |
| P498F | 1.02 |
| A496Y | 1.01 |
| P498G | 1.01 |
| K497Y | 0.99 |
| S457Y | 0.99 |
| A496W | 0.98 |
| A496F | 0.97 |
| K497G | 0.96 |
| K497F | 0.94 |
| A496S | 0.93 |
| K497S | 0.92 |
| P498W | 0.90 |
| P498P | 0.88 |
| P498M | 0.86 |
| P498D | 0.86 |
| P498E | 0.86 |
| K497R | 0.85 |
| K497A | 0.84 |
| A496M | 0.84 |
| S457K | 0.84 |
| K497W | 0.82 |
| A496G | 0.82 |
| A496P | 0.82 |
| S457N | 0.82 |
| K497D | 0.81 |
| P498Q | 0.81 |
| S457F | 0.80 |
| P498N | 0.80 |
| A496E | 0.80 |
| A496A | 0.76 |
| A496Q | 0.76 |
| S457M | 0.76 |
| S457D | 0.75 |

TABLE 5-continued

| Variant | GI |
|---|---|
| K497Q | 0.75 |
| P498C | 0.75 |
| A496D | 0.74 |
| S457W | 0.74 |
| S457E | 0.74 |
| K497M | 0.74 |
| K497N | 0.73 |
| K497E | 0.72 |
| A496C | 0.70 |
| K497P | 0.69 |
| A496N | 0.66 |
| S457G | 0.65 |
| P498A | 0.64 |
| K497C | 0.64 |
| S457L | 0.62 |
| S457V | 0.59 |
| S457C | 0.47 |
| S457I | 0.43 |
| S457A | 0.33 |
| S457P | 0.14 |
| Growth Index Ranking for Plate 026. | |
| G87K | 1.34 |
| S120L | 1.34 |
| G87T | 1.24 |
| G87L | 1.24 |
| S120I | 1.20 |
| S120K | 1.18 |
| G87V | 1.17 |
| G87Y | 1.17 |
| S120T | 1.16 |
| T240T | 1.15 |
| S120W | 1.14 |
| G87H | 1.12 |
| G87W | 1.11 |
| D25H | 1.11 |
| G87I | 1.10 |
| D25L | 1.10 |
| D25I | 1.09 |
| S120H | 1.08 |
| S120Y | 1.07 |
| D25T | 1.06 |
| S120V | 1.05 |
| G87M | 1.04 |
| G87R | 1.03 |
| D25V | 1.02 |
| S120F | 1.01 |
| D25K | 1.00 |
| D25Y | 1.00 |
| T240L | 0.99 |
| G87F | 0.99 |
| G87P | 0.98 |
| D25P | 0.97 |
| S120M | 0.96 |
| G87S | 0.96 |
| T240I | 0.96 |
| T240V | 0.95 |
| G87D | 0.94 |
| D25N | 0.93 |
| D25D | 0.93 |
| D25M | 0.90 |
| D25A | 0.89 |
| G87C | 0.89 |
| S120C | 0.88 |
| S120E | 0.88 |
| G87A | 0.88 |
| D25G | 0.88 |
| S120D | 0.88 |
| D25F | 0.88 |
| S120G | 0.87 |
| D25W | 0.86 |
| S120R | 0.84 |
| S120A | 0.82 |
| D25E | 0.82 |
| G87E | 0.81 |
| T240M | 0.81 |
| G87N | 0.80 |
| D25S | 0.80 |
| S120N | 0.80 |
| D25R | 0.77 |
| T240A | 0.76 |
| G87Q | 0.75 |
| S120Q | 0.74 |
| D25Q | 0.73 |
| S120S | 0.69 |
| T240N | 0.69 |
| T240C | 0.67 |
| T240Q | 0.67 |
| D25C | 0.66 |
| S120P | 0.60 |
| T240S | 0.56 |
| T240G | 0.35 |
| T240H | 0.15 |
| T240Y | 0.09 |
| T240E | 0.08 |
| T240W | 0.08 |
| T240F | 0.05 |
| T240D | 0.03 |
| T240K | 0.02 |
| T240P | 0.01 |
| T240R | 0.01 |
| G87G | −0.01 |
| Growth Index Ranking for Plate 027. | |
| F495L | 1.84 |
| F495T | 1.56 |
| S493T | 1.53 |
| G492A | 1.48 |
| F495Y | 1.45 |
| F495K | 1.45 |
| F495W | 1.44 |
| S493V | 1.40 |
| F495S | 1.40 |
| G492T | 1.38 |
| F495V | 1.38 |
| G492H | 1.38 |
| G492V | 1.37 |
| S493R | 1.35 |
| F495H | 1.31 |
| G492K | 1.30 |
| S493W | 1.29 |
| F495R | 1.28 |
| S493E | 1.27 |
| G492I | 1.26 |
| S493L | 1.26 |
| F495M | 1.25 |
| G492E | 1.25 |
| G492D | 1.24 |
| N476Y | 1.24 |
| S493K | 1.23 |
| S493G | 1.21 |
| S493I | 1.20 |
| S493S | 1.20 |
| G492L | 1.18 |
| G492W | 1.18 |
| F495Q | 1.16 |
| F495I | 1.15 |
| N476W | 1.15 |
| N476V | 1.14 |
| N476R | 1.13 |
| G492G | 1.11 |
| G492C | 1.11 |
| N476T | 1.09 |
| S493M | 1.09 |
| S493Y | 1.08 |
| F495F | 1.07 |
| G492Y | 1.07 |
| G492R | 1.06 |
| S493C | 1.04 |
| S493A | 1.03 |
| F495G | 1.02 |
| F495A | 1.02 |
| G492N | 0.99 |
| F495N | 0.98 |
| F495D | 0.96 |
| S493H | 0.95 |

TABLE 5-continued

| Variant | GI |
| --- | --- |
| F495C | 0.95 |
| F495P | 0.95 |
| G492F | 0.94 |
| F495E | 0.94 |
| G492Q | 0.93 |
| S493P | 0.93 |
| G492M | 0.89 |
| G492P | 0.89 |
| G492S | 0.86 |
| N476Q | 0.83 |
| S493Q | 0.83 |
| N476S | 0.82 |
| S493F | 0.81 |
| S493N | 0.79 |
| N476D | 0.73 |
| N476M | 0.71 |
| N476P | 0.64 |
| N476E | 0.62 |
| N476A | 0.02 |
| N476N | 0.01 |
| S493D | 0.00 |
| N476I | -0.01 |
| N476H | -0.01 |
| N476G | -0.02 |
| N476F | -0.04 |
| N476C | -0.04 |
| N476K | -0.05 |
| N476L | -0.08 |

Results/Discussion

Table 6 lists all variants identified that displayed growth indices of 1.2 or higher. Without being bound by theory, mutations at these positions may result in increased intracellular activity of IspS by several different means. Without being bound by theory, increased intracellular activity could be a result of one or a combination of any of the following properties of IspS: increased cellular viability, increased kcat, decreased Km, increased specific activity, increased solubility, decreased insolubility, improved ribosome binding, increased translation initiation rate, increased translation elongation rate, increased transcription initiation rate, increased transcription elongation rate, decreased secondary structure of DNA, decreased secondary structure of RNA, increased secondary structure of DNA, increased secondary structure of RNA, increased folding rates, increased affinity for intracellular chaperones, increased stability, decreased protein turnover, decreased exposure to intracellular protease, decreased affinity for intracellular protease, decreased localization to the periplasm, improved localization to the cytoplasm, decreased inclusion body formation, decreased membrane localization, increased expression due to a more favorable codon, increased DNA stability, increased RNA stability, and decreased RNA degradation.

Without being bound by theory, any mutation that has a positive effect on the properties of nucleic acid sequences (DNA and RNA) encoding or expressing IspS, or the biochemical properties of the IspS enzyme itself, could allow for greater activity within the cell. All variants with a growth index of 1.2 or higher are subjected to secondary growth assays in a matrix of mevalonic acid and IPTG. These variants are also pooled together and subjected to several rounds of enrichment under IPTG induction and mevalonic acid pathway flux to determine which enzymes allow for the best growth in competition experiments. The most promising variants are examined further for benefits to specific productivity in isoprene producing strains.

Figure 7:
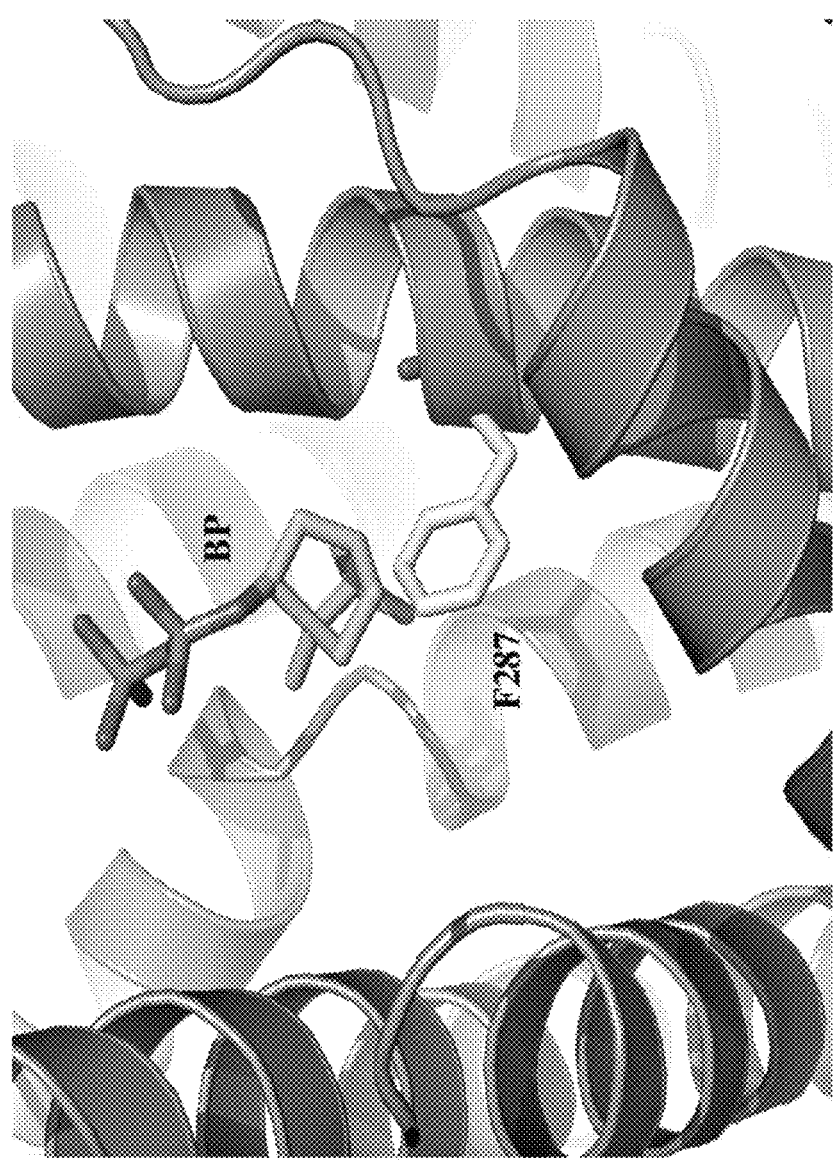
FIG. 7 shows a view of Wild Type IspS showing residue Phe287 in stick representation. (+)-bornyl diphospate (BP) is placed based on a structural alignment with PDB 1N24.

Residues listed in Table 7 are necessary for growth under high DMAPP pressure and thus, can be considered in one embodiment as immutable residues. Substitution of the wild type amino acid with any other residue results in minimal to no growth under the growth rate assay conditions. Growth index values for each position are shown in Table 7. Phenylalanine 287 (F287) is located in the active site, and defines the bottom of the active site cavity (FIG. 7). Based on structural alignments with other terpene synthases, F287 determines the length of the substrate that can be accommodated into the active site, thereby preventing access to the active site by isoprenoids with more than five carbons.

Figure 8:
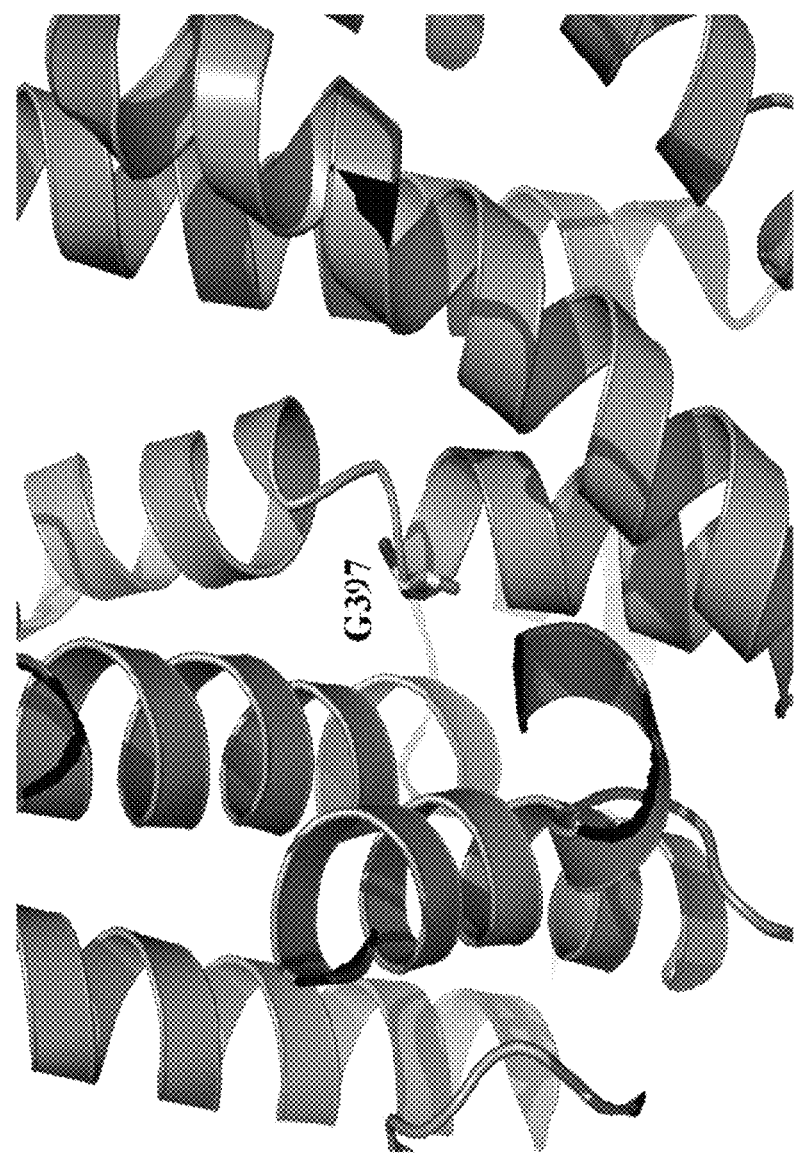
FIG. 8 shows a view of Wild Type IspS showing residue Gly397 in stick representation.

Glycine 397 (G397) is located on the side of the active site cavity (FIG. 8). This residue occurs at a kink in an alpha-helix, suggesting that the conformational flexibility of glycine (and other small amino acids) may be required at this position to allow the helix to bend. The bend in the helix is adjacent to the putative substrate binding position in the active site.

Figure 9:
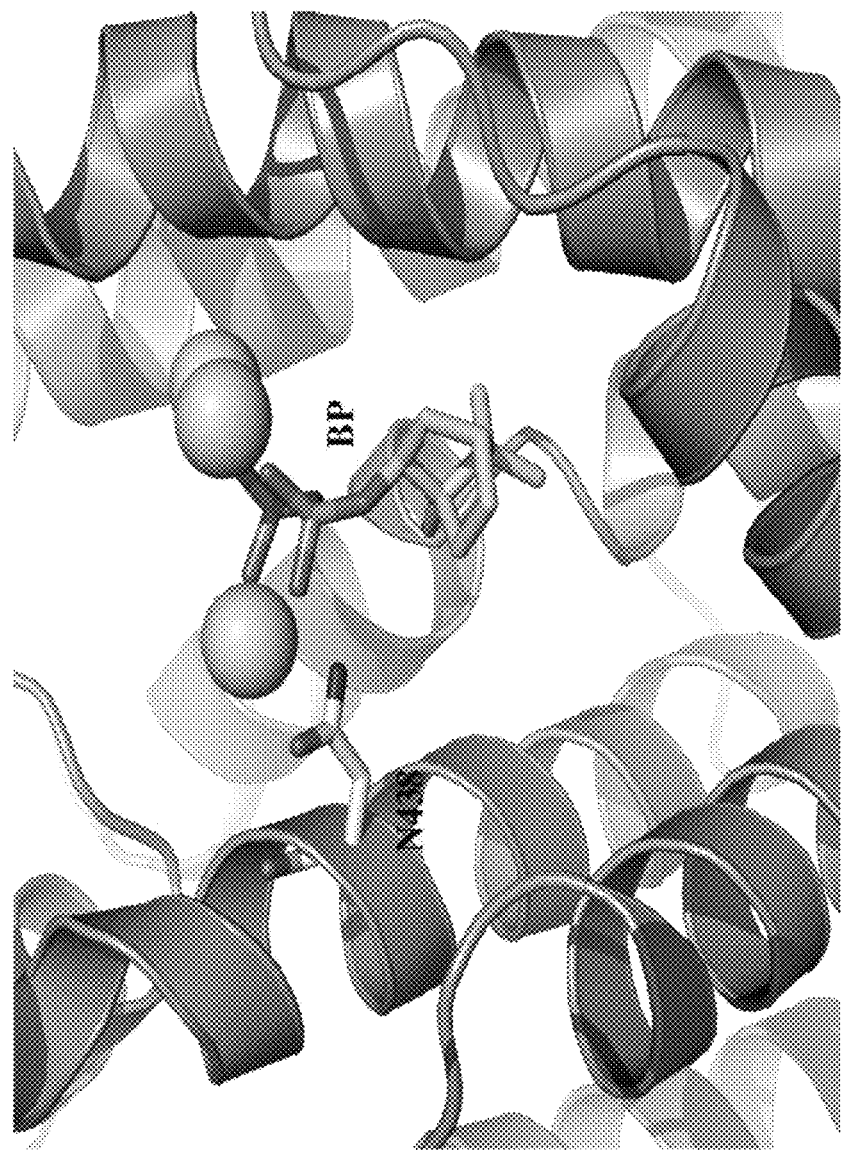
FIG. 9 shows an active site view of Wild Type IspS showing residue Asn438 in stick representation. (+)-bornyl diphospate (BP) and Mg2+ (spheres) are placed based on a structural alignment with PDB 1N24.

Asparagine 438 (N438) is positioned at the top of the active site (FIG. 9). Structural alignments with other terpene synthases indicate that N428 may be involved directly in coordination of the magnesium ions, as well as having possible interactions with the substrate.

Figure 10:
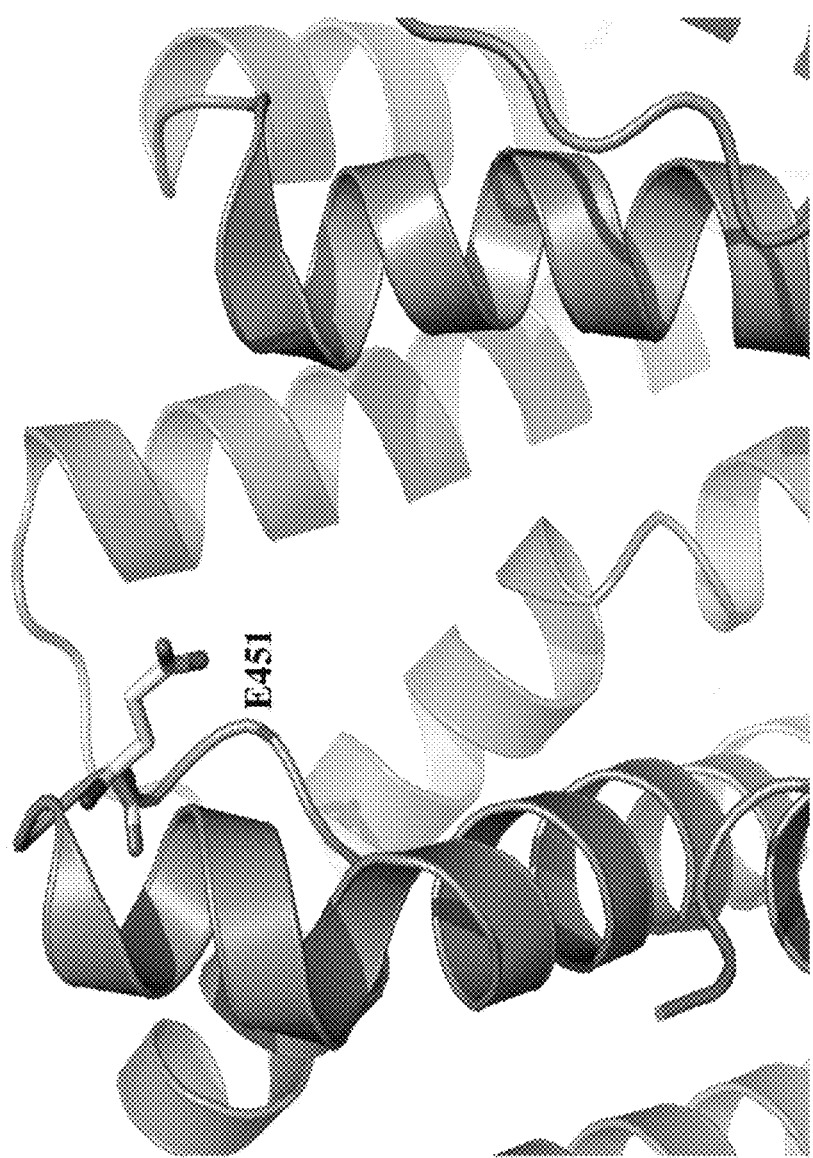
FIG. 10 shows a view of Wild Type IspS showing residue Glu451 in stick representation.

Glutamate 451 (E451) is on a substrate access loop located above the active site (FIG. 10). Based on homology modeling and structure-based alignments with other terpene synthases, these loops may have an open position for substrate capture, and then close over the active site once substrate is bound. Residue E451 is proposed to have a role in coordinating one or more magnesium ions during this process.

Figure 11:
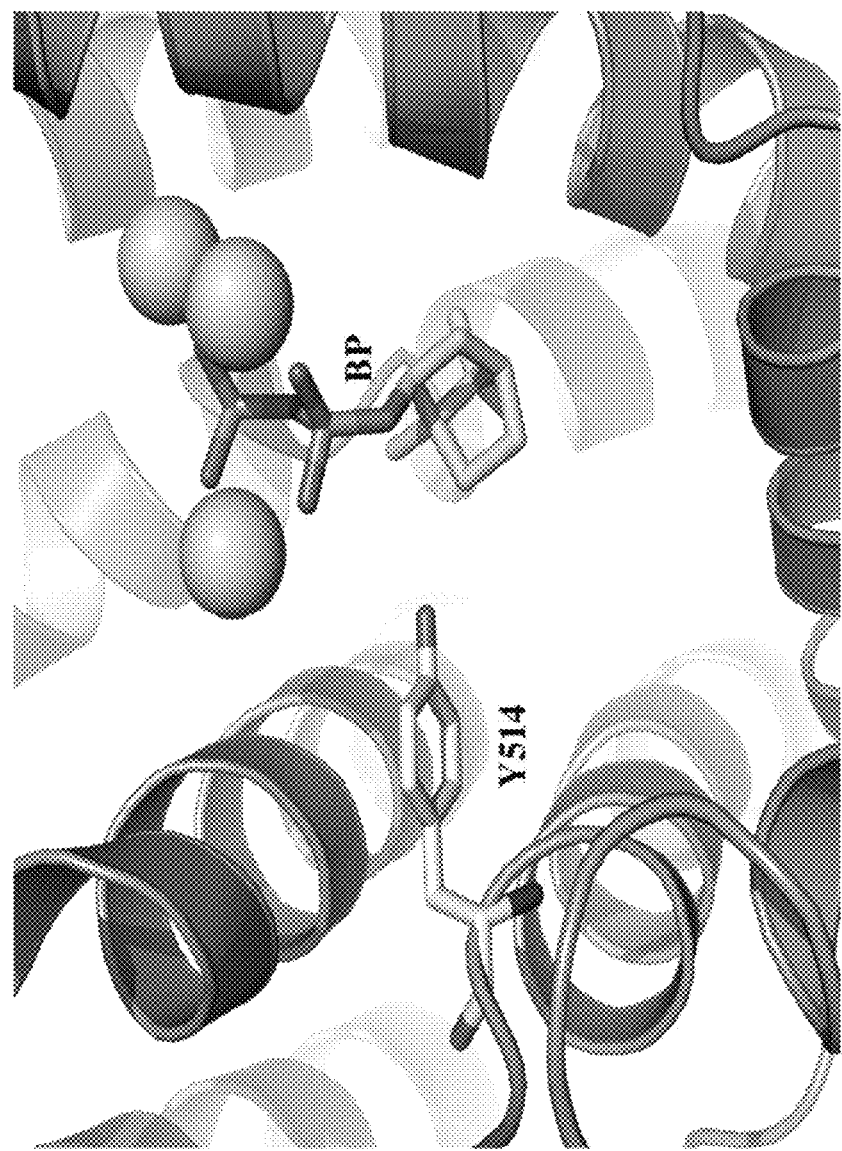
FIG. 11 shows an active site view of Wild Type IspS showing residue Tyr514 in stick representation. (+)-bornyl diphospate (BP) and Mg2+ (spheres) are placed based on a structural alignment with PDB 1N24.

Tyrosine 514 (Y514) is in the active site, below N438 (FIG. 11). Y514 may be involved in substrate binding, or it may play a direct role in catalysis.

TABLE 6

Variants with Growth Index value equal to or greater than 1.2.

| Variant | GI |
| --- | --- |
| L59H | 1.96 |
| F495L | 1.84 |
| L540V | 1.73 |
| V30L | 1.61 |
| L540T | 1.58 |
| G491I | 1.57 |
| F495T | 1.56 |
| S493T | 1.53 |
| V30K | 1.52 |
| L490I | 1.52 |
| D33T | 1.49 |
| Q509T | 1.49 |
| L59K | 1.49 |
| G492A | 1.48 |
| Q116V | 1.47 |
| L59I | 1.46 |
| E179L | 1.46 |
| L490H | 1.46 |
| I28T | 1.46 |
| D33V | 1.46 |
| I165Y | 1.46 |
| F495Y | 1.45 |
| F495K | 1.45 |
| V30Y | 1.45 |
| F53L | 1.44 |
| F495W | 1.44 |
| G99T | 1.43 |
| T462T | 1.43 |
| E117I | 1.42 |
| G491H | 1.41 |
| L59R | 1.41 |
| L490V | 1.41 |
| S493V | 1.40 |
| E179I | 1.40 |
| I539V | 1.40 |

TABLE 6-continued

Variants with Growth Index value equal to or greater than 1.2.

| Variant | GI |
|---|---|
| F495S | 1.40 |
| D33Y | 1.39 |
| Q421R | 1.39 |
| V30W | 1.39 |
| A3T | 1.39 |
| K487T | 1.39 |
| G492T | 1.38 |
| F495V | 1.38 |
| G492H | 1.38 |
| I28S | 1.38 |
| G492V | 1.37 |
| A443A | 1.36 |
| Q116W | 1.36 |
| G491V | 1.36 |
| Q116T | 1.36 |
| G491L | 1.36 |
| A448T | 1.35 |
| S493R | 1.35 |
| K489W | 1.35 |
| E179K | 1.35 |
| G153W | 1.34 |
| L490W | 1.34 |
| L540H | 1.34 |
| G87K | 1.34 |
| S120L | 1.34 |
| F53T | 1.34 |
| Q509V | 1.34 |
| G78L | 1.33 |
| K50I | 1.33 |
| K50L | 1.33 |
| R544T | 1.33 |
| E179H | 1.33 |
| G491W | 1.33 |
| G491T | 1.33 |
| Q116Y | 1.32 |
| G99V | 1.32 |
| F495H | 1.31 |
| G491Y | 1.31 |
| G78Y | 1.31 |
| T462V | 1.31 |
| L540I | 1.31 |
| I28R | 1.31 |
| G492K | 1.30 |
| Q509I | 1.30 |
| D33W | 1.30 |
| R44H | 1.30 |
| G491K | 1.29 |
| A139T | 1.29 |
| L130Y | 1.29 |
| E117L | 1.29 |
| S493W | 1.29 |
| F495R | 1.28 |
| R544W | 1.28 |
| L540K | 1.28 |
| L59G | 1.28 |
| A519W | 1.27 |
| S493E | 1.27 |
| F53W | 1.27 |
| E117W | 1.27 |
| G99I | 1.27 |
| G78W | 1.27 |
| R44T | 1.27 |
| E179W | 1.26 |
| A448H | 1.26 |
| F53V | 1.26 |
| Y377W | 1.26 |
| F53I | 1.26 |
| G492I | 1.26 |
| T462K | 1.26 |
| T462H | 1.26 |
| S493L | 1.26 |
| G177V | 1.26 |
| G78I | 1.26 |
| P498H | 1.26 |
| L59F | 1.26 |
| D33H | 1.26 |
| V30S | 1.26 |
| Q421H | 1.26 |
| I539T | 1.26 |
| R544V | 1.26 |
| F495M | 1.25 |
| E173H | 1.25 |
| G492E | 1.25 |
| L59A | 1.25 |
| G177T | 1.25 |
| G87T | 1.24 |
| G99K | 1.24 |
| V202H | 1.24 |
| S74K | 1.24 |
| G389K | 1.24 |
| G87L | 1.24 |
| G492D | 1.24 |
| Q421E | 1.24 |
| N476Y | 1.24 |
| I165H | 1.24 |
| F53Y | 1.24 |
| K489R | 1.24 |
| K36L | 1.23 |
| D33I | 1.23 |
| R544S | 1.23 |
| E179T | 1.23 |
| A448V | 1.23 |
| G99Y | 1.23 |
| E173W | 1.23 |
| S493K | 1.23 |
| G99L | 1.23 |
| E174I | 1.23 |
| E173T | 1.23 |
| D33S | 1.22 |
| G177L | 1.22 |
| V30F | 1.22 |
| K50W | 1.22 |
| Q116I | 1.22 |
| E179V | 1.22 |
| S74W | 1.22 |
| L59M | 1.22 |
| D33K | 1.21 |
| L490T | 1.21 |
| A3H | 1.21 |
| K489I | 1.21 |
| I539L | 1.21 |
| R44F | 1.21 |
| E117F | 1.21 |
| L59C | 1.21 |
| S493G | 1.21 |
| G69S | 1.21 |
| E173V | 1.20 |
| L540Y | 1.20 |
| S493I | 1.20 |
| S120I | 1.20 |
| Q116F | 1.20 |
| A496H | 1.20 |
| H254K | 1.20 |
| S74I | 1.20 |
| K489T | 1.20 |
| L376I | 1.20 |
| E174H | 1.20 |

TABLE 7

Growth index values for the immutable sites.

| Variant | GI |
|---|---|
| F287 | |
| F287A | 0.10 |
| F287C | 0.00 |
| F287D | −0.02 |

TABLE 7-continued

Growth index values for the immutable sites.

| Variant | GI |
|---|---|
| F287E | −0.02 |
| F287F | 0.74 |
| F287G | 0.02 |
| F287H | 0.09 |
| F287I | 0.01 |
| F287K | 0.08 |
| F287L | 0.39 |
| F287M | 0.26 |
| F287N | 0.01 |
| F287P | −0.01 |
| F287Q | 0.03 |
| F287R | 0.01 |
| F287S | 0.02 |
| F287T | 0.04 |
| F287V | 0.21 |
| F287W | 0.42 |
| F287Y | 0.19 |
| G397 | |
| G397A | 0.40 |
| G397C | 0.05 |
| G397D | −0.02 |
| G397E | −0.02 |
| G397F | −0.02 |
| G397G | 1.05 |
| G397H | −0.02 |
| G397I | 0.09 |
| G397K | −0.03 |
| G397L | −0.01 |
| G397M | 0.08 |
| G397N | 0.00 |
| G397P | 0.00 |
| G397Q | 0.00 |
| G397R | 0.00 |
| G397S | 0.00 |
| G397T | −0.03 |
| G397V | 0.16 |
| G397W | −0.03 |
| G397Y | 0.00 |
| N438 | |
| N438A | −0.02 |
| N438C | −0.05 |
| N438D | −0.04 |
| N438E | −0.04 |
| N438F | −0.04 |
| N438G | −0.07 |
| N438H | −0.04 |
| N438I | −0.05 |
| N438K | −0.06 |
| N438L | −0.05 |
| N438M | −0.05 |
| N438N | 1.27 |
| N438P | −0.06 |
| N438Q | −0.06 |
| N438R | −0.06 |
| N438S | −0.09 |
| N438T | −0.04 |
| N438V | −0.05 |
| N438W | −0.05 |
| N438Y | −0.06 |
| E451 | |
| E451A | −0.04 |
| E451C | −0.04 |
| E451D | −0.02 |
| E451E | 1.48 |
| E451E | 1.13 |
| E451F | −0.03 |
| E451G | −0.02 |
| E451H | −0.02 |
| E451I | −0.03 |
| E451K | −0.01 |
| E451L | −0.05 |
| E451N | −0.06 |
| E451P | −0.05 |
| E451Q | 0.06 |
| E451R | −0.03 |
| E451S | −0.06 |
| E451T | −0.04 |
| E451V | −0.04 |
| E451W | −0.01 |
| E451Y | −0.03 |
| Y514 | |
| Y514A | −0.02 |
| Y514C | −0.03 |
| Y514D | −0.02 |
| Y514E | −0.03 |
| Y514F | −0.04 |
| Y514G | −0.04 |
| Y514H | 0.01 |
| Y514I | −0.01 |
| Y514K | −0.03 |
| Y514L | −0.02 |
| Y514M | −0.04 |
| Y514N | −0.03 |
| Y514P | −0.02 |
| Y514Q | −0.03 |
| Y514R | −0.02 |
| Y514S | −0.02 |
| Y514T | 0.01 |
| Y514V | 0.00 |
| Y514W | −0.01 |
| Y514Y | 1.08 |

Example 3

Primary Specific Activity Assay for P. Alba IspS Complete Site Evaluation Libraries (SELs)

Site Evaluation Libraries (SELs) of the entire P. alba isoprene synthase (MEA P. alba) backbone (544 amino acids) were built in the parent vector pCL201 (FIG. 4), and screened for specific activity to identify isoprene synthase (IspS) molecules with improved characteristics. In most cases, the SEL at a given position contained all 20 possible amino acid substitutions including the wild type. Numbering of each library corresponds to the ORF of MEA P. alba (SEQ ID NO:1), where the starting methionine is position 1. Individual strains, built in the MD09-170 background, that contained variants for expression were arrayed into microtiter plates such that each well corresponded to a specific amino acid substitution at the given position in MEA P. alba. Microtiter plates contained four SELs, or four positions in MEA P. alba with all possible substitutions. Remaining wells were used for control strains. Plates were grown, induced, and lysed, in order to measure the amount of isoprene produced per the specific amount of IspS protein in each sample. Specific activity values were calculated for all variants in the entire set of SELs.

Methods

Cell Growth and Lysis

Glycerol stocks of MEA P. alba IspS libraries were thawed briefly and inoculated into microtiter plates (Cellstar) containing liquid LB medium with kanamycin at a concentration of 20 ug/ml. Cultures were grown overnight at 250 rpm, 30° C. to saturation in a shaking incubator using the Enzyscreen clamp system (Enzyscreen). The next day, cultures were removed and inoculated using a Liquidator96 pipettor (Rainin Instruments) at a ratio of 1:10 into TM3-glucose medium containing 50 ug/ml kanamycin and 50 uM IPTG. Wild type controls were grown separately and inoculated into each microtiter plate containing TM3-glucose with a titration of IPTG concentrations, from 30 uM to 65 uM, in separate wells. Plates were returned to the shaking incubator at 250 rpm, 30° C. and induced for five hours. Plates were then removed from the incubator and cultures were harvested into polypropylene microtiter plates (Nunc) by centrifugation at 3700 rpm for 20 minutes at 4° C. in a tabletop centrifuge. The supernatant was removed and pellets were stored at −80° C. prior to lysis, DMAPP assay, and protein determination.

Prior to cell lysis, plates were removed from the −80° C. freezer and thawed on the bench for 10 minutes. Pellets were thoroughly resuspended in 200 ul of lysis buffer (100 mM Tris, 100 mM NaCl pH 7.6 buffer, 1 mg/ml BSA, 50 U/ul Epicentre readylyse lysozyme, 0.1 mg/ml DNase, 0.5 mM PMSF/AEBSF, 5 mM MgCl2) using a Biomek automated workstation (Beckman Coulter), removed, and shaken at room temperature at 450 rpm for 30 minutes. Lysates were then spun at 3200 rpm at 4° C. for 10 minutes, and 150 ul of the supernatant was transferred using a Biomek to a new microtiter plate for DMAPP and dot blot assay.

DMAPP Assay

For the DMAPP assay, 25 ul of lysate was added to 75 ul of DMAPP assay buffer (100 mM Tris/100 mM NaCl pH 7.6, 1 mg/ml BSA, 50 mM MgCl2, 1 mM DMAPP) in a 96-well glass block (Zinser) using a Liquidator96 pipettor (Rainin Instruments). Glass blocks were sealed with aluminum foil seals (Beckman Coulter) and incubated at 450 rpm for one minute at room temperature. Blocks were then incubated at 34° C. in a water bath for 30 minutes, and the reaction was stopped by incubation at 70° C. for two minutes. Blocks were cooled briefly before loading onto the GC-MS.

Sealed glass blocks were loaded onto an Agilent 7890a Gas Chromatography (GC) System equipped with a flame ionization detector (FID) and a CTC CombiPAL autosampler. The GC FID method parameters are described below:

Column: ZB-5 ms
Dimensions: 15m×0.25 mm×0.25 μm
Oven:

| Ramp (° C./min) | Temperature (° C.) | Hold Time (min) |
|---|---|---|
| 0 | 37 | 28 |

| | |
|---|---|
| Total Run Time: | 28 minutes |
| Front Inlet Temperature: | 110° C. |
| Split Ratio: | 50:1 |
| Flow Rate: | 3.4 mL/min |
| Injection Volume: | 100 μL |
| Headspace Syringe Volume: | 1 mL |
| Detector Temperature: | 160° C. |
| Hydrogen Flow: | 40 mL/min |
| Air Flow: | 400 mL/min |
| Makeup Flow: | 0.1 mL/min |
| Makeup Gas Type: | Helium |

Chemstation software (version E.02.00.493) was used to control the GC and Cycle Composer software (version 1.5.2) was used to control the CTC autosampler. The Cycle Composer software was programmed to continuously inject one sample after another in sequence for a total of 48 injections. 0.2% v/v isoprene balanced with nitrogen gas from Air Liquide was used as the standard for determining calibration response factors. Three separate 2 mL vials were filled with the calibration gas and analyzed using the method described above to determine an average response factor. Calculated response factors allowed for the conversion of individual sample peak area counts to isoprene concentrations using Microsoft Excel.

Protein Determination

Prior to the protein determination assay, several wild type samples from each plate were analyzed by GC-MS for isoprene, and protein concentration was back-calculated from the known specific activity of MEA *P. alba* to determine the average amount of IspS for all samples in the microtiter plate. For the dot blot assay, nitrocellulose membranes (Invitrogen) were soaked in 1×PBS buffer (10 mM Sodium Phosphate, 150 mM NaCl, PH7.8+/−0.2) and equilibrated for at least 5 minutes. Lysates were then diluted in 1×PBS using a Hamilton MicroLab STAR liquid handling workstation to achieve loading concentration between 0.025-0.5 ug of *P. alba* IspS. Purified standards were added at concentrations between 0.025-1 ug. The blotting unit (Minifold-1, Whatman) was assembled according to the manufacturer's recommended protocol. Vacuum was applied briefly to remove excess 1×PBS buffer. Samples (approximately 200 ul of each) were transferred to the Minifold-1, and vacuum was applied at 20 kPa. After samples were filtered completely, wells were washed once with 200 ul of 1×PBS buffer. After the wash buffer passed completely through the membrane, the vacuum was removed, and membranes were removed carefully with forceps, labeled, and dried on clean filter paper.

Immunodetection of *P. alba* IspS molecules at each position on nitrocellulose membranes was carried out using the WesternBreeze kit from Invitrogen. Primary monoclonal or polyclonal antibody (anti-mouse against purified *P. alba* IspS, Prosci Incorporated) was diluted 1:5000 in blocking solution, and secondary antibody (Alexa Fluor 488 goat anti-mouse IgG (H+L), Invitrogen) was diluted to a concentration of 2 ug/ml in blocking solution. Fluorescent spots were quantified using a Storm 860 Molecular Imager (GMI, Inc.) and ImageQuant software (GE Healthcare), according to the manufacturers' recommended protocols, and specific protein concentrations for each sample were determined by comparison to known standards using Microsoft Excel.

Results

Specific activity values were calculated for every variant in the entire set of SELs by dividing the molar amount of isoprene produced in a given amount of time by the specific amount of protein in each sample. Performance index (PI) was calculated by dividing the specific activity of any given variant by the average of several WT specific activity measurements from the same microtiter plate. A variant that displayed a PI value of 1.5 for specific activity, for example, was 50% improved over WT. PIs for protein concentration and isoprene produced were also calculated in the same fashion, and these measurements were used for detailed data analysis.

Table 8 provides precise definitions for locations of the residues listed in Tables 9 and 10. For example, a residue listed as "N-term" in Table 9 or 10, is between residue 1 and 215 of reference sequence MEA *P. alba* IspS (SEQ ID NO:1).

TABLE 8

Definitions of locations of MEA *P. alba* IspS amino acid positions

| Location | Definition |
|---|---|
| N+31 term | Residues 1+31 215 |
| Hinge Region | Residues 216+31 245 |
| C+31 term | Residues 246+31 544 |
| N+31 term helices | Residues 134+31 179 |
| Dimer Interface | Residues 240+31 255 and 316+31 353 |
| Substrate Capture Loops | Residues 441+31 454 and 515+31 527 |

TABLE 8-continued

Definitions of locations of MEA *P. alba* IspS amino acid positions

| Location | Definition |
|---|---|
| Active Site | Residues within 8 Å of active site based on PDB 3N0G |
| Buried | Surface Accessibility below 35% and located internally |
| Surface | Residues located on the surface of the structure |
| Surface Loop | Residues in loops located on the surface of the structure |

Surface accessibilities and putative functions of amino acids of interest in the structure of MEA *P. alba* are also listed in Tables 9 and 10. Surface accessibility was calculated using the program MOE, which is written and supported by the Chemical Computing Group, Inc. An estimate for the water-accessible surface area of each residue was determined using a probe having a specified radius. The estimate was then compared against a library of peptides and the ratio between them was reported as the percent surface accessibility. Tables 9 and 10 also list the putative functions of each residue. For example, functions include but aren't limited to metal binding (in the active site), substrate capture, altered loop shape, alternative interactions in a pocket, and dimer formation.

Figure 15:
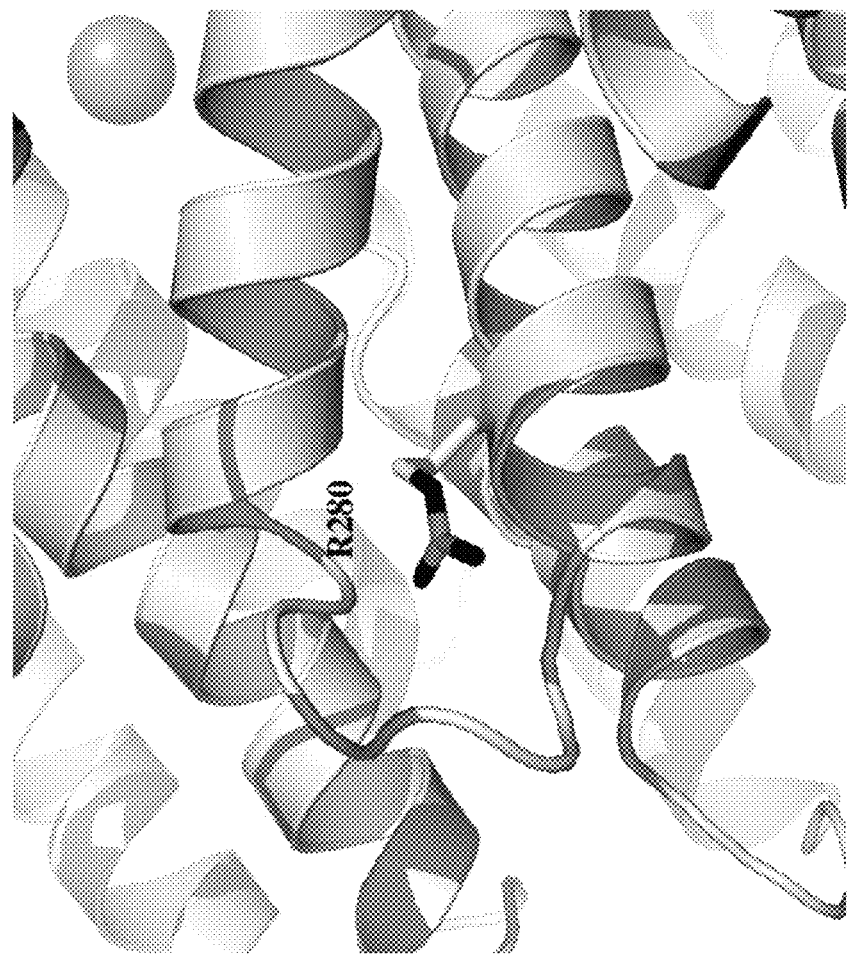
FIG. 15 shows the location of buried sites in IspS that do not tolerate substitution. $Mg^{2+}$ (spheres) are placed based on a structural alignment with PDB 1N24.
Figure 16:
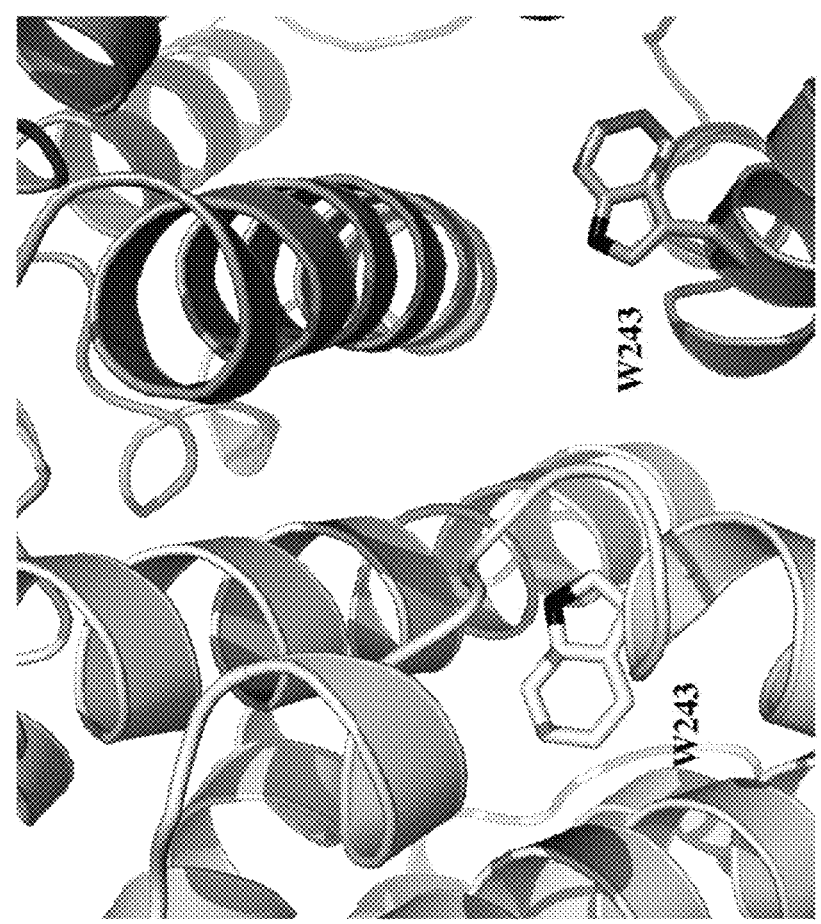
FIG. 16 shows residues located at the dimer interface of IspS that do not tolerate substitution. Chain A is light gray and chain B is dark gray.
Figure 17:
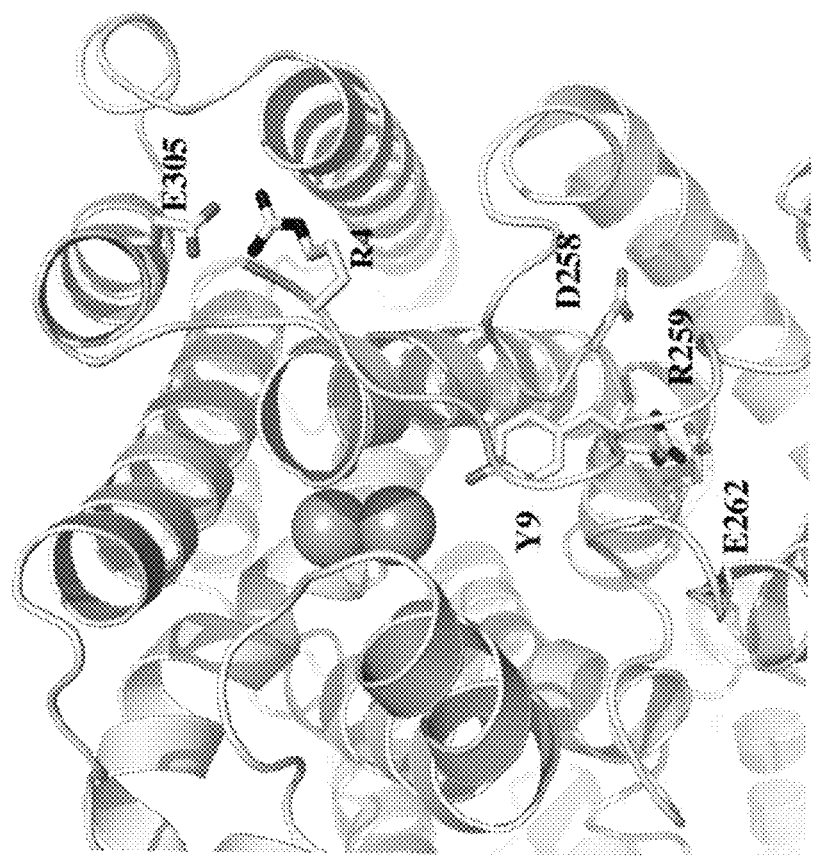
FIG. 17 shows the location of N-terminally located or interacting sites of IspS that do not tolerate substitution. $Mg^{2+}$ (spheres) and residues 1-50 are modeled based on a structural alignment with PDB 1N24.
Figure 18:
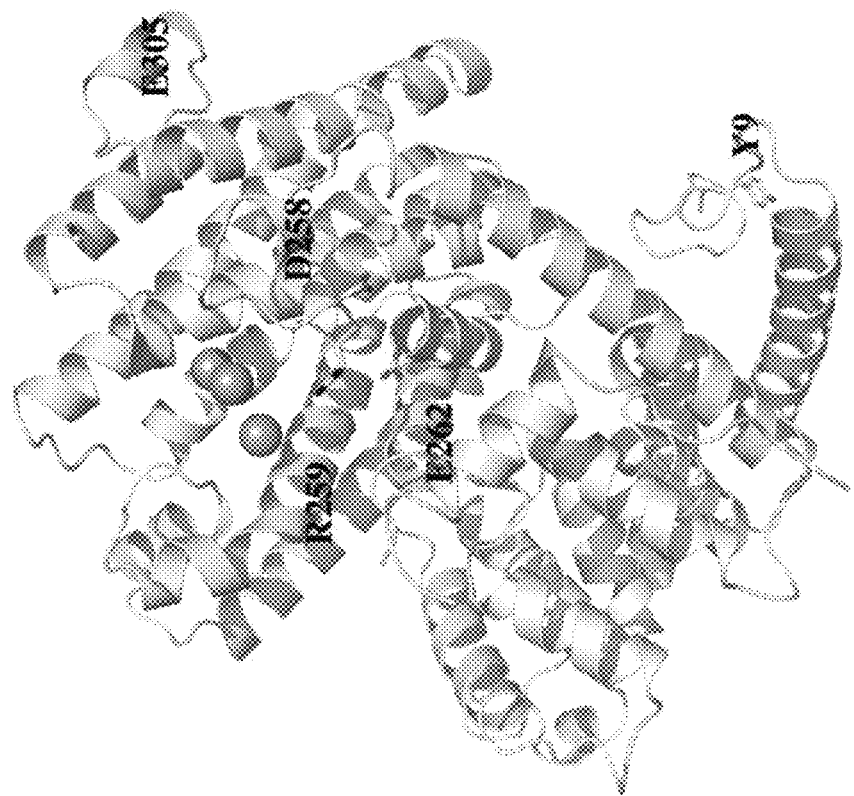
FIG. 18 shows the location of N-terminally located or interacting sites of IspS that do not tolerate substitution. $Mg^{2+}$ (spheres) are placed based on a structural alignment with PDB 1N24.
Figure 19:
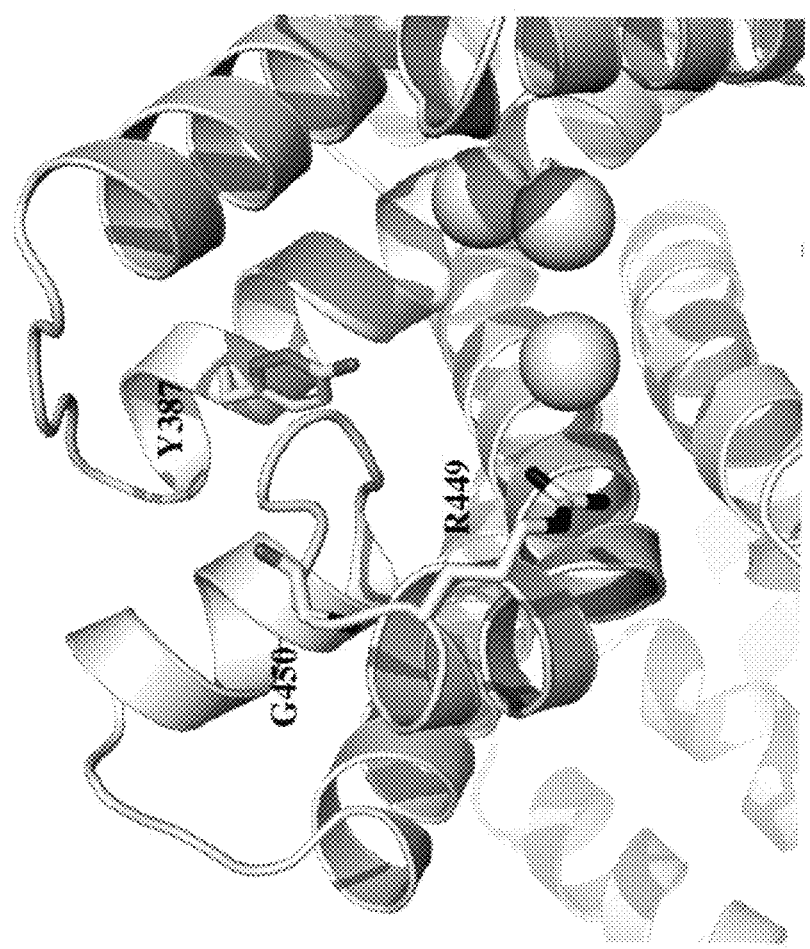
FIG. 19 shows the proposed substrate capture loop positions of IspS that do not tolerate substitution. $Mg^{2+}$ (spheres) are placed based on a structural alignment with PDB 1N24.

From the primary data, positions in MEA *P. alba* which tolerated no changes from the wild type residue were identified (see Table 9, FIGS. 13-19). MEA *P. alba* variants with amino acid substitutions other than wild type at these positions displayed specific activity no higher than 30% (PI≤0.3) of the value of WT, and were therefore functionally inactive. Wild type residues at these positions represent a minimum set that is required for the efficient conversion of DMAPP to isoprene by MEA *P. alba*. Many of these positions map to or near the active site of MEA *P. alba* (see FIG. 14), and are putatively involved in but are not limited to metal binding (for substrate orientation), substrate capture, substrate binding, and catalysis. FIG. 15, for example, shows a position that has an unknown role in enzyme function. FIG. 16 shows positions that may be involved in IspS dimer formation, and FIGS. 17 and 18 show positions that are in or interact with the N-terminus and may be involved in loop closure or function of the active site. FIG. 19 shows positions located in the substrate capture loops that tolerate no substitutions.

Figure 20:
FIG. 20 shows the monomer view of wild type IspS showing the location of sites where variants demonstrate improved specific activity.
Figure 21:
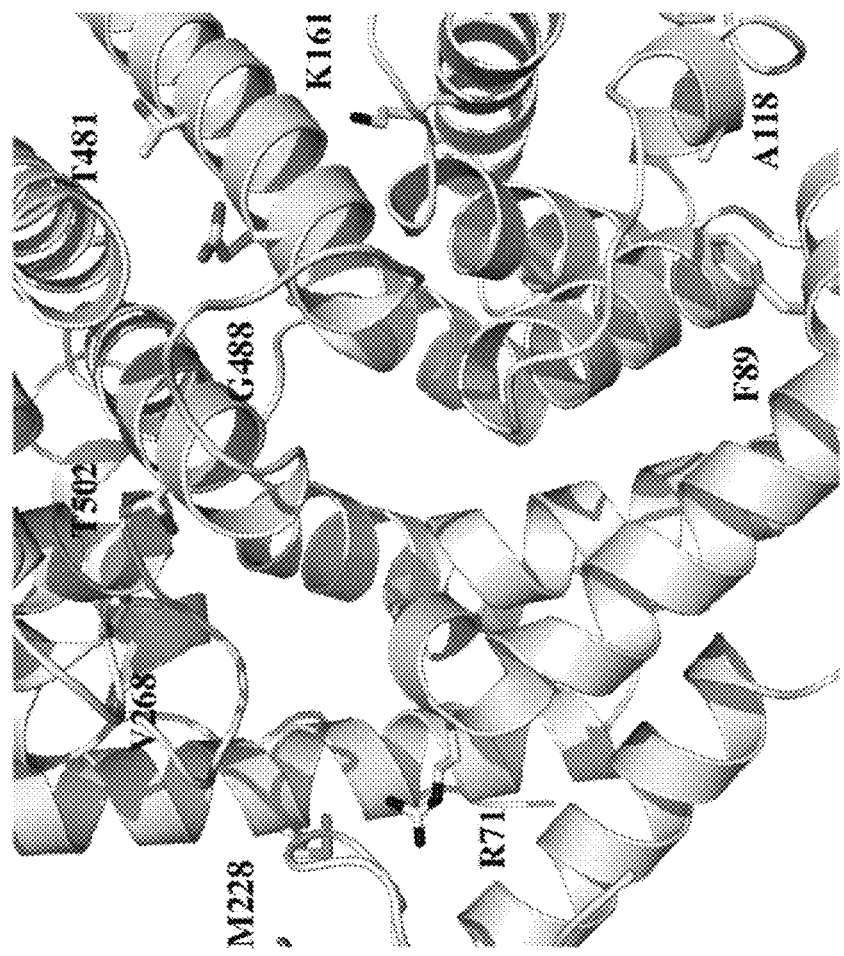
FIG. 21 shows the location of buried sites that are in or interact with the N-terminus of IspS, where variants demonstrated increased specific activity.
Figure 22:
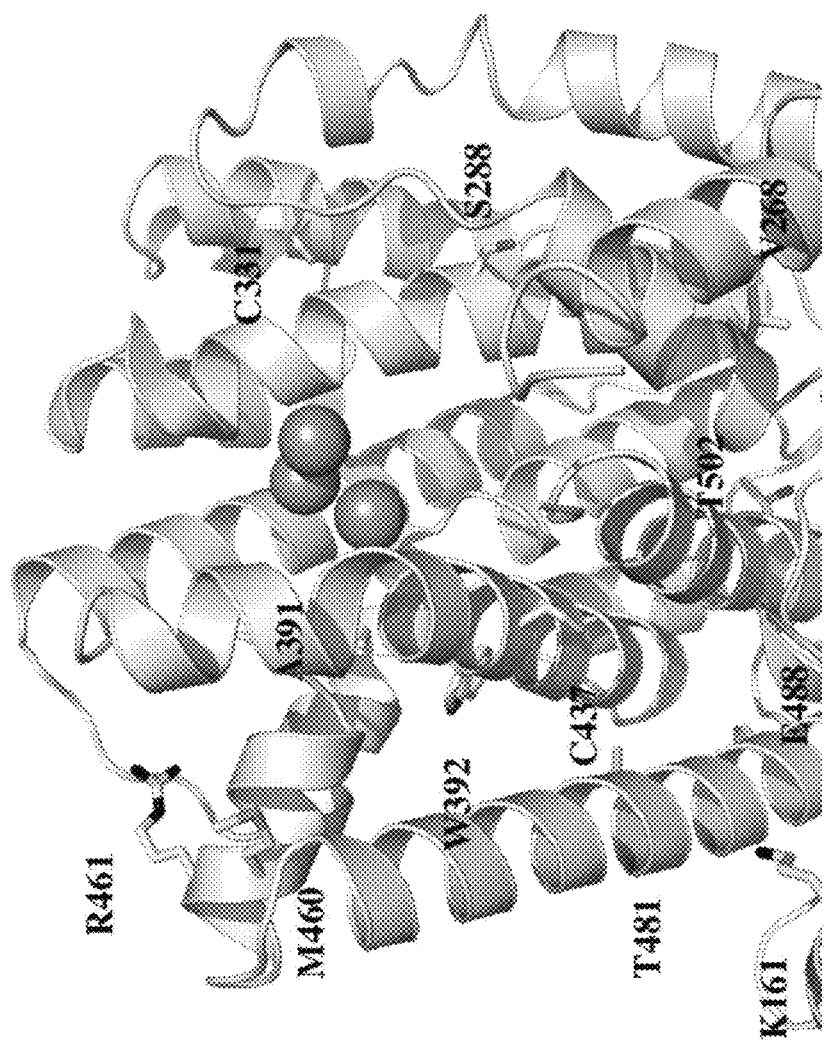
FIG. 22 shows the location of buried sites that are in or interact with the C-terminus of IspS, where variants demonstrated increased specific activity. $Mg^{2+}$ (spheres) are placed based on a structural alignment with PDB 1N24
Figure 23:
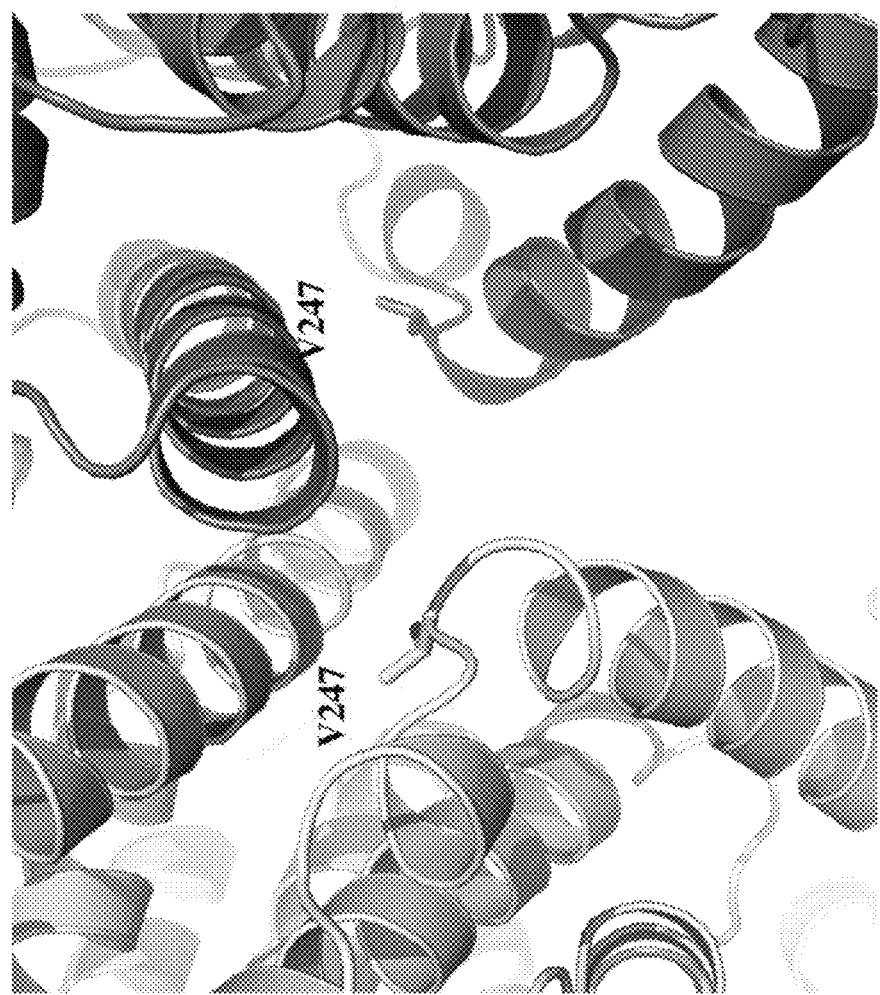
FIG. 23 shows the dimer interface of IspS, with chain A in light gray and chain B in dark gray. Variants at position 247 demonstrated improved specific activity.
Figure 24:
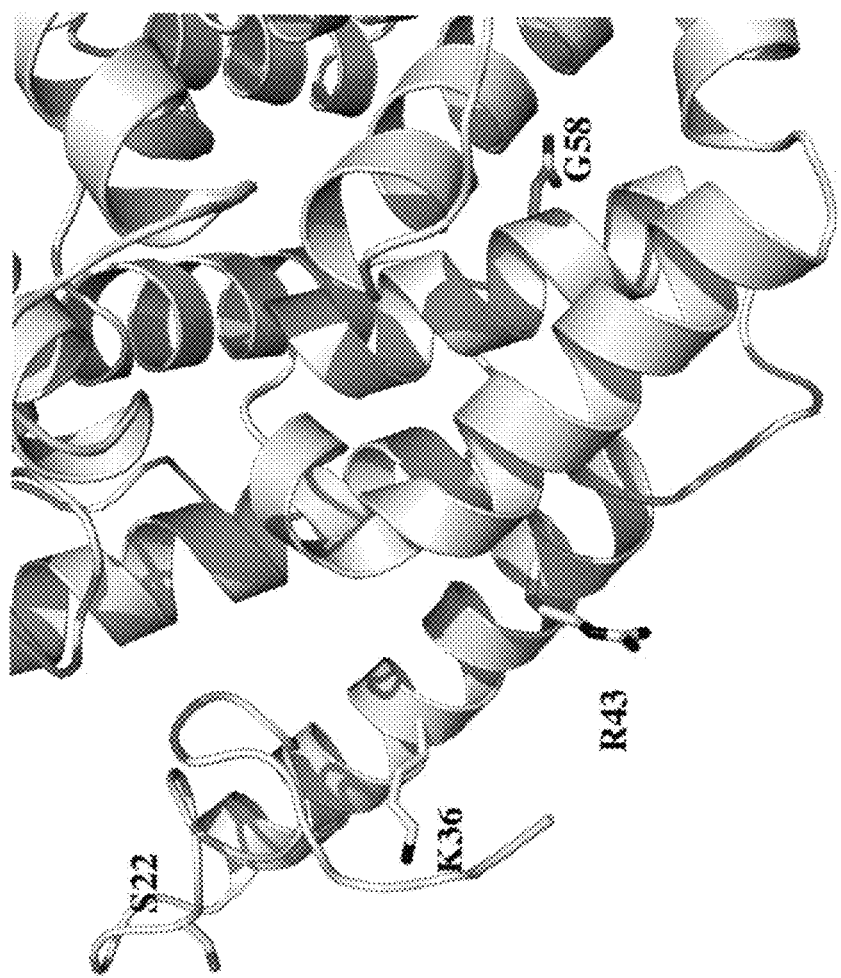
FIG. 24 shows the location of N-terminal sites of IspS where variants demonstrated improved specific activity.
Figure 25:
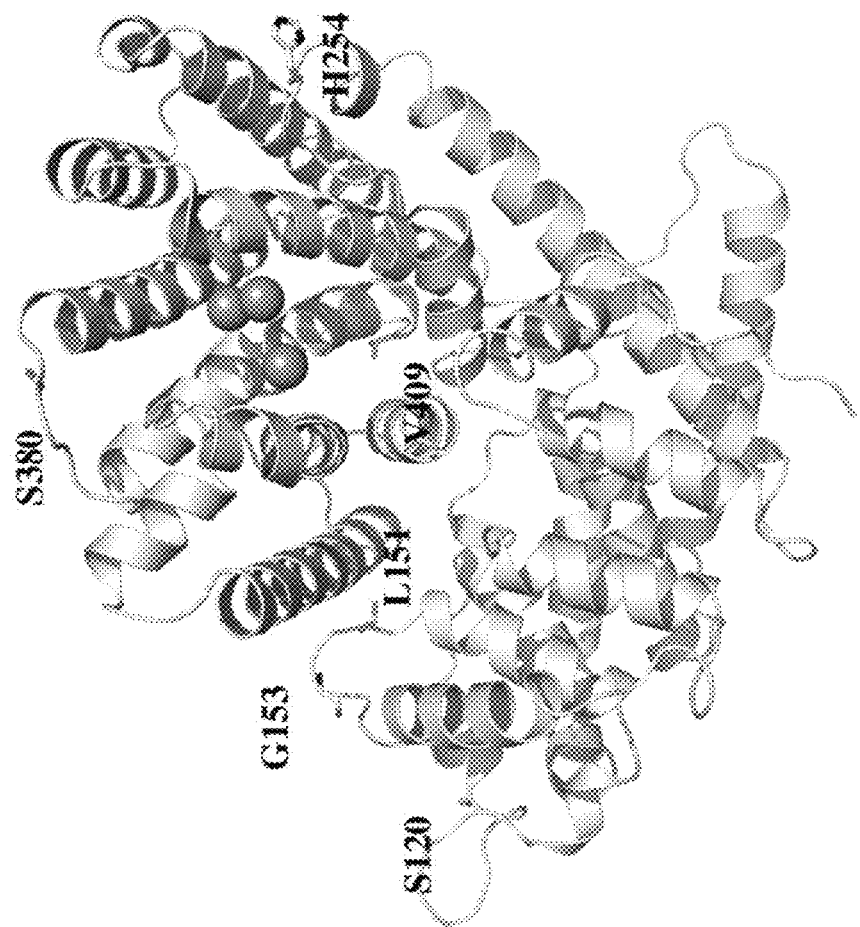
FIG. 25 shows the surface loop positions of IspS where variants demonstrated improved specific activity. $Mg^{2+}$ (spheres) are placed based on a structural alignment with PDB 1N24.
Figure 26:
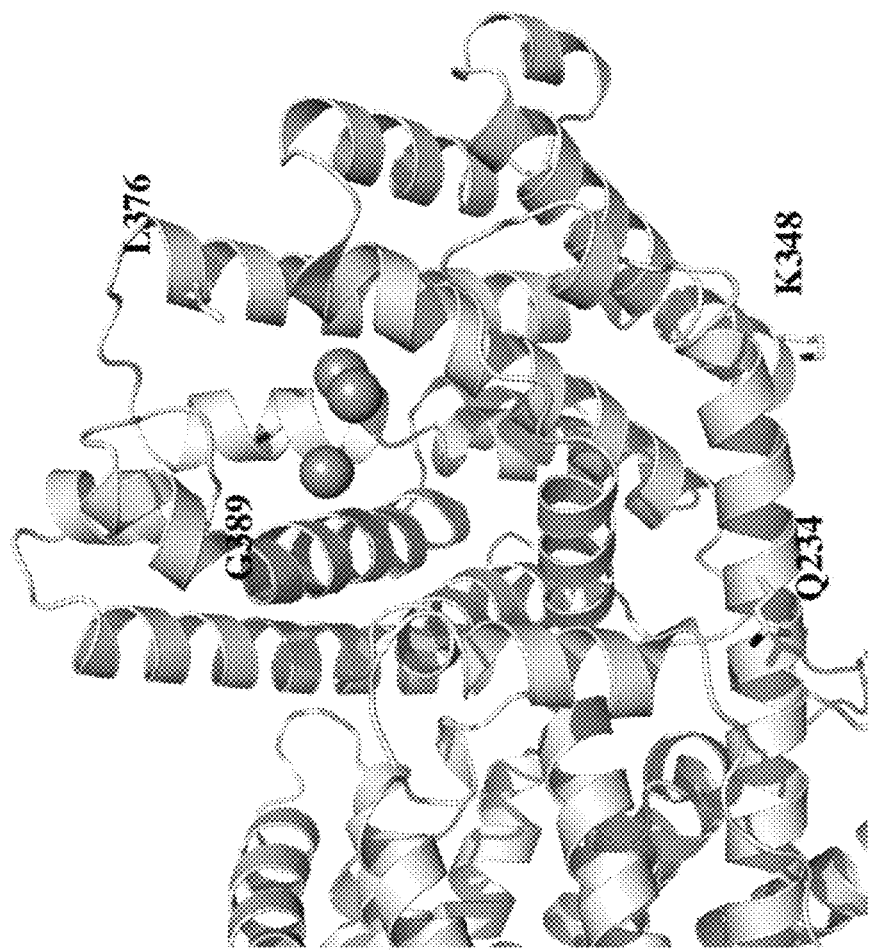
FIG. 26 shows the surface positions of IspS where variants demonstrated improved specific activity. $Mg^{2+}$ (spheres) are placed based on a structural alignment with PDB 1N24.
Figure 27:
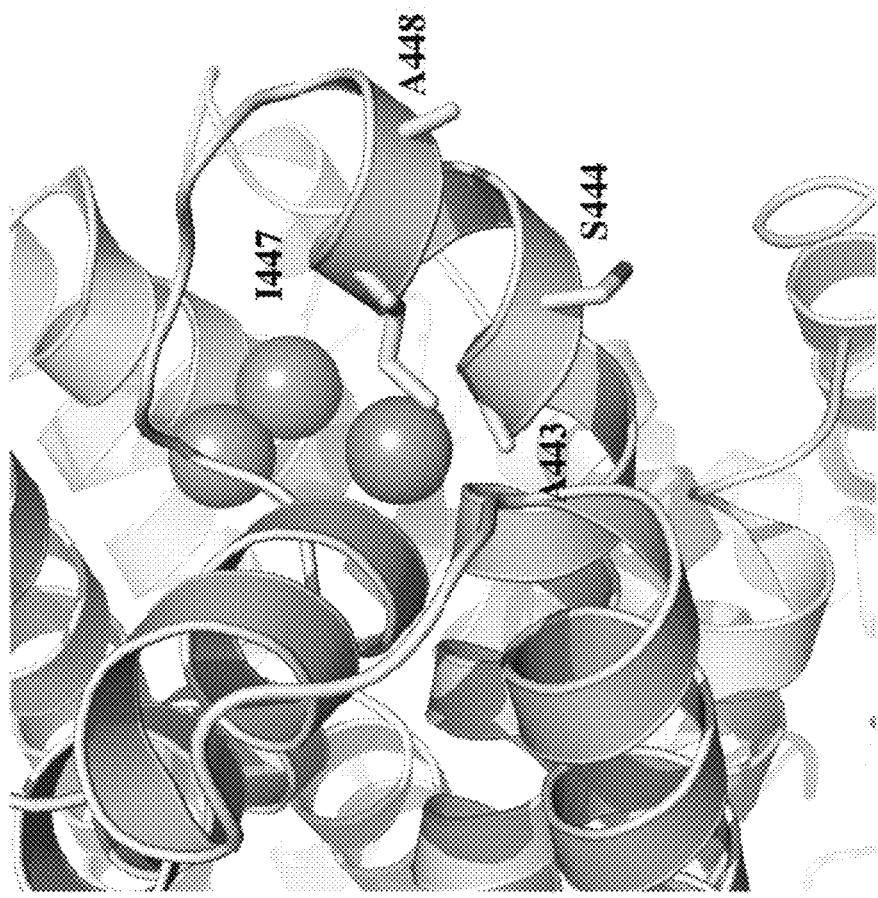
FIG. 27 shows the proposed substrate capture loop positions of IspS where variants demonstrated improved specific activity. $Mg^{2+}$ (spheres) are placed based on a structural alignment with PDB 1N24.

Variants that displayed specific activity higher than WT in the primary in vitro assay were selected for retesting. Variants were tested following the methods described above, except that polyclonal antibody in addition to monoclonal antibody was used for immunodetection, according to standard biochemical practices. Table 10 lists a set of retested variants that showed higher specific activity (a PI>1.3) than WT. FIG. 20 shows all positions in the crystal structure of IspS where variants displayed increased specific activity upon retest. In comparison to the wild type enzyme, these variants confer specific activity benefits to IspS by alteration/enhancement of the putative functions listed in Table 10. FIG. 21 shows buried positions in or that interact with the N-terminus of IspS and where variants displayed increased specific activity. FIG. 22 shows buried positions that are in or interact with the C-terminus of IspS, and where variants displayed increased specific activity. FIG. 23 shows position 247, where improved variants may positively affect dimerization of IspS, and FIG. 24 shows additional sites at the N-terminus where variants display clear specific activity benefits. FIG. 25 shows the locations of positions on surface loops where variants displayed high specific activity, and FIG. 26 shows positions on the surface of the enzyme that are not in loops, and where variants displayed increased specific activity. FIG. 27 shows positions in proposed substrate capture loops where variants displayed increased specific activity relative to wild type. Particular positions in this region have variants which displayed increased activity, whereas adjacent positions are immutable (see Table 9 and FIG. 19). This indicates that the proposed "substrate capture loops" in IspS are critical in the enzymatic conversion of DMAPP to isoprene, and are highly sensitive to perturbation, which can result in either negative or positive effects on activity. All variants listed in Table 10 and shown in FIGS. 20 through 27 or any combination thereof represent mutations in IspS that allow the enzyme to more efficiently convert DMAPP to isoprene.

TABLE 9

Positions in MEA *P. alba* displaying PI specific activity values ≤ 0.3 for all non+31 WT amino acid substitutions.

| Residue | Position | Location | % Surface Accessibility | Function |
|---|---|---|---|---|
| R | 4 | N+31 term | Not calc. | Conserved twin R presumably needed for N+31 term loop closure |
| Y | 9 | N+31 term | 65 | Based on model, this points into active site and interacts with D295 (part of DDxxD) |
| W | 243 | Dimer Interface | 9 | Base of dimer interface, in a hydrophobic pocket |
| D | 258 | N+31 term | 44 | Near active site; possible interaction with closed N+31 term tail (W244) |
| R | 259 | N+31 term | 29 | Near active site; possible interaction with closed N+31 term tail |
| E | 262 | N+31 term | 24 | Near active site; possible interaction with closed N+31 term tail |
| W | 266 | Active Site | 3 | Bottom of active site |
| R | 280 | Buried | 1 | Interacts with backbone of P274, possible loop stabilization |
| D | 294 | Active Site | 32 | Part of DDxxD motif |
| D | 295 | Active Site | 12 | Part of DDxxD motif |
| D | 298 | Active Site | 55 | Part of DDxxD motif |
| E | 305 | N+31 term | 19 | Possible interaction with R004 when N+31 term loop is closed |

TABLE 9-continued

Positions in MEA *P. alba* displaying PI specific activity values ≤ 0.3 for all non+31 WT amino acid substitutions.

| Residue | Position | Location | % Surface Accessibility | Function |
|---|---|---|---|---|
| Y | 387 | Substrate Capture Loops | 7 | Substrate capture loop; role unknown |
| S | 396 | Active TABLE 10-continued Retested variants of MEA P. alba displaying PI specific activity values > 1.3.

| Position | Mutation | Location | Charge Change | % Surface Accessibility | Function |
|---|---|---|---|---|---|
| 392 | C | Buried | 0 | 7 | alternate interactions in pocket |
| 392 | F | Buried | 0 | 7 | alternate interactions in pocket |
| 392 | M | Buried | 0 | 7 | alternate interactions in pocket |
| 392 | S | Buried | 0 | 7 | alternate interactions in pocket |
| 392 | V | Buried | 0 | 7 | alternate interactions in pocket |
| 392 | Y | Buried | 0 | 7 | alternate interactions in pocket |
| 409 | T | surface loop | 0 | 14 | alternate interactions in pocket |
| 437 | L | Buried | 0 | 7 | alternate interactions in pocket |
| 437 | M | Buried | 0 | 7 | alternate interactions in pocket |
| 443 | G | Substrate Capture Loops | 0 | 4 | affect shape of loop |
| 443 | Q | Substrate Capture Loops | 0 | 4 | affect shape of loop |
| 443 | R | Substrate Capture Loops | 1 | 4 | affect shape of loop |
| 443 | S | Substrate Capture Loops | 0 | 4 | affect shape of loop |
| 444 | D | Substrate Capture Loops | −1 | 56 | affect shape of loop |
| 444 | E | Substrate Capture Loops | −1 | 56 | affect shape of loop |
| 447 | T | Substrate Capture Loops | 0 | 23 | alternate interactions in pocket |
| 447 | V | Substrate Capture Loops | 0 | 23 | alternate interactions in pocket |
| 448 | V | Substrate Capture Loops | 0 | 77 | alternate surface interactions |
| 460 | A | Buried | 0 | 21 | alternate interactions in pocket |
| 461 | A | Buried | −1 | 32 | alternate interactions in pocket |
| 481 | Y | Buried | 0 | 0 | alternate interactions in pocket |
| 488 | L | Buried | 1 | 13 | alternate interactions in pocket |
| 502 | F | Buried | 0 | 1 | alternate interactions in pocket |
| 502 | M | Buried | 0 | 1 | alternate interactions in pocket |

Example 4

Growth Assay on 1024 Variants Selected from the Primary Screen

The primary in vitro specific activity screen identified variants of MEA P. alba that enhance the ability of the enzyme to catalyze the conversion DMAPP to isoprene. Since IspS must function inside a living cell, it was additionally necessary to measure the capability of the enzyme to convert DMAPP to isoprene in vivo. Examples 1 and 2 describe the methodology in determining the in vivo effectiveness of IspS. Essentially, by conversion of DMAPP to isoprene, IspS relieves the toxic effect of DMAPP on the growth of E. coli. Increased performance in comparison to wild type during the course of a growth curve indicates improved isoprene synthase function within a given strain. IspS variants that display both improved specific activity and the best growth performance are indicative of the enzymes best suited to improved isoprene production during fermentation.

Methods

Growth Assay and Specific Activity Measurements 1024 variants from the primary specific activity screen were selected for growth study and to confirm increased specific activity increases relative to the wild type MEA P. alba enzyme. Variants at positions that displayed high mutability (tolerance to mutation), and increased performance for both specific activity and expression not significantly less than wild type, were chosen for this study. Individual variants were isolated from their original glycerol stock plates and re-arrayed for the growth assay. Variants were induced at both low and high levels of IPTG, and their growth curves were determined in the presence of mevalonic acid (MVA). In these strains, MVA is taken up and drives flux through the mevalonic acid pathway to DMAPP, which is toxic to cell growth. Expression of functional P. alba IspS molecules allows for the conversion of DMAPP to isoprene, and the relief of growth inhibition. In these assays, better performing IspS molecules more effectively convert DMAPP to isoprene and result in improved growth.

Glycerol stocks of MEA P. alba IspS libraries were thawed briefly and inoculated into microtiter plates containing liquid LB with kanamycin at a concentration of 20 μg/ml. Cultures were grown overnight at 250 rpm, 30° C. to saturation in a shaking incubator. The next day, cultures were removed and inoculated at a ratio of 1:10 into TM3-glucose medium containing 50 ug/ml kanamycin and 40 or 100 uM IPTG (Sigma). Wild type controls were grown separately and inoculated into each microtiter plate containing TM3-glucose with a titration of IPTG concentrations, from 30 uM to 65 μM (for cultures induced at 40 μM), or 40 to 200 μM (for cultures induced at 100 μM), in separate wells. Plates were returned to the shaking incubator at 250 rpm, 30° C. and pre-induced for two hours. Cultures were then diluted into TM3-glucose medium containing 50 μg/ml kanamycin, 40 or 100 μM IPTG, and 20 mM MVA at a ratio of 1:10 in microtiter plates (Matrical). WT controls with or without MVA were included, as well as appropriate controls with titrations of IPTG. Plates were transferred to a Growth Profiler 1152 (Enzyscreen) and growth curves and optical densities (ODs) were determined according to the manufacturer's recommendation over a ten-hour time course. Performance indices (PIs) for growth of each strain were determined by comparison to four replicate WT strains induced at either 40 or 100 μM IPTG. PI values for OD at 300 minutes, Max OD, and area under the curve were calculated. Specific activity for all variants in this study, induced at the 40 µM IPTG level, was also determined according to the methods described in the previous example. Samples were isolated from the same pre-induction plate as the samples used in the growth assays.

Results

Figure 28:
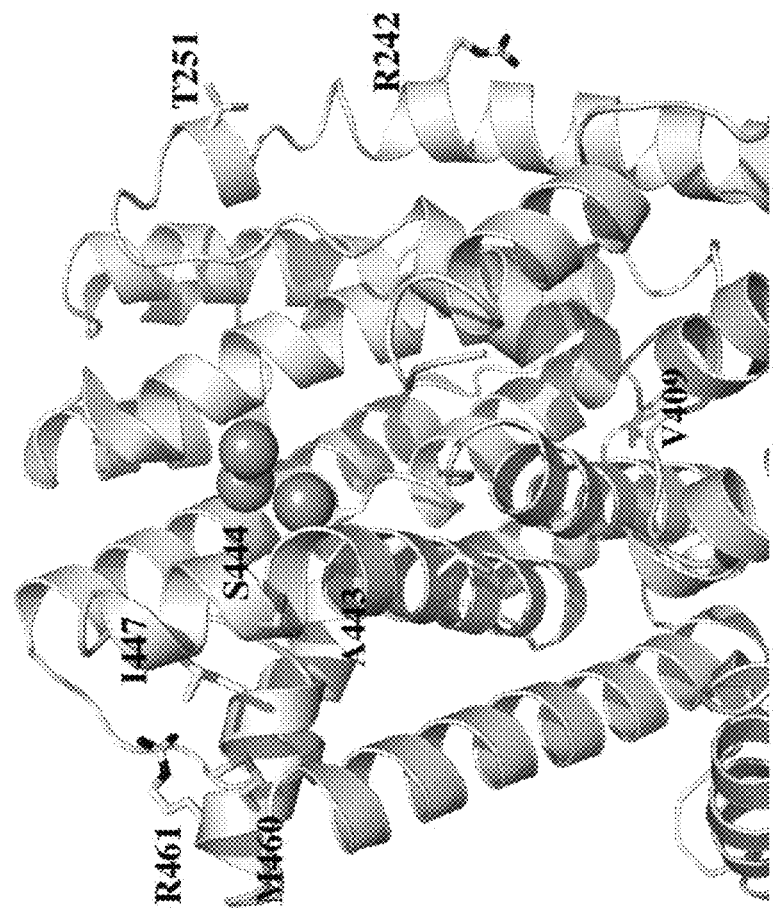
FIG. 28 shows positions of IspS demonstrating improved activity. $Mg^{2+}$ (spheres) are placed based on a structural alignment with PDB 1N24.
Figure 29:
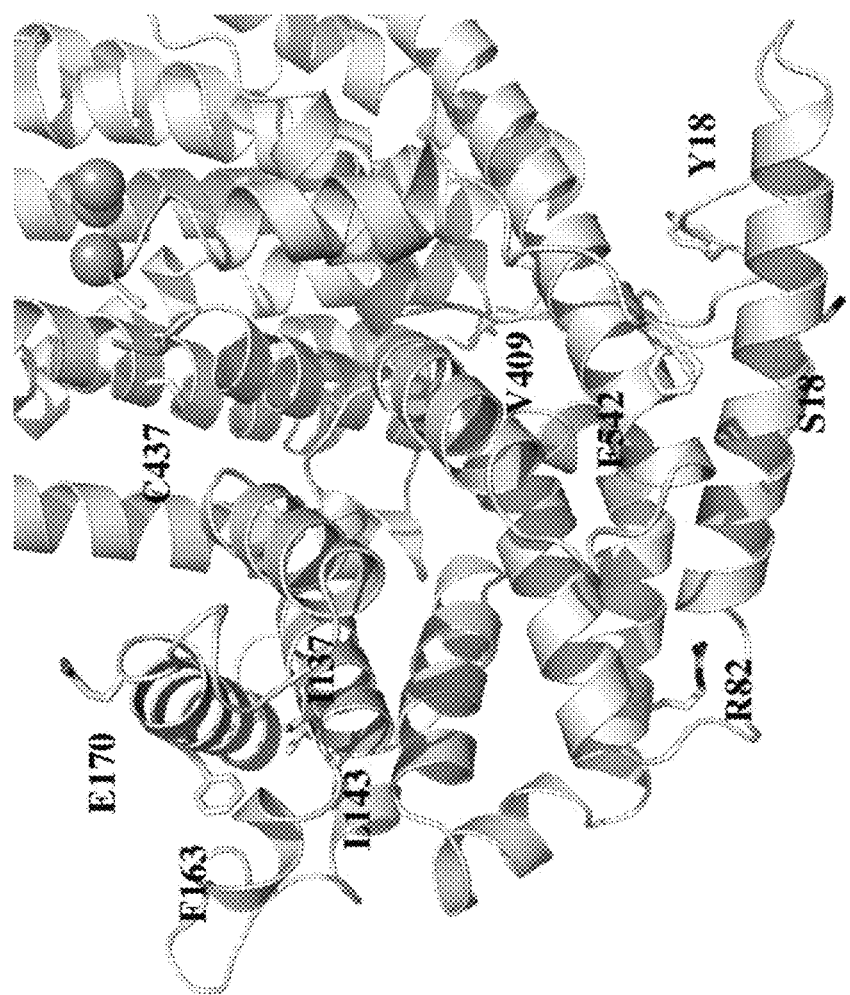
FIG. 29 shows positions of IspS demonstrating improved activity. $Mg^{2+}$ (spheres) are placed based on a structural alignment with PDB 1N24.

Table 8 provides definitions for locations of the residues listed in Tables 11 through 15. Table 11 lists all variants that displayed a PI value for specific activity greater than 1.4. Locations, surface accessibilities, and putative functions are also listed. Table 11 lists several variants that enhance the enzymatic efficiency of IspS, either alone or in combination. Locations of positions where variants displayed improved specific activity are shown in FIGS. 28 and 29. Variants with improved specific activity may allow for more efficient conversion of DMAPP to isoprene, and allow for improved cellular production of isoprene during fermentation.

Figure 30:
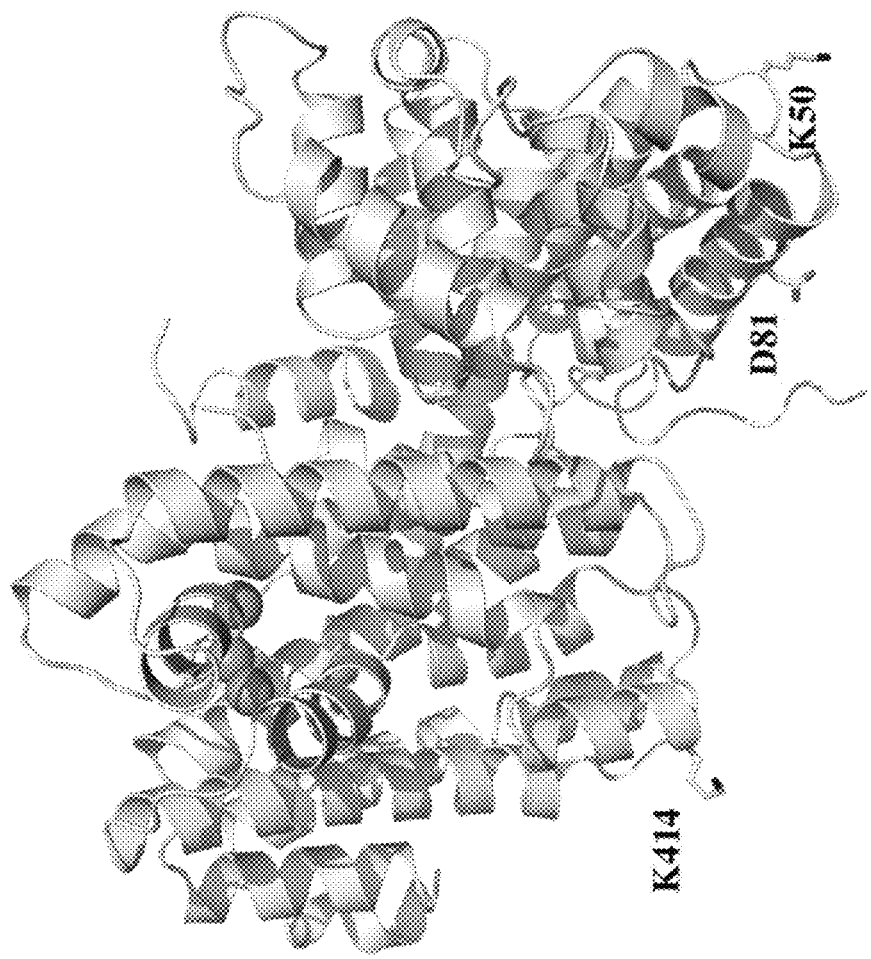
FIG. 30 shows monomer view of IspS showing N-terminal and Surface Loop positions demonstrating improved growth. $Mg^{2+}$ (spheres) are placed based on a structural alignment with PDB 1N24.
Figure 31:
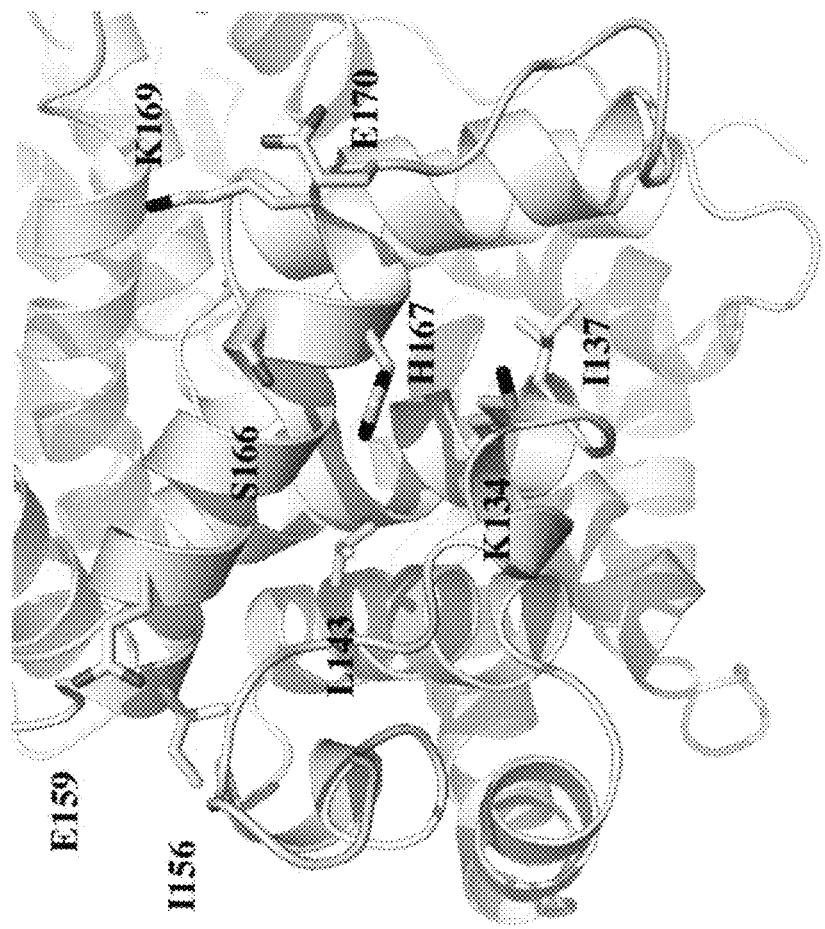
FIG. 31 shows monomer view of IspS showing N-terminal Helix positions demonstrating improved growth.
Figure 33:
FIG. 33 shows monomer view of IspS with location of sites where variants demonstrate improved growth colored dark gray. $Mg^{2+}$ (spheres) are placed based on a structural alignment with PDB 1N24.
Figure 34:
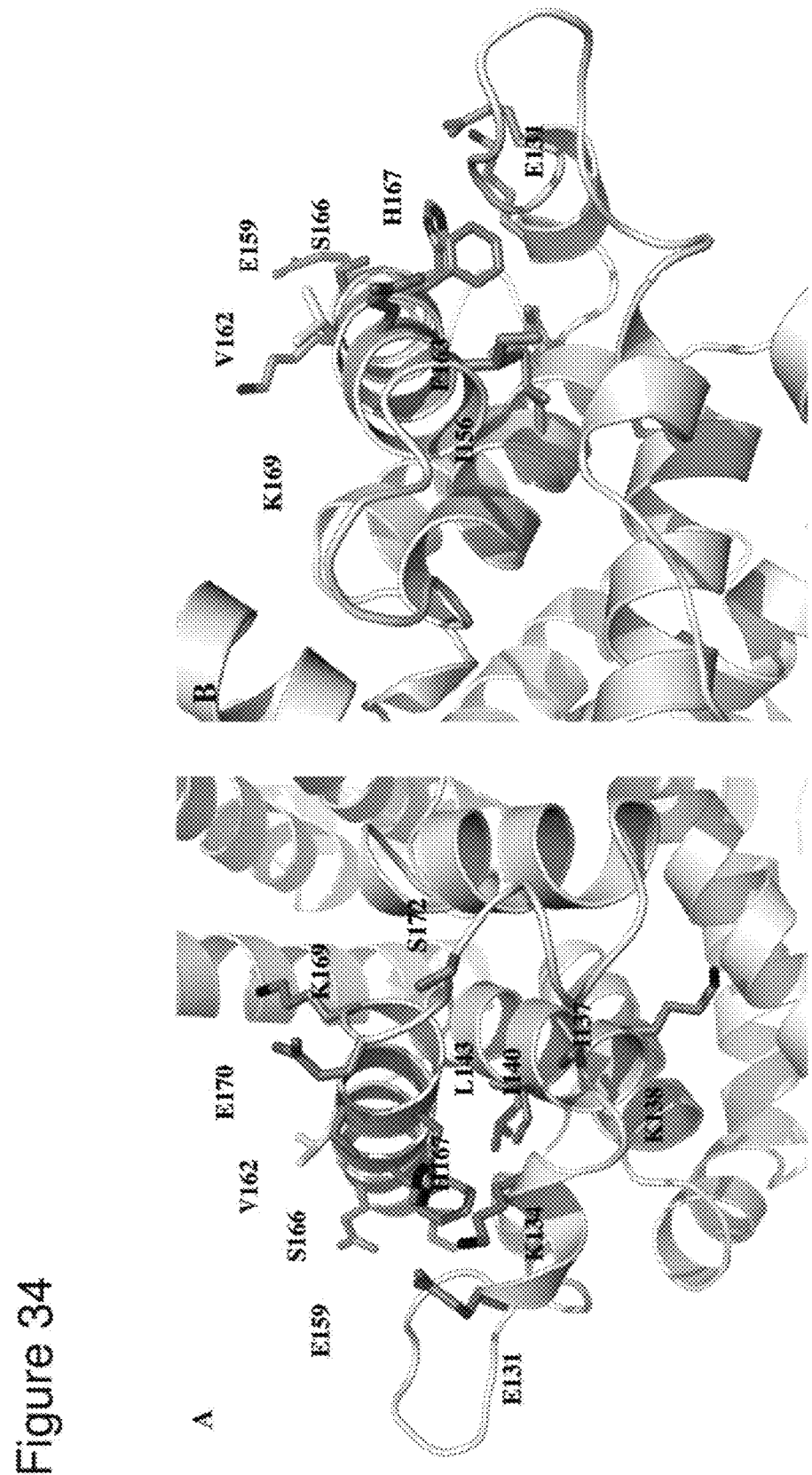
FIG. 34 shows view of IspS with location of sites where variants demonstrate improved growth shown as sticks. A and B are separated by 180°.

Tables 12 and 13 list variants with improved growth at the 40 uM and 100 uM induction level, respectively. While several different growth parameters were measured, all correlated well with each other, so only PI values for maximum OD (OD Max) were examined for variants listed in Tables 12 and 13. Listed variants displayed OD Max values that were 50% better than WT (PI of 1.5 or greater) at the given induction level. Variants that displayed improved growth (a PI value greater than 1.3 for OD Max) in both 40 uM and 100 uM IPTG induction conditions are listed in Table 14, and shown in FIGS. 30 and 31. These variants represent mutations that may allow for the highest overall growth performance and conversion of DMAPP to isoprene in cells expressing IspS. Several of these variants map near or within a particular N-terminal helix region of MEA *P. alba*, spanning residues 134 to 179. Several changes at or near this location ("N-term helices" in Tables 8, 12 through 15) displayed a growth benefit at either or both growth conditions. Not only do multiple variants map to this location in MEA *P. alba*, but the variants that displayed the largest benefit to growth are facing outwards from the helix and are located on the surface of the enzyme (see FIGS. 31, 33, and 34).

Figure 32:
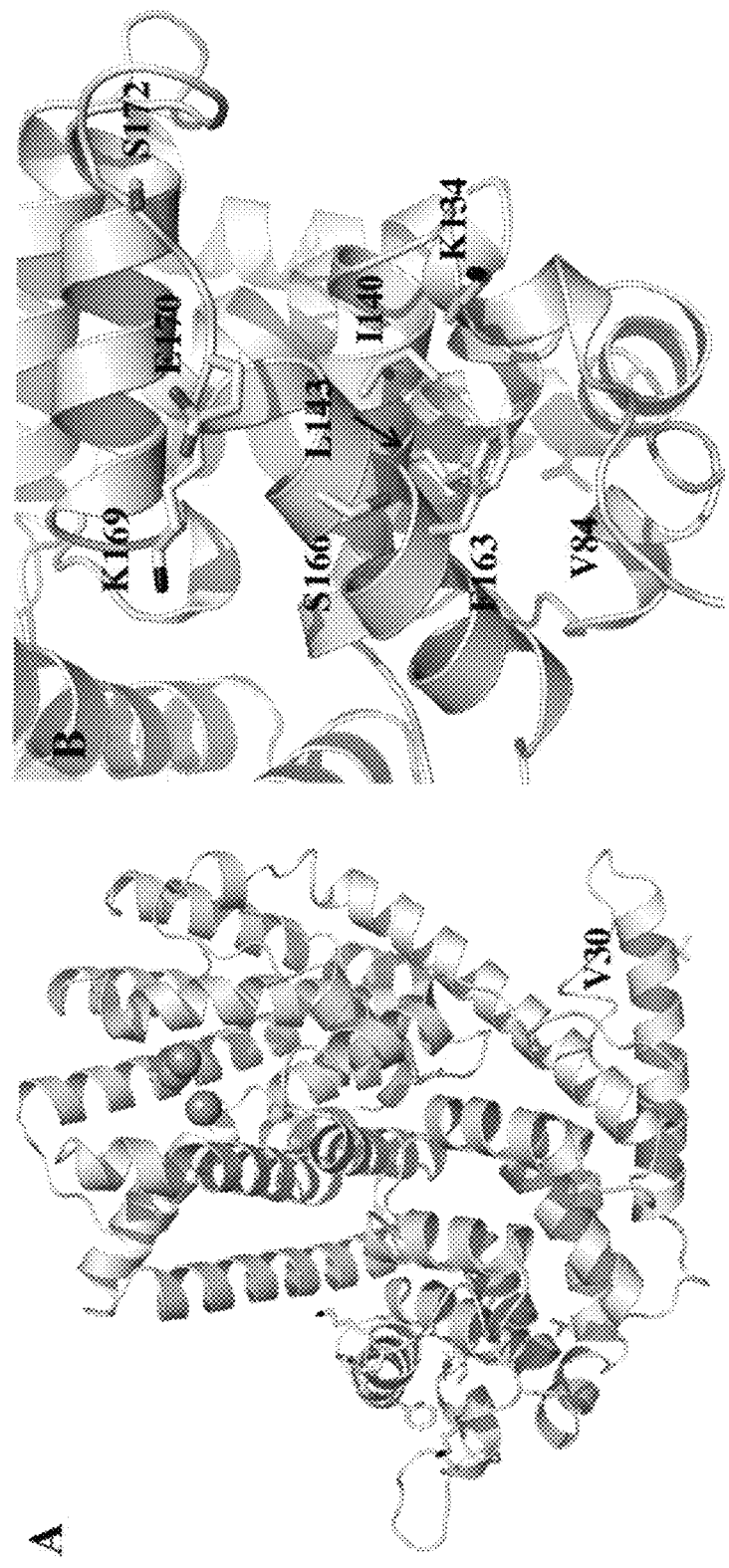
FIG. 32 shows monomer view of wild type IspS showing the location of sites from Table 15 (A). $Mg^{2+}$ (spheres) are placed based on a structural alignment with PDB 1N24. B) Close-up view of sites in A.

Table 15 lists variants that displayed improved performance (PI greater than 1.2) for all three parameters of specific activity, OD Max at 40 uM, and 100 uM IPTG. Several of these variants are listed in Table 14, and the majority of them are also located in or near the N-terminal helix described above, with the exceptions of V30K and V84T (see FIG. 32). This indicates that alterations at the helix spanning residues 150 to 172 are critical not only for improved growth of the host cell, but also for improved enzymatic activity. Since there is no obvious catalytic role for the N-terminal helix (see FIG. 33), these variants may influence IspS activity either intra-molecularly through conformational change of the enzyme structure, or inter-molecularly via the above-mentioned interactions with an unidentified enzyme, cellular process or structure. MEA *P. alba* enzymes harboring variants at this particular location, either alone or in combination with other variants conferring beneficial properties such as improved catalytic rates, likely will allow for improved growth rate of host strains, and improved isoprene production during fermentation.

TABLE 11

Retested variants of MEA *P. alba* that displayed PI values for specific activity >1.4.

| Position | Mutation | Location | Charge Change | % Surface Accessibility | Function |
|---|---|---|---|---|---|
| 18 | E | N-term | −1 | 64 | alternate interactions with nearby residues |
| 18 | D | N-term | −1 | 64 | alternate interactions with nearby residues |
| 18 | S | N-term | 0 | 64 | alternate interactions with nearby residues |
| 36 | P | N-term | −1 | 33 | alternate interactions with nearby residues |
| 82 | Q | N-term | −1 | 27 | alternate interactions with nearby residues |
| 87 | S | surface loop | 0 | 35 | alternate surface interactions |
| 87 | N | surface loop | 0 | 35 | alternate surface interactions |
| 87 | R | surface loop | 1 | 35 | alternate surface interactions |
| 137 | C | N-term helices | 0 | 15 | alternate interactions in pocket |
| 143 | N | N-term helices | 0 | 1 | alternate interactions in hydrophobic pocket |
| 163 | I | N-term helices | 0 | 10 | alternate interactions in pocket |
| 163 | Q | N-term helices | 0 | 10 | alternate interactions in pocket |
| 170 | G | N-term helices | 1 | 79 | alternate surface interactions |
| 242 | T | Dimer interface | −1 | 35 | improve dimer interface interactions |
| 251 | E | surface | −1 | 74 | alternate interactions with nearby residues |
| 409 | S | surface loop | 0 | 14 | alternate interactions in pocket |
| 437 | M | Buried | 0 | 7 | alternate interactions in pocket |
| 437 | K | Buried | 1 | 7 | alternate interactions in pocket |
| 443 | G | Substrate Capture Loops | 0 | 4 | affect shape of loop |
| 443 | S | Substrate Capture Loops | 0 | 4 | affect shape of loop |
| 443 | Q | Substrate Capture Loops | 0 | 4 | affect shape of loop |
| 444 | P | Substrate Capture Loops | 0 | 56 | affect shape of loop |
| 447 | Q | Substrate Capture Loops | 0 | 23 | alternate interactions in pocket |

TABLE 11-continued

Retested variants of MEA *P. alba* that displayed PI values for specific activity >1.4.

| Position | Mutation | Location | Charge Change | % Surface Accessibility | Function |
|---|---|---|---|---|---|
| 447 | T | Substrate Capture Loops | 0 | 23 | alternate interactions in pocket |
| 447 | M | Substrate Capture Loops | 0 | 23 | alternate interactions in pocket |
| 447 | E | Substrate Capture Loops | −1 | 23 | alternate interactions in pocket |
| 447 | S | Substrate Capture Loops | 0 | 23 | alternate interactions in pocket |
| 447 | R | Substrate Capture Loops | 1 | 23 | alternate interactions in pocket |
| 460 | Q | Buried | 0 | 21 | alternate interactions in pocket |
| 460 | S | Buried | 0 | 21 | alternate interactions in pocket |
| 460 | G | Buried | 0 | 21 | alternate interactions in pocket |
| 460 | A | Buried | 0 | 21 | alternate interactions in pocket |
| 461 | D | Buried | −2 | 32 | alternate interactions in pocket |
| 461 | S | Buried | −1 | 32 | alternate interactions in pocket |
| 461 | T | Buried | −1 | 32 | alternate interactions in pocket |
| 461 | E | Buried | −2 | 32 | alternate interactions in pocket |
| 542 | N | surface loop | 0 | 17 | alternate interactions with nearby residues |

TABLE 12

Variants of MEA *P. alba* that displayed PI values >1.5 for OD Max at 40 mM IPTG

| Position | Mutation | Location | Charge Change | % Surface Accessibility | Function |
|---|---|---|---|---|---|
| 134 | P | N-term helices | −1 | 37 | loop stabilization |
| 138 | C | N-term helices | −1 | 53 | alternate interctions with nearby residues |
| 143 | F | N-term helices | 0 | 1 | alternate interactions in hydrophobic pocket |
| 143 | V | N-term helices | 0 | 1 | alternate interactions in hydrophobic pocket |
| 156 | G | N-term helices | 0 | 13 | allow more flexibility in loop |
| 159 | G | N-term helices | 1 | 32 | alternate interctions with nearby residues |
| 159 | Q | N-term helices | 1 | 32 | alternate interctions with nearby residues |
| 163 | C | N-term helices | 0 | 10 | alternate interctions with nearby residues |
| 163 | E | N-term helices | −1 | 10 | alternate interctions with nearby residues |
| 163 | Q | N-term helices | 0 | 10 | alternate interctions with nearby residues |
| 163 | V | N-term helices | 0 | 10 | alternate interctions with nearby residues |
| 163 | Y | N-term helices | 0 | 10 | alternate interctions with nearby residues |
| 166 | C | N-term helices | 0 | 46 | alternate surface interactions |
| 166 | D | N-term helices | −1 | 46 | alternate surface interactions |
| 166 | G | N-term helices | 0 | 46 | alternate surface interactions |
| 166 | P | N-term helices | 0 | 46 | alternate surface interactions |
| 166 | V | N-term helices | 0 | 46 | alternate surface interactions |
| 167 | M | N-term helices | 0 | 21 | alternate interctions with nearby residues |
| 170 | G | N-term helices | 1 | 79 | alternate surface interactions |
| 170 | H | N-term helices | 1 | 79 | alternate surface interactions |
| 170 | K | N-term helices | 2 | 79 | alternate surface interactions |
| 170 | N | N-term helices | 1 | 79 | alternate surface interactions |
| 170 | R | N-term helices | 2 | 79 | alternate surface interactions |
| 170 | S | N-term helices | 1 | 79 | alternate surface interactions |
| 170 | W | N-term helices | 1 | 79 | alternate surface interactions |
| 414 | F | surface loop | −1 | 70 | alternate surface interactions |
| 414 | G | surface loop | −1 | 70 | alternate surface interactions |
| 414 | N | surface loop | −1 | 70 | alternate surface interactions |
| 414 | P | surface loop | −1 | 70 | alternate surface interactions |
| 421 | R | surface loop | 1 | 23 | alternate surface interactions |
| 491 | Q | surface loop | 0 | 58 | alternate surface interactions |

TABLE 12-continued

Variants of MEA *P. alba* that displayed PI values >1.5 for OD Max at 40 mM IPTG

| Position | Mutation | Location | Charge Change | % Surface Accessibility | Function |
| --- | --- | --- | --- | --- | --- |
| 491 | V | surface loop | 0 | 58 | alternate surface interactions |
| 491 | Y | surface loop | 0 | 58 | alternate surface interactions |

TABLE 13

Variants of MEA *P. alba* that displayed PI values >1.5 for OD Max at 100 mM IPTG

| Position | Mutation | Location | Charge Change | % Surface Accessibility | Function |
| --- | --- | --- | --- | --- | --- |
| 29 | N | N-term | 1 | 34 | alternate surface interactions |
| 47 | V | surface loop | 0 | 16 | affect shape of loop |
| 86 | C | surface loop | 0 | 59 | alternate interactions |
| 94 | A | surface loop | −1 | 73 | affect shape of loop |
| 131 | F | N-term helices | 1 | 58 | improved interaction with neighboring his |
| 134 | E | N-term helices | −2 | 37 | loop stabilization |
| 134 | P | N-term helices | −1 | 37 | loop stabilization |
| 156 | G | N-term helices | 0 | 13 | allow more flexibility in loop |
| 162 | P | N-term helices | 0 | 60 | loop stabilization |
| 169 | C | N-term helices | −1 | 60 | alternate surface interactions |
| 178 | E | N-term helices | −2 | 73 | alternate surface interactions |
| 179 | T | N-term helices | 1 | 46 | alternate surface interactions |
| 231 | D | hinge region | −1 | 33 | alternate surface interactions |
| 231 | K | hinge region | 1 | 33 | alternate surface interactions |
| 231 | R | hinge region | 1 | 33 | alternate surface interactions |
| 231 | T | hinge region | 0 | 33 | alternate surface interactions |
| 231 | V | hinge region | 0 | 33 | alternate surface interactions |
| 242 | N | dimer interface | −1 | 35 | improve dimer interface interactions |
| 242 | I | dimer interface | −1 | 35 | improve dimer interface interactions |
| 369 | C | active site | 0 | 2 | alter active site cavity |
| 414 | C | surface loop | −1 | 70 | alternate surface interactions |
| 414 | F | surface loop | −1 | 70 | alternate surface interactions |
| 414 | G | surface loop | −1 | 70 | alternate surface interactions |
| 414 | N | surface loop | −1 | 70 | alternate surface interactions |
| 421 | D | surface loop | −1 | 23 | alternate surface interactions |

TABLE 14

Variants of MEA *P. alba* that displayed PI values >1.3 for OD Max at 40 and 100 mM IPTG

| Position | Mutation | Location | Charge Change | % Surface Accessibility | Function |
| --- | --- | --- | --- | --- | --- |
| 50 | S | N-term | −1 | 86 | alternate surface interactions |
| 81 | F | N-term | 1 | 48 | alternate surface interactions |
| 134 | E | N-term helices | −2 | 37 | improved interaction with neighboring his |
| 134 | P | N-term helices | −1 | 37 | loop stabilization |
| 137 | N | N-term helices | 0 | 15 | alternate interactions in pocket |
| 143 | V | N-term helices | 0 | 1 | alternate interactions in hydrophobic pocket |
| 156 | G | N-term helices | 0 | 13 | allow more flexibility in loop |
| 159 | D | N-term helices | 0 | 32 | alternate interactions with nearby residues |
| 159 | G | N-term helices | 1 | 32 | allow more flexibility in loop |

TABLE 14-continued

Variants of MEA *P. alba* that displayed PI values >1.3 for OD Max at 40 and 100 mM IPTG

| Position | Mutation | Location | Charge Change | % Surface Accessibility | Function |
|---|---|---|---|---|---|
| 159 | Q | N-term helices | 1 | 32 | alternate interactions with nearby residues |
| 166 | C | N-term helices | 0 | 46 | alternate surface interactions |
| 166 | W | N-term helices | 0 | 46 | alternate surface interactions |
| 167 | M | N-term helices | 0 | 21 | alternate interactions with nearby residues |
| 167 | N | N-term helices | 0 | 21 | alternate interactions with nearby residues |
| 169 | C | N-term helices | −1 | 60 | alternate surface interactions |
| 170 | H | N-term helices | 1 | 79 | alternate surface interactions |
| 170 | K | N-term helices | 2 | 79 | alternate surface interactions |
| 170 | W | N-term helices | 1 | 79 | alternate surface interactions |
| 414 | C | surface loop | −1 | 70 | alternate surface interactions |
| 414 | F | surface loop | −1 | 70 | alternate surface interactions |
| 414 | G | surface loop | −1 | 70 | alternate surface interactions |
| 414 | N | surface loop | −1 | 70 | alternate surface interactions |
| 414 | P | surface loop | −1 | 70 | alternate surface interactions |

TABLE 15

Variants of MEA *P. alba* that displayed PI values >1.2 for Specific Activity, OD Max at 40 µM IPTG, and 100 µM IPTG

| Position | Mutation | Location | Charge Change | % Surface Accessibility | Function |
|---|---|---|---|---|---|
| 30 | K | N-term | 1 | 60 | replace surface hydrophobic w/charged |
| 84 | T | N-term | 0 | 30 | polar residue for better solvent interactions |
| 134 | C | N-term helices | −1 | 37 | size reduction, improved interaction with neighboring His |
| 134 | D | N-term helices | −2 | 37 | improved interaction with neighboring his |
| 134 | E | N-term helices | −2 | 37 | improved interaction with neighboring his |
| 140 | S | N-term helices | 0 | 1 | may improve interactions with other polar residues in pocket |
| 140 | T | N-term helices | 0 | 1 | may improve interactions with other polar residues in pocket |
| 143 | F | N-term helices | 0 | 1 | alternate interactions in hydrophobic pocket |
| 143 | I | N-term helices | 0 | 1 | alternate interactions in hydrophobic pocket |
| 143 | M | N-term helices | 0 | 1 | alternate interactions in hydrophobic pocket |
| 143 | V | N-term helices | 0 | 1 | alternate interactions in hydrophobic pocket |
| 163 | I | N-term helices | 0 | 10 | alternate interactions in pocket |
| 163 | M | N-term helices | 0 | 10 | alternate interactions in pocket |
| 166 | P | N-term helices | 0 | 45 | stabilize helix |
| 166 | V | N-term helices | 0 | 45 | alternate surface interactions |
| 169 | Q | N-term helices | −1 | 60 | alternate surface interactions |
| 170 | H | N-term helices | 1 | 80 | alternate surface interactions |
| 170 | K | N-term helices | 2 | 80 | alternate surface interactions |
| 172 | V | N-term helices | 0 | 47 | affect shape of loop |

Example 5

Specific Activity and Growth Assays on Combinatorial Libraries

Single variants of MEA *P. alba* IspS improved for specific activity, growth, or both traits were selected for combination into three seven-member libraries.

Methods

Libraries were constructed in the pCL201 vector and transformed into the MD09-170 screening strain (DNA2.0). 160 individual variants, representing approximately 80 to 90% of the 128 possible combinations in each library, were screened for both specific activity and growth following the methods described in the previous examples. Table 16 lists the variants chosen for combinatorial libraries, their locations in the crystal structure, surface accessibilities, and selection criteria (either specific activity, growth or both).

with other improved variants, is particularly beneficial for in vitro activity. M460A, A443G, and I447T also displayed this type of effect. Similarly, the V162P mutation was present in all combinatorial variants with improved properties for both specific activity and growth, suggesting that V162P works well in combination with other variants and may be an ideal mutation for more efficient conversion of DMAPP to isoprene within the host cell, for the reasons described in the previous paragraph. I156G and E170H also showed this effect. The variants G087R, R242N, and S288T also displayed improved specific activity in combination with other variants, but were not always among the highest performers for the in vitro assay. The combinatorial variants listed in Tables 17 and 18 may represent significantly improved IspS enzymes that allow for optimal conversion of DMAPP into isoprene during fermentation of host cells. The presence or absence of individual mutations in these particular combinatorial variants additionally may signify the best overall mutations that can be

TABLE 16

Variants chosen for combinatorial libraries

| Residue | Position | Mutation | Library | Location | % Surface Accessibility | Selection Criteria |
|---|---|---|---|---|---|---|
| S | 288 | C | ½ | C-term | 0 | Growth (Solubility) |
| S | 22 | R | 1 | N-term | 54 | Specific Activity |
| R | 71 | I | 1 | N-term | 3 | Specific Activity |
| S | 444 | D | ½ | SubLoop | 56 | Specific Activity |
| M | 460 | A | 1 | SubLoop | 21 | Specific Activity |
| A | 443 | G | 1 | SubLoop | 4 | Specific Activity |
| T | 502 | M | 1 | Buried | 1 | Specific Activity |
| V | 409 | T | 2 | surface loop | 14 | Growth/Specific Activity |
| R | 242 | N | 2 | DimInt | 35 | Growth/Specific Activity |
| K | 414 | F | 2 | surface loop | 70 | Growth |
| V | 162 | P | 2 | N-term helix | 60 | Growth |
| G | 87 | R | 2 | surface loop | 35 | Growth/Specific Activity |
| S | 288 | T | 3 | C-term | 0 | Growth/Specific Activity |
| N | 47 | V | 3 | surface loop | 16 | Growth |
| I | 447 | T | 3 | SubLoop | 23 | Specific Activity |
| E | 170 | H | 3 | N-term helix | 79 | Growth |
| S | 231 | T | 3 | hinge region | 33 | Growth |
| K | 414 | N | 3 | surface loop | 70 | Growth |
| I | 156 | G | 3 | N-term helix | 13 | Growth |

Results

Combinatorial variants displaying significantly improved specific activity and/or growth performance were identified. Table 17 contains a list of combinatorial variants that displayed performance index (PI) values for specific activity greater than 2.6. The left hand column lists the variant number, and the subsequent columns list the genotype for the 7 different positions in that library. Variants with improved specific activity allow for more efficient enzymatic conversion of DMAPP to isoprene, likely by improved kinetic parameters. Table 18 contains a list of combinatorial variants that displayed PI values greater than 1.3 for specific activity, OD Max at 40 uM, and OD Max at 100 uM. IspS variants improved for both specific activity and growth parameters also convert DMAPP to isoprene more efficiently than the WT enzyme, and likely are beneficial to growth of the host strain by mediation of a deleterious effect of IspS within the host.

Since each library member contained any combination of seven possible mutations, effects of variants were observed multiple times in different configurations. This provided a robust internal control to help identify the most effective combinations present in each library. For example, the S444D mutation was present in the highest specific activity combinatorial variants, suggesting that this variant, in combination combined in future variants of IspS, critical to the optimization of isoprene production by fermentation of microorganisms.

TABLE 17

Combinatorial variants of MEA *P. alba* displaying PI specific activity values > 2.6.

| Variant | Pos 1 | Pos 2 | Pos 3 | Pos 4 | Pos 5 | Pos 6 | Pos 7 |
|---|---|---|---|---|---|---|---|
| 1 | 022R | 071I | 288C | 443A | 444D | 460A | 502M |
| 2 | 022R | 071I | 288C | 443G | 444D | 460A | 502M |
| 3 | 022S | 071I | 288C | 443A | 444S | 460A | 502T |
| 4 | 022S | 071R | 288C | 443A | 444D | 460A | 502T |
| 5 | 087G | 162P | 242N | 288S | 409T | 414F | 444D |
| 6 | 087G | 162P | 242N | 288S | 409T | 414K | 444D |
| 7 | 087G | 162P | 242R | 288C | 409T | 414F | 444D |
| 8 | 087G | 162V | 242N | 288C | 409V | 414F | 444D |
| 9 | 087G | 162V | 242R | 288C | 409T | 414F | 444D |
| 10 | 087G | 162V | 242R | 288C | 409V | 414K | 444D |
| 11 | 087R | 162P | 242N | 288C | 409T | 414F | 444D |
| 12 | 087R | 162P | 242N | 288C | 409T | 414K | 444D |
| 13 | 087R | 162P | 242N | 288S | 409T | 414K | 444D |
| 14 | 087R | 162P | 242N | 288S | 409V | 414F | 444D |
| 15 | 087R | 162P | 242N | 288S | 409V | 414K | 444D |
| 16 | 087R | 162P | 242R | 288C | 409T | 414F | 444D |
| 17 | 087R | 162P | 242R | 288C | 409V | 414F | 444D |

TABLE 17-continued

Combinatorial variants of MEA *P. alba* displaying PI specific activity values > 2.6.

| Variant | Pos 1 | Pos 2 | Pos 3 | Pos 4 | Pos 5 | Pos 6 | Pos 7 |
|---|---|---|---|---|---|---|---|
| 18 | 087R | 162P | 242R | 288C | 409V | 414K | 444D |
| 19 | 087R | 162P | 242R | 288S | 409T | 414F | 444D |
| 20 | 087R | 162P | 242R | 288S | 409V | 414K | 444D |
| 21 | 087R | 162V | 242N | 288C | 409V | 414F | 444D |
| 22 | 087R | 162V | 242N | 288S | 409T | 414F | 444D |
| 23 | 087R | 162V | 242N | 288S | 409T | 414K | 444D |
| 24 | 087R | 162V | 242N | 288S | 409V | 414F | 444D |
| 25 | 087R | 162V | 242R | 288C | 409T | 414K | 444D |
| 26 | 087R | 162V | 242R | 288C | 409V | 414K | 444D |
| 27 | 087R | 162V | 242R | 288S | 409V | 414F | 444D |

TABLE 18

Combinatorial variants of MEA *P. alba* displaying PI > 1.3 for specific activity, OD Max at 40 µM IPTG, and OD Max at 100 µM IPTG.

Figure 36:
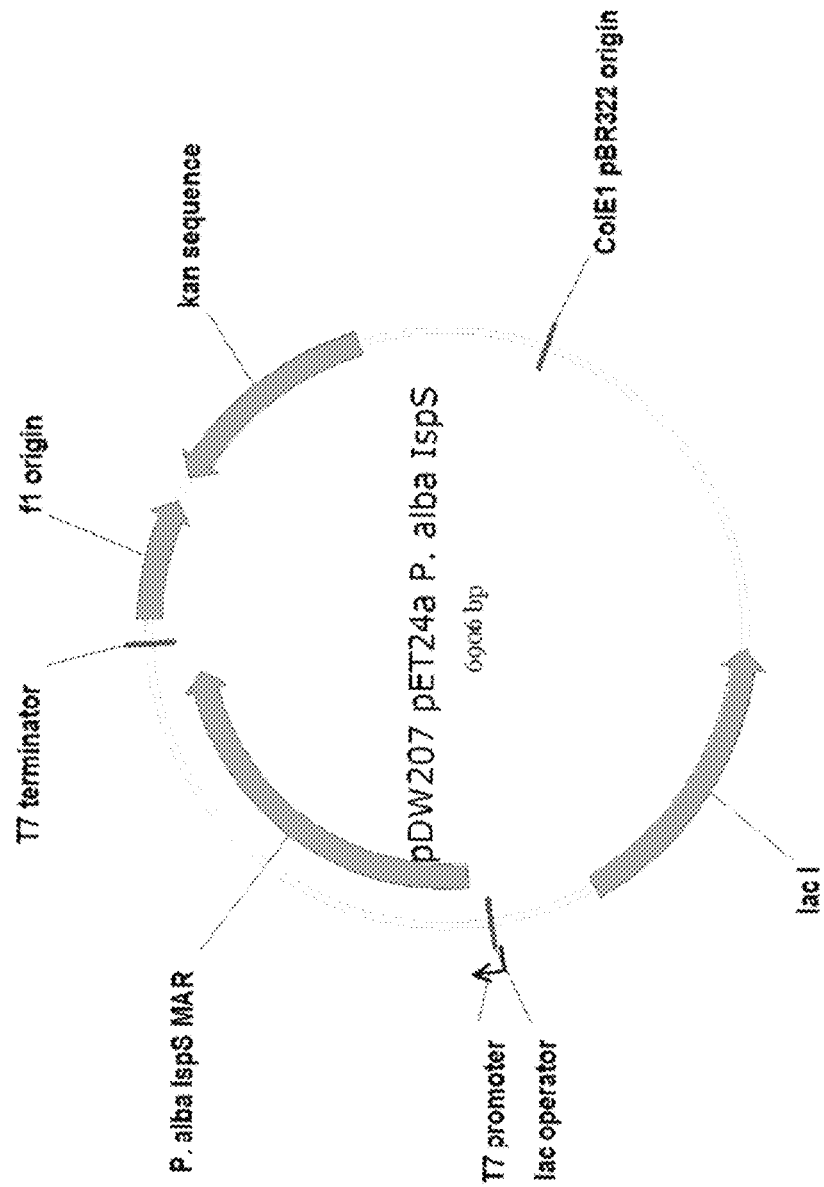
FIG. 36 shows a plasmid map of pDW207 harboring the *P. alba* IspS MAR variant.
Figure 37:
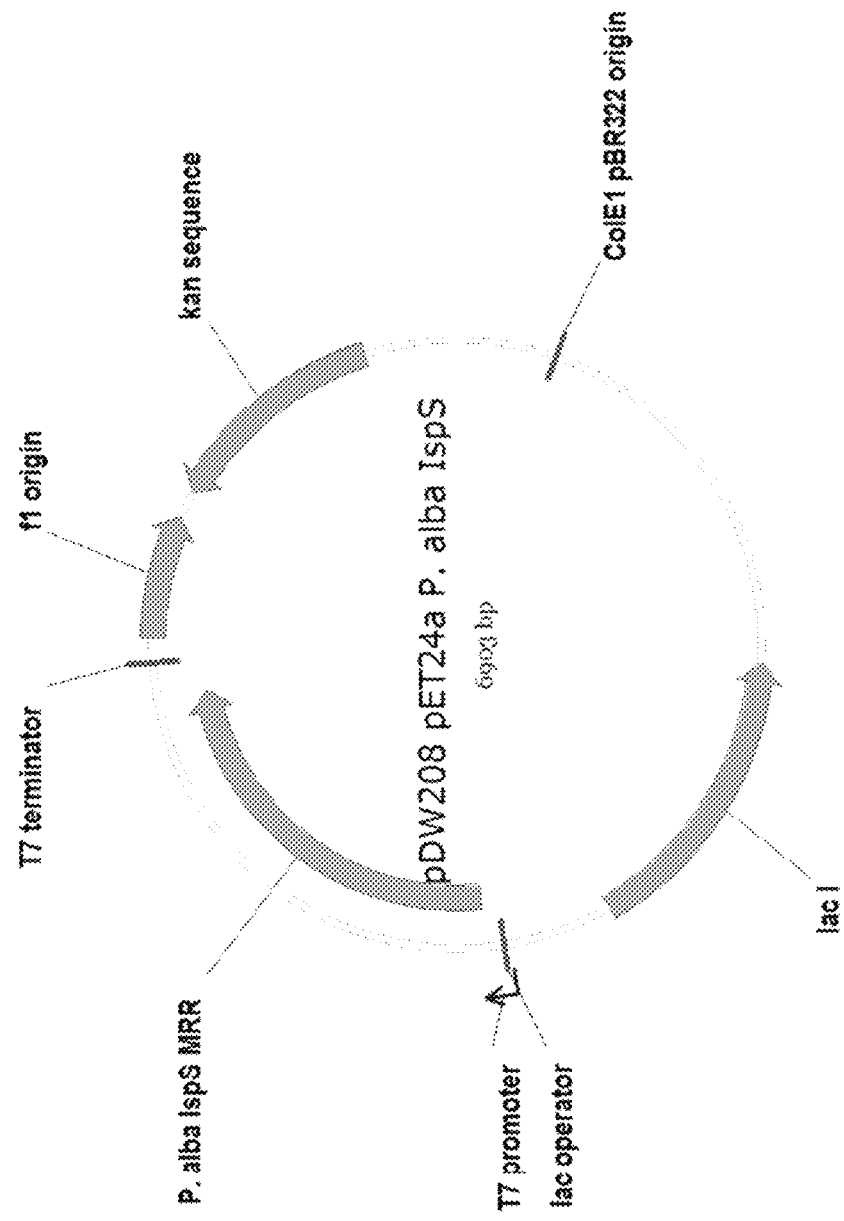
FIG. 37 shows a plasmid map of pDW208 harboring the *P. alba* IspS MRR variant.

| Variant | Pos 1 | Pos 2 | Pos 3 | Pos 4 | Pos 5 | Pos 6 | Pos 7 |
|---|---|---|---|---|---|---|---|
| 1 | 047N | 156G | 170H | 231S | 288T | 414K | 447I |
| 2 | 047V | 156G | 170H | 231S | 288T | 414K | 447I |
| 3 | 047V | 156I | 170H | 231S | 288T | 414F | 447I |
| 4 | 047V | 156I | 170H | 231T | 288T | 414K | 447I |
| 5 | 087G | 162P | 242N | 288C | 409T | 414F | 444S |
| 6 | 087G | 162P | 242N | 288C | 409V | 414K | 444S |
| 7 | 087G | 162P | 242N | 288S | 409T | 414F | 444S |
| 8 | 087G | 162P | 242R | 288C | 409T | 414K | 444S |
| 9 | 087G | 162P | 242R | 288S | 409T | 414K | 444S |
| 10 | 087R | 162P | 242N | 288C | 409T | 414F | 444S |
| 11 | 087R | 162P | 242N | 288C | 409V | 414K | 444S |
| 12 | 087R | 162P | 242R | 288C | 409V | 414K | 444S | product was treated with 1 µl DpnI (Roche) for 3 hours, and then 1 µl of the entire reaction was transformed into chemically competent *E. coli* Top10 cells (Invitrogen) according to the manufacturer's recommended protocol. Cells were recovered and plated on LB medium containing 50 µg/ml kanamycin. The next day, positive colonies were chosen for growth, plasmid purification (Qiagen) and sequencing (Quintara Biosciences). Plasmids which harbored the correct truncations were selected for sequencing of the entire open reading frame to confirm the integrity of the coding sequence. These plasmids, pDW207 (see FIG. 36) and pDW208 (see FIG. 37), were transformed by electroporation into the expression strain MD09-170 for determination of specific activity (see Table 20). Specific activity was determined as previously described. At least 30 replicates of each truncation were analyzed in comparison to MEA *P. alba*.

TABLE 19

Primers used for QuikChange Mutagenesis

| | | |
|---|---|---|
| HgS MRR Forward | TATACATATGCGTCGCTCT GCGAACTACGA | (SEQ ID NO: 23) |
| HgS MRR Reverse | CAGAGCGACGCATATGTAT ATCTCCTTCTT | (SEQ ID NO: 24) |
| HgS MAR Forward | TATACATATGGCACGTCGC TCTGCGAACTA | (SEQ ID NO: 25) |
| HgS MAR Reverse | AGCGACGTGCCATATGTAT ATCTCCTTCTT | (SEQ ID NO: 26) |

TABLE 20

Strains with N-terminal truncations

| Strain | Plasmid | Description |
|---|---|---|
| DW618 | pDW207 | BL21 (DE3) PL.2-mKKDyI + *P. alba* IspS MAR (−1 from MEA *P. alba*) |
| DW619 | pDW208 | BL21 (DE3) PL.2-mKKDyI + *P. alba* IspS MRR (−2 from MEA *P. alba*) |

Example 6

Figure 35:
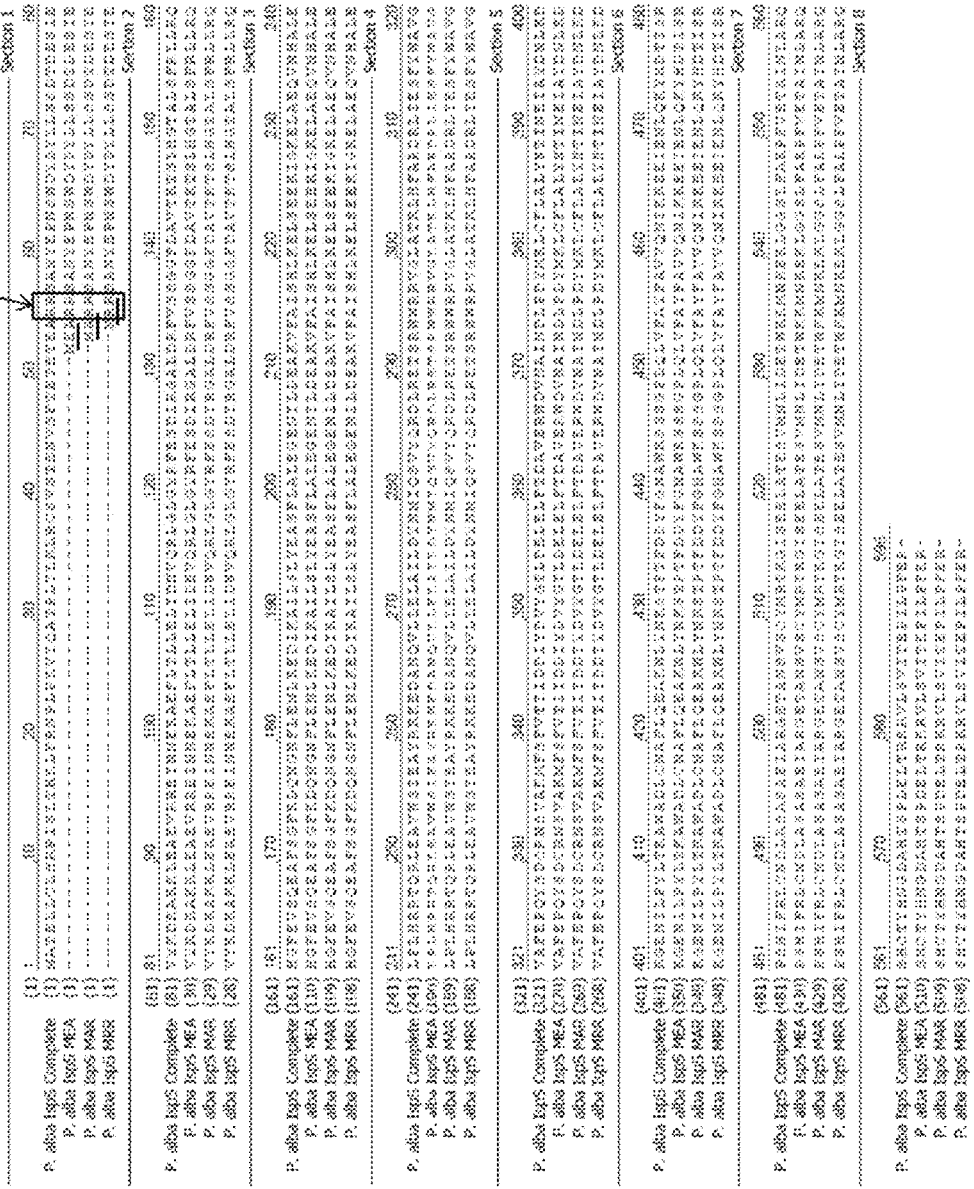
FIG. 35 shows an alignment of N-terminally truncated *P. alba* IspS molecules (SEQ ID NOS:31, 22, 27, and 29 respectively).

Specific Activity Determination of N-Terminal Truncations of MEA *P. Alba* IspS Isoprene synthase contains tandem arginine residues at the N-terminus that are necessary for proper enzymatic conversion of DMAPP to isoprene. As a truncated variant, MEA *P. alba* demonstrates high specific activity in comparison to enzymes with longer N-terminal regions, up to the naturally occurring chloroplast targeting peptide. The MEA *P. alba* enzyme has only two residues upstream of the tandem arginine residues (see FIG. 35), yet the function of these residues with regard to enzyme activity was not reported. N-terminal truncations of the MEA *P. alba* enzyme therefore were generated and assayed to determine if further truncations confer a specific activity benefit to IspS.

Methods

The two truncations of MEA *P. alba* were constructed by QuikChange (Stratagene) PCR on the template pCL201 (see Table 19 for primer sequences) as previously described following the manufacturer's recommended protocol. The PCR Results Specific activities of the truncated molecules of *P. alba* IspS expressed in strains DW618 (MAR) or DW619 (MRR) were either not improved or slightly lower, respectively, than the parental MEA *P. alba* enzyme. Table 21 shows performance index values for both the MAR and MRR truncations of *P. alba* IspS. The MAR truncation displayed specific activity that was approximately equivalent to the control MEA *P. alba* molecule, and the MRR truncation displayed specific activity that was approximately 81% of the control. Although these truncations did not have increased specific activity in comparison to MEA *P. alba*, they retained sufficient activity to be of potential future use in fermentation strains that convert DMAPP to isoprene via an IspS enzyme, where complete removal of the N-terminus up to but not including the tandem arginine residues is required.

TABLE 21

Performance index values for truncated variants of *P. alba* IspS

| Strain | Variant | PI Specific Activity | Standard Deviation |
|---|---|---|---|
| DW618 | MAR | 0.983189 | 0.091889 |
| DW619 | MRR | 0.813857 | 0.072938 |

Amino Acid Sequence of *P. alba* IspS MAR (SEQ ID NO: 27)

MARRSANYEPNSWDYDYLLSSDTDESIEVYKDKAKKLEAEVRREINNEKAEFLTLLELI

DNVQRLGLGYRFESDIRGALDRFVSSGGFDAVTKTSLHGTALSFRLLRQHGFEVSQEAF

SGFKDQNGNFLENLKEDIKAILSLYEASFLALEGENILDEAKVFAISHLKELSEEKIGKEL

AEQVNHALELPLHRRTQRLEAVWSIEAYRKKEDANQVLLELAILDYNMIQSVYQRDLR

ETSRWWRRVGLATKLHFARDRLIESFYWAVGVAFEPQYSDCRNSVAKMFSFVTIIDDIY

DVYGTLDELELFTDAVERWDVNAINDLPDYMKLCFLALYNTINEIAYDNLKDKGENILP

YLTKAWADLCNAFLQEAKWLYNKSTPTFDDYFGNAWKSSSGPLQLVFAYFAVVQNIK

KEEIENLQKYHDTISRPSHIFRLCNDLASASAEIARGETANSVSCYMRTKGISEELATESV

MNLIDETWKKMNKEKLGGSLFAKPFVETAINLARQSHCTYHNGDAHTSPDELTRKRVL

SVITEPILPFER

DNA Sequence of plasmid pDW207

(SEQ ID NO: 28)

tggcgaatgggacgcgccctgtagcggcgcattaagcgcggcgggtgtggtggttacgcgcagcgtgaccgctacacttgccagcgccc tagcgccccgctcctttcgctttcttcccttcctttctcgccacgttcgccggctttccccgtcaagctctaaatcggggggctcccttttagggttcc gatttagtgctttacggcacctcgaccccaaaaaacttgattagggtgatggttcacgtagtgggccatcgccctgatagacggttttttcgccc tttgacgttggagtccacgttctttaatagtggactcttgttccaaactggaacaacactcaaccctatctcggtctattcttttgatttataagggat tttgccgatttcggcctattggttaaaaaatgagctgatttaacaaaaatttaacgcgaattttaacaaaatattaacgtttacaatttcaggtggca cttttcggggaaatgtgcgcggaacccctatttgttattttctaaatacattcaaatatgtatccgctcatgaattaattcttagaaaaactcatcg agcatcaaatgaaactgcaatttattcatatcaggattatcaataccatattttgaaaaagccgtttctgtaatgaaggagaaaactcaccgag gcagttccataggatggcaagatcctggtatcggtctgcgattccgactcgtccaacatcaatacaacctattaatttcccctcgtcaaaaataa ggttatcaagtgagaaatcaccatgagtgacgactgaatccggtgagaatggcaaaagtttatgcatttcttttccagacttgttcaacaggcca gccattacgctcgtcatcaaaatcactcgcatcaaccaaaccgttattcattcgtgattgcgcctgagcgagacgaaatacgcgatcgctgtta aaaggacaattacaaacaggaatcgaatgcaaccggcgcaggaacactgccagcgcatcaacaatattttcacctgaatcaggatattcttc taatacctggaatgctgttttcccggggatcgcagtggtgagtaaccatgcatcatcaggagtacggataaaatgcttgatggtcggaagag gcataaattccgtcagccagtttagtctgaccatctcatctgtaacatcattggcaacgctacctttgccatgtttcagaaacaactctggcgcat cgggcttcccatacaatcgatagattgtcgcacctgattgcccgacattatcgcgagcccatttatacccatataaatcagcatccatgttggaa tttaatcgcggcctagagcaagacgtttcccgttgaatatggctcataacacccttgtattactgtttatgtaagcagacagttttattgttcatga ccaaaatcccttaacgtgagttttcgttccactgagcgtcagaccccgtagaaaagatcaaaggatcttcttgagatcctttttttctgcgcgtaa tctgctgcttgcaaacaaaaaaaccaccgctaccagcggtggtttgtttgccggatcaagagctaccaactctttttccgaaggtaactggctt cagcagagcgcagataccaaatactgtccttctagtgtagccgtagttaggccaccacttcaagaactctgtagcaccgcctacatacctcgc tctgctaatcctgttaccagtggctgctgccagtggcgataagtcgtgtcttaccgggttggactcaagacgatagttaccggataaggcgca gcggtcgggctgaacggggggttcgtgcacacagcccagcttggagcgaacgacctacaccgaactgagatacctacagcgtgagctat gagaaagcgccacgcttcccgaagggagaaaggcggacaggtatccggtaagcggcagggtcggaacaggagagcgcacgaggga gcttccaggggaaacgcctggtatctttatagtcctgtcgggtttcgccacctctgacttgagcgtcgatttttgtgatgctcgtcaggggg cggagcctatggaaaaacgccagcaacgcggcctttttacggttcctggccttttgctggccttttgctcacatgttctttcctgcgttatccct -continued

```
gattctgtggataaccgtattaccgcctttgagtgagctgataccgctcgccgcagccgaacgaccgagcgcagcgagtcagtgagcgag
gaagcggaagagcgcctgatgcggtattttctccttacgcatctgtgcggtatttcacaccgcatatatggtgcactctcagtacaatctgctct
gatgccgcatagttaagccagtatacactccgctatcgctacgtgactgggtcatggctgcgccccgacacccgccaacacccgctgacgc
gccctgacgggcttgtctgctcccggcatccgcttacagacaagctgtgaccgtctccgggagctgcatgtgtcagaggttttcaccgtcatc
accgaaacgcgcgaggcagctgcggtaaagctcatcagcgtggtcgtgaagcgattcacagatgtctgcctgttcatccgcgtccagctcg
ttgagtttctccagaagcgttaatgtctggcttctgataaagcgggccatgttaagggcggttttttcctgtttggtcactgatgcctccgtgtaag
ggggatttctgttcatgggggtaatgataccgatgaaacgagagaggatgctcacgatacgggttactgatgatgaacatgcccggttactg
gaacgttgtgagggtaaacaactggcggtatggatgcggcgggaccagagaaaaatcactcagggtcaatgccagcgcttcgttaataca
gatgtaggtgttccacagggtagccagcagcatcctgcgatgcagatccggaacataatggtgcagggcgctgacttccgcgtttccagac
tttacgaaacacggaaaccgaagaccattcatgttgttgctcaggtcgcagacgttttgcagcagcagtcgcttcacgttcgctcgcgtatcg
gtgattcattctgctaaccagtaaggcaaccccgccagcctagccgggtcctcaacgacaggagcacgatcatgcgcacccgtgggcc
gccatgccggcgataatggcctgcttctcgccgaaacgtttggtggcgggaccagtgacgaaggcttgagcgagggcgtgcaagattccg
aataccgcaagcgacaggccgatcatcgtcgcgctccagcgaaagcggtcctcgccgaaaatgacccagagcgctgccggcacctgtc
ctacgagttgcatgataaagaagacagtcataagtgcgggcgacgatagtcatgccccgcgcccaccggaaggagctgactggggttgaag
gctctcaagggcatcggtcgagatcccggtgcctaatgagtgagctaacttacattaattgcgttgcgctcactgcccgctttccagtcggga
aacctgtcgtgccagctgcattaatgaatcggccaacgcgcggggagaggcggtttgcgtattgggcgcagggtggttttcttttcacca
gtgagacgggcaacagctgattgcccttcaccgcctggccctgagagagttgcagcaagcggtccacgctggtttgcccccagcaggcga
aaatcctgtttgatggtggttaacggcgggatataacatgagctgtcttcggtatcgtcgtatcccactaccgagatatccgcaccaacgcgc
agcccggactcggtaatggcgcgcattgcgcccagcgccatctgatcgttggcaaccagcatcgcagtgggaacgatgccctcattcagc
atttgcatggtttgttgaaaaccggacatggcactccagtcgccttcccgttccgctatcggctgaatttgattgcgagtgagatatttatgccag
ccagccagacgcagacgcgccgagacagaacttaatgggcccgctaacagcgcgatttgctggtgacccaatgcgaccagatgctccac
gcccagtcgcgtaccgtcttcatgggagaaaataatactgttgatgggtgtctggtcagagacatcaagaaataacgccggaacattagtgc
aggcagcttccacagcaatggcatcctggtcatccagcggatagttaatgatcagcccactgacgcgttgcgcgagaagattgtgcaccgc
cgctttacaggcttcgacgccgcttcgttctaccatcgacaccaccacgctggcacccagttgatcggcgcgagatttaatcgccgcgacaa
tttgcgacggcgcgtgcagggccagactggaggtggcaacgccaatcagcaacgactgtttgcccgccagttgttgtgccacgcggttgg
gaatgtaattcagctccgccatcgccgcttccacttttcccgcgttttcgcagaaacgtggctggcctggttcaccacgcgggaaacggtct
gataagagacaccggcatactctgcgacatcgtataacgttactggtttcacattcaccaccctgaattgactctcttccgggcgctatcatgc
cataccgcgaaaggttttgcgccattcgatggtgtccgggatctcgacgctctcccttatgcgactcctgcattaggaagcagcccagtagta
ggttgaggccgttgagcaccgccgccaaggaatggtgcatgcaaggagatggcgcccaacagtcccccggccacgggcctgcca
ccatacccacgccgaaacaagcgctcatgagcccgaagtggcgagcccgatcttccccatcggtgatgtcggcgatataggcgccagca
accgcacctgtggcgccggtgatgccggccacgatgcgtccggcgtagaggatcgagatctcgatcccgcgaaattaatacgactcacta
tagggggaattgtgagcggataacaatttccctctagaaataattttgtttaactttaagaaggagatatacatatggcacgtcgctctgcgaact
acgaacctaacagctgggactatgattacctgctgtcctccgacacggacgagtccatcgaagtatacaaagacaaagcgaaaaagctgg
aagccgaagttcgtcgcgagattaataacgaaaaagcagaatttctgaccctgctggaactgattgacaacgtccagcgcctgggcctggg
ttaccgtttcgagtctgatatccgtggtgcgctggatcgcttcgtttcctccggcggcttcgatgcggtaaccaagacttccctgcacggtacg
gcactgtctttccgtctgctgcgtcaacacggttttgaggtttctcaggaagcgttcagcggcttcaaagaccaaaacggcaacttcctggag
aacctgaaggaagatatcaaagctatcctgagcctgtacgaggccagcttcctggctctggaaggcgaaaacatcctggacgaggcgaag
gttttcgcaatctctcatctgaaagaactgtctgaagaaaagatcggtaaagagctggcagaacaggtgaaccatgcactggaactgccact
gcatcgccgtactcagcgtctggaagcagtatggtctatcgaggcctaccgtaaaaaggaggacgcgaatcaggttctgctggagctggc
aattctggattacaacatgatccagtctgtataccagcgtgatctgcgtgaaacgtcccgttggtggcgtcgtgtgggtctggcgaccaaact
```

-continued

```
gcactttgctcgtgaccgcctgattgagagcttctactgggccgtgggtgtagcattcgaaccgcaatactccgactgccgtaactccgtcgc
aaaaatgttttctttcgtaaccattatcgacgatatctacgatgtatacggcaccctggacgaactggagctgtttactgatgcagttgagcgttg
ggacgtaaacgccatcaacgacctgccggattacatgaaactgtgctttctggctctgtataacactattaacgaaatcgcctacgacaacct
gaaagataaaggtgagaacatcctgccgtatctgaccaaagcctgggctgacctgtgcaacgctttcctgcaagaagccaagtggctgtac
aacaaatctactccgacctttgacgactacttcggcaacgcatggaaatcctcttctggcccgctgcaactggtgttcgcttacttcgctgtcgt
gcagaacattaaaaaggaagagatcgaaaacctgcaaaaataccatgacaccatctctcgtccttcccatatcttccgtctgtgcaatgacct
ggctagcgcgtctgcggaaattgcgcgtggtgaaaccgcaaatagcgtttcttgttacatgcgcactaaaggtatctccgaagaactggcta
ccgaaagcgtgatgaatctgatcgatgaaacctgaaaaagatgaacaaggaaaaactgggtggtagcctgttcgcgaaaccgttcgtgg
aaaccgcgatcaacctggcacgtcaatctcactgcacttatcataacggcgacgcgcatacctctccggatgagctgacccgcaaacgcgt
tctgtctgtaatcactgaaccgattctgccgtttgaacgctaaggatccgaattcgagctccgtcgacaagcttgcggccgcactcgagcacc
accaccaccactgagatccggctgctaacaaagcccgaaaggaagctgagttggctgctgccaccgctgagcaataactagcataac
cccttggggcctctaaacgggtcttgaggggttttttgctgaaaggaggaactatatccggat
```

Amino Acid Sequence of *P. alba* IspS MRR (SEQ ID NO: 29)

MRRSANYEPNSWDYDYLLSSDTDESIEVYKDKAKKLEAEVRREINNEKAEFLTLLELID
NVQRLGLGYRFESDIRGALDRFVSSGGFDAVTKTSLHGTALSFRLLRQHGFEVSQEAFS
GFKDQNGNFLENLKEDIKAILSLYEASFLALEGENILDEAKVFAISHLKELSEEKIGKELA
EQVNHALELPLHRRTQRLEAVWSIEAYRKKEDANQVLLELAILDYNMIQSVYQRDLRET
SRWWRRVGLATKLHFARDRLIESFYWAVGVAFEPQYSDCRNSVAKMFSFVTIIDDIYDV
YGTLDELELFTDAVERWDVNAINDLPDYMKLCFLALYNTINEIAYDNLKDKGENILPYL
TKAWADLCNAFLQEAKWLYNKSTPTFDDYFGNAWKSSSGPLQLVFAYFAVVQNIKKE
EIENLQKYHDTISRPSHIFRLCNDLASASAEIARGETANSVSCYMRTKGISEELATESVMN
LIDETWKKMNKEKLGGSLFAKPFVETAINLARQSHCTYHNGDAHTSPDELTRKRVLSVI
TEPILPFER

Sequence of plasmid pDW208 (SEQ ID NO: 30)

```
tggcgaatgggacgcgccctgtagcggcgcattaagcgcggcgggtgtggtggttacgcgcagcgtgaccgctacacttgccagcgccc
tagcgcccgctcctttcgctttcttcccttcctttctcgccacgttcgccggctttccccgtcaagctctaaatcggggggctcccctttagggttcc
gatttagtgctttacggcacctcgaccccaaaaaacttgattagggtgatggttcacgtagtgggccatcgccctgatagacggttttttcgccc
tttgacgttggagtccacgttctttaatagtggactcttgttccaaactggaacaacactcaaccctatctcggtctattctttgatttataagggat
tttgccgatttcggcctattggttaaaaaatgagctgatttaacaaaaatttaacgcgaattttaacaaaatattaacgtttacaatttcaggtggca
cttttcggggaaatgtgcgcggaacccctatttgtttatttttctaaatacattcaaatatgtatccgctcatgaattaattcttagaaaaactcatcg
agcatcaaatgaaactgcaatttattcatatcaggattatcaataccatattttttgaaaaagccgtttctgtaatgaaggagaaaactcaccgag
gcagttccataggatggcaagatcctggtatcggtctgcgattccgactcgtccaacatcaatacaacctattaatttcccctcgtcaaaaataa
ggttatcaagtgagaaatcaccatgagtgacgactgaatccggtgagaatggcaaaagtttatgcatttctttccagacttgttcaacaggcca
gccattacgctcgtcatcaaaatcactcgcatcaaccaaaccgttattcattcgtgattgcgcctgagcgagacgaaatacgcgatcgctgtta
aaaggacaattacaaacaggaatcgaatgcaaccggcgcaggaacactgccagcgcatcaacaatatttttcacctgaatcaggatattcttc
taatacctggaatgctgttttcccggggatcgcagtggtgagtaaccatgcatcatcaggagtacggataaaatgcttgatggtcggaagag
gcataaattccgtcagccagtttagtctgaccatctcatctgtaacatcattggcaacgctacctttgccatgtttcagaaacaactctggcgcat
cgggcttcccatacaatcgatagattgtcgcacctgattgcccgacattatcgcgagcccatttatacccatataaatcagcatccatgttggaa
tttaatcgcggcctagagcaagacgtttcccgttgaatatggctcataacaccccttgtattactgtttatgtaagcagacagttttattgttcatga
ccaaaatcccttaacgtgagttttcgttccactgagcgtcagaccccgtagaaaagatcaaaggatcttcttgagatcctttttttctgcgcgtaa
tctgctgcttgcaaacaaaaaaaccaccgctaccagcggtggtttgtttgccggatcaagagctaccaactctttttccgaaggtaactggctt
```

-continued cagcagagcgcagataccaaatactgtccttctagtgtagccgtagttaggccaccacttcaagaactctgtagcaccgcctacatacctcgc tctgctaatcctgttaccagtggctgctgccagtggcgataagtcgtgtcttaccggggttggactcaagacgatagttaccggataaggcgca gcggtcgggctgaacggggggttcgtgcacacagcccagcttggagcgaacgacctacaccgaactgagatacctacagcgtgagctat gagaaagcgccacgcttcccgaagggagaaaggcggacaggtatccggtaagcggcagggtcggaacaggagagcgcacgaggga gcttccaggggggaaacgcctggtatctttatagtcctgtcgggtttcgccacctctgacttgagcgtcgattttttgtgatgctcgtcaggggggg cggagcctatggaaaaacgccagcaacgcggccttttttacggttcctggccttttgctggccttttgctcacatgttctttcctgcgttatcccct gattctgtggataaccgtattaccgcctttgagtgagctgataccgctcgccgcagccgaacgaccgagcgcagcgagtcagtgagcgag gaagcggaagagcgcctgatgcggtattttctccttacgcatctgtgcggtatttcacaccgcatatatggtgcactctcagtacaatctgctct gatgccgcatagttaagccagtatacactccgctatcgctacgtgactgggtcatggctgcgccccgacacccgccaacacccgctgacgc gccctgacgggcttgtctgctcccggcatccgcttacagacaagctgtgaccgtctccgggagctgcatgtgtcagaggttttcaccgtcatc accgaaacgcgcgaggcagctgcggtaaagctcatcagcgtggtcgtgaagcgattcacagatgtctgcctgttcatccgcgtccagctcg ttgagtttctccagaagcgttaatgtctggcttctgataaagcgggccatgttaagggcggttttttcctgtttggtcactgatgcctccgtgtaag ggggatttctgttcatgggggtaatgataccgatgaaacgagagaggatgctcacgatacgggttactgatgatgaacatgcccggttactg gaacgttgtgagggtaaacaactggcggtatggatgcggcgggaccagagaaaaatcactcagggtcaatgccagcgcttcgttaataca gatgtaggtgttccacagggtagccagcagcatcctgcgatgcagatccggaacataatggtgcagggcgctgacttccgcgtttccagac tttacgaaacacggaaaccgaagaccattcatgttgttgctcaggtcgcagacgttttgcagcagcagtcgcttcacgttcgctcgcgtatcg gtgattcattctgctaaccagtaaggcaaccccgccagcctagccgggtcctcaacgacaggagcacgatcatgcgcacccgtgggggcc gccatgccggcgataatggcctgcttctcgccgaaacgtttggtggcgggaccagtgacgaaggcttgagcgagggcgtgcaagattccg aataccgcaagcgacaggccgatcatcgtcgcgctccagcgaaagcggtcctcgccgaaaatgacccagagcgctgccggcacctgtc ctacgagttgcatgataaagaagacagtcataagtgcggcgacgatagtcatgccccgcgcccaccggaaggagctgactgggttgaag gctctcaagggcatcggtcgagatcccggtgcctaatgagtgagctaacttacattaattgcgttgcgctcactgcccgctttccagtcggga aacctgtcgtgccagctgcattaatgaatcggccaacgcgcggggagaggcggtttgcgtattgggcgccagggtggttttctttttcacca gtgagacgggcaacagctgattgcccttcaccgcctggccctgagagagttgcagcaagcggtccacgctggtttgcccagcaggcga aaatcctgtttgatggtggttaacggcgggatataacatgagctgtcttcggtatcgtcgtatcccactaccgagatatccgcaccaacgcgc agcccggactcggtaatggcgcgcattgcgcccagcgccatctgatcgttggcaaccagcatcgcagtgggaacgatgccctcattcagc atttgcatggtttgttgaaaaccggacatggcactccagtcgccttcccgttccgctatcggctgaatttgattgcgagtgagatatttatgccag ccagccagacgcagacgcgccgagacagaacttaatgggcccgctaacagcgcgatttgctggtgacccaatgcgaccagatgctccac gcccagtcgcgtaccgtcttcatgggagaaaataatactgttgatgggtgtctggtcagagacatcaagaaataacgccggaacattagtgc aggcagcttccacagcaatggcatcctggtcatccagcggatagttaatgatcagcccactgacgcgttgcgcgagaagattgtgcaccgc cgctttacaggcttcgacgccgcttcgttctaccatcgacaccaccacgctggcacccagttgatcggcgcgagatttaatcgccgcgacaa tttgcgacggcgcgtgcagggccagactggaggtggcaacgccaatcagcaacgactgtttgcccgccagttgttgtgccacgcggttgg gaatgtaattcagctccgccatcgccgcttccactttttcccgcgttttcgcagaaacgtggctggcctggttcaccacgcgggaaacggtct gataagagacaccggcatactctgcgacatcgtataacgttactggtttcacattcaccaccctgaattgactctcttccgggcgctatcatgc cataccgcgaaaggttttgcgccattcgatggtgtccgggatctcgacgctctcccttatgcgactcctgcattaggaagcagcccagtagta ggttgaggccgttgagcaccgccgccaaggaatggtgcatgcaaggagatggcgcccaacagtcccccggccacgggcctgcca ccatacccacgccgaaacaagcgctcatgagcccgaagtggcgagcccgatcttccccatcggtgatgtcggcgatataggcgccagca accgcacctgtggcgccggtgatgccggccacgatgcgtccggcgtagaggatcgagatctcgatcccgcgaaattaatacgactcacta tagggaattgtgagcggataacaattcccctctagaaataattttgtttaactttaagaaggagatatacatatgcgtcgctctgcgaactacg aacctaacagctgggactatgattacctgctgtcctccgacacggacgagtccatcgaagtatacaaagacaaagcgaaaaagctggaag ccgaagttcgtcgcgagattaataacgaaaaagcagaatttctgaccctgctggaactgattgacaacgtccagcgcctgggcctgggttac -continued

```
cgtttcgagtctgatatccgtggtgcgctggatcgcttcgtttcctccggcggcttcgatgcggtaaccaagacttccctgcacggtacggca ctgtctttccgtctgctgcgtcaacacggttttgaggtttctcaggaagcgttcagcggcttcaaagaccaaaacggcaacttcctggagaac ctgaaggaagatatcaaagctatcctgagcctgtacgaggccagcttcctggctctggaaggcgaaaacatcctggacgaggcgaaggttt tcgcaatctctcatctgaaagaactgtctgaagaaaagatcggtaaagagctggcagaacaggtgaaccatgcactggaactgccactgca tcgccgtactcagcgtctggaagcagtatggtctatcgaggcctaccgtaaaaaggaggacgcgaatcaggttctgctggagctggcaatt ctggattacaacatgatccagtctgtataccagcgtgatctgcgtgaaacgtcccgttggtggcgtcgtgtgggtctggcgaccaaactgcac tttgctcgtgaccgcctgattgagagcttctactgggccgtgggtgtagcattcgaaccgcaatactccgactgccgtaactccgtcgcaaaa atgttttctttcgtaaccattatcgacgatatctacgatgtatacggcaccctggacgaactggagctgtttactgatgcagttgagcgttgggac gtaaacgccatcaacgacctgccggattacatgaaactgtgctttctggctctgtataacactattaacgaaatcgcctacgacaacctgaaa gataaaggtgagaacatcctgccgtatctgaccaaagcctgggctgacctgtgcaacgctttcctgcaagaagccaagtggctgtacaaca aatctactccgacctttgacgactacttcggcaacgcatggaaatcctcttctggcccgctgcaactggtgttcgcttacttcgctgtcgtgcag aacattaaaaaggaagagatcgaaaacctgcaaaaataccatgacaccatctctcgtccttcccatatcttccgtctgtgcaatgacctggcta gcgcgtctgcggaaattgcgcgtggtgaaaccgcaaatagcgtttcttgttacatgcgcactaaaggtatctccgaagaactggctaccgaa agcgtgatgaatctgatcgatgaaacctggaaaaagatgaacaaggaaaaactgggtggtagcctgttcgcgaaaccgttcgtggaaacc gcgatcaacctggcacgtcaatctcactgcacttatcataacggcgacgcgcatacctctccggatgagctgacccgcaaacgcgttctgtc tgtaatcactgaaccgattctgccgtttgaacgctaaggatccgaattcgagctccgtcgacaagcttgcggccgcactcgagcaccaccac caccaccactgagatccggctgctaacaaagcccgaaaggaagctgagttggctgctgccaccgctgagcaataactagcataacccctt ggggcctctaaacgggtcttgaggggttttttgctgaaaggaggaactatatccggat
```

Example 7

Productive Mutations, Combinable Mutations and Suitability Score

Productive positions are described as those positions within a molecule that are most useful for making combinatorial variants exhibiting an improved characteristic, where the position itself allows for at least one combinable mutation. Combinable mutations can be described as those substitutions in a molecule that can be used to make selected combinatorial variants. Combinable mutations do not significantly decrease expression, specific activity or growth, while at the same time improving at least one desired characteristic of the molecule such as growth or specific activity. Positions in IspS containing all combinable mutations were determined using performance index (PI) values resulting from the DMAPP assay for specific activity and protein determination, as described in Example 3. Productive positions are the positions which have shown a certain degree of tolerance for multiple substitutions, while at the same time meeting a set of criteria for combinability as set forth below.

When evaluating the data set, the most productive positions were determined when the following criteria were applied:

Positions containing substitutions where the minimum performance indices (PI) relative to wild type IspS for specific activity and expression are greater than or equal to a PI of 0.9 and where at least one PI relative to wild type IspS for specific activity or growth is greater than or equal to a PI of 1.0 (Group A).

Positions containing substitutions where the minimum performance indices (PI) relative to wild type IspS for specific activity and expression are greater than or equal to a PI of 0.8 and where at least one PI relative to wild type IspS for specific activity or growth is greater than or equal to a PI of 1.2 (Group B).

Positions containing substitutions where the minimum performance indices (PI) relative to wild type IspS for specific activity and expression are greater than or equal to a PI of 0.5 and where at least one PI relative to wild type IspS for specific activity or growth is greater than or equal to a PI of 1.5 (Group C).

Groups A, B, and C further contain positions that have differing degrees of tolerance for multiple substitutions. To measure this degree of substitutions tolerated, a Rank was assigned to each position. The Rank was assigned according to the percentage of the substitutions within each position that fall within groups A, B, or C. Combinable positions and substitutions are shown in Table 23.

The criteria to determine the Rank for productive positions are as follows:

Positions where less than 15% but greater than 0% of the substitutions at a given position fall within groups A, B, or C are given a Rank of "1".

Positions where less than 30%, but greater than, or equal to 15% of the substitutions at a given position fall within groups A, B, or C are given a Rank of "2".

Positions where less than 50%, but greater than, or equal to 30% of the substitutions at a given position fall within groups A, B, or C are given a Rank of "3".

Positions where greater than, or equal to 50% of the substitutions at a given position fall within groups A, B, or C are given a Rank of "4".

Substitutions are further assigned a Suitability Score based on the group(s) the substitution is a member of, and where a higher score represents a substitution more suitable for use in making combinatorial variants. Suitability scores are represented and defined in Table 23. Suitability scores and Rank for individual substitutions of IspS that fit the above criteria are represented in Table 23.

TABLE 22

Suitability Score for the defined groups.

| Substitutions Occur in Group(s): | Suitability Score |
|---|---|
| A, B and C | +++++ |
| A and B | ++++ |
| A or (B and C) | +++ |
| B | ++ |
| C | + |

TABLE 23

Suitability Score and Rank of positions in IspS with substitutions within the positions that are combinable.

| POSITION | RANK | VARIANTS SUITABILITY SCORE (+) | VARIANTS SUITABILITY SCORE (++) | VARIANTS SUITABILITY SCORE (+++) WT AA 1ST | VARIANTS SUITABILITY SCORE (++++) | VARIANTS SUITABILITY SCORE (+++++) |
|---|---|---|---|---|---|---|
| 2 | 4 | Q | FGLR | EHIS | CDNTV | AKP |
| 3 | 2 | | | AEGKNQRT | | |
| 6 | 1 | | | S | NT | |
| 13 | 2 | N | M | SQT | | |
| 17 | 1 | T | | DE | | |
| 18 | 3 | H | | YFMN | AQR | DEKS |
| 19 | 1 | | | LF | | Y |
| 20 | 2 | | | LIV | T | |
| 21 | 1 | M | | S | | W |
| 22 | 3 | AHKNRTY | | S | Q | |
| 23 | 2 | K | EG | DT | N | |
| 24 | 2 | AMS | | T | C | LV |
| 25 | 2 | | NQ | DAES | T | |
| 26 | 4 | Y | L | EGNQT | DHKMRSV | C |
| 27 | 4 | | RY | SEFKV | ACGHILMPQ | DN |
| 28 | 3 | | CW | IEFMP | DN | |
| 29 | 2 | | G | EDPRT | Q | N |
| 30 | 3 | | | VNQ | ADEMRT | |
| 31 | 2 | L | D | YQW | N | |
| 32 | 2 | | C | KDGNR | E | |
| 33 | 2 | K | E | DN | | |
| 34 | 2 | | | KDEQS | | |
| 36 | 4 | HTWY | GS | KFR | ACDEMNPQ | |
| 37 | 4 | | WY | KFI | AEGHMNRT | CDPQS |
| 40 | 3 | | | ACDEFMNPQV | | |
| 41 | 3 | M | | ECDFNQSV | | |
| 42 | 3 | C | L | VAST | FI | M |
| 43 | 2 | | G | RIQ | | |
| 44 | 2 | | | RADKMY | NQ | |
| 45 | 2 | | | ECMNQ | | |

TABLE 23 -continued

Suitability Score and Rank of positions in IspS with substitutions within the positions that are combinable.

| POSITION | RANK | VARIANTS SUITABILITY SCORE (+) | VARIANTS SUITABILITY SCORE (++) | VARIANTS SUITABILITY SCORE (+++) WT AA 1ST | VARIANTS SUITABILITY SCORE (++++) | VARIANTS SUITABILITY SCORE (+++++) |
|---|---|---|---|---|---|---|
| 46 | 1 | | | IFV | | |
| 47 | 4 | C | F | NEIKRV | AGHMQTW | DS |
| 48 | 4 | | | NACEFLQRS | HIK | DGT |
| 49 | 3 | | | EGHIRSW | AC | LV |
| 50 | 4 | | IQV | KCGMNPR | ADEFHSY | |
| 51 | 2 | | | AEGLQT | | |
| 52 | 1 | | D | E | | |
| 53 | 3 | | CGMS | FD | EHNPQV | |
| 54 | 2 | | | LACEHIQ | M | |
| 55 | 3 | | PW | TAHNQSY | CDE | |
| 56 | 4 | | | LHQRS | CN | EFGIKTVY |
| 57 | 1 | | | LI | | |
| 58 | 3 | ADFGHRSY | C | E | N | |
| 59 | 3 | | C | LFMSVY | HT | |
| 60 | 1 | | | ICV | | |
| 62 | 1 | | | NV | | |
| 63 | 1 | C | | V | | |
| 68 | 1 | | | L | I | |
| 69 | 1 | | AQ | G | | |
| 71 | 2 | HLV | | RI | KM | |
| 73 | 1 | | | ED | | |
| 74 | 3 | Q | AC | SGMP | DENY | |
| 75 | 1 | | | DE | | |
| 77 | 2 | | | RANTV | L | |
| 78 | 4 | | | GEIKNPQVW | ADFLM | |
| 79 | 3 | C | LN | AMRY | QT | |
| 81 | 4 | | W | DCEHLN | AFGMRSTV | Q |
| 82 | 4 | | D | RCFGLW | AEHIKMQS | NTVY |
| 83 | 2 | | | FGHILV | W | |
| 84 | 4 | | | VFHLNQRSTWY | A | M |
| 85 | 2 | | GM | SCLNR | | |
| 86 | 2 | | GQ | SCN | | ADM |
| 87 | 4 | | HMQSV | GCEFKLNT | DP | |
| 88 | 2 | | | GCDIVWY | | |
| 89 | 2 | | HM | FCI | | |
| 91 | 4 | | F | ACDEGHLRSTVY | KW | |

TABLE 23 -continued

Suitability Score and Rank of positions in IspS with substitutions within the positions that are combinable.

| POSITION | RANK | VARIANTS SUITABILITY SCORE (+) | VARIANTS SUITABILITY SCORE (++) | VARIANTS SUITABILITY SCORE (+++) WT AA 1ST | VARIANTS SUITABILITY SCORE (++++) | VARIANTS SUITABILITY SCORE (+++++) |
|---|---|---|---|---|---|---|
| 92 | 3 | | D | VACEFGILQW | | |
| 93 | 4 | | M | THIQVW | ADEGLNPY | CFRS |
| 94 | 4 | | FQ | KCVY | ADEHILMNRST | GP |
| 95 | 4 | | R | TCHKM | AEPQSVY | DFGINW |
| 96 | 2 | CG | DNQ | S | | |
| 97 | 2 | | | LAMP | F | |
| 98 | 4 | | P | HCSTVW | ADFGILMNQ | |
| 99 | 4 | | DNS | GACHPQT | EFM | |
| 100 | 2 | | C | TAILMV | | |
| 101 | 1 | | | AS | | |
| 102 | 1 | | | LM | | |
| 103 | 2 | | M | SACGL | | |
| 107 | 2 | | A | LCF | | |
| 109 | 2 | | | QCNS | E | |
| 110 | 1 | | A | H | | |
| 111 | 1 | | | GA | | |
| 113 | 2 | | MPQ | ECHV | | |
| 114 | 2 | | AM | VC | | |
| 115 | 2 | | | SDY | A | |
| 116 | 4 | | | QGHLSTV | ACDEIP | |
| 117 | 3 | | QW | EADI | CFLMV | |
| 118 | 2 | | | AIV | M | |
| 119 | 1 | | | FLM | | |
| 120 | 4 | IL | | SADEFKNRWY | HTV | CGMQ |
| 121 | 2 | | FM | GDLVW | | |
| 123 | 2 | | | KISWY | LT | V |
| 124 | 1 | | | DCE | | |
| 125 | 4 | | | CP | QADGHKLNSTVW | EIY |
| 126 | 4 | FR | GSY | N | ACDMTV | E |
| 127 | 3 | L | EMNS | GDFW | C | |
| 128 | 3 | | ELMST | NA | CDPQ | |
| 129 | 2 | | W | FLY | | |
| 130 | 3 | | | LACDQVY | E | |
| 131 | 4 | | N | EDFGR | ACPQSV | HKLMTWY |
| 132 | 4 | | QS | N | CDFHLRWY | IP |
| 133 | 3 | | | LEGIPQTVY | D | |

TABLE 23 -continued

Suitability Score and Rank of positions in IspS with substitutions within the positions that are combinable.

| POSITION | RANK | VARIANTS SUITABILITY SCORE (+) | VARIANTS SUITABILITY SCORE (++) | VARIANTS SUITABILITY SCORE (+++) WT AA 1ST | VARIANTS SUITABILITY SCORE (++++) | VARIANTS SUITABILITY SCORE (+++++) |
|---|---|---|---|---|---|---|
| 134 | 4 | | CFP | KDGHILNRWY | EMQSTV | A |
| 135 | 2 | G | | EHS | | |
| 136 | 1 | | | DN | E | |
| 137 | 4 | | | IACDGPQSV | EHN | T |
| 138 | 4 | L | FMQT | KCDEPRSV | IN | |
| 139 | 3 | DG | | APSTV | N | CQ |
| 140 | 3 | C | A | INQSTV | MW | |
| 143 | 4 | | I | LAFGNRW | S | CDEHKMQTVY |
| 146 | 1 | | | AM | | |
| 149 | 1 | | W | L | | |
| 150 | 1 | | GS | A | | |
| 151 | 4 | | | LEGMNQRSTVW | CHI | AF |
| 152 | 2 | | | EADIMP | | |
| 153 | 1 | | | GD | C | |
| 155 | 4 | | | NEKM | ITVY | ACGHQRSW |
| 156 | 4 | V | ACGMQS | IEKLRY | DNT | |
| 158 | 1 | | | DE | | |
| 159 | 2 | D | C | E | M | |
| 160 | 2 | | GY | AFHS | I | |
| 161 | 3 | M | | KLRSY | ACNQ | |
| 162 | 3 | | GH | VDFNPT | S | |
| 163 | 3 | | | FCHIMVWY | EQ | |
| 164 | 2 | C | S | A | T | |
| 165 | 1 | | D | I | | |
| 166 | 4 | | Y | SCEHKPQVW | ADG | N |
| 167 | 4 | | Y | HCLP | AEGKMRSTW | FINQV |
| 169 | 4 | | P | KEGR | DIMST | ACHNQV |
| 170 | 4 | | | EGINR | HKMQTV | LSWY |
| 171 | 4 | | | LCEGIMW | HKRS | ANQTVY |
| 172 | 3 | V | HKT | SGNQR | AC | |
| 173 | 1 | | Q | E | | |
| 175 | 4 | | | KAGHNPTV | S | CFIQR |
| 176 | 2 | | | IACNQV | M | |
| 177 | 3 | S | | GDEHNPT | AC | |
| 178 | 4 | | C | KDEGILMNPQVY | AFRST | |
| 179 | 4 | | | EGIPQSTVWYACLMN | D | |

TABLE 23 -continued

Suitability Score and Rank of positions in IspS with substitutions within the positions that are combinable.

| POSITION | RANK | VARIANTS SUITABILITY SCORE (+) | VARIANTS SUITABILITY SCORE (++) | VARIANTS SUITABILITY SCORE (+++) WT AA 1ST | VARIANTS SUITABILITY SCORE (++++) | VARIANTS SUITABILITY SCORE (+++++) |
|---|---|---|---|---|---|---|
| 180 | 4 | KMR | E | LFHVW | CQT | AI |
| 181 | 4 | GIK | CTY | AFMNW | HQSV | |
| 182 | 2 | | | EHN | S | |
| 183 | 2 | | M | QAL | | |
| 185 | 1 | | A | ND | | |
| 187 | 1 | | | ACS | | |
| 188 | 1 | | M | L | | |
| 190 | 2 | C | | L | IM | |
| 193 | 1 | | Q | HW | | |
| 194 | 2 | HWY | | RI | L | |
| 196 | 1 | | | TV | | |
| 197 | 3 | AEHIPT | | QG | S | CDN |
| 203 | 1 | | F | W | | |
| 204 | 2 | | | SAFMWY | C | |
| 208 | 1 | | A | Y | | |
| 210 | 1 | | | KM | | |
| 211 | 4 | L | C | KDEFGHIMRSTV | ANQ | |
| 212 | 2 | | | EADMPQT | | |
| 215 | 2 | | W | NDY | CH | |
| 216 | 2 | | | QAEN | | |
| 217 | 3 | AM | D | VCEKNPQT | I | |
| 218 | 1 | M | | LV | | |
| 219 | 2 | A | | LIMV | C | |
| 220 | 1 | | | EDN | | |
| 221 | 1 | | | L | M | |
| 222 | 1 | | | AS | | |
| 223 | 1 | | | IC | | |
| 224 | 2 | | | LACTV | | |
| 226 | 1 | | | YF | | |
| 228 | 2 | L | | MHR | FY | |
| 229 | 2 | | | IA | V | C |
| 231 | 4 | M | CI | SDGHRV | KQT | A |
| 232 | 1 | | | VQ | I | |
| 234 | 1 | | R | Q | | |
| 235 | 2 | | E | RADN | K | |
| 238 | 1 | K | | R | | |

TABLE 23 -continued

Suitability Score and Rank of positions in IspS with substitutions within the positions that are combinable.

| POSITION | RANK | VARIANTS SUITABILITY SCORE (+) | VARIANTS SUITABILITY SCORE (++) | VARIANTS SUITABILITY SCORE (+++) WT AA 1ST | VARIANTS SUITABILITY SCORE (++++) | VARIANTS SUITABILITY SCORE (+++++) |
|---|---|---|---|---|---|---|
| 240 | 2 | ILM | | TV | | C |
| 241 | 2 | L | | SC | AMT | |
| 242 | 4 | | | RKL | ADEHIMNQST | G |
| 245 | 4 | AEGN | | R | IL | CKMQTV |
| 246 | 2 | | E | RHQ | DK | N |
| 247 | 2 | I | | V | T | LM |
| 249 | 1 | I | | L | | |
| 251 | 3 | | | TH | AGKR | DENPQS |
| 253 | 1 | | | LM | | |
| 254 | 2 | R | CET | H | D | |
| 260 | 1 | | | LM | | |
| 268 | 1 | | | VI | | |
| 270 | 1 | | | VI | | |
| 271 | 2 | | | AS | CV | T |
| 272 | 2 | HS | | FQ | DGPW | |
| 275 | 1 | | | QE | | |
| 276 | 2 | | M | YFHQ | | |
| 278 | 4 | | FHIK | DLMRY | AENQSTVW | |
| 279 | 1 | | | C | A | |
| 282 | 3 | HIW | R | SC | AQ | Y |
| 296 | 1 | M | | I | V | |
| 297 | 1 | | F | Y | | |
| 302 | 1 | | | T | H | |
| 306 | 1 | | | L | | C |
| 307 | 1 | | | EQR | | |
| 308 | 1 | | S | L | | |
| 314 | 1 | | F | EH | | |
| 315 | 2 | M | | RGK | | |
| 317 | 2 | C | | DS | EQ | N |
| 319 | 1 | | | N | F | M |
| 320 | 2 | | | ANT | C | |
| 321 | 1 | | | ILM | | |
| 322 | 1 | | D | N | | |
| 323 | 1 | | | DIT | | |
| 327 | 2 | NQ | | Y | M | |
| 328 | 1 | | | ML | | |

TABLE 23 -continued

Suitability Score and Rank of positions in IspS with substitutions within the positions that are combinable.

| POSITION | RANK | VARIANTS SUITABILITY SCORE (+) | VARIANTS SUITABILITY SCORE (++) | VARIANTS SUITABILITY SCORE (+++) WT AA 1ST | VARIANTS SUITABILITY SCORE (++++) | VARIANTS SUITABILITY SCORE (+++++) |
|---|---|---|---|---|---|---|
| 329 | 2 | A | | KGQR | | |
| 331 | 1 | | | CT | P | |
| 332 | 1 | | | FY | | |
| 333 | 1 | | | LF | | |
| 336 | 1 | | M | Y | | |
| 343 | 1 | | | AIV | | |
| 345 | 1 | | | DY | | |
| 346 | 1 | | | NA | | |
| 348 | 2 | F | | K | RY | |
| 350 | 2 | | | KHWY | | |
| 351 | 2 | | | GEM | DN | |
| 352 | 2 | | | EFIMV | | |
| 356 | 1 | | | PMS | | |
| 357 | 2 | | N | YE | M | |
| 358 | 1 | M | A | L | | |
| 359 | 1 | A | | T | | |
| 360 | 1 | | | KQ | | |
| 361 | 2 | M | | AQSV | T | |
| 363 | 1 | | C | AS | | |
| 364 | 2 | | | DNT | EV | |
| 365 | 2 | | IV | L | CM | |
| 366 | 1 | | | CA | | |
| 367 | 2 | | | NDEM | | |
| 368 | 2 | LY | | ADQ | N | |
| 369 | 4 | | KW | FHQ | MNRTV | CDEGS |
| 370 | 4 | | | LADEFHNRSTV | GQ | |
| 371 | 4 | | | QGHINPRTWY | CS | F |
| 373 | 1 | | S | A | G | |
| 376 | 1 | | | L | | IM |
| 377 | 2 | FHV | | Y | W | |
| 378 | 1 | | | ND | | |
| 379 | 4 | CDNP | AHT | KERS | | GQ |
| 380 | 3 | | GR | SKN | ACDQTV | E |
| 383 | 1 | | | TQ | S | |
| 386 | 2 | | | DKS | EN | |
| 389 | 4 | F | L | GCMPRT | HI | ADEKNQSV |

TABLE 23 -continued

Suitability Score and Rank of positions in IspS with substitutions within the positions that are combinable.

| POSITION | RANK | VARIANTS SUITABILITY SCORE (+) | VARIANTS SUITABILITY SCORE (++) | VARIANTS SUITABILITY SCORE (+++) WT AA 1ST | VARIANTS SUITABILITY SCORE (++++) | VARIANTS SUITABILITY SCORE (+++++) |
|---|---|---|---|---|---|---|
| 390 | 1 | | T | NS | | |
| 392 | 3 | C | A | WFM | ISTV | Y |
| 393 | 3 | LM | | KHR | Q | CITV |
| 402 | 2 | | | VFIL | | |
| 403 | 2 | ACT | | F | | |
| 405 | 1 | | | YF | | |
| 407 | 1 | | | A | G | |
| 408 | 2 | | GN | VQS | I | T |
| 409 | 2 | | R | VCQS | HI | T |
| 410 | 4 | | PY | QEGHIR | CDKLMT | |
| 411 | 2 | CDE | | N | G | |
| 413 | 1 | | | KP | | |
| 414 | 3 | | A | KCHIQ | EGLNP | |
| 415 | 2 | MNP | S | E | | |
| 418 | 1 | | | EN | | |
| 421 | 2 | PW | | Q | | H |
| 422 | 4 | Y | CESV | KGHQR | ANT | D |
| 423 | 4 | ACDEFHMTV | | YG | Q | NS |
| 424 | 3 | | CN | HDGIST | EPQV | |
| 425 | 4 | ACEFKLMNQRSTV | | DP | | |
| 426 | 2 | GY | | TAMQ | | |
| 428 | 2 | AMN | R | SV | EQ | |
| 429 | 4 | M | SV | RACDGHKN | ILTWY | EFQ |
| 431 | 1 | | | SG | | |
| 432 | 2 | | QT | HAM | E | |
| 436 | 2 | I | | L | MY | |
| 437 | 3 | EFLW | H | CN | KT | M |
| 440 | 1 | M | | L | I | |
| 443 | 2 | G | | A | R | Q |
| 444 | 2 | | K | SNQT | P | DE |
| 445 | 1 | QS | | A | | |
| 447 | 3 | VY | | IKR | AEMQS | T |
| 448 | 3 | L | | AHST | EMNPQV | |
| 453 | 1 | V | | A | | |
| 455 | 1 | G | | S | | A |
| 457 | 2 | | Q | SD | NT | |

TABLE 23 -continued

Suitability Score and Rank of positions in IspS with substitutions within the positions that are combinable.

| POSITION | RANK | VARIANTS SUITABILITY SCORE (+) | VARIANTS SUITABILITY SCORE (++) | VARIANTS SUITABILITY SCORE (+++) WT AA 1ST | VARIANTS SUITABILITY SCORE (++++) | VARIANTS SUITABILITY SCORE (+++++) |
|---|---|---|---|---|---|---|
| 458 | 1 | | | C | | T |
| 460 | 2 | | C | MAEG | QRS | |
| 461 | 3 | F | | RN | DEGQST | A |
| 462 | 1 | | | TS | Q | |
| 463 | 2 | F | | KGN | ADE | |
| 464 | 4 | K | T | GADEFHVY | LR | CMNQS |
| 465 | 2 | | | I | ACGST | |
| 466 | 3 | | A | SEGKNT | P | D |
| 467 | 1 | | | EN | | |
| 468 | 2 | | | EANPQ | D | |
| 469 | 2 | Y | | LAN | | |
| 470 | 2 | | | A | M | IL |
| 471 | 2 | I | | TN | EHQ | |
| 472 | 2 | R | Q | EAGN | DS | |
| 473 | 2 | | | S | LV | I |
| 475 | 1 | | | MI | T | |
| 476 | 1 | E | | N | | |
| 480 | 2 | DV | MQ | E | N | |
| 481 | 1 | N | V | T | | |
| 484 | 2 | CH | | KA | | |
| 487 | 1 | L | | K | | |
| 488 | 1 | C | A | E | | |
| 489 | 4 | ADEFGMNSTV | Q | KR | | |
| 490 | 4 | CRS | NV | LIY | ADEFHM | |
| 491 | 4 | IL | D | GACMNQ | EKSTVY | |
| 492 | 2 | | A | GTV | C | |
| 493 | 3 | EM | APQ | SCGKV | | |
| 494 | 2 | | | LGIQV | D | |
| 495 | 1 | Y | | F | | |
| 496 | 2 | IK | EQS | A | PT | |
| 497 | 2 | L | GNR | KMT | | |
| 498 | 2 | A | ES | P | | |
| 499 | 1 | M | | F | | |
| 500 | 3 | | HQ | VIY | LM | AC |
| 501 | 1 | | | EN | D | |
| 502 | 3 | FL | QS | TH | ACRV | M |

TABLE 23 -continued

Suitability Score and Rank of positions in IspS with substitutions within the positions that are combinable.

| POSITION | RANK | VARIANTS SUITABILITY SCORE (+) | VARIANTS SUITABILITY SCORE (++) | VARIANTS SUITABILITY SCORE (+++) WT AA 1ST | VARIANTS SUITABILITY SCORE (++++) | VARIANTS SUITABILITY SCORE (+++++) |
|---|---|---|---|---|---|---|
| 503 | 2 | F |  | ALM | I |  |
| 504 | 1 |  |  | IL |  |  |
| 506 | 2 |  |  | LIV |  | M |
| 509 | 2 | STV |  | QA |  |  |
| 510 | 2 |  |  | ST | CV |  |
| 511 | 2 |  | Y | HIM |  |  |
| 512 | 1 | Q |  | C |  |  |
| 513 | 4 | AEILMQRY |  | TS | V | CGKN |
| 515 | 2 | AGV |  | HQ | N |  |
| 516 | 1 |  | DR | N |  |  |
| 517 | 1 |  |  | GP |  |  |
| 519 | 2 | W |  | AC | ST |  |
| 522 | 1 |  |  | SAK |  |  |
| 525 | 3 |  | G | E | ACPQS | FR |
| 528 | 1 |  |  | RK |  |  |
| 529 | 1 |  |  | KA |  |  |
| 531 | 4 | CD |  | VGN | AMT | EHKQRS |
| 534 | 2 | GM |  | VAS |  |  |
| 535 |  | AGM |  | ICST |  |  |
| 536 | 2 | K |  | TM | AFG |  |
| 537 | 2 | IV |  | EHNQ | KT |  |
| 538 | 1 | K |  | P |  |  |
| 539 | 1 |  |  | IV |  |  |
| 540 | 2 |  | D | LEQRV | AP |  |
| 541 | 1 | L |  | P | M |  |
| 542 | 2 | IL | QY | FM | P |  |
| 543 | 1 |  | D | E |  |  |
| 544 | 2 |  |  | RGNPQS | C |  |

Example 8

Less Combinable Improved Variants with Enhanced Specific Activity or Growth Activity Table 24 lists variants that were either in suitability groups B or C, or not listed in Table 23. These "less combinable" variants did not fit the criteria for combinability as described above, yet displayed improved performance for either specific activity or growth upon retest.

TABLE 24

| Positions in MEA *P. alba* with less combinable improved mutations that displayed PI specific activity values > 1.3 | | | | | | |
|---|---|---|---|---|---|---|
| Residue | Position | Mutation | Location | Charge Change | % Surface Accessibility | Function |
| S | 22 | K | N-term | 1 | 54 | alternate surface interactions |
| S | 22 | R | N-term | 1 | 54 | alternate surface interactions |
| K | 36 | H | N-term | −1 | 33 | alternate interactions with nearby residues |
| K | 36 | W | N-term | −1 | 33 | alternate interactions with nearby residues |
| R | 43 | E | N-term | −2 | 52 | alternate interactions with nearby residues |
| E | 58 | F | N-term | 1 | 20 | alternate interactions with nearby residues |
| G | 87 | S | surface loop | 0 | 35 | alternate surface interactions |
| G | 87 | R | surface loop | 1 | 35 | alternate surface interactions |
| F | 89 | D | Buried | −1 | 5 | alternate interactions in pocket |
| F | 89 | E | Buried | −1 | 5 | alternate interactions in pocket |
| A | 118 | E | Buried | −1 | 10 | alternate interactions in pocket |
| A | 118 | P | Buried | 0 | 10 | alternate interactions in pocket |
| L | 151 | Y | surface loop | 0 | 14 | alternate interactions in pocket |
| G | 153 | P | surface loop | 0 | 40 | affect shape of loop |
| Q | 234 | R | Hinge Region | 1 | 24 | alternate surface interactions |
| V | 247 | I | dimer interface | 0 | 5 | alternate interactions in pocket |
| H | 254 | C | surface loop | 0 | 89 | alternate surface interactions |
| S | 282 | H | Buried | 0 | 8 | alternate interactions in pocket |
| S | 282 | W | Buried | 0 | 8 | alternate interactions in pocket |
| S | 288 | A | Buried | 0 | 0 | alternate interactions in pocket |
| S | 288 | T | Buried | 0 | 0 | alternate interactions in pocket |
| S | 288 | Y | Buried | 0 | 0 | alternate interactions in pocket |
| A | 391 | G | Buried | 0 | 0 | alternate interactions in pocket |
| W | 392 | C | Buried | 0 | 7 | alternate interactions in pocket |
| C | 437 | L | Buried | 0 | 7 | alternate interactions in pocket |
| A | 443 | G | SubLoop | 0 | 4 | affect shape of loop |
| A | 443 | S | SubLoop | 0 | 4 | affect shape of loop |
| I | 447 | V | SubLoop | 0 | 23 | alternate interactions in pocket |
| T | 481 | Y | Buried | 0 | 0 | alternate interactions in pocket |
| E | 488 | L | Buried | 1 | 13 | alternate interactions in pocket |
| T | 502 | F | Buried | 0 | 1 | alternate interactions in pocket |
| F | 542 | N | surface loop | 0 | 17 | alternate interactions with nearby residues |

TABLE 25

| Positions in MEA *P. alba* with less combinable improved mutations that displayed PI values > 1.3 for OD Max at 40 uM and 100 uM IPTG | | | | | | |
|---|---|---|---|---|---|---|
| Residue | Position | Mutation | Location | Charge Change | % Surface Accessibility | Function |
| V | 30 | K | N-term | 1 | 60 | replace surface hydrophobic w/ charged |
| K | 134 | C | N-term helix | −1 | 37 | size reduction, improved interaction with neighboring His |
| K | 134 | P | N-term helix | −1 | 37 | loop stabilization |
| L | 143 | I | N-term helix | 0 | 1 | alternate interactions in hydrophobic pocket |
| I | 156 | G | N-term helix | 0 | 13 | allow more flexibility in loop |
| E | 159 | D | N-term helix | 0 | 32 | alternate interactions with nearby residues |
| E | 159 | G | N-term helix | 1 | 32 | alternate interactions with nearby residues |
| E | 159 | Q | N-term helix | 1 | 32 | alternate interactions with nearby residues |
| S | 172 | V | N-term helix | 0 | 47 | affect shape of loop |
| K | 414 | F | surface loop | −1 | 70 | alternate surface interactions |
| Q | 421 | R | surface loop | 1 | 23 | alternate surface interactions |
| Q | 421 | D | surface loop | −1 | 23 | alternate surface interactions |

Example 9

Identification of Isoprene Synthase Variants with Improved Kinetic Properties Isoprene synthase variants were previously selected based on improved specific activity in defined conditions compared to isoprene synthase variant MEA-$P.alba$. In this study, in vitro kinetic constants ($k_{cat}$, $K_M$ and $K_{iDMAPP}$) for the ability of the variant isoprene synthases to catalyze the conversion of DMAPP to isoprene were determined by fitting data to the following rate equation:

$$\frac{rate}{[\text{Isoprene synthase}]} = \frac{kcat * [DMAPP]}{KM + [DMAPP]\left(1 + \frac{[DMAPP]}{KiDMAPP}\right)}$$

Without being by theory, isoprene synthase variants that display increased $k_{cat}$ values have the potential ability to catalyze the conversion of DMAPP to isoprene more efficiently (if all other kinetic parameters are held constant). Isoprene synthase variants that display decreased $K_M$ values with respect to the parent isoprene synthase molecule have the potential to maintain decreased concentrations of DMAPP compared to the parent isoprene synthase (if all other kinetic parameters are held constant). Isoprene synthase variants that display increased $K_{iDMAPP}$ values have the potential to catalyze the conversion of DMAPP to isoprene more efficiently (if all other kinetic parameters are held constant). The described improvements in enzymatic properties can potentially benefit the production of isoprene for commercial applications.

Methods: Cell Growth

All chemicals were purchased from Sigma unless otherwise specified. All SEL strains were obtained from the isoprene synthase SEL screen as having desirable properties as described above. 96-well deep well plates (Axygen) containing 0.6 mL LB and 50 µg/mL kanamycin were inoculated with the E. coli strains and grown overnight at 34° C. at 600 rpm. The next day, 48-well plates (Axygen) containing 2 mL TM3 and 0.1% yeast extract, 1% glucose, 50 µg/mL kanamycin and 8 mM MgSO$_4$ was inoculated with 40 µL of each overnight culture. Cells were grown at 34° C. to OD$_{600}$ of approximately 0.5 and induced with 40 µM IPTG for all strains containing isoprene synthase variant genes and 25-60 µM IPTG (in 5 µM steps) for cells containing the parent isoprene synthase gene. Cells were grown for one additional hour and then 10 mM mevalonate was added to the cultures. The absorbance at 600 nm was measured every 1 h, starting at induction, using a Spectramax M5 UV-Vis spectrophotometer. 4 hours after mevalonate addition, the specific isoprene productivity was measured and then the cells were centrifuged for 20 minutes at 3000 RPM in a Sorvall Legend RT equipped with a 6445 swinging bucket rotor. Supernatant was removed and the pellets were frozen and stored at −80° C. until cell lysis was performed.

Specific Productivity Assay

100 µL of cells were transferred to a Zinsser 96-well glass block, sealed with aluminum foil lids, and incubated for 30 minutes at 34° C. in a Shel Lab shaking incubator at 600 RPM. The glass block was then transferred to an 80° C. water bath for 2 minutes followed by analysis of the headspace gas by GC-MS. The specific productivity of each culture was determined by combining the absorbance data for the cultures (immediately prior to the glass block procedure) with the isoprene production rate measured by GC-MS.

GC-MS Measurement of Isoprene

The amount of isoprene in units of nmole/$g_{wcm}$/hr can be measured as disclosed in U.S. Pat. No. 5,849,970, which is hereby incorporated by reference in its entirety, particularly with respect to the measurement of isoprene production. For example, two mL of headspace (e.g., headspace from a culture such as 2 mL of culture cultured in sealed vials at 32° C. with shaking at 200 rpm for approximately 3 hours) are analyzed for isoprene using a standard gas chromatography system, such as a system operated isothermally (85° C.) with an n-octane/porasil C column (Alltech Associates, Inc., Deerfield, Ill.) and coupled to a RGD2 mercuric oxide reduction gas detector (Trace Analytical, Menlo Park, Calif.) (see, for example, Greenberg et al, Atmos. Environ. 27A: 2689-2692, 1993; Silver et al., Plant Physiol. 97:1588-1591, 1991, which are each hereby incorporated by reference in their entireties, particularly with respect to the measurement of isoprene production). The gas chromatography area units are converted to nmol isoprene via a standard isoprene concentration calibration curve. In some embodiments, the value for the grams of cells for the wet weight of the cells is calculated by obtaining the $A_{600}$ value for a sample of the cell culture, and then converting the $A_{600}$ value to grams of cells based on a calibration curve of wet weights for cell cultures with a known $A_{600}$ value. In some embodiments, the grams of the cells is estimated by assuming that one liter of broth (including cell medium and cells) with an $A_{600}$ value of 1 has a wet cell weight of 1 gram. The value is also divided by the number of hours the culture has been incubating for, such as three hours.

Cell Lysis

Materials: Tris/NaCl pH 7.6, MgCl$_2$, 4-(2-Aminoethyl) benzenesulfonyl fluoride Hydrochloride (AEBSF), DNase I, DMAPP Triammonium salt(Cayman chemicals), Lysozyme (Epicentre), 96-well Zinsser Glass Block, Seal & Sample Aluminum foil lids (Part No:538619)(Beckman coulter), Nunc*MicroWell*96-Well Plates, Polypropylene, High Volume (Part No:2449946), (Thermo Scientific) (VWR).

Procedure:

200 µL lysis buffer (100 mM Tris, 100 mM NaCl pH 7.6, 1 mg/ml BSA, 50 U/µl Epicentre readylyse lysozyme, 0.1 mg/ml DNAase, 0.5 mM AEBSF, 5 mM MgCl$_2$) was added to each well of the 48-well plate, the pellets were re-suspended, and the plate was sealed with aluminum foil lids. The resuspended cells were re-frozen at −80° C. for 10 minutes. The plate was then removed from the −80° C. freezer and mixed at 450 rpm for 30 minutes at room temperature using the Thermomixer (Eppindorf). The mixture was then centrifuged at 3200 rpm for 10 minutes at 4° C. The supernatant was collected for use in enzymatic activity assays.

Isoprene Synthase Enzymatic Activity Assay

25 µL of E. coli lysate, containing isoprene synthase, was incubated with 0.25, 0.5, 1, 3, 5, 7, 10 and 20 mM DMAPP, in 100 µL reactions containing 50 mM MgCl$_2$ and 100 mM Tris/NaCl in a Zinsser 96-well glass block sealed with aluminum foil lids for 30 minutes at 34° C. The glass blocks were then transferred to an 80° C. water bath for 2 minutes. Next, the glass blocks were analyzed by GC-FID (see below) to determine the concentration of isoprene generated in the reactions.

GC-FID Analysis

Equipment and Materials:

Gas chromatograph (GC), 7890 (Agilent Technologies), Flame ionization detector (FID) 7890 (Agilent Technologies), HP-5 ms column, 5%-phenyl-methylpolysiloxane, 15 m×0.25 mm×0.25 µm (Agilent Technologies), CTC autosampler (Leap Technologies), 0.2% v/v isoprene, balance nitrogen (Air Liquide), Chemstation with Enhanced Data Analysis (D.03.00.611)

Procedure:

96-well glass blocks were analyzed using GC-FID with the following parameters:

Oven:

| Rate (° C./min) | Temperature (° C.) | Time (min) |
|---|---|---|
| 0 | 37 | 28 |

Run Time: 28 minutes

| FRONT INLET | |
|---|---|
| Front Inlet Temperature | 110° C. |
| Flow Rate | 3.4 mL/min |
| Flow Mode | Constant Flow |
| Split Ratio | 50:1 |
| Carrier Gas | Helium |

| FLAME IONIZATION DETECTOR | |
|---|---|
| Detector Temperature | 160° C. |
| Hydrogen Flow | 40 mL/min |
| Air Flow | 400 mL/min |
| Makeup Flow | 0.1 mL/min |
| Makeup Gas Type | Helium |

SYRINGE CYCLE
syringe:1.0 ml-HS
JN(37,100,0,1000,GC Inj-2,500,50,50,10,600)
[MACRO JN]
Syringe Temperature (° C.);50;30;150
Fill Speed (μl/s);SYR.Fill Speed;SYR.Min Speed;SYR.Max Speed
Fill Strokes ( );SYR.Fill Strokes;0;99
Pullup Delay (ms);SYR.Pullup De1;0;10000
Inject to;INJECTOR
Injection Speed (μl/s);SYR.Inject Speed;SYR.Min Speed; SYR.Max Speed
Pre Inject Delay (ms);500;0;99000
Post Inject Delay (ms);500;0;99000
Flush Time (s);10;0;600
GC Runtime (s);600;30;86400
SET_TEMP(SYR,Syringe Temperature,0,)
MOVETO_OBJECT(Home,,,)
WAIT_FOR_DS( )
WAIT_SYNC_SIG(Start,)
GET_SAMPLE(SL.tray,1,SL.volume,0,,,Fill Speed,Pullup Delay,,Fill Strokes,Off,,,)
INJ_SAMPLE(Inject to,Inject,Injected,,,Pre Inject Delay,Injection Speed,Post Inject Delay,1,)
MOVETO_OBJECT(Home,,,)
START_FLUSH(Flush Time,)
WAIT(Flush Time,)
STOP_FLUSH( )
GET_SAMPLE(SL.tray,2,SL.volume,0,,,Fill Speed,Pullup Delay,,Fill Strokes,Off,,,)
INJ_SAMPLE(Inject to,Inject,Injected,,,Pre Inject Delay,Injection Speed,Post Inject Delay,1,)
MOVETO_OBJECT(Home,,,)
START_FLUSH(Flush Time,)
WAIT(Flush Time,)
STOP_FLUSH( )
GET_SAMPLE(SL.tray,3,SL.volume,0,,,Fill Speed,Pullup Delay,,Fill Strokes,Off,,,)
INJ_SAMPLE(Inject to,Inject,Injected,,,Pre Inject Delay,Injection Speed,Post Inject Delay,1,)
MOVETO_OBJECT(Home,,,)
START_FLUSH(Flush Time,)
WAIT(Flush Time,)
STOP_FLUSH( )

Calculations/Data Analysis

The peak areas were converted to isoprene concentrations by dividing the peak area by the response factor calculated from 0.2% v/v isoprene in nitrogen calibration standards.

HPLC Analysis

Equipment and Materials:

96-well polypropylene plates, 46600-666 (Thermo Scientific), Zone Free Films, plate covers, Z721646 (Sigma Aldrich), High Performance Liquid Chromatography, 1200 (Agilent Technologies), Diode Array Detector, G1315D (Agilent Technologies), ProSwift RP-2H column, 4.6×50 mm (Dionex), In-line filter with 0.46 μm stainless steel frits[1], 5067-1562 (Agilent Technologies), Trifluoroacetic Acid, 1 mL ampules, 91707 (Sigma Aldrich), Acetonitrile, 9017-03 (J. T. Baker), Isopropanol, 9079-05 (J. T. Baker), Software, Chemstation (B.04.01).

Procedure:

10 μL of 2% TFA in water was added to 200 μL of each sample and the samples were transferred to a 96-well polypropylene plate (see above). A Zone Free Film plate cover was used on the 96-well plate. Mobile phase A consisted of 0.1% TFA in 55:25:20 water:acetonitrile:isopropanol. Mobile phase B consisted of 0.1% TFA in isopropanol. Samples were analyzed by HPLC-UV with the following parameters:

Gradient:

A: 0.1% TFA in 55:25:20 water:acetonitrile:isopropanol.
B: 0.1% TFA in isopropanol

| Time (min) | % B | Flow Rate (mL/min) |
|---|---|---|
| 0 | 0 | 1.5 |
| 0.2 | 0 | 1.5 |
| 2.0 | 30 | 1.5 |
| 2.5 | 100 | 1.5 |
| 4.5 | 100 | 1.5 |
| 5.0 | 0 | 1.5 |
| 6.0 | 0 | 1.5 |

| | |
|---|---|
| Run Time | 6 minutes |
| Injection Volume | 40 μL |
| Column Temperature | 70° C. |
| UV Detection Wavelength | 220 nm |

Calculations and Data Analysis

Chemstation was used to capture and process the data.

Calculation of Isoprene Synthase Kinetic Parameters:

Data from the isoprene synthase kinetic assays were fit to the following modified version of the Henri-Michaelis-Menten equation that takes into account substrate inhibition using Kaleidagraph 4.0 (Synergy Software) to determine $K_M$, $k_{cat}$ and $k_{iDMAPP}$ values for each isoprene synthase analyzed:

$$\frac{\text{rate}}{[\text{Isoprene synthase}]} = \frac{kcat * [DMAPP]}{KM + [DMAPP]\left(1 + \frac{[DMAPP]}{KiDMAPP}\right)}$$

All $K_M$, $k_{cat}$ and $k_{iDMAPP}$ data were normalized to the average value calculated from 43 replicates of the isoprene synthase parent molecule.

Table 26 shows exemplary isoprene synthase variants that display improved $k_{cat}$ values for the conversion of DMAPP to isoprene. All $k_{cat}$ values are normalized to the $k_{cat}$ of the parent isoprene synthase molecule. Isoprene synthase variants with Kcat of 1.240593 to 4.720585 are shown in Table 26 and are designated as +++. Isoprene synthase variants with Kcat of 1.130066 to 1.239277 are shown in Table 26 and are designated as ++. Isoprene synthase variants with Kcat of 1.001492 to 1.128037 are shown in Table 26 and are designated as +.

TABLE 26

| Variant | $k_{cat}$ |
|---|---|
| D323F | +++ |
| A118E | +++ |
| K36W | +++ |
| S22K | +++ |
| M228Y | +++ |
| A448L | +++ |
| E488F | +++ |
| E467H | +++ |
| A443S | +++ |
| C331P | +++ |
| A453I | +++ |
| R71K | +++ |
| R71L | +++ |
| A448I | +++ |
| R71M | +++ |
| W392Y | +++ |
| A448V | +++ |
| S282H | +++ |
| T383Y | +++ |
| D323Y | +++ |
| H511Y | +++ |
| A448E | +++ |
| L376M | +++ |
| E488L | +++ |
| S120E | +++ |
| R461A | +++ |
| K414I | +++ |
| S282W | +++ |
| R071K | +++ |
| S493E | +++ |
| W392S | +++ |
| A448Q | +++ |
| S282Y | +++ |
| E537N | +++ |
| I447Y | +++ |
| T240C | +++ |
| A443Q | +++ |
| P538R | +++ |
| S510C | +++ |
| G389D | ++ |
| T383H | ++ |
| K36E | ++ |
| L436Y | ++ |
| I447V | ++ |
| W392F | ++ |
| K161R | ++ |
| G99D | ++ |
| G99E | ++ |
| K161C | ++ |
| K414S | ++ |
| E537T | ++ |
| K393V | ++ |
| A443G | ++ |
| S510V | ++ |

TABLE 26-continued

| Variant | $k_{cat}$ |
|---|---|
| K36N | ++ |
| W392A | ++ |
| K161A | ++ |
| H254R | ++ |
| E472C | ++ |
| K161Q | ++ |
| K36Y | ++ |
| E537C | ++ |
| E41Y | ++ |
| K161M | ++ |
| R43L | ++ |
| S120A | ++ |
| G087M | ++ |
| K36S | ++ |
| K36H | ++ |
| K348Y | ++ |
| E467W | ++ |
| S288T | ++ |
| I447T | ++ |
| D025N | ++ |
| V268I | + |
| E488M | + |
| E480I | + |
| T240V | + |
| M460A | + |
| R071L | + |
| K36Q | + |
| A118P | + |
| K36T | + |
| S282I | + |
| V409I | + |
| R071I | + |
| V409T | + |
| L436F | + |
| K348F | + |
| A118Q | + |
| I342Y | + |
| S74Q | + |
| E41P | + |
| C437Y | + |
| W392T | + |
| F89D | + |
| E41M | + |
| S510E | + |
| K36P | + |
| K393I | + |
| R71I | + |
| T381M | + |
| K374Y | + |
| E58Y | + |
| L526Q | + |
| E543F | + |
| T240M | + |
| G111S | + |
| K463T | + |
| S120M | + |
| E135G | + |
| WT | 1 |

Table 27 shows isoprene synthase variants that display KM values less than 1 compared to the parent isoprene synthase molecule for the conversion of DMAPP to isoprene. All $K_M$ values are normalized to the $K_M$ of the parent isoprene synthase molecule. The variants with KM values from 0.105 to 0.587 are designated as +++. The variants with KM values from 0.608 to 0.844 are designated as ++. The variants with KM values from 0.846 to 0.998 are designated as +.

TABLE 27

| Variant | KM |
|---|---|
| S22K | +++ |
| K348F | +++ |

TABLE 27-continued

| Variant | KM |
|---|---|
| W392V | +++ |
| W392F | +++ |
| E488C | +++ |
| S22R | +++ |
| R71V | +++ |
| A443R | +++ |
| Q234R | +++ |
| A453V | +++ |
| C437Y | +++ |
| W392C | +++ |
| K463F | +++ |
| P538K | +++ |
| K393L | +++ |
| H254C | +++ |
| L436Y | +++ |
| S21R | +++ |
| C437L | +++ |
| S444D | +++ |
| K374Y | +++ |
| A363L | +++ |
| I447V | +++ |
| S444E | +++ |
| R71I | +++ |
| I504F | +++ |
| E488W | +++ |
| R71H | +++ |
| K36P | +++ |
| T381I | +++ |
| L436F | +++ |
| M460A | +++ |
| A443G | +++ |
| S288A | +++ |
| W392T | +++ |
| E537I | +++ |
| K374Y | +++ |
| R242G | +++ |
| C437M | +++ |
| L436I | +++ |
| L376I | +++ |
| S288Y | +++ |
| W392M | +++ |
| I342Y | ++ |
| K414W | ++ |
| R461A | ++ |
| A443S | ++ |
| W392A | ++ |
| K463T | ++ |
| E488T | ++ |
| L526Q | ++ |
| T502F | ++ |
| T502M | ++ |
| E488M | ++ |
| K36Y | ++ |
| K414R | ++ |
| R071I | ++ |
| K36W | ++ |
| T502L | ++ |
| T481Y | ++ |
| E472R | ++ |
| K36H | ++ |
| K36T | ++ |
| E415Y | ++ |
| E415H | ++ |
| E58Y | ++ |
| T381M | ++ |
| T481V | ++ |
| F89E | ++ |
| E480I | ++ |
| K36Q | ++ |
| F89D | ++ |
| H254R | ++ |
| K161N | ++ |
| R071L | ++ |
| H424P | ++ |
| E415V | ++ |
| S22K | ++ |
| E58L | ++ |
| W392S | ++ |
| V268I | ++ |
| W392I | ++ |
| L526E | ++ |
| E537V | ++ |
| K36D | ++ |
| K393I | + |
| E41M | + |
| D025N | + |
| K36N | + |
| A118Q | + |
| G389E | + |
| S282W | + |
| K348Y | + |
| T383L | + |
| S510V | + |
| D323Y | + |
| D323F | + |
| T383H | + |
| E41P | + |
| S288T | + |
| K36S | + |
| A453I | + |
| I447T | + |
| E472I | + |
| L376M | + |
| K161E | + |
| E488L | + |
| T381L | + |
| R071K | + |
| V409T | + |
| W392Y | + |
| E135G | + |
| F542L | + |
| M228Y | + |
| A118P | + |
| E543F | + |
| K36E | + |
| WT | 1.000 |

Table 28 shows isoprene synthase variants that display $K_{iDMAPP}$ values greater than 1 compared to the parent isoprene synthase molecule for the conversion of DMAPP to isoprene. All $K_{iDMAPP}$ values are normalized to the $K_{iDMAPP}$ of the parent isoprene synthase molecule. The variants with Ki from 1.506 to 5.745 and even no substrate inhibition are designated as +++. The variants with Ki from 1.078 to 1.422 are designated as ++. The variants with Ki from 1.002 to 1.074 are designated as +.

TABLE 28

| Variant | Ki |
|---|---|
| E472R | +++ |
| G389E | +++ |
| R242G | +++ |
| L376I | +++ |
| K161N | +++ |
| S288C | +++ |
| T240V | +++ |
| T481Y | +++ |
| K463F | +++ |
| K393L | +++ |
| S120Q | ++ |
| E58L | ++ |
| T240M | ++ |
| A453V | ++ |
| E543F | + |
| S74Q | + |
| K414R | + |
| E415H | + |
| E415V | + |
| WT | 1.000 |

Example 10

Figure 39:
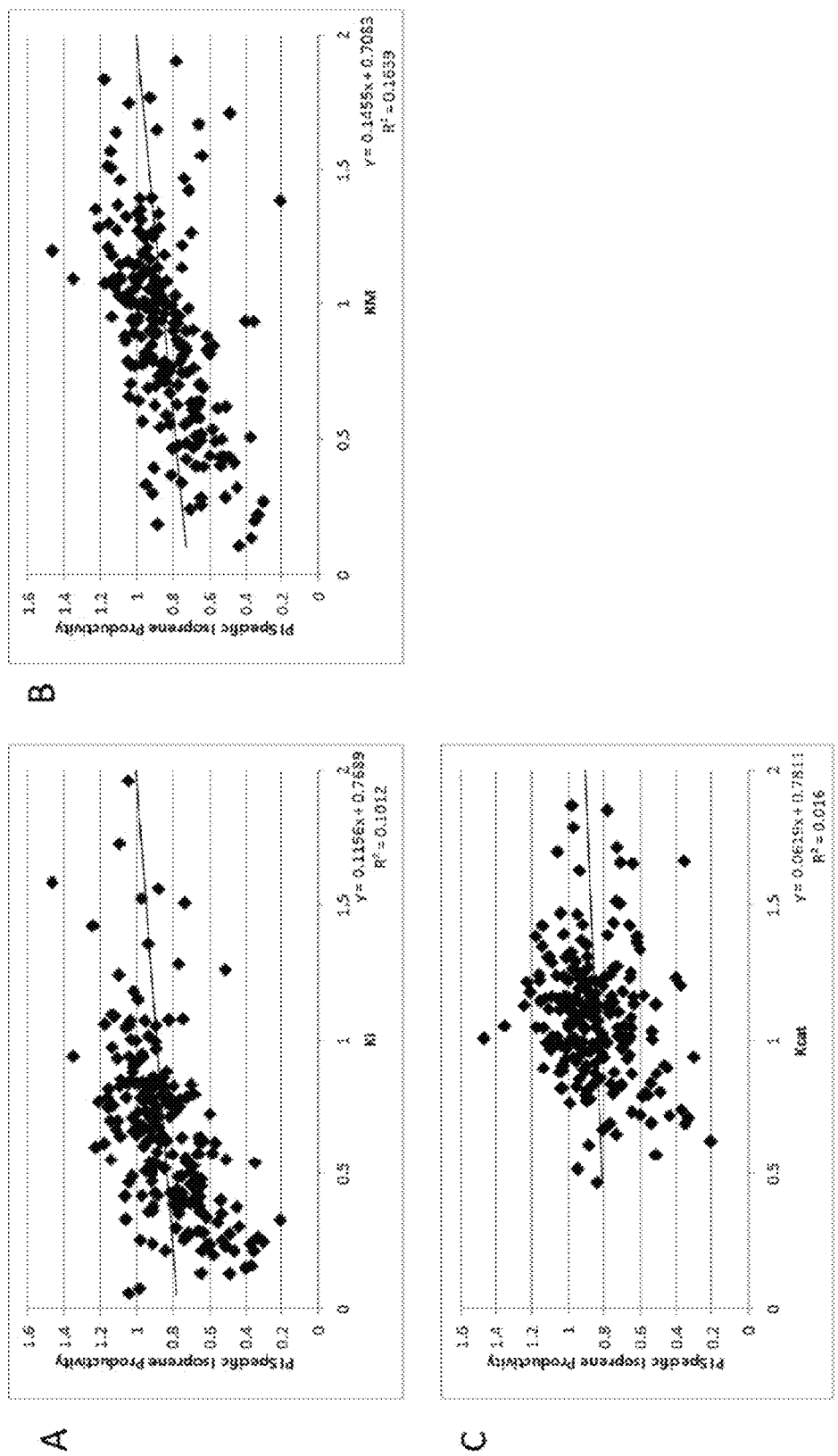
FIG. 39A-C.

Correlation of Isoprene Synthase Kinetic Parameters with Specific Isoprene Productivity The specific isoprene productivity for *E. coli* BL21 strains that express isoprene synthase variants was plotted against the corresponding kinetic parameters for each isoprene synthase variant to determine if specific properties of isoprene synthase variants could be used to predict increased specific isoprene productivity. The specific isoprene productivity was positively correlated with decreased substrate inhibition ($K_{iDMAPP}$)(FIG. 39A, Table 29). In addition, the specific isoprene productivity was positively correlated with decreased $K_M$ values (FIG. 39B, Table 29). There was no correlation between the specific isoprene productivity and $k_{cat}$ values (FIG. 39C, Table 29).

TABLE 29

| Variant | Specific Isoprene Productivity |
| --- | --- |
| S510E | +++ |
| K161M | +++ |
| S120Q | +++ |
| S120E | +++ |
| K161R | +++ |
| S120A | +++ |
| S493E | +++ |
| A448E | +++ |
| T240V | +++ |
| T240M | +++ |
| E537T | +++ |
| K161N | ++ |
| I447Y | ++ |
| T502M | ++ |
| E537N | ++ |
| K348Y | ++ |
| E543F | ++ |
| C331P | ++ |
| E537C | ++ |
| S120M | ++ |
| S288C | ++ |
| K161Q | ++ |
| K161A | + |
| T481V | + |
| G087M | + |
| E467W | + |
| A448V | + |
| T502L | + |
| L376M | + |

What is claimed is:

1. A recombinant host cell comprising a nucleic acid encoding a polypeptide having isoprene synthase activity, wherein the polypeptide comprises one or more amino acid substitution(s) at one or more residue position(s) corresponding to positions in the amino acid sequence of SEQ ID NO:1, wherein said one or more amino acid substitution(s) is selected from the group consisting of: X118E, X36W, X22K, X228Y, X448L, X488F, X467H, X331P, X448I, X392Y, X448V, X282H, X383Y, X511Y, X448E, X376M, X488L, X461A, X414I, X282W, X493E, X392S, X448Q, X282Y, X537N, X447Y, X240C, X538R, and X510C, and wherein the polypeptide has increased $k_{cat}$ compared to a parent polypeptide which does not comprise said one or more amino acid substitution(s), and wherein said polypeptide has at least 80% sequence identity with SEQ ID NO:1.

2. The host cell of claim 1 wherein the host cell is a bacterial, algal, or fungal cell.

3. The host cell of claim 2 wherein the host cell is a bacterial cell.

4. The host cell of claim 3 wherein the bacterial cell is a gram-positive bacterial cell or gram-negative bacterial cell.

5. The host cell of claim 3 wherein the bacterial cell is selected from the group consisting of *E. coli, L. acidophilus, P. citrea, B. subtilis, B. licheniformis, B. lentos, B. brevis, B. stearothennophilus, B. alkalophilus, B. amyloliquefaciens, B. clausii, B. halodurans, B. megaterium, B. coagulans, B. circulars, B. lautus, B. thuringiensis, S. albus, S. lividans, S. coelicolor, S. griseus, Pseudomonas* sp., *P. alcaligenes, Clostridium* sp., *Corynebacterium* sp., and *C. glutamicum* cell.

6. The host cell of claim 3, wherein the bacterial cell is a cyanobacterial or Clostridial cell.

7. The host cell of claim 2 wherein the host cell is an algal cell.

8. The host cell of claim 7 wherein the algal cell is selected from the group consisting of green algae, red algae, glaucophytes, chlorarachniophytes, euglenids, chromista, and dinoflagellates.

9. The host cell of claim 2 wherein the host cell is a fungal cell.

10. The host cell of claim 9 wherein the fungal cell is a filamentous fungi.

11. The host cell of claim 9 wherein the fungal cell is a yeast cell.

12. The host cell of claim 11 wherein the yeast cell is selected from the group consisting of *Saccharomyces* sp., *Schizosaccharomyces* sp., *Pichia* sp., and *Candida* sp.

13. The host cell of claim 12 wherein the yeast cell is a *Saccharomyces cerevisiae* cell.

14. A method for producing isoprene comprising (a) culturing the host cells of claim 1 under conditions suitable for the production of isoprene and (b) producing isoprene.

15. The method of claim 14 further comprising recovering the isoprene.

* * * * *

```
                      SEQUENCE LISTING

<160> NUMBER OF SEQ ID NOS: 32

<210> SEQ ID NO 1
<211> LENGTH: 544
<212> TYPE: PRT
<213> ORGANISM: Artificial Sequence
<220> FEATURE:
<223> OTHER INFORMATION: Synthetic Construct

<400> SEQUENCE: 1

Met Glu Ala Arg Arg Ser Ala Asn Tyr Glu Pro Asn Ser Trp Asp Tyr
1               5                   10                  15

Asp Tyr Leu Leu Ser Ser Asp Thr Asp Glu Ser Ile Glu Val Tyr Lys
            20                  25                  30

Asp Lys Ala Lys Lys Leu Glu Ala Glu Val Arg Arg Glu Ile Asn Asn
        35                  40                  45

Glu Lys Ala Glu Phe Leu Thr Leu Leu Glu Leu Ile Asp Asn Val Gln
    50                  55                  60

Arg Leu Gly Leu Gly Tyr Arg Phe Glu Ser Asp Ile Arg Gly Ala Leu
65                  70                  75                  80

Asp Arg Phe Val Ser Ser Gly Gly Phe Asp Ala Val Thr Lys Thr Ser
                85                  90                  95

Leu His Gly Thr Ala Leu Ser Phe Arg Leu Leu Arg Gln His Gly Phe
            100                 105                 110

Glu Val Ser Gln Glu Ala Phe Ser Gly Phe Lys Asp Gln Asn Gly Asn
        115                 120                 125

Phe Leu Glu Asn Leu Lys Glu Asp Ile Lys Ala Ile Leu Ser Leu Tyr
    130                 135                 140

Glu Ala Ser Phe Leu Ala Leu Glu Gly Glu Asn Ile Leu Asp Glu Ala
145                 150                 155                 160

Lys Val Phe Ala Ile Ser His Leu Lys Glu Leu Ser Glu Glu Lys Ile
                165                 170                 175
```

Gly Lys Glu Leu Ala Glu Gln Val Asn His Ala Leu Glu Leu Pro Leu
            180                 185                 190

His Arg Arg Thr Gln Arg Leu Glu Ala Val Trp Ser Ile Glu Ala Tyr
            195                 200                 205

Arg Lys Lys Glu Asp Ala Asn Gln Val Leu Leu Glu Leu Ala Ile Leu
        210                 215                 220

Asp Tyr Asn Met Ile Gln Ser Val Tyr Gln Arg Asp Leu Arg Glu Thr
225                 230                 235                 240

Ser Arg Trp Trp Arg Arg Val Gly Leu Ala Thr Lys Leu His Phe Ala
                245                 250                 255

Arg Asp Arg Leu Ile Glu Ser Phe Tyr Trp Ala Val Gly Val Ala Phe
            260                 265                 270

Glu Pro Gln Tyr Ser Asp Cys Arg Asn Ser Val Ala Lys Met Phe Ser
            275                 280                 285

Phe Val Thr Ile Ile Asp Asp Ile Tyr Asp Val Tyr Gly Thr Leu Asp
            290                 295                 300

Glu Leu Glu Leu Phe Thr Asp Ala Val Glu Arg Trp Asp Val Asn Ala
305                 310                 315                 320

Ile Asn Asp Leu Pro Asp Tyr Met Lys Leu Cys Phe Leu Ala Leu Tyr
                325                 330                 335

Asn Thr Ile Asn Glu Ile Ala Tyr Asp Asn Leu Lys Asp Lys Gly Glu
            340                 345                 350

Asn Ile Leu Pro Tyr Leu Thr Lys Ala Trp Ala Asp Leu Cys Asn Ala
            355                 360                 365

Phe Leu Gln Glu Ala Lys Trp Leu Tyr Asn Lys Ser Thr Pro Thr Phe
            370                 375                 380

Asp Asp Tyr Phe Gly Asn Ala Trp Lys Ser Ser Ser Gly Pro Leu Gln
385                 390                 395                 400

Leu Val Phe Ala Tyr Phe Ala Val Val Gln Asn Ile Lys Lys Glu Glu
                405                 410                 415

Ile Glu Asn Leu Gln Lys Tyr His Asp Thr Ile Ser Arg Pro Ser His
            420                 425                 430

Ile Phe Arg Leu Cys Asn Asp Leu Ala Ser Ala Ser Ala Glu Ile Ala
            435                 440                 445

Arg Gly Glu Thr Ala Asn Ser Val Ser Cys Tyr Met Arg Thr Lys Gly
        450                 455                 460

Ile Ser Glu Glu Leu Ala Thr Glu Ser Val Met Asn Leu Ile Asp Glu
465                 470                 475                 480

Thr Trp Lys Lys Met Asn Lys Glu Lys Leu Gly Gly Ser Leu Phe Ala
                485                 490                 495

Lys Pro Phe Val Glu Thr Ala Ile Asn Leu Ala Arg Gln Ser His Cys
            500                 505                 510

Thr Tyr His Asn Gly Asp Ala His Thr Ser Pro Asp Glu Leu Thr Arg
            515                 520                 525

Lys Arg Val Leu Ser Val Ile Thr Glu Pro Ile Leu Pro Phe Glu Arg
        530                 535                 540

<210> SEQ ID NO 2
<211> LENGTH: 329
<212> TYPE: PRT
<213> ORGANISM: Artificial Sequence
<220> FEATURE:
<223> OTHER INFORMATION: Synthetic Construct

<400> SEQUENCE: 2

Met Thr Asp Val Arg Phe Arg Ile Ile Gly Thr Gly Ala Tyr Val Pro
1               5                   10                  15

Glu Arg Ile Val Ser Asn Asp Glu Val Gly Ala Pro Ala Gly Val Asp
            20                  25                  30

Asp Asp Trp Ile Thr Arg Lys Thr Gly Ile Arg Gln Arg Arg Trp Ala
        35                  40                  45

Ala Asp Asp Gln Ala Thr Ser Asp Leu Ala Thr Ala Ala Gly Arg Ala
    50                  55                  60

Ala Leu Lys Ala Ala Gly Ile Thr Pro Glu Gln Leu Thr Val Ile Ala
65                  70                  75                  80

Val Ala Thr Ser Thr Pro Asp Arg Pro Gln Pro Pro Thr Ala Ala Tyr
                85                  90                  95

Val Gln His His Leu Gly Ala Thr Gly Thr Ala Phe Asp Val Asn
            100                 105                 110

Ala Val Cys Ser Gly Thr Val Phe Ala Leu Ser Ser Val Ala Gly Thr
        115                 120                 125

Leu Val Tyr Arg Gly Gly Tyr Ala Leu Val Ile Gly Ala Asp Leu Tyr
    130                 135                 140

Ser Arg Ile Leu Asn Pro Ala Asp Arg Lys Thr Val Leu Phe Gly
145                 150                 155                 160

Asp Gly Ala Gly Ala Met Val Leu Gly Pro Thr Ser Gly Thr Gly
                165                 170                 175

Pro Ile Val Arg Arg Val Ala Leu His Thr Phe Gly Gly Leu Thr Asp
            180                 185                 190

Leu Ile Arg Val Pro Ala Gly Gly Ser Arg Gln Pro Leu Asp Thr Asp
        195                 200                 205

Gly Leu Asp Ala Gly Leu Gln Tyr Phe Ala Met Asp Gly Arg Glu Val
    210                 215                 220

Arg Arg Phe Val Thr Glu His Leu Pro Gln Leu Ile Lys Gly Phe Leu
225                 230                 235                 240

His Glu Ala Gly Val Asp Ala Ala Asp Ile Ser His Phe Val Pro His
                245                 250                 255

Gln Ala Asn Gly Val Met Leu Asp Glu Val Phe Gly Glu Leu His Leu
            260                 265                 270

Pro Arg Ala Thr Met His Arg Thr Val Glu Thr Tyr Gly Asn Thr Gly
        275                 280                 285

Ala Ala Ser Ile Pro Ile Thr Met Asp Ala Val Arg Ala Gly Ser
    290                 295                 300

Phe Arg Pro Gly Glu Leu Val Leu Leu Ala Gly Phe Gly Gly Gly Met
305                 310                 315                 320

Ala Ala Ser Phe Ala Leu Ile Glu Trp
                325

<210> SEQ ID NO 3
<211> LENGTH: 125
<212> TYPE: DNA
<213> ORGANISM: Artificial Sequence
<220> FEATURE:
<223> OTHER INFORMATION: Synthetic Construct

<400> SEQUENCE: 3
aattcatata aaaacatac agataaccat ctgcggtgat aaattatctc tggcggtgtt      60
gacataaata ccactggcgg tgatactgag cacatcagca ggacgcactg accaccatga     120
aggtg                                                                 125

<210> SEQ ID NO 4
<211> LENGTH: 47
<212> TYPE: DNA
<213> ORGANISM: Artificial Sequence
<220> FEATURE:
<223> OTHER INFORMATION: Synthetic Construct

<400> SEQUENCE: 4
ggagatatac atatggaagc acgtcgctct gcgaactacg aacctaa    47

<210> SEQ ID NO 5
<211> LENGTH: 47
<212> TYPE: DNA
<213> ORGANISM: Artificial Sequence
<220> FEATURE:
<223> OTHER INFORMATION: Synthetic Construct

<400> SEQUENCE: 5
ttaggttcgt agttcgcaga gcgacgtgct tccatatgta tatctcc    47

<210> SEQ ID NO 6
<211> LENGTH: 20
<212> TYPE: DNA
<213> ORGANISM: Artificial Sequence
<220> FEATURE:
<223> OTHER INFORMATION: Synthetic Construct

<400> SEQUENCE: 6
taatacgact cactataggg    20

<210> SEQ ID NO 7
<211> LENGTH: 2439
<212> TYPE: DNA
<213> ORGANISM: Artificial Sequence
<220> FEATURE:
<223> OTHER INFORMATION: Synthetic Construct

<400> SEQUENCE: 7
atggttaaag acattgtaat aattgatgcc ctccgtactc ccatcggtaa gtaccgcggt    60
cagctctcaa agatgacggc ggtggaattg gaaccgcag ttacaaaggc tctgttcgag    120
aagaacgacc aggtcaaaga ccatgtagaa caagtcattt ttggcaacgt tttacaggca    180
gggaacggcc agaatcccgc ccgtcagatc gcccttaatt ctggcctgtc cgcagagata    240
ccggcttcga ctattaacca ggtgtgtggt tctggcctga agcaataag catggcgcgc    300 caacagatcc tactcggaga agcggaagta atagtagcag gaggtatcga atccatgacg    360
aatgcgccga gtattacata ttataataaa gaagaagaca ccctctcaaa gcctgttcct    420
acgatgacct tcgatggtct gaccgacgcg tttagcggaa agattatggg tttaacagcc    480
gaaaatgttg ccgaacagta cggcgtatca cgtgaggccc aggacgcctt tgcgtatgga    540
tcgcagatga aagcagcaaa ggcccaagaa cagggcattt tcgcagctga atactgcct    600 cttgaaatag gggacgaagt tattactcag gacgaggggg ttcgtcaaga gaccaccctc    660
gaaaaattaa gtctgcttcg gaccatttt aaagaagatg gtactgttac agcgggcaac    720
gcctcaacga tcaatgatgg cgcctcagcc gtgatcattg catcaaagga gtttgctgag    780
acaaaccaga ttccctacct tgcgatcgta catgatatta cagagatagg cattgatcca    840
tcaataatgg gcattgctcc cgtgagtgcg atcaataaac tgatcgatcg taaccaaatt    900
agcatggaag aaatcgatct cttttgaaatt aatgaggcat ttgcagcatc ctcggtggta    960

```
gttcaaaaag agttaagcat tcccgatgaa aagatcaata ttggcggttc cggtattgca    1020
ctaggccatc ctcttggcgc cacaggagcg cgcattgtaa ccaccctagc gcaccagttg    1080
aaacgtacac acggacgcta tggtattgcc tccctgtgca ttggcggtgg ccttggccta    1140
gcaatattaa tagaagtgcc tcaggaagat cagccggtta aaaaatttta tcaattggcc    1200
cgtgaggacc gtctggctag acttcaggag caagccgtga tcagcccagc tacaaaacat    1260
gtactggcag aaatgacact tcctgaagat attgccgaca atctgatcga aaatcaaata    1320
tctgaaatgg aaatccctct tggtgtggct ttgaatctga gggtcaatga taagagttat    1380
accatcccac tagcaactga ggaaccgagt gtaatcgctg cctgtaataa tggtgcaaaa    1440
atggcaaacc acctgggcgg ttttcagtca gaattaaaag atggtttcct gcgtgggcaa    1500
attgtactta tgaacgtcaa agaacccgca actatcgagc atacgatcac ggcagagaaa    1560
gcggcaattt ttcgtgccgc agcgcagtca catccatcga ttgtgaaacg aggtgggggt    1620
ctaaaagaga tagtagtgcg tacgttcgat gatgatccga cgttcctgtc tattgatctg    1680
atagttgata ctaaagacgc aatgggcgct aacatcatta caccattct cgagggtgta    1740 gccggctttc tgagggaaat ccttaccgaa gaaattctgt tctctatttt atctaattac    1800
gcaaccgaat caattgtgac cgccagctgt cgcataccTt acgaagcact gagtaaaaaa    1860
ggtgatggta aacgaatcgc tgaaaaagtg gctgctgcat ctaaatttgc ccagttagat    1920
ccttatcgag ctgcaaccca aacaaaggt attatgaatg gtattgaggc cgtcgttttg    1980
gcctcaggaa atgacacacg ggcggtcgcg gcagccgcac atgcgtatgc ttcacgcgat    2040
cagcactatc ggggcttaag ccagtggcag gttcagaag gcgcgttaca cggggagatc    2100
agtctaccac ttgcactcgg cagcgttggc ggtgcaattg aggtcttgcc taaagcgaag    2160
gcggcattcg aaatcatggg gatcacagag gcgaaggagc tggcagaagt cacagctgcg    2220
gtagggctgg cgcaaaacct ggcggcgtta agagcgcttg ttagtgaagg aatacagcaa    2280
ggtcacatgt cgctccaggc tcgctctctt gcattatcgg taggtgctac aggcaaggaa    2340
gttgaaatcc tggccgaaaa attacagggc tctcgtatga atcaggcgaa cgctcagacc    2400
atactcgcag agatcagatc gcaaaaagtt gaattgtga                           2439
```

<210> SEQ ID NO 8
<211> LENGTH: 1158
<212> TYPE: DNA
<213> ORGANISM: Artificial Sequence
<220> FEATURE:
<223> OTHER INFORMATION: Synthetic Construct

<400> SEQUENCE: 8

```
atgaccatga acgttggaat cgataaaatg tcattctttg ttccaccta ctttgtggac     60 atgactgatc tggcagtagc acgggatgtc gatcccaata agtttctgat ggtattggc    120 caggaccaga tggcagttaa tccgaaaacg caggatattg tgacatttgc cacaaatgct    180
gccaaaaaca tactgtcagc tgaggacctt gataaaattg atatggtcat agtcggcacc    240
gagagtggaa tcgatgaatc caaagcgagt gccgtagtgc ttcacaggtt gctcggtatc    300
cagaagtttg ctcgctccct tgaaatcaaa gaagcctgtt atgggggtac cgcggcttta    360
cagttcgctg taaaccacat taggaatcat cctgaatcaa aggttcttgt agttgcatca    420
gatatcgcga atacggcct ggcttctgga ggtgaaccaa cgcaaggtgc aggcgctgtg    480
gctatgctcg tctcaactga ccctaagatc attgctttca cgacgatag cctcgcgctt    540 acacaagata tctatgactt ctggcgacca gttggacatg actatcctat ggtcgacggg    600
```

```
cctcttagta cagagaccta catccagtca tttcagaccg tatggcagga atacacaaaa      660
cggtcgcagc atgcactggc agactttgct gcccttagct ttcatatccc gtatactaaa      720
atgggcaaaa aggcgctgct tgcaatcctt gaaggcgaat cagaggaggc tcagaaccgt      780
atactagcaa aatatgaaaa gagtatagcc tactccagaa aggcgggtaa cctgtatacc      840
ggtagcctgt atctaggact tatttcactt ctggaaaatg cagaagacct taaagctggt      900
gatttaatag gcctcttttc ttacggttcc ggtgctgttg cggagttttt ctcaggaagg      960
ctggttgagg actatcagga acagctactt aaaacaaaac atgccgaaca gctggcccat     1020
agaaagcaac tgacaatcga ggagtacgaa acgatgttct ccgatcgctt ggacgtggac     1080
aaagacgccg aatacgaaga cacattagct tatagcattt cgtcagtccg aaacaccgta     1140
cgtgagtaca ggagttga                                                   1158
```

<210> SEQ ID NO 9
<211> LENGTH: 2442
<212> TYPE: DNA
<213> ORGANISM: Artificial Sequence
<220> FEATURE:
<223> OTHER INFORMATION: Synthetic Construct

<400> SEQUENCE: 9

```
atgaaagaag tggttatgat tgatgcggct cgcacaccca ttgggaaata cagaggtagt       60
cttagtcctt ttacagcggt ggagctgggg acactggtca cgaaagggct gctggataaa      120
acaaagctta agaaagacaa gatagaccaa gtgatattcg gcaatgtgct tcaggcagga      180
aacggacaaa acgttgcaag acaaatagcc ctgaacagtg gcttaccagt tgacgtgccg      240
gcgatgacta ttaacgaagt ttgcgggtcc ggaatgaaag cggtgatttt agcccgccag      300
ttaatacagt taggggaggc agagttggtc attgcagggg gtacggagtc aatgtcacaa      360
gcacccatgc tgaaaccttg ccagtcagag accaacgaat acggagagcc gatatcatca      420
atggttaatg acgggctgac ggatgcgttt tccaatgctc acatgggtct tactgccgaa      480
aaggtggcga cccagttttc agtgtcgcgc gaggaacaag accggtacgc attgtccagc      540
caattgaaag cagcgcacgc ggttgaagcc ggggtgttct cagaagagat tattccggtt      600
aagattagcg acgaggatgt cttgagtgaa gacgaggcag taagaggcaa cagcactttg      660
gaaaaactgg gcaccttgcg gacggtgttt tctgaagagg gcacggttac cgctggcaat      720
gcttcaccgc tgaatgacgg cgctagtgtc gtgattcttg catcaaaaga atacgcggaa      780
aacaataatc tgccttacct ggcgacgata aaggaggttg cggaagttgg tatcgatcct      840
tctatcatgg gtattgcccc aataaaggcc attcaaaagt taacagatcg gtcgggcatg     900
aacctgtcca cgattgatct gttcgaaatt aatgaagcat cgcggcatc tagcattgtt      960 gtttctcaag agctgcaatt ggacgaagaa aaagtgaata tctatggcgg ggcgatagct     1020
ttaggccatc caatcggcgc aagcggagcc cggatactga caaccttagc atacggcctc     1080
ctgcgtgagc aaaagcgtta tggtattgcg tcattatgta tcggcggtgg tcttggtctg     1140
gccgtgctgt tagaagctaa tatggagcag acccacaaag acgttcagaa gaaaaagttt     1200
taccagctta ccccctccga gcggagatcg cagcttatcg agaagaacgt tctgactcaa     1260
gaaacggcac ttattttcca ggagcagacg ttgtccgaag aactgtccga tcacatgatt     1320
gagaatcagg tctccgaagt ggaaattcca atgggaattg cacaaaattt tcagattaat     1380
ggcaagaaaa aatggattcc tatggcgact gaagaacctt cagtaatagc ggcagcatcg     1440
```

```
aacggcgcca aaatctgcgg gaacatttgc gcggaaacgc ctcagcggct tatgcgcggg    1500
cagattgtcc tgtctggcaa atcagaatat caagccgtga taaatgccgt gaatcatcgc    1560
aaagaagaac tgattctttg cgcaaacgag tcgtacccga gtattgttaa acgcggggga    1620
ggtgttcagg atatttctac gcgggagttt atgggttctt ttcacgcgta tttatcaatc    1680
gactttctgg tggacgtcaa ggacgcaatg ggggcaaaca tgatcaactc tattctcgaa    1740
agcgttgcaa ataaactgcg tgaatggttc cggaagagg aaatactgtt ctccatcctg     1800
tcaaacttcg ctacggagtc cctggcatct gcatgttgcg agattccttt tgaaagactt    1860
ggtcgtaaca aagaaattgg tgaacagatc gccaagaaaa ttcaacaggc aggggaatat    1920
gctaagcttg acccttaccg cgcggcaacc cataacaagg ggattatgaa cggtatcgaa    1980
gccgtcgttg ccgcaacggg aaacgacaca cgggctgttt ccgcttctat tcacgcatac    2040
gccgcccgta atggcttgta ccaaggttta acggattggc agatcaaggg cgataaactg    2100
gttggtaaat taacagtccc actggctgtg gcgactgtcg gtggcgcgtc gaacatatta    2160
ccaaaagcca aagcttccct cgccatgctg gatattgatt ccgcaaaaga actggcccaa    2220
gtgatcgccg cggtaggttt agcacagaat ctggcggcgt tacgtgcatt agtgacagaa    2280
ggcattcaga aggacacat gggcttgcaa gcacgttctt tagcgatttc gataggtgcc    2340
atcggtgagg agatagagca agtcgcgaaa aaactgcgtg aagctgaaaa aatgaatcag    2400
caaacggcaa tacagatttt agaaaaaatt cgcgagaaat ga                       2442
```

<210> SEQ ID NO 10
<211> LENGTH: 1155
<212> TYPE: DNA
<213> ORGANISM: Artificial Sequence
<220> FEATURE:
<223> OTHER INFORMATION: Synthetic Construct

<400> SEQUENCE: 10

```
atgaaaatcg gtattgaccg tctgtccttc ttcatcccga atttgtattt ggacatgact      60
gagctggcag aatcacgcgg ggatgatcca gctaaatatc atattggaat cggacaagat    120
cagatggcag tgaatcgcgc aaacgaggac atcataacac tgggtgcaaa cgctgcgagt    180
aagatcgtga cagagaaaga ccgcgagttg attgatatgg taatcgttgg cacggaatca    240
ggaattgacc actccaaagc aagcgccgtg attattcacc atctccttaa aattcagtcg    300
ttcgcccgtt ctttcgaggt aaaagaagct tgctatggcg gaactgctgc cctgcacatg    360
gcgaaggagt atgtcaaaaa tcatccggag cgtaaggtct tggtaattgc gtcagacatc    420
gcgcgttatg gtttggccag cggaggagaa gttactcaag gcgtgggggc cgtagccatg    480
atgattacac aaaaccccg gattctttcg attgaagacg atagtgtttt tctcacagag    540
gatatctatg atttctggcg gcctgattac tccgagttcc ctgtagtgga cgggcccctt    600
tcaaactcaa cgtatataga gagttttcag aaagtttgga accggcacaa ggaattgtcc    660
ggaagagggc tggaagatta tcaagctatt gcttttcaca tacccatac gaagatgggt     720 aagaaagcgc tccagagtgt tttagaccaa accgatgaag ataaccagga gcgcttaatg    780
gctagatatg aggagtctat tcgctatagc cggagaattg gtaacctgta cacaggcagc    840
ttgtaccttg gtcttacaag cttgttggaa aactctaaaa gtttacaacc gggagatcgg    900
atcggcctct tttcctatgg cagtggtgcg gtgtccgagt tctttaccgg gtatttagaa    960
gaaaattacc aagagtacct gttcgctcaa agccatcaag aaatgctgga tagccggact   1020
cggattacgg tcgatgaata cgagaccatc ttttcagaga ctctgccaga acatggtgaa   1080
```

```
tgcgccgaat atacgagcga cgtccccttt tctataacca agattgagaa cgacattcgt   1140
tattataaaa tctga                                                    1155

<210> SEQ ID NO 11
<211> LENGTH: 2448
<212> TYPE: DNA
<213> ORGANISM: Artificial Sequence
<220> FEATURE:
<223> OTHER INFORMATION: Synthetic Construct

<400> SEQUENCE: 11
atggaagaag tggtaattat agatgcacgt cggactccga ttggtaaata tcacgggtcg     60
ttgaagaagt tttcagcggt ggcgctgggg acggccgtgg ctaaagacat gttcgaacgc    120
aaccagaaaa tcaaagagga gatcgcgcag gtcataattg gtaatgtctt gcaggcagga    180
aatggccaga accccgcgcg gcaagttgct cttcaatcag ggttgtccgt tgacattccc    240
gcttctacaa ttaacgaggt tgtgggtct ggtttgaaag ctatcttgat gggcatggaa     300
caaatccaac tcggcaaagc gcaagtagtg ctggcaggcg gcattgaatc aatgacaaat    360
gcgccaagcc tgtcccacta taacaaggcg aggatacgt atagtgtccc agtgtcgagc     420
atgacactgg atggtctgac agacgcattt tctagtaaac ctatgggatt aacagcggaa    480
aacgtcgcac agcgctacgg tatctcccgt gaggcgcaag atcaattcgc atatcaatct    540
cagatgaaag cagcaaaagc gcaggcagaa acaaattcg ctaaggaaat tgtgccactg     600
gcgggtgaaa ctaaaaccat cacagctgac gaagggatca gatcccaaac aacgatggag    660
aaactggcaa gtctcaaacc tgttttaaa accgatggca ctgtaaccgc agggaatgct    720
agcaccatta tgacggggc cgcccttgtg ctgcttgcta gcaaaactta ctgcgaaact    780
aatgacatac cgtaccttgc gacaatcaaa gaaattgttg aagttggaat cgatccggag    840
attatgggca tctctccgat aaaagcgata caaacattgt tacaaaatca aaaagttagc    900
ctcgaagata ttggagtttt tgaaataaat gaagcctttg ccgcaagtag catagtggtt    960
gaatctgagt tgggattaga tccggctaaa gttaaccgtt atgggggtgg tatatcctta   1020
ggtcatgcaa ttgggcaac cggcgctcgc ctggccactt cactggtgta tcaaatgcag   1080
gagatacaag cacgttatgg tattgcgagc ctgtgcgttg gtggtggact tggactggca   1140 atgctttag aacgtccaac tattgagaag gctaaaccga cagacaaaaa gttctatgaa    1200
ttgtcaccag ctgaacggtt gcaagagctg gaaaatcaac agaaaatcag ttctgaaact    1260
aaacagcagt tatctcagat gatgcttgcc gaggacactg caaaccattt gatagaaaat    1320
caaatatcag agattgaact cccaatgggc gtcgggatga acctgaaggt tgatgggaaa    1380
gcctatgttg tgccaatggc gacggaagag ccgtccgtca tcgcggccat gtctaatggt    1440
gccaaaatgg ccggcgaaat tcacactcag tcgaaagaac ggctgctcag aggtcagatt    1500
gttttcagcg cgaagaatcc gaatgaaatc gaacagagaa tagctgagaa ccaagctttg    1560
attttcgaac gtgccgaaca gtcctatcct tccattgtga aaagagaggg aggtctccgc    1620
cgcattgcac ttcgtcattt tcctgccgat tctcagcagg agtctgcgga ccagtccaca    1680 ttttatcag tggacctttt tgtagatgtg aaagacgcga tggggcaaa tatcataaat    1740 gcaatacttg agggcgtcgc agccctgttt cgcgaatggt tccccaatga ggaaattctt    1800
ttttctattc tctcgaactt ggctacggag agcttagtca cggctgtttg tgaagtccca    1860
tttagtgcac ttagcaagag aggtggtgca acggtggccc agaaaattgt gcaggcgtcg    1920
```

```
ctcttcgcaa agacagaccc ataccgcgca gtgacccaca acaaagggat tatgaacggt    1980
gtagaggctg ttatgcttgc cacaggcaac gacacgcgcg cagtctcagc cgcttgtcat    2040
ggatacgcag cgcgcaccgg tagctatcag ggtctgacta actggacgat tgagtcggat    2100
cgcctggtag gcgagataac actgccgctg gccatcgcta cagttggagg cgctaccaaa    2160
gtgttgccca agctcaagc ggcactggag attagtgatg ttcactcttc tcaagagctt     2220
gcagccttag cggcgtcagt aggtttagta caaaatctcg cggccctgcg cgcactggtt    2280
tccgaaggta tacaaaaagg gcacatgtcc atgcaagccc ggtctctcgc aatcgcggtc    2340
ggtgctgaaa aagccgagat cgagcaggtc gccgaaaagt tgcggcagaa cccgccaatg    2400
aatcagcagc aggcgctccg tttttcttggc gagatccgcg aacaatga                2448
```

<210> SEQ ID NO 12
<211> LENGTH: 1155
<212> TYPE: DNA
<213> ORGANISM: Artificial Sequence
<220> FEATURE:
<223> OTHER INFORMATION: Synthetic Construct

<400> SEQUENCE: 12

```
atgaacgtcg gcattgacaa aattaatttt ttcgttccac cgtattatct ggatatggtc      60
gacctggccc acgcacgcga gtggacccg aacaaattta caattggaat tggacaggat      120
cagatggctg tgagcaaaaa gacgcacgat atcgtaacat tcgcggctag tgccgcgaag    180
gaaattttag aacctgagga cttgcaagct atagacatgg ttatagttgg taccgaatcg    240
ggcattgacg agagcaaagc atccgcggtc gttttacatc gtttgttggg cgtacaacct    300
ttcgctcgca gttttgaaat taagaagcc tgttacgggg caaccgcagg cattcagttt     360
gccaagactc atatacaagc gaacccggag agcaaggtcc tggtaattgc aagcgatata    420
gctcggtatg gtcttcggtc aggtggagag cccacacaag gcgcaggggc agttgctatg    480
cttctcacgg caaatcccag aatcctgacc ttcgaaaacg acaatctgat gttaacgcag    540
gatatttatg acttctggag accacttggt cacgcttacc ctatggtaga tggccacctt    600
tccaatcaag tctatattga cagttttaag aaggtctggc aagcacattg cgaacgcaat    660
caagcttcta tatccgacta tgccgcgatt agttttcata ttccgtatac aaaaatgggt    720
aagaaagccc tgctcgctgt ttttgcagat gaagtggaaa ctgaacagga acgcgttatg    780
gcacggtatg aagagtctat cgtatattca cgccggatcg gcaacttgta tacgggatca    840
ttgtacctgg ggctgatatc cttattggaa aacagttctc acctgtcggc gggcgaccgg    900
ataggattgt ttagttatgg gagtggcgct gtcagcgaat tttctccgg tcgtttagtg     960 gcaggctatg aaaatcaatt gaacaaagag gcgcataccc agctcctgga tcagcgtcag    1020
aagctttcca tcgaagagta tgaggcgatt tttacagatt ccttagaaat tgatcaggat    1080
gcagcgttct cggatgacct gccatattcc atccgcgaga taaaaaacac gattcggtac    1140
tataaggaga gctga                                                     1155
```

<210> SEQ ID NO 13
<211> LENGTH: 2475
<212> TYPE: DNA
<213> ORGANISM: Artificial Sequence
<220> FEATURE:
<223> OTHER INFORMATION: Synthetic Construct

<400> SEQUENCE: 13

```
atggaagaag ttgtcatcat tgacgcactg cgtactccaa taggaaagta ccacggttcg     60
```

-continued

```
ctgaaagatt acacagctgt tgaactgggg acagtagcag caaaggcgtt gctggcacga      120
aatcagcaag caaaagaaca catagcgcaa gttattattg caacgtcct gcaagccgga       180 agtgggcaga atccaggccg acaagtcagt ttacagtcag gattgtcttc tgatatcccc      240
gctagcacga tcaatgaagt gtgtggctcg ggtatgaaag cgattctgat gggtatggag      300
caaattcagc tgaacaaagc ctctgtggtc ttaacaggcg gaattgaaag catgaccaac      360
gcgccgctgt ttagttatta caacaaggct gaggatcaat attcggcgcc ggttagcaca      420
atgatgcacg atggtctaac agatgctttc agttccaaac caatgggctt aaccgcagag      480
accgtcgctg agagatatgg aattacgcgt aaggaacaag atgaatttgc ttatcactct      540
caaatgaagg cggccaaagc ccaggcggcg aaaaagtttg atcaggaaat tgtaccccctg     600 acggaaaaat ccggaacggt tctccaggac gaaggcatca gagccgcgac aacagtcgag      660
aagctagctg agcttaaaac ggtgttcaaa aaagacggaa cagttacagc gggtaacgcc      720
tctacgataa atgatggcgc tgctatggta ttaatagcat caaaatctta ttgcgaagaa      780
caccagattc cttatctggc cgttataaag gagatcgttg aggtgggttt tgccccccgaa     840 ataatgggta tttcccccat taaggctata gacacccctgc tgaaaaatca agcactgacc     900
atagaggata taggaatatt tgagattaat gaagcctttg ctgcgagttc gattgtggta      960
gaacgcgagt tgggcctgga ccccaaaaaa gttaatcgct atggcggtgg tatatcactc     1020
ggccacgcaa ttggggcgac gggagctcgc attgcgacga ccgttgctta tcagctgaaa     1080
gatacccagg agcgctacgg tatagcttcc ttatgcgttg gtgggggtct tggattggcg     1140
atgcttctgg aaaacccatc ggccactgcc tcacaaacta attttgatga ggaatctgct     1200
tccgaaaaaa ctgagaagaa gaagttttat gcgctagctc ctaacgaacg cttagcgttt     1260
ttggaagccc aaggcgctat taccgctgct gaaaccctgg tcttccagga gatgacctta     1320
aacaaagaga cagccaatca cttaatcgaa accaaatca gcgaagttga aattcccttta    1380 ggcgtgggcc tgaacttaca ggtgaatggg aaagcgtata atgttcctct ggccacggag     1440
gaaccgtccg ttatcgctgc gatgtcgaat ggcgccaaaa tggctggtcc tattacaaca     1500
acaagtcagg agaggctgtt acggggtcag attgtcttca tggacgtaca ggacccagaa     1560
gcaatattag cgaaagttga atccgagcaa gctaccatttt tcgcggtggc aaatgaaaca     1620
tacccgtcta tcgtgaaaag aggaggaggt ctgcgtagag tcattggcag gaatttcagt     1680
ccggccgaaa gtgacttagc cacggcgtat gtatcaattg acctgatggt agatgttaag     1740
gatgcaatgg gtgctaatat catcaatagt atcctagaag gtgttgcgga attgtttaga     1800
aaatggttcc cagaagaaga aatcctgttc tcaattctct ccaatctcgc gacagaaagt     1860
ctggtaacgc gacgtgctc agttccgttt gataaattgt ccaaaactgg gaatggtcga     1920
caagtagctg gtaaaatagt gcacgcggcg gactttgcta agatagatcc atacagagct     1980
gccacacaca ataaaggtat tatgaatggc gttgaagcgt taatcttagc caccggtaat     2040
gacacccgtg cggtgtcggc tgcatgccac ggttacgcgg cacgcaatgg gcgaatgcaa     2100
gggcttacct cttggacgat tatcgaagat cggctgatag gctctatcac attaccttg      2160 gctattgcga cagtgggggg tgccacaaaa atccttgcca aagcacaggc cgccctggcg     2220
ctaactggcg ttgagacggc gtcggaactg gccagcctgg cggcgagtgt gggattagtt     2280
caaaatttgg ccgcttttacg agcactagtg agcgagggca ttcagcaagg gcacatgagt     2340
atgcaagcta gatccctggc cattagcgta ggtgcgaaag gtactgaaat agagcaacta     2400
```

```
gctgcgaagc tgagggcagc gacgcaaatg aatcaggagc aggctcgtaa atttctgacc    2460
gaaataagaa attaa                                                     2475

<210> SEQ ID NO 14
<211> LENGTH: 1161
<212> TYPE: DNA
<213> ORGANISM: Artificial Sequence
<220> FEATURE:
<223> OTHER INFORMATION: Synthetic Construct

<400> SEQUENCE: 14
atgaacgttg gaattgataa aatcaattttt ttcgttccgc cctatttcat tgatatggtg     60
gatctcgctc atgcaagaga agttgacccc aacaagttca ctataggaat aggccaagat    120
cagatggcag taaacaagaa aacgcaagat atcgtaacgt tcgcgatgca cgccgcgaag    180
gatattctga ctaaggaaga tttacaggcc atagatatgg taatagtggg gactgagtct    240
gggatcgacg agagcaaggc aagtgctgtc gtattgcatc ggcttttagg tattcagcct    300
tttgcgcgct cctttgaaat taaggaggca tgctatgggg ccactgccgg ccttcagttt    360
gcaaaagctc atgtgcaggc taatccccag agcaaggtcc tggtggtagc ttccgatata    420
gcacgctacg gactggcatc cggaggagaa ccgactcaag tgtaggtgc tgtggcaatg    480 ttgatttccg ctgatccagc tatcttgcag ttagaaaatg ataatctcat gttgacccaa    540
gatatatacg attttttggcg cccggtcggg catcaatatc ctatggtaga cggccatctg    600
tctaatgccg tctatatagga cagctttaaa caagtctggc aagcacattg cgagaaaaac    660
caacggactg ctaaagatta tgctgcattg tcgttccata ttccgtacac gaaaatgggt    720
aagaaagctc tgttagcggt ttttgcggag gaagatgaga cagaacaaaa gcggttaatg    780
gcacgttatg aagaatcaat tgtatacagt cgtcggactg gaaatctgta tactggctca    840
ctctatctgg gcctgatttc cttactggag aatagtagca gtttacaggc gaacgatcgc    900
ataggtctgt ttagctatgg ttcaggggcc gttgcggaat ttttcagtgg cctcttggta    960
ccgggttacg agaaacaatt agcgcaagct gcccatcaag ctcttctgga cgaccggcaa   1020
aaactgacta tcgcagagta cgaagccatg tttaatgaaa ccattgatat tgatcaggac   1080
cagtcatttg aggatgactt actgtactcc atcagagaga tcaaaaacac tattcgctac   1140
tataacgagg agaatgaata a                                             1161

<210> SEQ ID NO 15
<211> LENGTH: 19
<212> TYPE: DNA
<213> ORGANISM: Artificial Sequence
<220> FEATURE:
<223> OTHER INFORMATION: Synthetic Construct

<400> SEQUENCE: 15
gctagttatt gctcagcgg                                                  19

<210> SEQ ID NO 16
<211> LENGTH: 22
<212> TYPE: DNA
<213> ORGANISM: Artificial Sequence
<220> FEATURE:
<223> OTHER INFORMATION: Synthetic Construct

<400> SEQUENCE: 16
gcactgtctt tccgtctgct gc                                              22
```

-continued

```
<210> SEQ ID NO 17
<211> LENGTH: 22
<212> TYPE: DNA
<213> ORGANISM: Artificial Sequence
<220> FEATURE:
<223> OTHER INFORMATION: Synthetic Construct

<400> SEQUENCE: 17
gcactgtctt tccgtctgct gc                                              22

<210> SEQ ID NO 18
<211> LENGTH: 20
<212> TYPE: DNA
<213> ORGANISM: Artificial Sequence
<220> FEATURE:
<223> OTHER INFORMATION: Synthetic Construct

<400> SEQUENCE: 18
cttcggcaac gcatggaaat                                                 20

<210> SEQ ID NO 19
<211> LENGTH: 20
<212> TYPE: DNA
<213> ORGANISM: Artificial Sequence
<220> FEATURE:
<223> OTHER INFORMATION: Synthetic Construct

<400> SEQUENCE: 19
ctcgtacagg ctcaggatag                                                 20

<210> SEQ ID NO 20
<211> LENGTH: 20
<212> TYPE: DNA
<213> ORGANISM: Artificial Sequence
<220> FEATURE:
<223> OTHER INFORMATION: Synthetic Construct

<400> SEQUENCE: 20
ttacgtccca acgctcaact                                                 20

<210> SEQ ID NO 21
<211> LENGTH: 6909
<212> TYPE: DNA
<213> ORGANISM: Artificial Sequence
<220> FEATURE:
<223> OTHER INFORMATION: Synthetic Construct

<400> SEQUENCE: 21
tggcgaatgg gacgcgccct gtagcggcgc attaagcgcg gcgggtgtgg tggttacgcg      60
cagcgtgacc gctacacttg ccagcgccct agcgcccgct cctttcgctt tcttcccttc     120
ctttctcgcc acgttcgccg gctttccccg tcaagctcta aatcggggc  tcccttt agg    180 gttccgattt agtgctttac ggcacctcga ccccaaaaaa cttgattagg gtgatggttc     240
acgtagtggg ccatcgccct gatagacggt ttttcgccct ttgacgttgg agtccacgtt     300
ctttaatagt ggactcttgt tccaaactgg aacaacactc aaccctatct cggtctattc     360
ttttgattta tagggatttt tgccgatttc ggcctattgg ttaaaaaatg agctgattta     420
acaaaatttt aacgcgaatt ttaacaaaat attaacgttt acaatttcag gtggcacttt     480
tcggggaaat gtgcgcggaa cccctatttg tttatttttc taaatacatt caaatatgta     540
tccgctcatg aattaattct tagaaaaact catcgagcat caaatgaaac tgcaatttat     600
tcatatcagg attatcaata ccatattttt gaaaagccg tttctgtaat gaaggagaaa      660
```

```
actcaccgag gcagttccat aggatggcaa gatcctggta tcggtctgcg attccgactc    720
gtccaacatc aatacaacct attaatttcc cctcgtcaaa ataaggttta tcaagtgaga    780
aatcaccatg agtgacgact gaatccggtg agaatggcaa aagtttatgc atttctttcc    840
agacttgttc aacaggccag ccattacgct cgtcatcaaa atcactcgca tcaaccaaac    900
cgttattcat tcgtgattgc gcctgagcga gacgaaatac gcgatcgctg ttaaaaggac    960
aattacaaac aggaatcgaa tgcaaccggc gcaggaacac tgccagcgca tcaacaatat   1020
tttcacctga atcaggatat tcttctaata cctggaatgc tgttttcccg gggatcgcag   1080
tggtgagtaa ccatgcatca tcaggagtac ggataaaatg cttgatggtc ggaagaggca   1140
taaattccgt cagccagttt agtctgacca tctcatctgt aacatcattg gcaacgctac   1200
ctttgccatg tttcagaaac aactctggcg catcgggctt cccatacaat cgatagattg   1260
tcgcacctga ttgcccgaca ttatcgcgag cccatttata cccatataaa tcagcatcca   1320
tgttggaatt taatcgcggc ctagagcaag acgtttcccg ttgaatatgg ctcataacac   1380
cccttgtatt actgtttatg taagcagaca gtttttattgt tcatgaccaa aatcccttaa   1440
cgtgagtttt cgttccactg agcgtcagac cccgtagaaa agatcaaagg atcttcttga   1500
gatccttttt ttctgcgcgt aatctgctgc ttgcaaacaa aaaaaccacc gctaccagcg   1560
gtggtttgtt tgccggatca agagctacca actcttttc cgaaggtaac tggcttcagc   1620
agagcgcaga taccaaatac tgtccttcta gtgtagccgt agttaggcca ccacttcaag   1680
aactctgtag caccgcctac atacctcgct ctgctaatcc tgttaccagt ggctgctgcc   1740
agtggcgata agtcgtgtct taccgggttg gactcaagac gatagttacc ggataaggcg   1800
cagcggtcgg gctgaacggg gggttcgtgc acacagccca gcttggagcg aacgacctac   1860
accgaactga gatacctaca gcgtgagcta tgagaaagcg ccacgcttcc gaagggaga    1920
aaggcggaca ggtatccggt aagcggcagg gtcggaacag gagagcgcac gagggagctt   1980
ccagggggaa acgcctggta tctttatagt cctgtcgggt ttcgccacct ctgacttgag   2040
cgtcgatttt tgtgatgctc gtcaggggg cggagcctat ggaaaaacgc cagcaacgcg   2100
gcctttttac ggttcctggc cttttgctgg ccttttgctc acatgttctt tcctgcgtta   2160
tcccctgatt ctgtggataa ccgtattacc gcctttgagt gagctgatac cgctcgccgc   2220
agccgaacga ccgagcgcag cgagtcagtg agcgaggaag cggaagagcg cctgatgcgg   2280
tattttctcc ttacgcatct gtgcggtatt tcacaccgca tatatggtgc actctcagta   2340
caatctgctc tgatgccgca tagttaagcc agtatacact ccgctatcgc tacgtgactg   2400
ggtcatggct gcgccccgac acccgccaac acccgctgac gcgccctgac gggcttgtct   2460
gctcccggca tccgcttaca gacaagctgt gaccgtctcc gggagctgca tgtgtcagag   2520
gttttcaccg tcatcaccga aacgcgcgag gcagctgcgg taaagctcat cagcgtggtc   2580
gtgaagcgat tcacagatgt ctgcctgttc atccgcgtcc agctcgttga gtttctccag   2640
aagcgttaat gtctggcttc tgataaagcg ggccatgtta agggcggttt ttcctgtttt   2700
ggtcactgat gcctccgtgt aagggggatt tctgttcatg ggggtaatga taccgatgaa   2760
acgagagagg atgctcacga tacgggttac tgatgatgaa catgcccggt tactggaacg   2820
ttgtgagggt aaacaactgg cggtatggat gcggcgggac cagagaaaaa tcactcaggg   2880
tcaatgccag cgcttcgtta atacagatgt aggtgttcca gggtagcc agcagcatcc   2940
tgcgatgcag atccggaaca taatggtgca gggcgctgac ttccgcgttt ccagacttta   3000
cgaaacacgg aaaccgaaga ccattcatgt tgttgctcag gtcgcagacg ttttgcagca   3060
```

```
gcagtcgctt cacgttcgct cgcgtatcgg tgattcattc tgctaaccag taaggcaacc    3120
ccgccagcct agccgggtcc tcaacgacag gagcacgatc atgcgcaccc gtggggccgc    3180
catgccggcg ataatggcct gcttctcgcc gaaacgtttg gtggcgggac cagtgacgaa    3240
ggcttgagcg agggcgtgca agattccgaa taccgcaagc gacaggccga tcatcgtcgc    3300
gctccagcga aagcggtcct cgccgaaaat gacccagagc gctgccggca cctgtcctac    3360
gagttgcatg ataaagaaga cagtcataag tgcggcgacg atagtcatgc cccgcgccca    3420
ccggaaggag ctgactgggt tgaaggctct caagggcatc ggtcgagatc ccggtgccta    3480
atgagtgagc taacttacat taattgcgtt gcgctcactg cccgctttcc agtcgggaaa    3540
cctgtcgtgc cagctgcatt aatgaatcgg ccaacgcgcg gggagaggcg gtttgcgtat    3600
tgggcgccag gtggtttttt cttttcacca gtgagacggg caacagctga ttgcccttca    3660
ccgcctggcc ctgagagagt tgcagcaagc ggtccacgct ggtttgcccc agcaggcgaa    3720
aatcctgttt gatggtggtt aacggcggga tataacatga gctgtcttcg gtatcgtcgt    3780
atcccactac cgagatatcc gcaccaacgc gcagcccgga ctcggtaatg gcgcgcattg    3840
cgcccagcgc catctgatcg ttggcaacca gcatcgcagt gggaacgatg ccctcattca    3900
gcatttgcat ggtttgttga aaaccggaca tggcactcca gtcgccttcc cgttccgcta    3960
tcggctgaat ttgattgcga gtgagatatt tatgccagcc agccagacgc agacgcgccg    4020
agacagaact taatgggccc gctaacagcg cgatttgctg gtgacccaat gcgaccagat    4080
gctccacgcc cagtcgcgta ccgtcttcat gggagaaaat aatactgttg atgggtgtct    4140
ggtcagagac atcaagaaat aacgccggaa cattagtgca ggcagcttcc acagcaatgg    4200
catcctggtc atccagcgga tagttaatga tcagcccact gacgcgttgc gcgagaagat    4260
tgtgcaccgc cgctttacag gcttcgacgc cgcttcgttc taccatcgac accaccacgc    4320
tggcacccag ttgatcggcg cgagatttaa tcgccgcgac aatttgcgac ggcgcgtgca    4380
gggccagact ggaggtggca acgccaatca gcaacgactg tttgcccgcc agttgttgtg    4440
ccacgcggtt gggaatgtaa ttcagctccg ccatcgccgc ttccactttt tcccgcgttt    4500
tcgcagaaac gtggctggcc tggttcacca cgcgggaaac ggtctgataa gagacaccgg    4560
catactctgc gacatcgtat aacgttactg gtttcacatt caccaccctg aattgactct    4620
cttccgggcg ctatcatgcc ataccgcgaa aggttttgcg ccattcgatg gtgtccggga    4680
tctcgacgct ctcccttatg cgactcctgc attaggaagc agcccagtag taggttgagg    4740
ccgttgagca ccgccgccgc aaggaatggt gcatgcaagg agatggcgcc caacagtccc    4800
ccggccacgg ggcctgccac catacccacg ccgaaacaag cgctcatgag cccgaagtgg    4860
cgagcccgat cttccccatc ggtgatgtcg gcgatatagg cgccagcaac cgcacctgtg    4920
gcgccggtga tgccggccac gatgcgtccg gcgtagagga tcgagatctc gatcccgcga    4980
aattaatacg actcactata ggggaattgt gagcggataa caattcccct ctagaaataa    5040
ttttgtttaa ctttaagaag gagatataca tatggaagca cgtcgctctg cgaactacga    5100
acctaacagc tgggactatg attacctgct gtcctccgac acggacgagt ccatcgaagt    5160
atacaaagac aaagcgaaaa agctggaagc cgaagttcgt cgcgagatta ataacgaaaa    5220
agcagaattt ctgaccctgc tggaactgat tgacaacgtc cagcgcctgg gcctgggtta    5280
ccgtttcgag tctgatatcc gtggtgcgct ggatcgcttc gtttcctccg gcggcttcga    5340
tgcggtaacc aagacttccc tgcacggtac ggcactgtct ttccgtctgc tgcgtcaaca    5400
```

-continued

```
cggttttgag gtttctcagg aagcgttcag cggcttcaaa gaccaaaacg gcaacttcct    5460
ggagaacctg aaggaagata tcaaagctat cctgagcctg tacgaggcca gcttcctggc    5520
tctggaaggc gaaacatcc tggacgaggc gaaggttttc gcaatctctc atctgaaaga    5580
actgtctgaa gaaaagatcg gtaaagagct ggcagaacag gtgaaccatg cactggaact    5640
gccactgcat cgccgtactc agcgtctgga agcagtatgg tctatcgagg cctaccgtaa    5700
aaaggaggac gcgaatcagg ttctgctgga gctggcaatt ctggattaca acatgatcca    5760
gtctgtatac cagcgtgatc tgcgtgaaac gtcccgttgg tggcgtcgtg tgggtctggc    5820
gaccaaactg cactttgctc gtgaccgcct gattgagagc ttctactggg ccgtgggtgt    5880
agcattcgaa ccgcaatact ccgactgccg taactccgtc gcaaaaatgt tttctttcgt    5940
aaccattatc gacgatatct acgatgtata cggcaccctg gacgaactgg agctgtttac    6000
tgatgcagtt gagcgttggg acgtaaacgc catcaacgac ctgccggatt acatgaaact    6060 gtgcttctg gctctgtata acactattaa cgaaatcgcc tacgacaacc tgaaagataa    6120
aggtgagaac atcctgccgt atctgaccaa agcctgggct gacctgtgca cgctttcct    6180 gcaagaagcc aagtggctgt acaacaaatc tactccgacc tttgacgact acttcggcaa    6240
cgcatggaaa tcctcttctg gcccgctgca actggtgttc gcttacttcg ctgtcgtgca    6300
gaacattaaa aaggaagaga tcgaaaacct gcaaaaatac catgacacca tctctcgtcc    6360
ttcccatatc ttccgtctgt gcaatgacct ggctagcgcg tctgcggaaa ttgcgcgtgg    6420
tgaaaccgca aatagcgttt cttgttacat gcgcactaaa ggtatctccg aagaactggc    6480
taccgaaagc gtgatgaatc tgatcgatga aacctggaaa aagatgaaca aggaaaaact    6540
gggtggtagc ctgttcgcga accgttcgt ggaaaccgcg atcaacctgg cacgtcaatc    6600
tcactgcact tatcataacg cgacgcgca tacctctccg gatgagctga cccgcaaacg    6660
cgttctgtct gtaatcactg aaccgattct gccgtttgaa cgctaaggat ccgaattcga    6720
gctccgtcga caagcttgcg gccgcactcg agcaccacca ccaccaccac tgagatccgg    6780
ctgctaacaa agcccgaaag gaagctgagt tggctgctgc caccgctgag caataactag    6840 cataaccct gggggcctct aaacgggtct tgaggggttt tttgctgaaa ggaggaacta    6900
tatccggat                                                            6909
```

<210> SEQ ID NO 22
<211> LENGTH: 544
<212> TYPE: PRT
<213> ORGANISM: Artificial Sequence
<220> FEATURE:
<223> OTHER INFORMATION: Synthetic Construct

<400> SEQUENCE: 22

```
Met Glu Ala Arg Arg Ser Ala Asn Tyr Glu Pro Asn Ser Trp Asp Tyr
  1               5                  10                  15

Asp Tyr Leu Leu Ser Ser Asp Thr Asp Glu Ser Ile Glu Val Tyr Lys
             20                  25                  30

Asp Lys Ala Lys Lys Leu Glu Ala Glu Val Arg Arg Glu Ile Asn Asn
         35                  40                  45

Glu Lys Ala Glu Phe Leu Thr Leu Leu Glu Leu Ile Asp Asn Val Gln
     50                  55                  60

Arg Leu Gly Leu Gly Tyr Arg Phe Glu Ser Asp Ile Arg Gly Ala Leu
 65                  70                  75                  80

Asp Arg Phe Val Ser Ser Gly Gly Phe Asp Ala Val Thr Lys Thr Ser
                 85                  90                  95
```

```
Leu His Gly Thr Ala Leu Ser Phe Arg Leu Leu Arg Gln His Gly Phe
            100                 105                 110

Glu Val Ser Gln Glu Ala Phe Ser Gly Phe Lys Asp Gln Asn Gly Asn
        115                 120                 125

Phe Leu Glu Asn Leu Lys Glu Asp Ile Lys Ala Ile Leu Ser Leu Tyr
    130                 135                 140

Glu Ala Ser Phe Leu Ala Leu Glu Gly Glu Asn Ile Leu Asp Glu Ala
145                 150                 155                 160

Lys Val Phe Ala Ile Ser His Leu Lys Glu Leu Ser Glu Glu Lys Ile
                165                 170                 175

Gly Lys Glu Leu Ala Glu Gln Val Asn His Ala Leu Glu Leu Pro Leu
            180                 185                 190

His Arg Arg Thr Gln Arg Leu Glu Ala Val Trp Ser Ile Glu Ala Tyr
        195                 200                 205

Arg Lys Lys Glu Asp Ala Asn Gln Val Leu Leu Glu Leu Ala Ile Leu
    210                 215                 220

Asp Tyr Asn Met Ile Gln Ser Val Tyr Gln Arg Asp Leu Arg Glu Thr
225                 230                 235                 240

Ser Arg Trp Trp Arg Arg Val Gly Leu Ala Thr Lys Leu His Phe Ala
                245                 250                 255

Arg Asp Arg Leu Ile Glu Ser Phe Tyr Trp Ala Val Gly Val Ala Phe
            260                 265                 270

Glu Pro Gln Tyr Ser Asp Cys Arg Asn Ser Val Ala Lys Met Phe Ser
        275                 280                 285

Phe Val Thr Ile Ile Asp Asp Ile Tyr Asp Val Tyr Gly Thr Leu Asp
    290                 295                 300

Glu Leu Glu Leu Phe Thr Asp Ala Val Glu Arg Trp Asp Val Asn Ala
305                 310                 315                 320

Ile Asn Asp Leu Pro Asp Tyr Met Lys Leu Cys Phe Leu Ala Leu Tyr
                325                 330                 335

Asn Thr Ile Asn Glu Ile Ala Tyr Asp Asn Leu Lys Asp Lys Gly Glu
            340                 345                 350

Asn Ile Leu Pro Tyr Leu Thr Lys Ala Trp Ala Asp Leu Cys Asn Ala
        355                 360                 365

Phe Leu Gln Glu Ala Lys Trp Leu Tyr Asn Lys Ser Thr Pro Thr Phe
    370                 375                 380

Asp Asp Tyr Phe Gly Asn Ala Trp Lys Ser Ser Gly Pro Leu Gln
385                 390                 395                 400

Leu Val Phe Ala Tyr Phe Ala Val Val Gln Asn Ile Lys Lys Glu Glu
                405                 410                 415

Ile Glu Asn Leu Gln Lys Tyr His Asp Thr Ile Ser Arg Pro Ser His
            420                 425                 430

Ile Phe Arg Leu Cys Asn Asp Leu Ala Ser Ala Ser Ala Glu Ile Ala
        435                 440                 445

Arg Gly Glu Thr Ala Asn Ser Val Ser Cys Tyr Met Arg Thr Lys Gly
    450                 455                 460

Ile Ser Glu Glu Leu Ala Thr Glu Ser Val Met Asn Leu Ile Asp Glu
465                 470                 475                 480

Thr Trp Lys Lys Met Asn Lys Glu Lys Leu Gly Gly Ser Leu Phe Ala
                485                 490                 495

Lys Pro Phe Val Glu Thr Ala Ile Asn Leu Ala Arg Gln Ser His Cys
            500                 505                 510
```

```
Thr Tyr His Asn Gly Asp Ala His Thr Ser Pro Asp Glu Leu Thr Arg
    515                 520                 525

Lys Arg Val Leu Ser Val Ile Thr Glu Pro Ile Leu Pro Phe Glu Arg
    530                 535                 540
```

<210> SEQ ID NO 23
<211> LENGTH: 30
<212> TYPE: DNA
<213> ORGANISM: Artificial Sequence
<220> FEATURE:
<223> OTHER INFORMATION: Synthetic Construct

<400> SEQUENCE: 23
tatacatatg cgtcgctctg cgaactacga                              30

<210> SEQ ID NO 24
<211> LENGTH: 30
<212> TYPE: DNA
<213> ORGANISM: Artificial Sequence
<220> FEATURE:
<223> OTHER INFORMATION: Synthetic Construct

<400> SEQUENCE: 24
cagagcgacg catatgtata tctccttctt                              30

<210> SEQ ID NO 25
<211> LENGTH: 30
<212> TYPE: DNA
<213> ORGANISM: Artificial Sequence
<220> FEATURE:
<223> OTHER INFORMATION: Synthetic Construct

<400> SEQUENCE: 25
tatacatatg gcacgtcgct ctgcgaacta                              30

<210> SEQ ID NO 26
<211> LENGTH: 30
<212> TYPE: DNA
<213> ORGANISM: Artificial Sequence
<220> FEATURE:
<223> OTHER INFORMATION: Synthetic Construct

<400> SEQUENCE: 26
agcgacgtgc catatgtata tctccttctt                              30

<210> SEQ ID NO 27
<211> LENGTH: 543
<212> TYPE: PRT
<213> ORGANISM: Artificial Sequence
<220> FEATURE:
<223> OTHER INFORMATION: Synthetic Construct

<400> SEQUENCE: 27

```
Met Ala Arg Arg Ser Ala Asn Tyr Glu Pro Asn Ser Trp Asp Tyr Asp
 1               5                  10                  15

Tyr Leu Leu Ser Ser Asp Thr Asp Glu Ser Ile Glu Val Tyr Lys Asp
                20                  25                  30

Lys Ala Lys Lys Leu Glu Ala Glu Val Arg Arg Glu Ile Asn Asn Glu
            35                  40                  45

Lys Ala Glu Phe Leu Thr Leu Leu Glu Leu Ile Asp Asn Val Gln Arg
        50                  55                  60

Leu Gly Leu Gly Tyr Arg Phe Glu Ser Asp Ile Arg Gly Ala Leu Asp
 65                  70                  75                  80
```

```
Arg Phe Val Ser Ser Gly Gly Phe Asp Ala Val Thr Lys Thr Ser Leu
                85                  90                  95

His Gly Thr Ala Leu Ser Phe Arg Leu Leu Arg Gln His Gly Phe Glu
            100                 105                 110

Val Ser Gln Glu Ala Phe Ser Gly Phe Lys Asp Gln Asn Gly Asn Phe
        115                 120                 125

Leu Glu Asn Leu Lys Glu Asp Ile Lys Ala Ile Leu Ser Leu Tyr Glu
    130                 135                 140

Ala Ser Phe Leu Ala Leu Glu Gly Glu Asn Ile Leu Asp Glu Ala Lys
145                 150                 155                 160

Val Phe Ala Ile Ser His Leu Lys Glu Leu Ser Glu Glu Lys Ile Gly
                165                 170                 175

Lys Glu Leu Ala Glu Gln Val Asn His Ala Leu Glu Leu Pro Leu His
            180                 185                 190

Arg Arg Thr Gln Arg Leu Glu Ala Val Trp Ser Ile Glu Ala Tyr Arg
        195                 200                 205

Lys Lys Glu Asp Ala Asn Gln Val Leu Glu Leu Ala Ile Leu Asp
    210                 215                 220

Tyr Asn Met Ile Gln Ser Val Tyr Gln Arg Asp Leu Arg Glu Thr Ser
225                 230                 235                 240

Arg Trp Trp Arg Arg Val Gly Leu Ala Thr Lys Leu His Phe Ala Arg
                245                 250                 255

Asp Arg Leu Ile Glu Ser Phe Tyr Trp Ala Val Gly Val Ala Phe Glu
            260                 265                 270

Pro Gln Tyr Ser Asp Cys Arg Asn Ser Val Ala Lys Met Phe Ser Phe
        275                 280                 285

Val Thr Ile Ile Asp Asp Ile Tyr Asp Val Tyr Gly Thr Leu Asp Glu
    290                 295                 300

Leu Glu Leu Phe Thr Asp Ala Val Glu Arg Trp Asp Val Asn Ala Ile
305                 310                 315                 320

Asn Asp Leu Pro Asp Tyr Met Lys Leu Cys Phe Leu Ala Leu Tyr Asn
                325                 330                 335

Thr Ile Asn Glu Ile Ala Tyr Asp Asn Leu Lys Asp Lys Gly Glu Asn
            340                 345                 350

Ile Leu Pro Tyr Leu Thr Lys Ala Trp Ala Asp Leu Cys Asn Ala Phe
        355                 360                 365

Leu Gln Glu Ala Lys Trp Leu Tyr Asn Lys Ser Thr Pro Thr Phe Asp
    370                 375                 380

Asp Tyr Phe Gly Asn Ala Trp Lys Ser Ser Gly Pro Leu Gln Leu
385                 390                 395                 400

Val Phe Ala Tyr Phe Ala Val Val Gln Asn Ile Lys Lys Glu Glu Ile
                405                 410                 415

Glu Asn Leu Gln Lys Tyr His Asp Thr Ile Ser Arg Pro Ser His Ile
            420                 425                 430

Phe Arg Leu Cys Asn Asp Leu Ala Ser Ala Ser Ala Glu Ile Ala Arg
        435                 440                 445

Gly Glu Thr Ala Asn Ser Val Ser Cys Tyr Met Arg Thr Lys Gly Ile
    450                 455                 460

Ser Glu Glu Leu Ala Thr Glu Ser Val Met Asn Leu Ile Asp Glu Thr
465                 470                 475                 480

Trp Lys Lys Met Asn Lys Glu Lys Leu Gly Gly Ser Leu Phe Ala Lys
                485                 490                 495

Pro Phe Val Glu Thr Ala Ile Asn Leu Ala Arg Gln Ser His Cys Thr
```

```
                500           505           510
Tyr His Asn Gly Asp Ala His Thr Ser Pro Asp Glu Leu Thr Arg Lys
            515                 520                 525

Arg Val Leu Ser Val Ile Thr Glu Pro Ile Leu Pro Phe Glu Arg
            530                 535                 540

<210> SEQ ID NO 28
<211> LENGTH: 6906
<212> TYPE: DNA
<213> ORGANISM: Artificial Sequence
<220> FEATURE:
<223> OTHER INFORMATION: Synthetic Construct

<400> SEQUENCE: 28
tggcgaatgg gacgcgccct gtagcggcgc attaagcgcg gcgggtgtgg tggttacgcg     60
cagcgtgacc gctacacttg ccagcgccct agcgcccgct cctttcgctt tcttcccttc    120
ctttctcgcc acgttcgccg gctttccccg tcaagctcta atcggggggc tcccctttagg   180 gttccgattt agtgctttac ggcacctcga ccccaaaaaa cttgattagg gtgatggttc    240
acgtagtggg ccatcgccct gatagacggt ttttcgccct ttgacgttgg agtccacgtt    300
ctttaatagt ggactcttgt tccaaactgg aacaacactc aaccctatct cggtctattc    360
ttttgattta agggatttt tgccgatttc ggcctattgg ttaaaaaatg agctgattta    420
acaaaatttt aacgcgaatt ttaacaaaat attaacgttt acaatttcag gtggcacttt    480
tcggggaaat gtgcgcggaa cccctatttg tttatttttc taaatacatt caaatatgta    540
tccgctcatg aattaattct tagaaaaact catcgagcat caaatgaaac tgcaatttat    600
tcatatcagg attatcaata ccatattttt gaaaaagccg tttctgtaat gaaggagaaa    660
actcaccgag gcagttccat aggatggcaa gatcctggta tcggtctgcg attccgactc    720
gtccaacatc aatacaacct attaatttcc cctcgtcaaa aataaggtta tcaagtgaga    780
aatcaccatg agtgacgact gaatccggtg agaatggcaa aagtttatgc atttctttcc    840
agacttgttc aacaggccag ccattacgct cgtcatcaaa atcactcgca tcaaccaaac    900
cgttattcat tcgtgattgc gcctgagcga cgaaatac gcgatcgctg ttaaaaggac    960
aattacaaac aggaatcgaa tgcaaccggc gcaggaacac tgccagcgca tcaacaatat   1020
tttcacctga tcaggatat tcttctaata cctggaatgc tgttttcccg gggatcgcag   1080
tggtgagtaa ccatgcatca tcaggagtac ggataaaatg cttgatggtc ggaagaggca   1140
taaattccgt cagccagttt agtctgacca tctcatctgt aacatcattg gcaacgctac   1200
ctttgccatg tttcagaaac aactctggcg catcgggctt cccatacaat cgatagattg   1260
tcgcacctga ttgcccgaca ttatcgcgag cccatttata cccatataaa tcagcatcca   1320
tgttggaatt taatcgcggc ctagagcaag acgtttcccg ttgaatatgg ctcataacac   1380
cccttgtatt actgtttatg taagcagaca gttttattgt tcatgaccaa atcccttaa   1440 cgtgagtttt cgttccactg agcgtcagac cccgtagaaa agatcaaagg atcttcttga   1500
gatccttttt ttctgcgcgt aatctgctgc ttgcaaacaa aaaaaccacc gctaccagcg   1560
gtggtttgtt tgccggatca agagctacca actctttttc cgaaggtaac tggcttcagc   1620
agagcgcaga taccaaatac tgtccttcta gtgtagccgt agttaggcca ccacttcaag   1680
aactctgtag caccgcctac atacctcgct ctgctaatcc tgttaccagt ggctgctgcc   1740
agtggcgata agtcgtgtct taccgggttg gactcaagac gatagttacc ggataaggcg   1800
cagcggtcgg gctgaacggg gggttcgtgc acacagccca gcttggagcg aacgacctac   1860
```

```
accgaactga gatacctaca gcgtgagcta tgagaaagcg ccacgcttcc cgaagggaga    1920
aaggcggaca ggtatccggt aagcggcagg gtcggaacag gagagcgcac gagggagctt    1980
ccagggggaa acgcctggta tctttatagt cctgtcgggt ttcgccacct ctgacttgag    2040
cgtcgatttt tgtgatgctc gtcagggggg cggagcctat ggaaaaacgc cagcaacgcg    2100 gccttttac ggttcctggc cttttgctgg ccttttgctc acatgttctt tcctgcgtta    2160
tcccctgatt ctgtggataa ccgtattacc gcctttgagt gagctgatac cgctcgccgc    2220
agccgaacga ccgagcgcag cgagtcagtg agcgaggaag cggaagagcg cctgatgcgg    2280
tattttctcc ttacgcatct gtgcggtatt tcacaccgca tatatggtgc actctcagta    2340
caatctgctc tgatgccgca tagttaagcc agtatacact ccgctatcgc tacgtgactg    2400
ggtcatggct gcgccccgac acccgccaac acccgctgac gcgccctgac gggcttgtct    2460
gctcccggca tccgcttaca gacaagctgt gaccgtctcc gggagctgca tgtgtcagag    2520
gttttcaccg tcatcaccga aacgcgcgag gcagctgcgg taaagctcat cagcgtggtc    2580
gtgaagcgat tcacagatgt ctgcctgttc atccgcgtcc agctcgttga gtttctccag    2640
aagcgttaat gtctggcttc tgataaagcg ggccatgtta agggcggttt tttcctgttt    2700
ggtcactgat gcctccgtgt aagggggatt tctgttcatg ggggtaatga taccgatgaa    2760
acgagagagg atgctcacga tacgggttac tgatgatgaa catgcccggt tactggaacg    2820
ttgtgagggt aaacaactgg cggtatggat gcggcgggac cagagaaaaa tcactcaggg    2880
tcaatgccag cgcttcgtta atacagatgt aggtgttcca cagggtagcc agcagcatcc    2940
tgcgatgcag atccggaaca taatggtgca gggcgctgac ttccgcgttt ccagacttta    3000
cgaaacacgg aaaccgaaga ccattcatgt tgttgctcag gtcgcagacg ttttgcagca    3060
gcagtcgctt cacgttcgct cgcgtatcgg tgattcattc tgctaaccag taaggcaacc    3120
ccgccagcct agccgggtcc tcaacgacag gagcacgatc atgcgcaccc gtggggccgc    3180
catgccggcg ataatggcct gcttctcgcc gaaacgtttg gtggcgggac cagtgacgaa    3240
ggcttgagcg agggcgtgca agattccgaa taccgcaagc gacaggccga tcatcgtcgc    3300
gctccagcga aagcggtcct cgccgaaaat gacccagagc gctgccggca cctgtcctac    3360
gagttgcatg ataaagaaga cagtcataag tgcggcgacg atagtcatgc cccgcgccca    3420
ccggaaggag ctgactgggt tgaaggctct caagggcatc ggtcgagatc ccggtgccta    3480
atgagtgagc taacttacat taattgcgtt gcgctcactg cccgctttcc agtcgggaaa    3540
cctgtcgtgc cagctgcatt aatgaatcgg ccaacgcgcg gggagaggcg gtttgcgtat    3600
tgggcgccag ggtggttttt cttttcacca gtgagacggg caacagctga ttgcccttca    3660
ccgcctggcc ctgagagagt tgcagcaagc ggtccacgct ggtttgcccc agcaggcgaa    3720
aatcctgttt gatggtggtt aacggcggga tataacatga gctgtcttcg gtatcgtcgt    3780
atcccactac cgagatatcc gcaccaacgc gcagcccgga ctcggtaatg gcgcgcattg    3840
cgcccagcgc catctgatcg ttggcaacca gcatcgcagt gggaacgatg ccctcattca    3900
gcatttgcat ggtttgttga aaaccggaca tggcactcca gtcgccttcc cgttccgcta    3960
tcggctgaat ttgattgcga gtgagatatt tatgccagcc agccagacgc agacgcgccg    4020
agacagaact taatgggccc gctaacagcg cgatttgctg gtgacccaat gcgaccagat    4080
gctccacgcc cagtcgcgta ccgtcttcat gggagaaaat aatactgttg atgggtgtct    4140
ggtcagagac atcaagaaat aacgccggaa cattagtgca ggcagcttcc acagcaatgg    4200
```

```
catcctggtc atccagcgga tagttaatga tcagcccact gacgcgttgc gcgagaagat    4260
tgtgcaccgc cgctttacag gcttcgacgc cgcttcgttc taccatcgac accaccacgc    4320
tggcacccag ttgatcggcg cgagatttaa tcgccgcgac aatttgcgac ggcgcgtgca    4380
gggccagact ggaggtggca acgccaatca gcaacgactg tttgcccgcc agttgttgtg    4440
ccacgcggtt gggaatgtaa ttcagctccg ccatcgccgc ttccactttt tcccgcgttt    4500
tcgcagaaac gtggctggcc tggttcacca cgcgggaaac ggtctgataa agacaccgg    4560
catactctgc gacatcgtat aacgttactg gtttcacatt caccaccctg aattgactct    4620
cttccgggcg ctatcatgcc ataccgcgaa aggttttgcg ccattcgatg gtgtccggga    4680
tctcgacgct ctcccttatg cgactcctgc attaggaagc agcccagtag taggttgagg    4740
ccgttgagca ccgccgccgc aaggaatggt gcatgcaagg agatggcgcc caacagtccc    4800
ccggccacgg ggcctgccac catacccacg ccgaaacaag cgctcatgag cccgaagtgg    4860
cgagcccgat cttccccatc ggtgatgtcg gcgatatagg cgccagcaac cgcacctgtg    4920
gcgccggtga tgccggccac gatgcgtccg gcgtagagga tcgagatctc gatcccgcga    4980
aattaatacg actcactata ggggaattgt gagcggataa caattcccct ctagaaataa    5040
ttttgtttaa ctttaagaag gagatataca tatggcacgt cgctctgcga actacgaacc    5100
taacagctgg gactatgatt acctgctgtc ctccgacacg gacgagtcca tcgaagtata    5160
caaagacaaa gcgaaaaagc tggaagccga agttcgtcgc gagattaata cgaaaaagc    5220
agaatttctg accctgctgg aactgattga caacgtccag cgcctgggcc tgggttaccg    5280
tttcgagtct gatatccgtg gtgcgctgga tcgcttcgtt tcctccggcg gcttcgatgc    5340
ggtaaccaag acttccctgc acggtacggc actgtctttc cgtctgctgc gtcaacacgg    5400
ttttgaggtt tctcaggaag cgttcagcgg cttcaaagac caaaacggca acttcctgga    5460
gaacctgaag gaagatatca agctatcct gagcctgtac gaggccagct tcctggctct    5520
ggaaggcgaa aacatcctgg acgaggcgaa ggttttcgca atctctcatc tgaaagaact    5580
gtctgaagaa aagatcggta aagagctggc agaacaggtg aaccatgcac tggaactgcc    5640
actgcatcgc cgtactcagc gtctggaagc agtatggtct atcgaggcct accgtaaaaa    5700
ggaggacgcg aatcaggttc tgctggagct ggcaattctg gattacaaca tgatccagtc    5760
tgtataccag cgtgatctgc gtgaaacgtc ccgttggtgg cgtcgtgtgg gtctggcgac    5820
caaactgcac tttgctcgtg accgcctgat tgagagcttc tactgggccg tgggtgtagc    5880
attcgaaccg caatactccg actgccgtaa ctccgtcgca aaaatgtttt ctttcgtaac    5940
cattatcgac gatatctacg atgtatacgg caccctggac gaactggagc tgtttactga    6000
tgcagttgag cgttgggacg taaacgccat caacgacctg ccggattaca tgaaactgtg    6060
cttcctggct ctgtataaca ctattaacga aatcgcctac gacaacctga agataaagg    6120
tgagaacatc ctgccgtatc tgaccaaagc ctgggctgac ctgtgcaacg ctttcctgca    6180
agaagccaag tggctgtaca acaaatctac tccgaccttt gacgactact tcggcaacgc    6240
atggaaatcc tcttctggcc cgctgcaact ggtgttcgct tacttcgctg tcgtgcagaa    6300
cattaaaaag gaagagatcg aaaacctgca aaaataccat gacaccatct tcgtccttc    6360
ccatatcttc gtctgtgca atgacctggc tagcgcgtct gcggaaattg cgcgtggtga    6420
aaccgcaaat agcgttttctt gttacatgcg cactaaaggt atctccgaag aactggctac    6480
cgaaagcgtg atgaatctga tcgatgaaac ctggaaaaag atgaacaagg aaaaactggg    6540
tggtagcctg ttcgcgaaac cgttcgtgga aaccgcgatc aacctggcac gtcaatctca    6600
```

```
ctgcacttat cataacggcg acgcgcatac ctctccggat gagctgaccc gcaaacgcgt    6660
tctgtctgta atcactgaac cgattctgcc gtttgaacgc taaggatccg aattcgagct    6720
ccgtcgacaa gcttgcggcc gcactcgagc accaccacca ccaccactga gatccggctg    6780
ctaacaaagc ccgaaaggaa gctgagttgg ctgctgccac cgctgagcaa taactagcat    6840
aaccccttgg ggcctctaaa cgggtcttga ggggttttttt gctgaaagga ggaactatat    6900
ccggat                                                                6906
```

<210> SEQ ID NO 29
<211> LENGTH: 542
<212> TYPE: PRT
<213> ORGANISM: Artificial Sequence
<220> FEATURE:
<223> OTHER INFORMATION: Synthetic Construct

<400> SEQUENCE: 29

```
Met Arg Arg Ser Ala Asn Tyr Glu Pro Asn Ser Trp Asp Tyr Asp Tyr
  1               5                  10                  15

Leu Leu Ser Ser Asp Thr Asp Glu Ser Ile Glu Val Tyr Lys Asp Lys
             20                  25                  30

Ala Lys Lys Leu Glu Ala Glu Val Arg Arg Glu Ile Asn Asn Glu Lys
         35                  40                  45

Ala Glu Phe Leu Thr Leu Leu Glu Leu Ile Asp Asn Val Gln Arg Leu
     50                  55                  60

Gly Leu Gly Tyr Arg Phe Glu Ser Asp Ile Arg Gly Ala Leu Asp Arg
 65                  70                  75                  80

Phe Val Ser Ser Gly Gly Phe Asp Ala Val Thr Lys Thr Ser Leu His
                 85                  90                  95

Gly Thr Ala Leu Ser Phe Arg Leu Leu Arg Gln His Gly Phe Glu Val
            100                 105                 110

Ser Gln Glu Ala Phe Ser Gly Phe Lys Asp Gln Asn Gly Asn Phe Leu
        115                 120                 125

Glu Asn Leu Lys Glu Asp Ile Lys Ala Ile Leu Ser Leu Tyr Glu Ala
    130                 135                 140

Ser Phe Leu Ala Leu Glu Gly Glu Asn Ile Leu Asp Glu Ala Lys Val
145                 150                 155                 160

Phe Ala Ile Ser His Leu Lys Glu Leu Ser Glu Glu Lys Ile Gly Lys
                165                 170                 175

Glu Leu Ala Glu Gln Val Asn His Ala Leu Glu Leu Pro Leu His Arg
            180                 185                 190

Arg Thr Gln Arg Leu Glu Ala Val Trp Ser Ile Glu Ala Tyr Arg Lys
        195                 200                 205

Lys Glu Asp Ala Asn Gln Val Leu Leu Glu Leu Ala Ile Leu Asp Tyr
    210                 215                 220

Asn Met Ile Gln Ser Val Tyr Gln Arg Asp Leu Arg Glu Thr Ser Arg
225                 230                 235                 240

Trp Trp Arg Arg Val Gly Leu Ala Thr Lys Leu His Phe Ala Arg Asp
                245                 250                 255

Arg Leu Ile Glu Ser Phe Tyr Trp Ala Val Gly Val Ala Phe Glu Pro
            260                 265                 270

Gln Tyr Ser Asp Cys Arg Asn Ser Val Ala Lys Met Phe Ser Phe Val
        275                 280                 285

Thr Ile Ile Asp Asp Ile Tyr Asp Val Tyr Gly Thr Leu Asp Glu Leu
        290                 295                 300
```

Glu Leu Phe Thr Asp Ala Val Glu Arg Trp Asp Val Asn Ala Ile Asn
305                 310                 315                 320

Asp Leu Pro Asp Tyr Met Lys Leu Cys Phe Leu Ala Leu Tyr Asn Thr
            325                 330                 335

Ile Asn Glu Ile Ala Tyr Asp Asn Leu Lys Asp Lys Gly Glu Asn Ile
        340                 345                 350

Leu Pro Tyr Leu Thr Lys Ala Trp Ala Asp Leu Cys Asn Ala Phe Leu
    355                 360                 365

Gln Glu Ala Lys Trp Leu Tyr Asn Lys Ser Thr Pro Thr Phe Asp Asp
370                 375                 380

Tyr Phe Gly Asn Ala Trp Lys Ser Ser Ser Gly Pro Leu Gln Leu Val
385                 390                 395                 400

Phe Ala Tyr Phe Ala Val Val Gln Asn Ile Lys Lys Glu Glu Ile Glu
            405                 410                 415

Asn Leu Gln Lys Tyr His Asp Thr Ile Ser Arg Pro Ser His Ile Phe
        420                 425                 430

Arg Leu Cys Asn Asp Leu Ala Ser Ala Ser Ala Glu Ile Ala Arg Gly
    435                 440                 445

Glu Thr Ala Asn Ser Val Ser Cys Tyr Met Arg Thr Lys Gly Ile Ser
450                 455                 460

Glu Glu Leu Ala Thr Glu Ser Val Met Asn Leu Ile Asp Glu Thr Trp
465                 470                 475                 480

Lys Lys Met Asn Lys Glu Lys Leu Gly Gly Ser Leu Phe Ala Lys Pro
            485                 490                 495

Phe Val Glu Thr Ala Ile Asn Leu Ala Arg Gln Ser His Cys Thr Tyr
        500                 505                 510

His Asn Gly Asp Ala His Thr Ser Pro Asp Glu Leu Thr Arg Lys Arg
    515                 520                 525

Val Leu Ser Val Ile Thr Glu Pro Ile Leu Pro Phe Glu Arg
530                 535                 540

<210> SEQ ID NO 30
<211> LENGTH: 6903
<212> TYPE: DNA
<213> ORGANISM: Artificial Sequence
<220> FEATURE:
<223> OTHER INFORMATION: Synthetic Construct

<400> SEQUENCE: 30
tggcgaatgg gacgcgccct gtagcggcgc attaagcgcg gcgggtgtgg tggttacgcg     60
cagcgtgacc gctacacttg ccagcgccct agcgcccgct cctttcgctt tcttcccttc    120
ctttctcgcc acgttcgccg gctttccccg tcaagctcta atcgggggc tcccttagg     180 gttccgattt agtgctttac ggcacctcga ccccaaaaaa cttgattagg gtgatggttc    240
acgtagtggg ccatcgccct gatagacggt ttttcgccct ttgacgttgg agtccacgtt    300
ctttaatagt ggactcttgt tccaaactgg aacaacactc aaccctatct cggtctattc    360
ttttgattta tagggattt tgccgatttc ggcctattgg ttaaaaaatg agctgattta    420
acaaaaattt aacgcgaatt ttaacaaaat attaacgttt acaatttcag gtggcacttt    480
tcggggaaat gtgcgcggaa cccctatttg tttatttttc taaatacatt caaatatgta    540
tccgctcatg aattaattct tagaaaaact catcgagcat caaatgaaac tgcaatttat    600
tcatatcagg attatcaata ccatattttt gaaaagccg tttctgtaat gaaggagaaa    660
actcaccgag gcagttccat aggatggcaa gatcctggta tcggtctgcg attccgactc    720

```
gtccaacatc aatacaacct attaatttcc cctcgtcaaa ataaggtta tcaagtgaga    780 aatcaccatg agtgacgact gaatccggtg agaatggcaa aagtttatgc atttctttcc    840
agacttgttc aacaggccag ccattacgct cgtcatcaaa atcactcgca tcaaccaaac    900
cgttattcat tcgtgattgc gcctgagcga gacgaaatac gcgatcgctg ttaaaaggac    960
aattacaaac aggaatcgaa tgcaaccggc gcaggaacac tgccagcgca tcaacaatat   1020
tttcacctga atcaggatat tcttctaata cctggaatgc tgttttcccg gggatcgcag   1080
tggtgagtaa ccatgcatca tcaggagtac ggataaaatg cttgatggtc ggaagaggca   1140
taaattccgt cagccagttt agtctgacca tctcatctgt aacatcattg gcaacgctac   1200
ctttgccatg tttcagaaac aactctggcg catcgggctt cccatacaat cgatagattg   1260
tcgcacctga ttgcccgaca ttatcgcgag cccatttata cccatataaa tcagcatcca   1320
tgttggaatt taatcgcggc ctagagcaag acgtttcccg ttgaatatgg ctcataacac   1380
cccttgtatt actgtttatg taagcagaca gttttattgt tcatgaccaa aatcccttaa   1440
cgtgagtttt cgttccactg agcgtcagac cccgtagaaa agatcaaagg atcttcttga   1500
gatccttttt ttctgcgcgt aatctgctgc ttgcaaacaa aaaaaccacc gctaccagcg   1560
gtggtttgtt tgccggatca agagctacca actctttttc cgaaggtaac tggcttcagc   1620
agagcgcaga taccaaatac tgtccttcta gtgtagccgt agttaggcca ccacttcaag   1680
aactctgtag caccgcctac atacctcgct ctgctaatcc tgttaccagt ggctgctgcc   1740
agtggcgata gtcgtgtct taccggggttg gactcaagac gatagttacc ggataaggcg   1800
cagcggtcgg gctgaacggg gggttcgtgc acacagccca gcttggagcg aacgacctac   1860
accgaactga gatacctaca gcgtgagcta tgagaaagcg ccacgcttcc cgaagggaga   1920
aaggcggaca ggtatccggt aagcggcagg gtcggaacag gagagcgcac gagggagctt   1980
ccagggggaa acgcctggta tctttatagt cctgtcgggt ttcgccacct ctgacttgag   2040
cgtcgatttt tgtgatgctc gtcaggggggg cggagcctat ggaaaaacgc cagcaacgcg   2100
gcctttttac ggttcctggc cttttgctgg ccttttgctc acatgttctt tcctgcgtta   2160
tcccctgatt ctgtggataa ccgtattacc gcctttgagt gagctgatac cgctcgccgc   2220
agccgaacga ccgagcgcag cgagtcagtg agcgaggaag cggaagagcg cctgatgcgg   2280
tattttctcc ttacgcatct gtgcggtatt tcacaccgca tatatggtgc actctcagta   2340
caatctgctc tgatgccgca tagttaagcc agtatacact ccgctatcgc tacgtgactg   2400
ggtcatggct gcgccccgac acccgccaac acccgctgac gcgccctgac gggcttgtct   2460
gctcccggca tccgcttaca gacaagctgt gaccgtctcc gggagctgca tgtgtcagag   2520
gttttcaccg tcatcaccga aacgcgcgag gcagctgcgg taaagctcat cagcgtggtc   2580
gtgaagcgat tcacagatgt ctgcctgttc atccgcgtcc agctcgttga gtttctccag   2640
aagcgttaat gtctggcttc tgataaagcg ggccatgtta agggcggttt tttcctgttt   2700
ggtcactgat gcctccgtgt aagggggatt tctgttcatg ggggtaatga taccgatgaa   2760
acgagagagg atgctcacga tacgggttac tgatgatgaa catgcccggt tactggaacg   2820
ttgtgagggt aaacaactgg cggtatggat gcggcgggac cagagaaaaa tcactcaggg   2880
tcaatgccag cgcttcgtta atacagatgt aggtgttcca cagggtagcc agcagcatcc   2940
tgcgatgcag atccggaaca taatggtgca gggcgctgac ttccgcgttt ccagacttta   3000
cgaaacacgg aaaccgaaga ccattcatgt tgttgctcag gtcgcagacg ttttgcagca   3060
```

```
gcagtcgctt cacgttcgct cgcgtatcgg tgattcattc tgctaaccag taaggcaacc    3120
ccgccagcct agccgggtcc tcaacgacag gagcacgatc atgcgcaccc gtggggccgc    3180
catgccggcg ataatggcct gcttctcgcc gaaacgtttg gtggcgggac cagtgacgaa    3240
ggcttgagcg agggcgtgca agattccgaa taccgcaagc gacaggccga tcatcgtcgc    3300
gctccagcga aagcggtcct cgccgaaaat gacccagagc gctgccggca cctgtcctac    3360
gagttgcatg ataaagaaga cagtcataag tgcggcgacg atagtcatgc cccgcgccca    3420
ccggaaggag ctgactgggt tgaaggctct caagggcatc ggtcgagatc ccggtgccta    3480
atgagtgagc taacttacat taattgcgtt gcgctcactg cccgctttcc agtcgggaaa    3540
cctgtcgtgc cagctgcatt aatgaatcgg ccaacgcgcg gggagaggcg gtttgcgtat    3600
tgggcgccag gtggtttttt cttttcacca gtgagacggg caacagctga ttgcccttca    3660
ccgcctggcc ctgagagagt tgcagcaagc ggtccacgct ggtttgcccc agcaggcgaa    3720
aatcctgttt gatggtggtt aacggcggga tataacatga gctgtcttcg gtatcgtcgt    3780
atcccactac cgagatatcc gcaccaacgc gcagcccgga ctcggtaatg gcgcgcattg    3840
cgcccagcgc catctgatcg ttggcaacca gcatcgcagt gggaacgatg ccctcattca    3900
gcatttgcat ggtttgttga aaaccggaca tggcactcca gtcgccttcc cgttccgcta    3960
tcggctgaat ttgattgcga gtgagatatt tatgccagcc agccagacgc agacgcgccg    4020
agacagaact taatgggccc gctaacagcg cgatttgctg gtgacccaat gcgaccagat    4080
gctccacgcc cagtcgcgta ccgtcttcat gggagaaaat aatactgttg atgggtgtct    4140
ggtcagagac atcaagaaat aacgccgaaa cattagtgca ggcagcttcc acagcaatgg    4200
catcctggtc atccagcgga tagttaatga tcagcccact gacgcgttgc gcgagaagat    4260
tgtgcaccgc cgctttacag gcttcgacgc cgcttcgttc taccatcgac accaccacgc    4320
tggcacccag ttgatcggcg cgagatttaa tcgccgcgac aatttgcgac ggcgcgtgca    4380
gggccagact ggaggtggca acgccaatca gcaacgactg tttgcccgcc agttgttgtg    4440
ccacgcggtt gggaatgtaa ttcagctccg ccatcgccgc ttccactttt tcccgcgttt    4500
tcgcagaaac gtggctggcc tggttcacca cgcgggaaac ggtctgataa gagacaccgg    4560
catactctgc gacatcgtat aacgttactg gtttcacatt caccaccctg aattgactct    4620
cttccgggcg ctatcatgcc ataccgcgaa aggttttgcg ccattcgatg gtgtccggga    4680
tctcgacgct ctcccttatg cgactcctgc attaggaagc agcccagtag taggttgagg    4740
ccgttgagca ccgccgccgc aaggaatggt gcatgcaagg agatggcgcc caacagtccc    4800
ccggccacgg ggcctgccac catacccacg ccgaaacaag cgctcatgag cccgaagtgg    4860
cgagcccgat cttccccatc ggtgatgtcg gcgatatagg cgccagcaac cgcacctgtg    4920
gcgccggtga tgccggccac gatgcgtccg gcgtagagga tcgagatctc gatcccgcga    4980
aattaatacg actcactata ggggaattgt gagcggataa caattcccct ctagaaataa    5040
ttttgtttaa ctttaagaag gagatataca tatgcgtcgc tctgcgaact acgaacctaa    5100
cagctgggac tatgattacc tgctgtcctc cgacacggac gagtccatcg aagtatacaa    5160
agacaaagcg aaaagctgg aagccgaagt tcgtcgcgag attaataacg aaaaagcaga    5220
atttctgacc ctgctggaac tgattgacaa cgtccagcgc ctgggcctgg ttaccgtttt    5280
cgagtctgat atccgtggtg cgctggatcg cttcgtttcc tccggcggct tcgatgcggt    5340
aaccaagact tccctgcacg gtacggcact gtctttccgt ctgctgcgtc aacacggttt    5400
tgaggtttct caggaagcgt tcagcggctt caaagaccaa aacggcaact tcctggagaa    5460
```

```
cctgaaggaa gatatcaaag ctatcctgag cctgtacgag gccagcttcc tggctctgga    5520
aggcgaaaac atcctggacg aggcgaaggt tttcgcaatc tctcatctga agaactgtc    5580 tgaagaaaag atcggtaaag agctggcaga acaggtgaac catgcactgg aactgccact    5640
gcatcgccgt actcagcgtc tggaagcagt atggtctatc gaggcctacc gtaaaaagga    5700
ggacgcgaat caggttctgc tggagctggc aattctggat tacaacatga tccagtctgt    5760
ataccagcgt gatctgcgtg aaacgtcccg ttggtggcgt cgtgtgggtc tggcgaccaa    5820
actgcacttt gctcgtgacc gcctgattga gagcttctac tgggccgtgg gtgtagcatt    5880
cgaaccgcaa tactccgact gccgtaactc cgtcgcaaaa atgttttctt tcgtaaccat    5940
tatcgacgat atctacgatg tatacggcac cctggacgaa ctggagctgt tactgatgc    6000 agttgagcgt tgggacgtaa acgccatcaa cgacctgccg gattacatga aactgtgctt    6060
tctggctctg tataacacta ttaacgaaat cgcctacgac aacctgaaag ataaaggtga    6120
gaacatcctg ccgtatctga ccaaagcctg ggctgacctg tgcaacgctt cctgcaagaa    6180
agccaagtgg ctgtacaaca atctactcc gacctttgac gactacttcg caacgcatg    6240 gaaatcctct tctggcccgc tgcaactggt gttcgcttac ttcgctgtcg tgcagaacat    6300
taaaaaggaa gagatcgaaa acctgcaaaa ataccatgac accatctctc gtccttccca    6360
tatcttccgt ctgtgcaatg acctggctag gcgtctgcg gaaattgcgc gtggtgaaac    6420
cgcaaatagc gtttcttgtt acatgcgcac taaaggtatc tccgaagaac tggctaccga    6480
aagcgtgatg aatctgatcg atgaaacctg gaaaaagatg aacaaggaaa aactgggtgg    6540
tagcctgttc gcgaaaccgt tcgtggaaac cgcgatcaac ctggcacgtc aatctcactg    6600
cacttatcat aacggcgacg cgcataccct ccggatgag ctgacccgca aacgcgttct    6660
gtctgtaatc actgaaccga ttctgccgtt tgaacgctaa ggatccgaat tcgagctccg    6720
tcgacaagct tgcggccgca ctcgagcacc accaccacca ccactgagat ccggctgcta    6780
acaaagcccg aaaggaagct gagttggctg ctgccaccgc tgagcaataa ctagcataac    6840 ccccttgggcc ctctaaacgg gtcttgaggg gttttttgct gaaaggagga actatatccg    6900
gat                                                                 6903
```

<210> SEQ ID NO 31
<211> LENGTH: 595
<212> TYPE: PRT
<213> ORGANISM: Artificial Sequence
<220> FEATURE:
<223> OTHER INFORMATION: Synthetic Construct

<400> SEQUENCE: 31

```
Met Ala Thr Glu Leu Leu Cys Leu His Arg Pro Ile Ser Leu Thr His
 1               5                  10                  15

Lys Leu Phe Arg Asn Pro Leu Pro Lys Val Ile Gln Ala Thr Pro Leu
            20                  25                  30

Thr Leu Lys Leu Arg Cys Ser Val Ser Thr Glu Asn Val Ser Phe Thr
        35                  40                  45

Glu Thr Glu Thr Glu Ala Arg Arg Ser Ala Asn Tyr Glu Pro Asn Ser
    50                  55                  60

Trp Asp Tyr Asp Tyr Leu Leu Ser Ser Asp Thr Asp Glu Ser Ile Glu
65                  70                  75                  80

Val Tyr Lys Asp Lys Ala Lys Lys Leu Glu Ala Glu Val Arg Arg Glu
                85                  90                  95
```

```
Ile Asn Asn Glu Lys Ala Glu Phe Leu Thr Leu Leu Glu Leu Ile Asp
            100                 105                 110

Asn Val Gln Arg Leu Gly Leu Gly Tyr Arg Phe Glu Ser Asp Ile Arg
        115                 120                 125

Gly Ala Leu Asp Arg Phe Val Ser Ser Gly Phe Asp Ala Val Thr
130                 135                 140

Lys Thr Ser Leu His Gly Thr Ala Leu Ser Phe Arg Leu Leu Arg Gln
145                 150                 155                 160

His Gly Phe Glu Val Ser Gln Glu Ala Phe Ser Gly Phe Lys Asp Gln
                165                 170                 175

Asn Gly Asn Phe Leu Glu Asn Leu Lys Glu Asp Ile Lys Ala Ile Leu
            180                 185                 190

Ser Leu Tyr Glu Ala Ser Phe Leu Ala Leu Glu Gly Glu Asn Ile Leu
        195                 200                 205

Asp Glu Ala Lys Val Phe Ala Ile Ser His Leu Lys Glu Leu Ser Glu
210                 215                 220

Glu Lys Ile Gly Lys Glu Leu Ala Glu Gln Val Asn His Ala Leu Glu
225                 230                 235                 240

Leu Pro Leu His Arg Arg Thr Gln Arg Leu Glu Ala Val Trp Ser Ile
                245                 250                 255

Glu Ala Tyr Arg Lys Glu Asp Ala Asn Gln Val Leu Leu Glu Leu
            260                 265                 270

Ala Ile Leu Asp Tyr Asn Met Ile Gln Ser Val Tyr Gln Arg Asp Leu
        275                 280                 285

Arg Glu Thr Ser Arg Trp Trp Arg Arg Val Gly Leu Ala Thr Lys Leu
290                 295                 300

His Phe Ala Arg Asp Arg Leu Ile Glu Ser Phe Tyr Trp Ala Val Gly
305                 310                 315                 320

Val Ala Phe Glu Pro Gln Tyr Ser Asp Cys Arg Asn Ser Val Ala Lys
                325                 330                 335

Met Phe Ser Phe Val Thr Ile Ile Asp Asp Ile Tyr Asp Val Tyr Gly
            340                 345                 350

Thr Leu Asp Glu Leu Glu Leu Phe Thr Asp Ala Val Glu Arg Trp Asp
        355                 360                 365

Val Asn Ala Ile Asn Asp Leu Pro Asp Tyr Met Lys Leu Cys Phe Leu
370                 375                 380

Ala Leu Tyr Asn Thr Ile Asn Glu Ile Ala Tyr Asp Asn Leu Lys Asp
385                 390                 395                 400

Lys Gly Glu Asn Ile Leu Pro Tyr Leu Thr Lys Ala Trp Ala Asp Leu
                405                 410                 415

Cys Asn Ala Phe Leu Gln Glu Ala Lys Trp Leu Tyr Asn Lys Ser Thr
            420                 425                 430

Pro Thr Phe Asp Asp Tyr Phe Gly Asn Ala Trp Lys Ser Ser Ser Gly
        435                 440                 445

Pro Leu Gln Leu Val Phe Ala Tyr Phe Ala Val Val Gln Asn Ile Lys
450                 455                 460

Lys Glu Glu Ile Glu Asn Leu Gln Lys Tyr His Asp Thr Ile Ser Arg
465                 470                 475                 480

Pro Ser His Ile Phe Arg Leu Cys Asn Asp Leu Ala Ser Ala Ser Ala
                485                 490                 495

Glu Ile Ala Arg Gly Glu Thr Ala Asn Ser Val Ser Cys Tyr Met Arg
            500                 505                 510

Thr Lys Gly Ile Ser Glu Glu Leu Ala Thr Glu Ser Val Met Asn Leu
```

```
              515                 520                 525
Ile Asp Glu Thr Trp Lys Lys Met Asn Lys Glu Lys Leu Gly Gly Ser
530                 535                 540

Leu Phe Ala Lys Pro Phe Val Glu Thr Ala Ile Asn Leu Ala Arg Gln
545                 550                 555                 560

Ser His Cys Thr Tyr His Asn Gly Asp Ala His Thr Ser Pro Asp Glu
                565                 570                 575

Leu Thr Arg Lys Arg Val Leu Ser Val Ile Thr Glu Pro Ile Leu Pro
                580                 585                 590

Phe Glu Arg
        595

<210> SEQ ID NO 32
<211> LENGTH: 560
<212> TYPE: PRT
<213> ORGANISM: Artificial Sequence
<220> FEATURE:
<223> OTHER INFORMATION: Synthetic Construct

<400> SEQUENCE: 32

Met Arg Cys Ser Val Ser Thr Glu Asn Val Ser Phe Thr Glu Thr Glu
1               5                   10                  15

Thr Glu Ala Arg Arg Ser Ala Asn Tyr Glu Pro Asn Ser Trp Asp Tyr
                20                  25                  30

Asp Tyr Leu Leu Ser Ser Asp Thr Asp Glu Ser Ile Glu Val Tyr Lys
            35                  40                  45

Asp Lys Ala Lys Lys Leu Glu Ala Glu Val Arg Arg Glu Ile Asn Asn
50                  55                  60

Glu Lys Ala Glu Phe Leu Thr Leu Leu Glu Leu Ile Asp Asn Val Gln
65                  70                  75                  80

Arg Leu Gly Leu Gly Tyr Arg Phe Glu Ser Asp Ile Arg Gly Ala Leu
                85                  90                  95

Asp Arg Phe Val Ser Ser Gly Gly Phe Asp Ala Val Thr Lys Thr Ser
            100                 105                 110

Leu His Gly Thr Ala Leu Ser Phe Arg Leu Leu Arg Gln His Gly Phe
        115                 120                 125

Glu Val Ser Gln Glu Ala Phe Ser Gly Phe Lys Asp Gln Asn Gly Asn
    130                 135                 140

Phe Leu Glu Asn Leu Lys Glu Asp Ile Lys Ala Ile Leu Ser Leu Tyr
145                 150                 155                 160

Glu Ala Ser Phe Leu Ala Leu Glu Gly Glu Asn Ile Leu Asp Glu Ala
                165                 170                 175

Lys Val Phe Ala Ile Ser His Leu Lys Glu Leu Ser Glu Glu Lys Ile
            180                 185                 190

Gly Lys Glu Leu Ala Glu Gln Val Asn His Ala Leu Glu Leu Pro Leu
        195                 200                 205

His Arg Arg Thr Gln Arg Leu Glu Ala Val Trp Ser Ile Glu Ala Tyr
    210                 215                 220

Arg Lys Lys Glu Asp Ala Asn Gln Val Leu Leu Glu Leu Ala Ile Leu
225                 230                 235                 240

Asp Tyr Asn Met Ile Gln Ser Val Tyr Gln Arg Asp Leu Arg Glu Thr
                245                 250                 255

Ser Arg Trp Trp Arg Arg Val Gly Leu Ala Thr Lys Leu His Phe Ala
            260                 265                 270

Arg Asp Arg Leu Ile Glu Ser Phe Tyr Trp Ala Val Gly Val Ala Phe
```

```
                275                 280                 285
Glu Pro Gln Tyr Ser Asp Cys Arg Asn Ser Val Ala Lys Met Phe Ser
    290                 295                 300
Phe Val Thr Ile Ile Asp Asp Ile Tyr Asp Val Tyr Gly Thr Leu Asp
305                 310                 315                 320
Glu Leu Glu Leu Phe Thr Asp Ala Val Glu Arg Trp Asp Val Asn Ala
                325                 330                 335
Ile Asn Asp Leu Pro Asp Tyr Met Lys Leu Cys Phe Leu Ala Leu Tyr
                340                 345                 350
Asn Thr Ile Asn Glu Ile Ala Tyr Asp Asn Leu Lys Asp Lys Gly Glu
            355                 360                 365
Asn Ile Leu Pro Tyr Leu Thr Lys Ala Trp Ala Asp Leu Cys Asn Ala
        370                 375                 380
Phe Leu Gln Glu Ala Lys Trp Leu Tyr Asn Lys Ser Thr Pro Thr Phe
385                 390                 395                 400
Asp Asp Tyr Phe Gly Asn Ala Trp Lys Ser Ser Ser Gly Pro Leu Gln
                405                 410                 415
Leu Val Phe Ala Tyr Phe Ala Val Val Gln Asn Ile Lys Lys Glu Glu
                420                 425                 430
Ile Glu Asn Leu Gln Lys Tyr His Asp Thr Ile Ser Arg Pro Ser His
            435                 440                 445
Ile Phe Arg Leu Cys Asn Asp Leu Ala Ser Ala Ser Ala Glu Ile Ala
        450                 455                 460
Arg Gly Glu Thr Ala Asn Ser Val Ser Cys Tyr Met Arg Thr Lys Gly
465                 470                 475                 480
Ile Ser Glu Glu Leu Ala Thr Glu Ser Val Met Asn Leu Ile Asp Glu
                485                 490                 495
Thr Trp Lys Lys Met Asn Lys Glu Lys Leu Gly Gly Ser Leu Phe Ala
            500                 505                 510
Lys Pro Phe Val Glu Thr Ala Ile Asn Leu Ala Arg Gln Ser His Cys
        515                 520                 525
Thr Tyr His Asn Gly Asp Ala His Thr Ser Pro Asp Glu Leu Thr Arg
    530                 535                 540
Lys Arg Val Leu Ser Val Ile Thr Glu Pro Ile Leu Pro Phe Glu Arg
545                 550                 555                 560
```